US011147759B2

(12) United States Patent
Kang et al.

(10) Patent No.: US 11,147,759 B2
(45) Date of Patent: *Oct. 19, 2021

(54) COVALENT TREATMENT FOR KERATIN-CONTAINING MATERIALS

(71) Applicant: Living Proof, Inc., Boston, MA (US)

(72) Inventors: Soo-Young Kang, Bedford, MA (US); Zhaoxia Ji, Boston, MA (US); Sara A. Johnson, Boston, MA (US); Dinara A. Villanueva, Boston, MA (US); Jeremiah A. Johnson, Cambridge, MA (US); Xu Qin, Boston, MA (US)

(73) Assignee: Living Proof, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/193,385

(22) Filed: Nov. 16, 2018

(65) Prior Publication Data

US 2019/0160001 A1 May 30, 2019

Related U.S. Application Data

(60) Provisional application No. 62/587,896, filed on Nov. 17, 2017.

(51) Int. Cl.
*A61K 8/91* (2006.01)
*A61K 8/44* (2006.01)
*A61K 8/55* (2006.01)
*A61K 8/365* (2006.01)
*A61Q 5/00* (2006.01)
*A61K 8/49* (2006.01)
*A61K 8/81* (2006.01)
*A61Q 3/00* (2006.01)
*A61Q 1/10* (2006.01)

(52) U.S. Cl.
CPC .............. *A61K 8/91* (2013.01); *A61K 8/365* (2013.01); *A61K 8/447* (2013.01); *A61K 8/498* (2013.01); *A61K 8/55* (2013.01); *A61K 8/8105* (2013.01); *A61K 8/8135* (2013.01); *A61K 8/8152* (2013.01); *A61K 8/8158* (2013.01); *A61Q 1/10* (2013.01); *A61Q 3/00* (2013.01); *A61Q 5/002* (2013.01); *A61K 2800/10* (2013.01); *A61K 2800/54* (2013.01); *A61K 2800/95* (2013.01)

(58) Field of Classification Search
CPC .......... A61K 8/91; A61K 8/365; A61K 8/447; A61K 8/498; A61K 8/55; A61K 8/8105; A61K 8/8135; A61K 8/8152; A61K 8/8158; A61K 2800/10; A61K 2800/54; A61K 2800/95; A61Q 1/10; A61Q 3/00; A61Q 5/002
See application file for complete search history.

(56) References Cited

U.S. PATENT DOCUMENTS

| 3,634,022 A | 1/1972 | Robbins et al. |
| 3,676,550 A | 7/1972 | Anzuino |
| 5,241,973 A * | 9/1993 | Salce ........................ A61Q 5/04 132/202 |
| 5,641,477 A * | 6/1997 | Syed ........................ A61K 8/43 132/204 |
| 2003/0140429 A1 | 7/2003 | Legrand et al. |
| 2005/0002886 A1* | 1/2005 | Philippe ................... A61K 8/46 424/70.5 |
| 2007/0134185 A1* | 6/2007 | Samain ..................... A61K 8/46 424/70.4 |
| 2010/0028281 A1* | 2/2010 | Robinson ................. A61K 8/44 424/70.2 |
| 2010/0202998 A1 | 8/2010 | Ramos-Stanbury et al. |
| 2011/0229430 A1* | 9/2011 | Hawkins ................ A61Q 5/004 424/70.12 |
| 2015/0034117 A1 | 2/2015 | Pressly et al. |
| 2016/0346182 A1* | 12/2016 | Itaya ........................ A61K 8/19 |

FOREIGN PATENT DOCUMENTS

| EP | 3388052 A1 | 10/2018 |
| GB | 1198857 A | 7/1970 |
| GB | 1198857 A | 7/1970 |
| WO | 2015/017768 A1 | 2/2015 |
| WO | 2017/099436 A1 | 6/2017 |

OTHER PUBLICATIONS

Shang. Process control in dyeing of textiles. 2013, p. 307, in "Process Control in Textile Manufacturing". (Year: 2013).*
International Search Report and Written Opinion for International Application No. PCT/US2018/061505 dated Feb. 4, 2019.
International Search Report and Written Opinion for Application No. PCT/US2018/061505, dated Feb. 4, 2019, 16 pages.

* cited by examiner

*Primary Examiner* — Robert A Wax
*Assistant Examiner* — Olga V. Tcherkasskaya
(74) *Attorney, Agent, or Firm* — McCarter & English, LLP; Michael J. DeGrazia

(57) ABSTRACT

Disclosed are methods of grafting monomeric and polymeric materials on keratin-containing material to provide a covalent coating on keratin-containing material. A mixture comprising a reducing agent is applied to the keratin-containing material sample. The keratin-containing material sample then comprises a plurality of free thiol groups. A monomer is applied to the keratin-containing material sample. The free thiol groups react with the monomer to form a plurality of covalent bonds between the free thiol groups and the monomers. The reducing agent and the monomer can be applied separately, semi-simultaneously, or simultaneously. The disclosed methods can be carried out with or without catalyst. The disclosed methods can be carried out with or without an additive.

15 Claims, 84 Drawing Sheets

R, R' = hydrocarbons; linear or branched, saturated or unsaturated

R, R' = hydrocarbons; linear or branched, saturated or unsaturated

R, R' = hydrocarbons; linear or branched, saturated or unsaturated

Table 6

Figure 30

Table 14.

| Monomer | Structure |
|---|---|
| 2-(dimethylamino)ethyl acrylate | 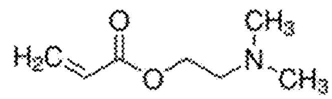 |
| 2-ethylhexyl acrylate | 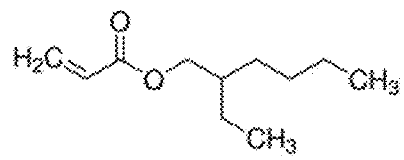 |
| Butyl acrylate | 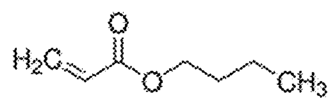 |
| Dodecyl acrylate | 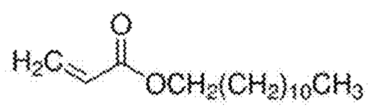 |
| Ethyl acrylate | 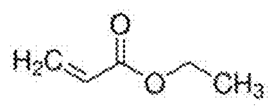 |
| Isodecyl acrylate | 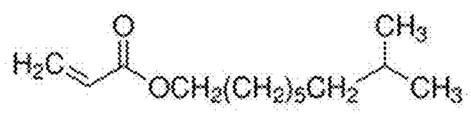 |
| Isobornyl acrylate | 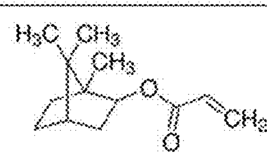 |
| Tert-butyl acrylate | 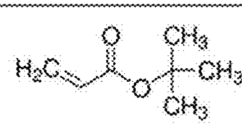 |

Figure 76A
 

Figure 76B
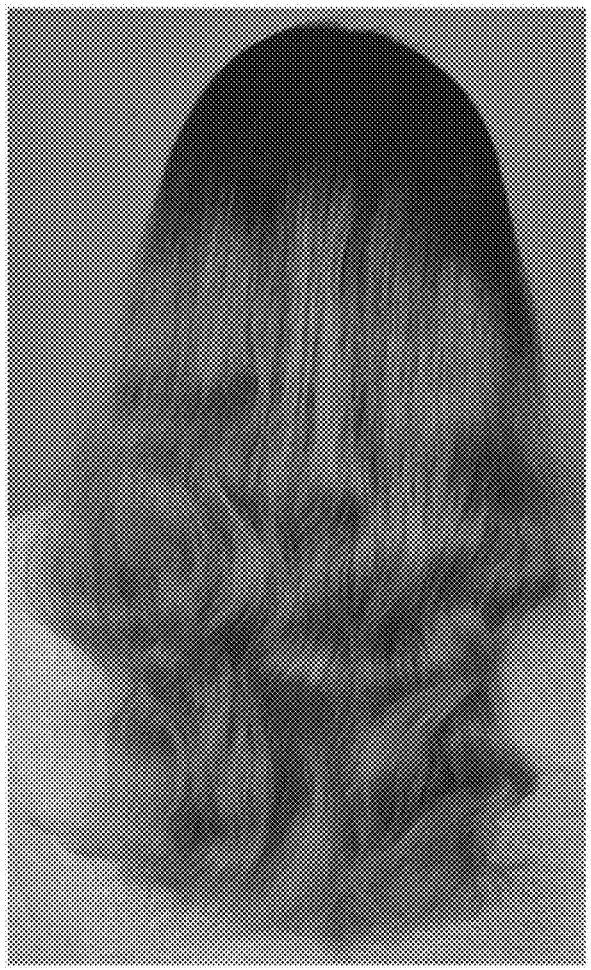
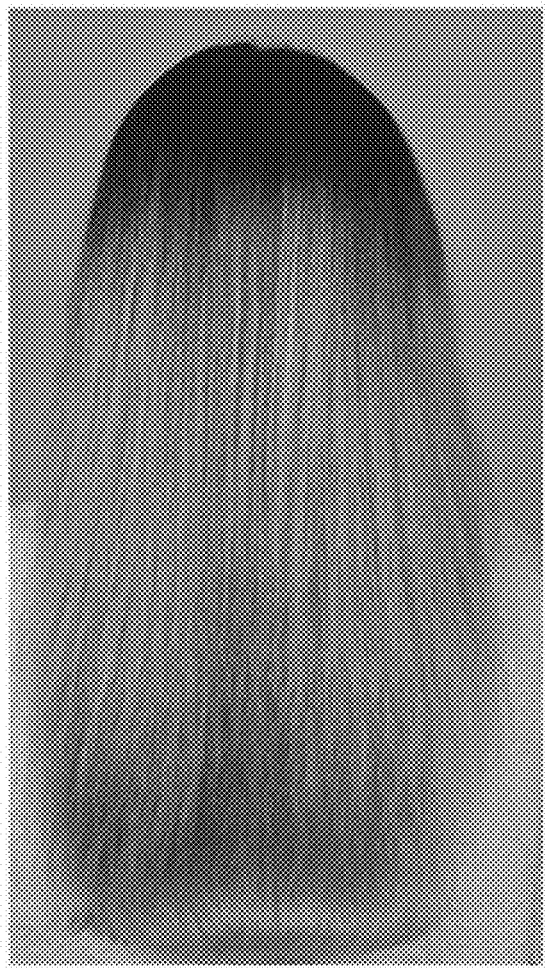

Figure 77
 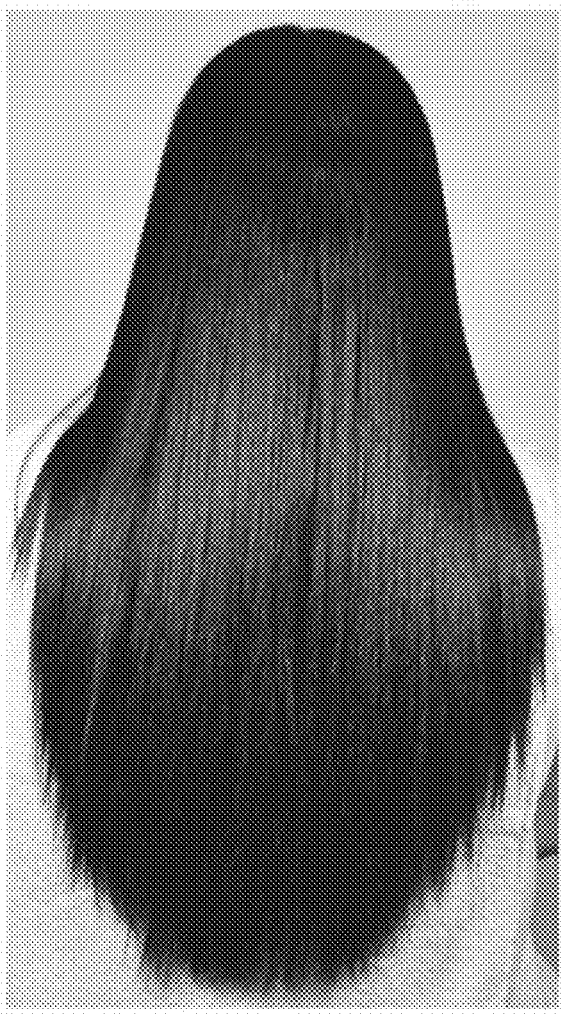

COVALENT TREATMENT FOR KERATIN-CONTAINING MATERIALS

RELATED APPLICATIONS

This application claims the benefit of priority to U.S. Provisional Patent Application Ser. No. 62/587,896, filed Nov. 17, 2017.

BACKGROUND

The human body includes a number of keratinous components, including hair, eyebrows, eyelashes, fingernails and toenails. These protein-based structures serve in various ways to enhance the body's functions—for example, hair helps protect the body from extreme temperatures, eyelashes and eyebrows stop debris from falling into the eyes, and fingernails provide a counterpressure to the fingertips that improve dexterity.

These keratinous substances consist primarily of the protein keratin, but in their virgin form also contain important small molecule components that improve functionality. For instance, fingernails and toenails function best (i.e. have optimal mechanical properties and flexibility) when they contain functional phospholipid molecules. See, e.g., Finlay, A. Y.; Frost, P.; Keith, A. D.; Snipes, W. Br. J. Dermatol. 1980, 103, 357-365. These molecules can be removed during normal wear and tear, and are particularly susceptible to harsh cleaning solvents. The consumer can partially mitigate this functional degradation through the use of moisturizers, but they must frequently spend time re-applying these products. A long-term method for achieving healthy, virgin-like nails is still an unmet need.

Likewise, upon emerging from the follicle, mammalian hair is covered with a thin covalently bound lipid layer of 18-methyl eicosanoic acid (18-MEA) bonded to the outermost proteinaceous cell membrane layer (FIG. 1). The 18-MEA molecule is covalently attached to the outermost keratin layer of the cuticle via a thioester linkage, and lends the hair enhanced hydrophobicity and a conditioned, smooth feeling while acting as a boundary lubricant to decrease friction resistance. See, e.g., Robbins, C. R. Chemical and Physical Behavior of Human Hair. $5^{th}$ ed. 2012; Kalkbrenner, U.; Koener, H.; Hoecker, H.; Rivett, D. E. Proc. $8^{th}$ Int. Wool Text. Res. Conf., Christchurch, New Zealand. 1990, 1, 398-407; Carr, C. M.; Leaver, I. H.; Hughes, A. E. Textile Res. 1986, 56, 457; Breakspear, S.; Smith, J. R., Luengo, G. J. Struct. Biol. 2005, 149, 235-242; Torre, C.A.; Bhusham, B.; Yang, J.-Z.; Torgerson, P. M. J. Cosmet. Sci., 2006, 57, 37-56.

When hair is repeatedly weathered in response to stresses such as washing, drying, brushing, combing, rubbing, styling, and sun exposure, the 18-MEA layer is lost and the hair surface becomes more hydrophilic, negatively charged, and damaged-feeling. There are many products to address this need including conditioners, leave-on creams, and smoothing oils. These products contain emollient and conditioning molecules such as natural oil derivatives, long-chain alcohols, carboxylic acids, and quaternary compounds, but since the conditioning molecules in these products are only deposited on the surface of the hair via non-covalent interactions, they are routinely washed out of the hair and the effect is short-lived. Therefore, the consumer must frequently spend time re-applying these products. A long-term method for achieving healthy, virgin-like hair is still an unmet need.

SUMMARY

In one aspect, the disclosure provides a method for treating a keratin-containing material, comprising:
i) providing a keratin-containing material sample comprising a plurality of disulfide bonds;
ii) applying to the keratin-containing material sample for a period of time a mixture, comprising a reducing agent in a concentration of about 0.1% by weight to about 15% by weight, thereby producing a reduced keratin-containing material sample, wherein the reduced keratin-containing material sample comprises a plurality of free thiol groups; and
iii) applying a monomer to the reduced keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers.

In another aspect, the disclosure provides a method for treating a keratin-containing material, comprising:
i) providing a keratin-containing material sample comprising a plurality of disulfide bonds;
ii) applying to the keratin-containing material sample for a period of time a mixture, comprising a reducing agent in a concentration of about 0.1% by weight to about 15% by weight and a catalyst, wherein the keratin-containing material sample comprises a plurality of free thiol groups; and
iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers.

In another aspect, the disclosure provides a method for treating a keratin-containing material, comprising:
i) providing a keratin-containing material sample comprising a plurality of disulfide bonds; and
ii) applying to the keratin-containing material sample for a period of time a mixture, comprising a reducing agent in a concentration of about 0.1% by weight to about 15% by weight, and a monomer; wherein the monomer is selected from the group consisting of an acrylate, a methacrylate, a monomer comprising a vinyl group, a monomer comprising an alkyne group, and a monomer comprising a maleimide group, thereby forming a plurality of free thiol groups which react with the monomer to form a plurality of covalent bonds between the free thiol groups and the monomers.

In another aspect, the disclosure provides a method for treating a keratin-containing material, wherein hydrophobicity of a keratin-containing material is improved, comprising:
i) providing a keratin-containing material sample comprising a plurality of disulfide bonds;
ii) applying to the keratin-containing material sample for a period of time a mixture, comprising a reducing agent, wherein the keratin-containing material sample comprises a plurality of free thiol groups; and
iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the hydrophobicity of the keratin-containing material.

In another aspect, the disclosure provides a method for treating a keratin-containing material, wherein hydrophobicity of the keratin-containing material is improved, comprising:
i) providing a keratin-containing material sample comprising a plurality of disulfide bonds;
ii) applying to the keratin-containing material sample for a period of time a mixture, comprising a reducing agent and a catalyst, wherein the keratin-containing material sample comprises a plurality of free thiol groups; and
iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the hydrophobicity of the keratin-containing material.

In another aspect, the disclosure provides a method for treating a keratin-containing material, wherein hydrophobicity of the keratin-containing material is improved, comprising:
i) providing a keratin-containing material sample comprising a plurality of disulfide bonds; and
ii) applying to the keratin-containing material sample for a period of time a mixture, comprising a reducing agent and a monomer; wherein the monomer is selected from the group consisting of an acrylate, a methacrylate, a monomer comprising a vinyl group, a monomer comprising an alkyne group, and a monomer comprising a maleimide group, thereby forming a plurality of free thiol groups which react with the monomer to form a plurality of covalent bonds between the free thiol groups and the monomers;

thereby improving the hydrophobicity of the keratin-containing material.

In another aspect, the disclosure provides a method for treating a keratin-containing material, wherein an ultimate tensile strength of the keratin-containing material is improved, comprising:
i) providing a keratin-containing material sample comprising a plurality of disulfide bonds;
ii) applying to the keratin-containing material sample for a period of time a mixture, comprising a reducing agent, wherein the keratin-containing material sample comprises a plurality of free thiol groups; and
iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the ultimate tensile strength of the keratin-containing material.

In another aspect, the disclosure provides a method for treating a keratin-containing material, wherein an ultimate tensile strength of the keratin-containing material is improved, comprising:
i) providing a keratin-containing material sample comprising a plurality of disulfide bonds;
ii) applying to the keratin-containing material sample for a period of time a mixture, comprising a reducing agent and a catalyst, wherein the keratin-containing material sample comprises a plurality of free thiol groups; and
iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the ultimate tensile strength of the keratin-containing material.

In another aspect, the disclosure provides a method for treating keratin-containing material, wherein an ultimate tensile strength of the keratin-containing material is improved, comprising:
i) providing a keratin-containing material sample comprising a plurality of disulfide bonds; and
ii) applying to the keratin-containing material sample for a period of time a mixture, comprising a reducing agent and a monomer; wherein the monomer is selected from the group consisting of an acrylate, a methacrylate, a monomer comprising a vinyl group, a monomer comprising an alkyne group, and a monomer comprising a maleimide group, thereby forming a plurality of free thiol groups which react with the monomer to form a plurality of covalent bonds between the free thiol groups and the monomers;

thereby improving the ultimate tensile strength of the keratin-containing material.

In another aspect, the disclosure provides a method for treating a keratin-containing material, wherein a protein loss value of the keratin-containing material is improved, comprising:
i) providing a keratin-containing material sample comprising a plurality of disulfide bonds;
ii) applying to the keratin-containing material sample for a period of time a mixture, comprising a reducing agent, wherein the keratin-containing material sample comprises a plurality of free thiol groups; and
iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the protein loss value of the keratin-containing material.

In another aspect, the disclosure provides a method for treating a keratin-containing material, wherein a protein loss value of the keratin-containing material is improved, comprising:
i) providing a keratin-containing material sample comprising a plurality of disulfide bonds;
ii) applying to the keratin-containing material sample for a period of time a mixture, comprising a reducing agent and a catalyst, wherein the keratin-containing material sample comprises a plurality of free thiol groups; and iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the protein loss value of the keratin-containing material.

In another aspect, the disclosure provides a method for treating a keratin-containing material, wherein a protein loss value of the keratin-containing material is improved, comprising:

i) providing a keratin-containing material sample comprising a plurality of disulfide bonds; and ii) applying to the keratin-containing material sample for a period of time a mixture, comprising a reducing agent and a monomer; wherein the monomer is selected from the group consisting of an acrylate, a methacrylate, a monomer comprising a vinyl group, a monomer comprising an alkyne group, and a monomer comprising a maleimide group, thereby forming a plurality of free thiol groups which react with the monomer to form a plurality of covalent bonds between the free thiol groups and the monomers;

thereby improving the protein loss value of the keratin-containing material.

In another aspect, the disclosure provides a method for treating a keratin-containing material, wherein a denaturation temperature of the keratin-containing material is improved, comprising:

i) providing a keratin-containing material sample comprising a plurality of disulfide bonds;

ii) applying to the keratin-containing material sample for a period of time a mixture, comprising a reducing agent, wherein the keratin-containing material sample comprises a plurality of free thiol groups; and iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the denaturation temperature of the keratin-containing material.

In another aspect, the disclosure provides a method for treating a keratin-containing material, wherein denaturation temperature of the keratin-containing material is improved, comprising:

i) providing a keratin-containing material sample comprising a plurality of disulfide bonds;

ii) applying to the keratin-containing material sample for a period of time a mixture, comprising a reducing agent and a catalyst, wherein the keratin-containing material sample comprises a plurality of free thiol groups; and iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the denaturation temperature of the keratin-containing material.

In another aspect, the disclosure provides a method for treating a keratin-containing material, wherein denaturation temperature of the keratin-containing material is improved, comprising:

i) providing a keratin-containing material sample comprising a plurality of disulfide bonds; and ii) applying to the keratin-containing material sample for a period of time a mixture, comprising a reducing agent and a monomer; wherein the monomer is selected from the group consisting of an acrylate, a methacrylate, a monomer comprising a vinyl group, a monomer comprising an alkyne group, and a monomer comprising a maleimide group, thereby forming a plurality of free thiol groups which react with the monomer to form a plurality of covalent bonds between the free thiol groups and the monomers;

thereby improving the denaturation temperature of the keratin-containing material.

BRIEF DESCRIPTION OF THE FIGURES

FIG. 30 depicts exemplary acrylate monomers for simultaneous grafting.

FIG. 76A depicts images showing a subject with wavy and frizzy hair before and after semi-simultaneous grafting with an exemplary PEG-diacrylate monomer and post-treatment with gluconolactone and citric acid.

FIG. 76B depicts images showing a subject with bleached and curly hair before and after semi-simultaneous grafting with an exemplary PEG-diacrylate monomer and post-treatment with gluconolactone and citric acid.

FIG. 77 depicts images showing a subject with straight and frizzy hair before and after semi-simultaneous grafting with an exemplary PEG-diacrylate monomer and post-treatment with gluconolactone and citric acid.

DETAILED DESCRIPTION

Overview

Figure 1:
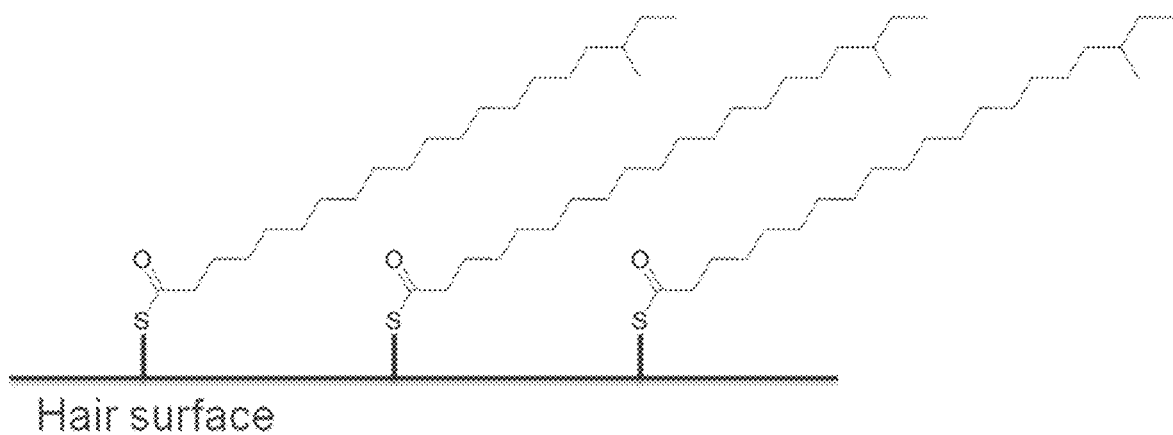
FIG. 1 depicts a cartoon illustrating the covalent attachment of the hydrophobic molecule 18-MEA to the surface of hair via a thioester linkage.

A keratin-containing material is weathered and damaged in response to stresses, including normal wear and tear, harsh cleaning solvents, washing, drying, brushing, combing, rubbing, styling, bleaching, dyeing, and sun exposure. Damage leads to functional degradation of a keratin-containing material. For example, when the natural 18-MEA layer is lost, and the hair surface becomes more hydrophilic, negatively charged, and damaged-feeling. Many products attempt to address this need, including moisturizers, conditioners, leave-on creams, and smoothing oils. These products contain emollient and conditioning molecules such as natural oil derivatives, long-chain alcohols, carboxylic acids, and quaternary compounds. However, the conditioning molecules in these products are deposited only on the surface of the keratin-containing material via non-covalent interactions, they are routinely washed out of the keratin-containing material and the effect is short-lived. Therefore, the consumer must frequently spend time re-applying these products. A long-term method for achieving healthy, virgin-like keratin-containing material, e.g., nails and hair, is still an unmet need.

Exemplary Methods for Treating a Keratin-Containing Material

Grafting monomeric and polymeric materials to a keratin-containing material can provide a covalent coating on a keratin-containing material. A keratin-containing material sample comprises a plurality of disulfide bonds. A mixture comprising a reducing agent is applied to the keratin-containing material sample. The keratin-containing material sample then comprises a plurality of free thiol groups. A monomer is applied to the keratin-containing material sample. The free thiol groups react with the monomer to form a plurality of covalent bonds between the free thiol groups and the monomers.

In some embodiments, the keratin-containing material is selected from the group consisting of hair (including facial hair such as eyebrows, eyelashes, beards, and moustaches), fingernails and toenails. In some embodiments, the keratin-containing material is selected from the group consisting of hair, eyebrows, eyelashes, fingernails and toenails. In some embodiments, the keratin-containing material is hair. In some embodiments, the keratin-containing material is a fingernail or a toenail.

In one aspect, the disclosure provides a method for treating keratin-containing material, comprising:
i) providing a keratin-containing material sample comprising a plurality of disulfide bonds;
ii) applying to the keratin-containing material sample for a period of time a mixture, comprising a reducing agent in a concentration of about 0.1% by weight to about 15% by weight, thereby producing a reduced keratin-containing material sample, wherein the reduced keratin-containing material sample comprises a plurality of free thiol groups; and
iii) applying a monomer to the reduced keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers.

Figure 2A:
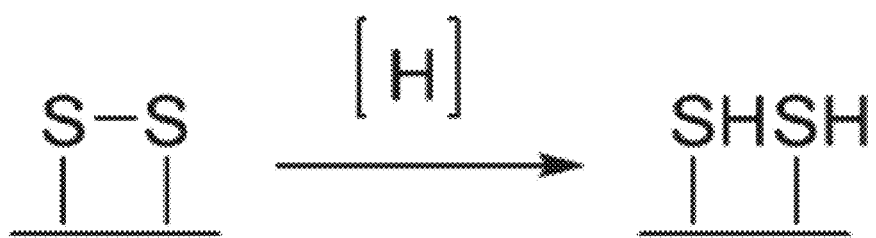
FIG. 2A depicts the conversion to free thiols of disulfide functional groups comprising the amino acid cysteine in the presence of a reducing agent.

In some embodiments, the method is a two-step method for the attachment of functional molecules to keratin-containing material. In some embodiments, the functional molecules are hydrophobic. First, functional groups are generated for the covalent attachment of monomers. Keratin-containing material, which consists primarily of the cysteine-rich protein keratin, contains a high concentration of disulfide bonds. In some embodiments, the first step of the grafting process is a reduction step to convert these disulfide bonds into free thiol functional groups (FIG. 2A). Keratin reduction is commonly used today in salon services such as permanent waving (perming) and permanent straightening (Japanese perming), and has been studied extensively for these purposes. See, e.g., Kuzuhara, A., Hori, T. J. Appl. Polym. Sci 2004, 94, 1131-1138; Kuzuhara, A. Hori, T. J. Mol. Struct. 2013, 1037, 85-92; Manuszak, M.A.; Borish, E.T.; Wickett, R.R. J. Soc. Cosmet. Sci. 1996, 47, 49-58; Manuszak, M.A.; Borish, E.T.; Wickett, R.R. J. Soc. Cosmet. Sci. 1996, 47, 213-227. Although the reduction chemistry is well-known, reducing the keratin-containing material with minimal keratin-containing material damage has not been evaluated. In some embodiments, a reduced keratin-containing material sample is provided after applying a reducing agent followed by a grafted keratin-containing material sample after applying a monomer.

In some embodiments of the methods disclosed herein, the method further comprises rinsing the keratin-containing material sample between steps ii) and iii). In some embodiments, the method further comprises washing the keratin-containing material sample between steps ii) and iii). In some embodiments, the method further comprises drying the keratin-containing material sample after washing and before step iii). In some embodiments, the method further comprises washing, rinsing, and drying the keratin-containing material sample between steps ii) and iii).

In some embodiments of the methods disclosed herein, the method is semi-simultaneous. In some embodiments, the keratin-containing material sample is first soaked in a solution of a reducing agent and, optionally, a catalyst, and then monomer is directly added to the keratin-containing material sample.

In some embodiments of the methods disclosed herein, a keratin-containing material sample is not rinsed between steps ii) and iii). In some embodiments, a keratin-containing material sample is not washed between steps ii) and iii). In some embodiments, a keratin-containing material sample is not washed nor dried between steps ii) and iii). In some embodiments, a keratin-containing material sample is not rinsed, washed, or dried between steps ii) and iii).

In another aspect, the disclosure provides a method for treating keratin-containing material, comprising:
i) providing a keratin-containing material sample comprising a plurality of disulfide bonds;
ii) applying to the keratin-containing material sample for a period of time a mixture, comprising a reducing agent in a concentration of about 0.1% by weight to about 15% by weight and a catalyst, wherein the keratin-containing material sample comprises a plurality of free thiol groups; and
iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers.

In some embodiments of the methods disclosed herein, the method is simultaneous. In some embodiments, the method is one-step and encompasses simultaneous reduction and grafting processes. In some embodiments, as disulfide bonds convert into thiol groups upon exposure to the reducing solution, the functional monomer molecules present in the solution immediately bind to the free thiol groups via thiol-Michael addition reaction. In some embodiments, a mixture comprising a reducing agent and a monomer is applied to a keratin-containing material sample. In some embodiments, the simultaneous method reduced treatment time and overall keratin-containing material damage. See, e.g., Schumacher, F.F.; Nobles, M.; Ryan, C.P.; Smith, M.E.B.; 11,12 Tinker, A.; Caddick, S.; Baker, J.R. Bioconjugate Chem. 2011, 22, 132-136; Richards, D.A.; Fletcher, S.A.; Nobles, M.; Kossen, H.; Tedaldi, L.; Chudasama; V.; Tinker, A.; Backer, J.R. Org. Biomol. Chem. 2016, 14, 455-459.

In another aspect, the disclosure provides a method for treating keratin-containing material, comprising:
i) providing a keratin-containing material sample comprising a plurality of disulfide bonds; and
ii) applying to the keratin-containing material sample for a period of time a mixture, comprising a reducing agent in a concentration of about 0.1% by weight to about 15% by weight, and a monomer; wherein the monomer is selected from the group consisting of an acrylate, a methacrylate, a monomer comprising a vinyl group, a monomer comprising an alkyne group, and a monomer comprising a maleimide group, thereby forming a plurality of free thiol groups which react with the monomer to form a plurality of covalent bonds between the free thiol groups and the monomers.

In some embodiments, the reducing agent is selected from the group consisting of ammonium thioglycolate, L-cysteine, N-acetyl L-cysteine, glutathione, ascorbic acid, beta-mercaptoethanol, 2-mercaptoethylamine, 2-mercaptoethylamine hydrochloride, dithiothreitol (DTT), thiolactic acid, thiosalicylic acid, tris-2-carboxyethylphospine hydrochloride (TCEP), sodium hydrosulfite, sodium thiosulfate, potassium disulfite, sodium disulfite, sodium bisulfate, sodium bisulfite, ammonium bisulfite, thioglycolic acid, calcium thioglycolate, potassium thioglycolate, sodium thioglycolate, cysteine hydrochloride, ammonium thiolactate, thioglycerin, mercaptopropionic acid, glycerol thioglycolate and dithiolbutylamine (DTBA). In some embodiments, the reducing agent is selected from the group consisting of ammonium thioglycolate, L-cysteine, glutathione, beta-mercaptoethanol, 2-mercaptoethylamine, DTT, thiolactic acid, TCEP, DTBA, sodium hydrosulfite, and sodium thiosulfate. In some embodiments, the reducing agent is selected from the group consisting of ammonium thioglycolate, L-cysteine, glutathione, and thiolactic acid. In some embodiments, the reducing agent is ammonium thioglycolate or L-cysteine. In some embodiments, the reducing agent is ammonium thioglycolate. In some embodiments, the mixture further comprises diammonium dithioglycolate.

In some embodiments, a commercial treatment comprises a reducing agent. In some embodiments, the mixture comprises a commercial treatment comprising a reducing agent. In some embodiments, the mixture of step ii) comprises a commercial treatment comprising a reducing agent. In some embodiments, the mixture comprises a commercial treatment comprising ammonium thioglycolate. In some embodiments, the mixture comprises a commercial treatment comprising a reducing agent and a monomer. In some embodiments, a mixture is formed by adding a monomer to a commercial treatment comprising a reducing agent.

In some embodiments, the reducing agent is a mild reducing agent. In some embodiments, the method for treating keratin-containing material minimizes keratin-containing material damage. In some embodiments, the keratin-containing material is hair. In some embodiments, the disclosed methods for treating hair are less damaging than a method of permanently waving hair. In some embodiments, applying the disclosed methods for treating hair are less damaging than a method of permanently straightening hair.

In some embodiments, the concentration of the reducing agent in the mixture is selected from the group consisting of about 0.1%, about 0.2%, about 0.3%, about 0.4%, about 0.5%, about 0.6%, about 0.7%, about 0.8%, about 0.9%, about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, about 5%, about 5.25%, about 5.5%, about 5.75%, about 6%, about 6.25%, about 6.5%, about 6.75%, about 7%, about 7.25%, about 7.5%, about 7.75%, about 8%, about 8.25%, about 8.5%, about 8.75%, about 9%, about 9.25%, about 9.5%, about 9.75%, about 10%, about 10.25%, about 10.5%, about 10.75%, about 11%, about 11.25%, about 11.5%, about 11.75%, about 12%, about 12.25%, about 12.5%, about 12.75%, about 13%, about 13.25%, about 13.5%, about 13.75%, about 14%, about 14.25%, about 14.5%, about 14.75%, and about 15% by weight. In some embodiments of the methods disclosed herein, the concentration of the reducing agent in the mixture is about 0.1% by weight to about 11% by weight. In some embodiments, the concentration of the reducing agent in the mixture is about 5% by weight to about 20% by weight. In some embodiments, the concentration of the reducing agent in the mixture is about 0.1% by weight to about 5% by weight. In some embodiments, the concentration of the reducing agent in the mixture is about 0.5% by weight to about 5% by weight. In some embodiments, the concentration of the reducing agent in the mixture is about 2.5% by weight to about 7% by weight. In some embodiments, the concentration of the reducing agent in the mixture is about 2.5% by weight to about 5% by weight. In some embodiments, the concentration of the reducing agent in the mixture is about 1% by weight to about 4% by weight. In some embodiments, the concentration of the reducing agent in the mixture is about 2.5% by weight. In some embodiments, the concentration of the reducing agent in the mixture is about 5% by weight.

In some embodiments, the concentration of the reducing agent in the mixture is low. In some embodiments, the concentration of the reducing agent in the mixture is less than about 11% by weight. In some embodiments, the concentration of the reducing agent in the mixture is less than about 8% by weight. In some embodiments, the concentration of the reducing agent in the mixture is less than about 6% by weight.

In some embodiments of the methods disclosed herein, the ratio by weight of the mixture to the keratin-containing material sample (also referred to herein as liquor ratio) is about 1:10 to about 500:1. In some embodiments, the ratio is selected from the group consisting of about 1:10, about 2:10, about 3:10, about 4:10, about 5:10, about 6:10, about 7:10, about 8:10, about 9:10, about 1:1, about 1.1:1, about 1.2:1, about 1.3:1, about 1.4:1, about 1.5:1, about 1.6:1, about 1.7:1, about 1.8:1, about 1.9:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, about 20:1, about 21:1, about 22:1, about 23:1, about 24:1, about 25:1, about 26:1, about 27:1, about 28:1, about 29:1, about 30:1, about 31:1, about 32:1, about 33:1, about 34:1, about 35:1, about 36:1, about 37:1, about 38:1, about 39:1, about 40:1, about 41:1, about 42:1, about 43:1, about 44:1, about 45:1, about 46:1, about 47:1, about 48:1, about 49:1, about 50:1, about 51:1, about 52:1, about 53:1, about 54:1, about 55:1, about 56:1, about 57:1, about 58:1, about 59:1, about 60:1, about 61:1, about 62:1, about 63:1, about 64:1, about 65:1, about 66:1, about 67:1, about 68:1, about 69:1, about 70:1, about 71:1, about 72:1, about 73:1, about 74:1, about 75:1, about 76:1, about 77:1, about 78:1, about 79:1, about 80:1, about 81:1, about 82:1, about 83:1, about 84:1, about 85:1, about 86:1, about 87:1, about 88:1, about 89:1, about 90:1, about 91:1, about 92:1, about 93:1, about 94:1, about 95:1, about 96:1, about 97:1, about 98:1, about 99:1, about 100:1, about 101:1, about 102:1, about 103:1, about 104:1, about 105:1, about 106:1, about 107:1, about 108:1, about 109:1, about 110:1, about 115:1, about 120:1, about 125:1, about 130:1, about 135:1, about 140:1, about 145:1, about 150:1, about 155:1, about 160:1, about 165:1, about 170:1, about 175:1, about 180:1, about 185:1, about 190:1, about 195:1, about 200:1, about 205:1, about 210:1, about 215:1, about 220:1, about 225:1, about 230:1, about 235:1, about 240:1, about 245:1, about 250:1, about 255:1, about 260:1, about 265:1, about 270:1, about 275:1, about 280:1, about 285:1, about 290:1, about 295:1, about 300:1, about 310:1, about 320:1, about 330:1, about 340:1, about 350:1, about 360:1, about 370:1, about 380:1, about 390:1, about 400:1, about 410:1, about 420:1, about 430:1, about 440:1, about 450:1, about 460:1, about 470:1, about 480:1, about 490:1, and about 500:1. In some embodiments, the ratio is about 1:10 to about 100:1. In some embodiments, the ratio is about 1:1 to about 100:1. In some embodiments, the ratio is about 1:1 to about 20:1. In some embodiments, the ratio is about 2:1 to about 10:1. In some embodiments, the ratio is about 3:1 to about 10:1. In some embodiments, the ratio is about 5:1. In some embodiments, the ratio is about 1:10 to about 5:1. In some embodiments, the ratio is about 5:10 to about 2:1. In some embodiments, the ratio is about 5:10 to about 1.5:1. In some embodiments, the ratio is about 1.1:1.

In some embodiments, the liquor ratio is low. In some embodiments, the ratio is less than about 50:1. In some embodiments, the ratio is less than about 20:1. In some embodiments, the ratio is less than about 10:1. In some embodiments, the ratio is less than about 5:1. In some embodiments, the ratio is less than about 2:1.

In some embodiments of the methods disclosed herein, the mixture is applied overnight. In some embodiments of the methods disclosed herein, the mixture is applied for about 1 hour to about 12 hours. In some embodiments, the mixture is applied for a period of time selected from the group consisting of about 1 hour, about 1.25 hours, about 1.5 hours, about 1.75 hours, about 2 hours, about 2.25 hours, about 2.5 hours, about 2.75 hours, about 3 hours, about 3.25 hours, about 3.5 hours, about 3.75 hours, about 4 hours, about 4.25 hours, about 4.5 hours, about 4.75 hours, about 5 hours, about 5.25 hours, about 5.5 hours, about 5.75 hours, about 6 hours, about 6.25 hours, about 6.5 hours, about 6.75 hours, about 7 hours, about 7.25 hours, about 7.5 hours, about 7.75 hours, about 8 hours, about 8.25 hours, about 8.5 hours, about 8.75 hours, about 9 hours, 9.25 hours, about 9.5 hours, about 9.75 hours, about 10 hours, about 10.25 hours, about 10.5 hours, about 10.75 hours, about 11 hours, about 11.25 hours, about 11.5 hours, about 11.75 hours, and about 12 hours. In some embodiments, the mixture is applied for about 5 hours to about 12 hours. In some embodiments, the mixture is applied for about 6 hours to about 10 hours. In some embodiments, the mixture comprises a reducing agent. In some embodiments, the mixture comprises a reducing agent in a concentration of about 0.1% by weight to about 15% by weight.

In some embodiments of the methods disclosed herein, the mixture is applied for about 30 seconds to about 180 minutes. In some embodiments, the mixture is applied for a period of time selected from the group consisting of about 15 seconds, about 30 seconds, about 45 seconds, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, about 120 minutes, about 125 minutes, about 130 minutes, about 135 minutes, about 140 minutes, about 145 minutes, about 150 minutes, about 155 minutes, about 160 minutes, about 165 minutes, about 170 minutes, about 175 minutes, and about 180 minutes. In some embodiments, the mixture is applied for about 30 seconds to about 60 minutes. In some embodiments, the mixture is applied for about 1 minute to about 30 minutes. In some embodiments, the mixture is applied for about 15 minutes to about 30 minutes. In some embodiments, the mixture is applied for about 15 minutes. In some embodiments, the mixture is applied for about 1 minute to about 10 minutes. In some embodiments, the mixture is applied for about 2 minutes. In some embodiments, the mixture comprises a reducing agent and a catalyst. In some embodiments, the mixture comprises a reducing agent and a monomer.

In some embodiments, the mixture is applied for a short time. In some embodiments, the mixture is applied for less than about 60 minutes. In some embodiments, the mixture is applied for less than about 30 minutes. In some embodiments, the mixture is applied for less than about 20 minutes. In some embodiments, the mixture is applied for less than about 15 minutes. In some embodiments, the mixture is applied for less than about 5 minutes.

In some embodiments, the monomer is applied to the keratin-containing material sample within about 30 minutes after applying the mixture to the keratin-containing material sample. In some embodiments, the monomer is applied to the keratin-containing material sample within a period of time selected from the group consisting of about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, and about 30 minutes after applying the mixture to the keratin-containing material sample. In some embodiments, the monomer is applied to the keratin-containing material sample within about 15 minutes of applying the mixture to the keratin-containing material sample. In some embodiments, the monomer is applied to the keratin-containing material sample within about 10 minutes of applying the mixture to the keratin-containing material sample. In some embodiments, the monomer is applied to the keratin-containing material sample within about 5 minutes of applying the mixture to the keratin-containing material sample. In some embodiments, the monomer is applied to the keratin-containing material sample within about 1 minute of applying the mixture to the keratin-containing material sample.

In some embodiments, the monomer is applied to the keratin-containing material sample after applying the mixture to the keratin-containing material sample.

In some embodiments of the methods disclosed herein, the monomer is applied for about 30 seconds to about 180 minutes. In some embodiments, the monomer is applied for a period of time selected from the group consisting of about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, about 120 minutes, about 125 minutes, about 130 minutes, about 135 minutes, about 140 minutes, about 145 minutes, about 150 minutes, about 155 minutes, about 160 minutes, about 165 minutes, about 170 minutes, about 175 minutes, and about 180 minutes. In some embodiments, the monomer is applied for about 30 seconds to about 60 minutes. In some embodiments, the monomer is applied for about 1 minute to about 30 minutes. In some embodiments, the monomer is applied for about 15 minutes to about 30 minutes. In some embodiments, the monomer is applied for about 30 minutes. In some embodiments, the monomer is applied for about 15 minutes. In some embodiments, the monomer is applied for about 1 minute to about 10 minutes.

In some embodiments of the methods disclosed herein, the mixture further comprises a buffer solution. In some embodiments, the buffer solution is selected from the group consisting of phosphate, phosphate buffered saline, imidazole-HCl, 4-morpholineethanesulfonic acid (MES); bis(2-hydroxyethyl)-amino-tris(hydroxymethyl)methane (bis-Tris); N-(2-acetamido)iminodiacetic acid; N-(2-acetamido)-2-aminoethanesulfonic acid; 1,4-piperazinediethanesulfonic acid; 3-morpholino-2-hydroxypropanesulfonic acid (MOPSO); 1,3-bis[tris(hydroxymethyl)methyl-amino]propane; N,N-bis(2-hydroxyethyl)-2-aminoethanesulfonic acid; 4-morpholinepropanesulfonic acid (MOPS); 2-[(2-hydroxy-1,1-bis(hydroxymethyl)ethyl)-amino]ethanesulfonic acid; 4-(2-hydroxyethyl)piperazine-1-ethanesulfonic acid (HEPES); 3-(N,N-bis[2-hydroxyethyl]amino)-2-hydroxypropanesulfonic acid; 4-(N-morpholino)butane-sulfonic acid; 2-hydroxy-3-[tris(hydroxymethyl)methylamino]-1-propanesulfonic acid; tris(hydroxymethyl)aminomethane; piperazine-N,N'-bis(2-hydroxypropanesulfonic acid); 4-(2-hydroxyethyl)-1-piperazinepropane-sulfonic acid; N-[tris(hydroxymethyl)methyl]glycine; diglycine; N,N-bis(2-hydroxyethyl)-glycine, N-(2-hydroxyethyl)piperazine-N'-(4-butanesulfonic acid); N-[tris(hydroxymethyl)-methyl]-3-aminopropanesulfonic acid; N-(1,1-dimethyl-2-hydroxyethyl)-3-amino-2-hydroxypropanesulfonic acid; 2-(cyclohexylamino)-ethanesulfonic acid; 3-(cyclohexylamino)-2-hydroxy-1-propanesulfonic acid; 2-amino-2-methyl-2-propanol; sodium carbonate-sodium bicarbonate; 3-(cyclohexylamino)-1-propanesulfonic acid; and 4-(cyclohexylamino)-1-butanesulfonic acid.

In some embodiments of the methods disclosed herein, the pH of the mixture is about 5 to about 11. In some embodiments of the methods disclosed herein, the pH of the mixture is selected from the group consisting of about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, about 10.1, about 10.2, about 10.3, about 10.4, about 10.5, about 10.6, about 10.7, about 10.8, about 10.9, and about 11. In some embodiments, the pH of the mixture is about 7 to about 11. In some embodiments, the pH of the mixture is about 7 to about 10. In some embodiments, the pH of the mixture is about 7.5 to about 10.5. In some embodiments, the pH of the mixture is about 9.5. In some embodiments, the pH of the mixture is about 7.0 to about 9.5. In some embodiments, the pH of the mixture is about 8.5 to about 9.5. In some embodiments, the pH of the mixture is about 8.5.

In some embodiments of the methods disclosed herein, the monomer is selected from the group consisting of an acrylate, a methacrylate, a monomer comprising a vinyl group, and a monomer comprising a maleimide group. In some embodiments, the monomer is selected from the group consisting of an acrylate, a methacrylate, a monomer comprising a vinyl group, a monomer comprising an alkyne group. In some embodiments, the monomer is an acrylate, a methacrylate, or a monomer comprising a vinyl group. In some embodiments, the monomer is an acrylate, a methacrylate, or a monomer comprising a maleimide group. In some embodiments, the monomer is an acrylate or a methacrylate. In some embodiments, the monomer is an alkyl acrylate or a cycloalkyl acrylate.

In some embodiments, the monomer is hydrophobic. In some embodiments, the monomer forms a coating on the keratin-containing material sample.

In some embodiments, the coating mimics the behavior of the natural lipid layer (18-methyleicosanoic acid, 18-MEA) found on naïve (or virgin) hair emerging from the follicle. 18-MEA functions as a protective barrier and leaves the hair with a smooth feeling and enhanced fiber alignment that lasts much longer compared to wash-off conditioning treatments.

In some embodiments, the coating mimics the behavior of virgin keratin-containing material. In some embodiments, the monomer is a long-chain acrylate. In some embodiments, the monomer is a branched monomer. In some embodiments, the monomer is a branched alkyl acrylate.

In some embodiments, the covalent attachment of the monomer to the keratin-containing material sample is a click chemistry reaction. Click chemistry reactions feature fast and complete conversion, and high functional group tolerance. See, e.g., Chatani, S.; Nair, D.P.; Bowman, C.N. Polym. Chem. 2013, 4, 1048-1055; Lowe, A.B.; Hoyle, C.E.; Bowman, C.N. J. Mater. Chem. 2010, 20, 4745-4750.

Figure 2B:
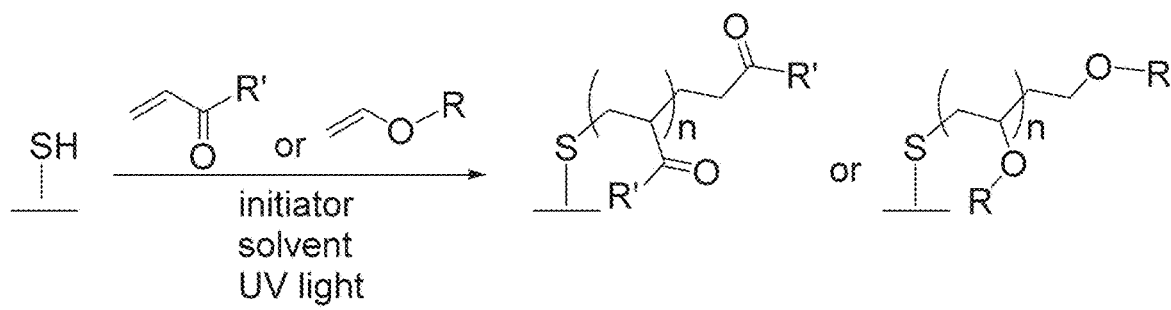
FIG. 2B is a schematic representation of free thiol functional groups initiating a polymerization with olefin-containing molecules, such as acrylates or vinyl ethers, using a radical thiol-ene reaction mediated by a photoinitiator and UV light.

In some embodiments, the covalent attachment of terminal "ene" molecules to the free thiols is via a thiol-ene radical addition (FIG. 2B). Without being bound by any theory, it is proposed that when utilizing the radical thiol-ene mechanism, the ene monomers propagate from thiols on the keratin-containing material to generate surface bound polymers and oligomers. If the ene monomers are capable of polymerizing without thiol functional groups, it is also possible to obtain free homopolymers that are not attached to the keratin-containing material. See, e.g., Hoyle, C.E.; Bowman, C.N. Angew. Chem. Int. Ed. 2010, 49, 1540-1573.

Figure 2C:
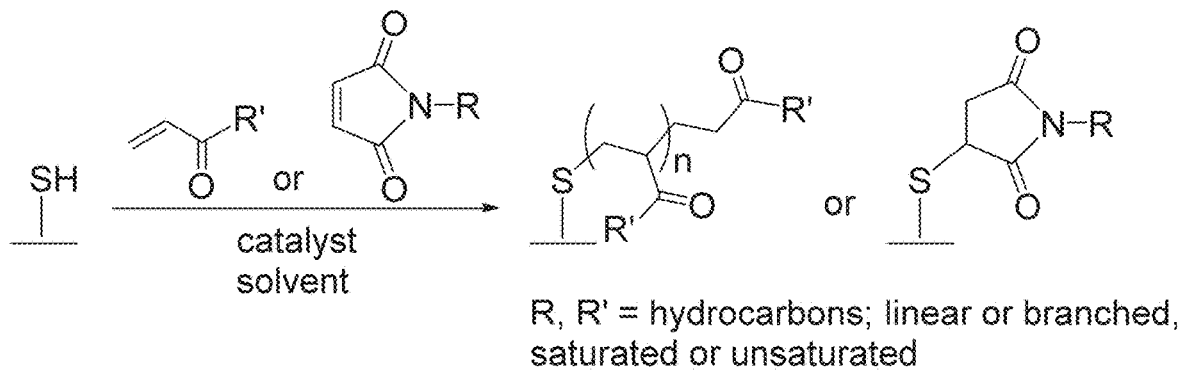
FIG. 2C is a schematic representation of free thiol functional groups acting as nucleophiles, and adding across the double bond of electrophilic olefin-containing monomers, such as acrylates or maleimides.

In some embodiments, the covalent attachment of terminal "ene" molecules to the free thiols is by thiol-Michael addition (FIG. 2C). The thiol-Michael addition allows grafting of monomers onto keratin-containing material fibers without generating unwanted homopolymer byproduct. Without being bound by any theory, it is proposed that this mechanism consists solely of the addition of a nucleophilic thiol adds across one electrophilic ene monomer. See, e.g., Mather, B.D.; Viswanathan, K.; Miller, K.M.; Long, T.E. Prog. Polym. Sci. 2006, 31, 487-531.

In some embodiments, the monomer is selected from the group consisting of ethyl acrylate; propyl acrylate; isobutyl acrylate; butyl acrylate; pentyl acrylate; tert-butyl acrylate; hexyl acrylate; heptyl acrylate; octyl acrylate; isooctyl acrylate; nonyl acrylate; decyl acrylate; isodecyl acrylate; dodecyl acrylate; tridecyl acrylate; tetradecyl acrylate; hexadecyl acrylate; octadecyl acrylate; cyclopentyl acrylate; cyclohexyl acrylate; cycloheptyl acrylate; cyclooctyl acrylate; 2-(dimethylamino)ethyl acrylate; 2-(diethylamino) ethyl acrylate; 2-ethylhexyl acrylate; 3,5,5-trimethylhexyl acrylate; 8-methylnonyl acrylate; 3-isobutylnonyl acrylate; 3-(cyclohexylmethyl)nonyl acrylate; 3-butyl-7,11-dimethyldodecyl acrylate; (E)-3-butyl-7,11-dimethyldodec-2-en-1-yl acrylate; isobornyl acrylate; a poly(ethylene glycol) (PEG) acrylate; 1,6-hexanediol diacrylate; octafluoropentyl acrylate; fluorescein-o-acrylate; fluorescein-o-o-diacrylate; and a PEG-diacrylate. In some embodiments, the monomer is selected from the group consisting of isobutyl acrylate; butyl acrylate; tert-butyl acrylate; hexyl acrylate; isodecyl acrylate; dodecyl acrylate; tetradecyl acrylate; hexadecyl acrylate; octadecyl acrylate; cyclohexyl acrylate; 2-(dimethylamino)ethyl acrylate; 2-ethylhexyl acrylate; 8-methylnonyl acrylate; 3-isobutylnonyl acrylate; 3-(cyclohexylmethyl) nonyl acrylate; 3-butyl-7,11-dimethyldodecyl acrylate; (E)-3-butyl-7,11-dimethyldodec-2-en-1-yl acrylate; isobornyl acrylate; a PEG acrylate; 1,6-hexanediol diacrylate; octafluoropentyl acrylate; fluorescein-o-acrylate; fluorescein-o-o-diacrylate; and a PEG-diacrylate. In some embodiments, the monomer is selected from the group consisting of hexyl acrylate; isodecyl acrylate; dodecyl acrylate; tetradecyl acrylate; hexadecyl acrylate; octadecyl acrylate; 2-ethylhexyl acrylate; 3-isobutylnonyl acrylate; 3-(cyclohexylmethyl)nonyl acrylate; 3-butyl-7,11-dimethyldodecyl acrylate; (E)-3-butyl-7,11-dimethyldodec-2-en-1-yl acrylate; isobornyl acrylate; a PEG acrylate; and a PEG diacrylate. In some embodiments, the monomer is selected from the group consisting of hexyl acrylate; isodecyl acrylate; dodecyl acrylate; octadecyl acrylate; 2-ethylhexyl acrylate; 3-butyl-7,11-dimethyldodecyl acrylate; (E)-3-butyl-7,11-dimethyldodec-2-en-1-yl acrylate; isobornyl acrylate; a PEG acrylate; and a PEG diacrylate. In some embodiments, the monomer is hexyl acrylate or dodecyl acrylate. In some embodiments, the monomer is a PEG-diacrylate. In some embodiments, the monomer is a poly(ethylene glycol)-diacrylate or polyethylene glycol diacrylate (PEG diacrylate or PEG-DA) selected from the group consisting of PEG-DA 250, PEG-DA 575, PEG-DA 700, PEG-DA 1 k, PEG-DA 1.5 k, PEG-DA 2 k, and PEG-DA 6 k. In some embodiments, the monomer is selected from the group consisting of PEG-DA 700, PEG-DA 1 k, and PEG-DA 2 k. In some embodiments, the monomer is PEG-DA 700. In some embodiments, the monomer is PEG-DA 1.5 k. In some embodiments, the monomer is PEG-DA 2 k. The numbers refer to the number average molecular weight. That is, PEG-DA 700 refers to poly(ethylene glycol) diacrylate with a number average molecular weight of 700, and PEG-DA 1.5 k refers to poly(ethylene glycol) diacrylate with a number average molecular weight of 1,500. In some embodiments, the monomer is an acrylate, which is a multi-arm PEG-acrylate (PEG-AA). In some embodiments, the monomer is a multi-arm PEG-acrylate selected from the group consisting of 4-arm PEG-AA 2 k, 4-arm PEG-AA 5 k, 4-arm PEG-AA 10 k, 8-arm PEG-AA 5 k, and 8-arm PEG-AA 20 k.

In some embodiments, the monomer is a monomer comprising a vinyl group. In some embodiments, the monomer comprising a vinyl group is selected from the group consisting of a vinyl sulfone, an acrylate group, a methacrylate group, a styrene group, an acrylamide group, a methacrylamide group, a maleimide group, a maleate group, a fumarate group, and an itaconate group. In some embodiments, the monomer is selected from the group consisting of ethyl vinyl ether; propyl vinyl ether; isobutyl vinyl ether; butyl vinyl ether; pentyl vinyl ether; tert-butyl vinyl ether; hexyl vinyl ether; heptyl vinyl ether; octyl vinyl ether; isooctyl vinyl ether; nonyl vinyl ether; decyl vinyl ether; dodecyl vinyl ether; tetradecyl vinyl ether; hexadecyl vinyl ether; octadecyl vinyl ether; N,N-dimethyl-2-(vinyloxy)-ethylamine; cyclopentyl vinyl ether; cyclohexyl vinyl ether; cycloheptyl vinyl ether; cyclooctyl vinyl ether; 2-(dimethylamino)ethyl vinyl ether; 2-(diethylamino)ethyl vinyl ether; 2-ethylhexyl vinyl ether; 1-(vinyloxy)adamantane; vinyloxy-trimethylsilane; and vinyloxy-triethylsilane. In some embodiments, the monomer is selected from the group consisting of isobutyl vinyl ether; butyl vinyl ether; dodecyl vinyl ether; octadecyl vinyl ether; cyclohexyl vinyl ether; and vinyloxy-triethylsilane.

In some embodiments, the monomer is a monomer comprising a maleimide group. In some embodiments, the monomer is selected from the group consisting of N-ethylmaleimide; N-cyclohexylmaleimide; N-arachidonylmaleimide; fluorescein-5-maleimide; a succinimidyl-[(N-maleimidopropionamido)-diethyleneglycol] ester (an NHS-PEG$_n$-maleimide); a poly(ethylene glycol) (PEG)-maleimide; a PEG-methyl ether maleimide (an mPEG-maleimide); and a methoxy-PEG-maleimide. In some embodiments, the monomer is selected from the group consisting of N-ethylmaleimide; an NHS-PEG$_n$-maleimide; a PEG-maleimide; an mPEG-maleimide; and a methoxy-PEG-maleimide. In some embodiments, the monomer is N-ethylmaleimide or a PEG-maleimide.

In some embodiments, the monomer is selected from the group consisting of hexyl acrylate; dodecyl acrylate; N-ethylmaleimide; and a PEG-maleimide.

In some embodiments of the methods disclosed herein, the molar ratio of the monomer to the free thiol groups is about 100:1 to about 1:10. In some embodiments, the molar ratio of the monomer to the free thiol groups is selected from the group consisting of about 100:1, about 99:1, about 98:1, about 97:1, about 96:1, about 95:1, about 94:1, about 93:1, about 92:1, about 91:1, about 90:1, about 89:1, about 88:1, about 87:1, about 86:1, about 85:1, about 84:1, about 83:1, about 82:1, about 81:1, about 80:1, about 79:1, about 78:1, about 77:1, about 76:1, about 75:1, about 74:1, about 73:1, about 72:1, about 71:1, about 70:1, about 69:1, about 68:1, about 67:1, about 66:1, about 65:1, about 64:1, about 63:1, about 62:1, about 61:1, about 60:1, about 59:1, about 58:1, about 57:1, about 56:1, about 55:1, about 54:1, about 53:1, about 52:1, about 51:1, about 50:1, about 49:1, about 48:1, about 47:1, about 46:1, about 45:1, about 44:1, about 43:1, about 42:1, about 41:1, about 40:1, about 39:1, about 38:1, about 37:1, about 36:1, about 35:1, about 34:1, about 33:1, about 32:1, about 31:1, about 30:1, about 29:1, about 28:1, about 27:1, about 26:1, about 25:1, about 24:1, about 23:1, about 22:1, about 21:1, about 20:1, about 19:1, about 18:1, about 17:1, about 16:1, about 15:1, about 14:1, about 13:1, about 12:1, about 11:1, about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2.5:1, about 2:1, about 1.5:1, about 1:1, about 9:10, about 8:10, about 7:10, about 6:10, about 5:10, about 4:10, about 3:10, about 2:10, and about 1:10. In some embodiments, the molar ratio of the monomer to the free thiol groups is about 20:1 to about 1:1. In some embodiments, the molar ratio of the monomer to the free thiol groups is about 10:1 to about 1:1. In some embodiments, the molar ratio of the monomer to the free thiol groups is about 5:1. In some embodiments, the molar ratio of the monomer to the free thiol groups is about 2.5:1.

In some embodiments, the molar ratio of the monomer to the free thiol groups is about 0.001:1 to about 2.5:1. In some embodiments, the molar ratio of the monomer to the free thiol groups is selected from the group consisting of about 0.001:1, about 0.005:1, about 0.01:1, about 0.011:1, about 0.012:1, about 0.013:1, about 0.014:1, about 0.015:1, about 0.016:1, about 0.017:1, about 0.018:1, about 0.019:1, about 0.02:1, about 0.021:1, about 0.022:1, about 0.023:1, about 0.024:1, about 0.025:1, about 0.026:1, about 0.027:1, about 0.028:1, about 0.029:1, about 0.03:1, about 0.031:1, about 0.032:1, about 0.033:1, about 0.034:1, about 0.035:1, about 0.036:1, about 0.037:1, about 0.038:1, about 0.039:1, about 0.04:1, about 0.041:1, about 0.042:1, about 0.043:1, about 0.044:1, about 0.045:1, about 0.046:1, about 0.047:1, about 0.048:1, about 0.049:1, about 0.05:1, about 0.051:1, about 0.052:1, about 0.053:1, about 0.054:1, about 0.055:1, about 0.056:1, about 0.057:1, about 0.058:1, about 0.059:1, about 0.06:1, about 0.061:1, about 0.062:1, about 0.063:1, about 0.064:1, about 0.065:1, about 0.066:1, about 0.067:1, about 0.068:1, about 0.069:1, about 0.07:1, about 0.071:1, about 0.072:1, about 0.073:1, about 0.074:1, about 0.075:1, about 0.076:1, about 0.077:1, about 0.078:1, about 0.079:1, about 0.08:1, about 0.081:1, about 0.082:1, about 0.083:1, about 0.084:1, about 0.085:1, about 0.086:1, about 0.087:1, about 0.088:1, about 0.089:1, about 0.09:1, about 0.091:1, about 0.092:1, about 0.093:1, about 0.094:1, about 0.095:1, about 0.096:1, about 0.097:1, about 0.098:1, about 0.099:1, about 0.1:1, about 0.11:1, about 0.12:1, about 0.13:1, about 0.14:1, about 0.15:1, about 0.16:1, about 0.17:1, about 0.18:1, about 0.19:1, about 0.2:1, about 0.21:1, about 0.22:1, about 0.23:1, about 0.24:1, about 0.25:1, about 0.26:1, about 0.27:1, about 0.28:1, about 0.29:1, about 0.3:1, about 0.31:1, about 0.32:1, about 0.33:1, about 0.34:1, about 0.35:1, about 0.36:1, about 0.37:1, about 0.38:1, about 0.39:1, about 0.4:1, about 0.41:1, about 0.42:1, about 0.43:1, about 0.44:1, about 0.45:1, about 0.46:1, about 0.47:1, about 0.48:1, about 0.49:1, about 0.5:1, about 0.51:1, about 0.52:1, about 0.53:1, about 0.54:1, about 0.55:1, about 0.56:1, about 0.57:1, about 0.58:1, about 0.59:1, about 0.6:1, about 0.65:1, about 0.7:1, about 0.75:1, about 0.8:1, about 0.85:1, about 0.9:1, about 1:1, about 1.05:1, about 1.1:1, about 1.15:1, about 1.2:1, about 1.25:1, about 1.3:1, about 1.35:1, about 1.4:1, about 1.45:1, about 1.5:1, about 1.55:1, about 1.6:1, about 1.65:1, about 1.7:1, about 1.75:1, about 1.8:1, about 1.85:1, about 1.9:1, about 2:1, about 2.1:1, about 2.2:1, about 2.3:1, about 2.4:1, and about 2.5:1. In some embodiments, the molar ratio of the monomer to the free thiol groups is about 0.05:1 to about 2.5:1. In some embodiments, the molar ratio of the monomer to the free thiol groups is about 0.1:1 to about 1:1. In some embodiments, the molar ratio of the monomer to the free thiol groups is about 0.2:1 to about 0.6:1. In some embodiments, the molar ratio of the monomer to the free thiol groups is about 0.38:1. In some embodiments, the molar ratio of the monomer to the free thiol groups is about 0.02:1 to about 0.06:1. In some embodiments, the molar ratio of the monomer to the free thiol groups is about 0.04:1.

In some embodiments of the methods disclosed herein, the concentration of the monomer is about 0.5% by weight to about 95% by weight. In some embodiments, the concentration of the monomer is selected from the group consisting of about 0.5%, about 0.75%, about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, about 5%, about 5.25%, about 5.5%, about 5.75%, about 6%, about 6.25%, about 6.5%, about 6.75%, about 7%, about 7.25%, about 7.5%, about 7.75%, about 8%, about 8.25%, about 8.5%, about 8.75%, about 9%, about 9.25%, about 9.5%, about 9.75%, about 10%, about 10.5%, about 11%, about 11.5%, about 12%, about 12.5%, about 13%, about 13.5%, about 14%, about 14.5%, about 15%, about 15.5%, about 16%, about 16.5%, about 17%, about 17.5%, about 18%, about 18.5%, about 19%, about 19.5%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, and about 95% by weight. In some embodiments, the concentration of the monomer is about 0.5% by weight to about 70% by weight. In some embodiments, the concentration of the monomer is about 2% by weight to about 60% by weight. In some embodiments, the concentration of the monomer is about 2% by weight to about 30% by weight. In some embodiments, the concentration of the monomer is about 0.5% by weight to about 40% by weight. In some embodiments, the concentration of the monomer is about 2% by weight to about 30% by weight.

In some embodiments of the methods disclosed herein, the method for treating a keratin-containing material comprises:
  i) providing a keratin-containing material sample comprising a plurality of disulfide bonds;
  ii) applying to the keratin-containing material sample for a period of time a mixture, comprising a reducing agent in a concentration of about 2.5% by weight to about 7% by weight, thereby producing a reduced keratin-containing material sample, wherein the reduced keratin-containing material sample comprises a plurality of free thiol groups; and
  iii) applying a monomer to the reduced keratin-containing material sample, wherein the monomer is a poly(ethylene glycol) diacrylate (PEG-DA), thereby forming a plurality of covalent bonds between the free thiol groups and the monomers.

In some embodiments of the methods disclosed herein, the method for treating a keratin-containing material comprises:
  i) providing a keratin-containing material sample comprising a plurality of disulfide bonds;
  ii) applying to the keratin-containing material sample for a period of time a mixture, comprising a reducing agent in a concentration of about 2.5% by weight to about 7% by weight and a catalyst, wherein the keratin-containing material sample comprises a plurality of free thiol groups; and
  iii) applying a monomer to the keratin-containing material sample, wherein the monomer is a PEG-DA, thereby forming a plurality of covalent bonds between the free thiol groups and the monomers.

In some embodiments of the methods disclosed herein, the method for treating a keratin-containing material comprises:
  i) providing a keratin-containing material sample comprising a plurality of disulfide bonds; and ii) applying to the keratin-containing material sample for a period of time a mixture, comprising a reducing agent in a concentration of about 2.5% by weight to about 7% by weight, and a monomer; wherein the monomer is a PEG-DA, thereby forming a plurality of free thiol groups which react with the monomer to form a plurality of covalent bonds between the free thiol groups and the monomers.

In some embodiments, the reducing agent is ammonium thioglycolate. In some embodiments, the reducing agent concentration is about 5% by weight. In some embodiments, the ratio by weight of the mixture to the keratin-containing material sample (the liquor ratio) is about 1.1:1. In some embodiments, the PEG-DA is PEG-DA 1.5 k or PEG-DA 2 k. In some embodiments, the reducing agent is ammonium thioglycolate, and the PEG-DA is PEG-DA 1.5 k or PEG-DA 2 k.

In some embodiments, the methods disclosed herein further comprise applying a catalyst to the keratin-containing material sample. In some embodiments, the catalyst is selected from the group consisting of an amine, a phosphine, and a radical initiator.

In some embodiments, the catalyst is an amine. In some embodiments, the catalyst is a primary amine or a secondary amine. In some embodiments, the catalyst is a tertiary amine. In some embodiments, the amine is selected from the group consisting of N,N-diisopropylethylamine, N-ethyldiisopropylamine, di-n-propylamine, trimethylamine, triethylamine, ethanolamine, diethanolamine, and triethanolamine. In some embodiments, the amine is di-n-propylamine or triethylamine. In some embodiments, the amine is triethylamine.

In some embodiments, the catalyst is a phosphine. In some embodiments, the catalyst is a tertiary phosphine. In some embodiments, the phosphine is selected from the group consisting of dimethylphenylphosphine, diethylphenylphosphine, methyldiphenyl-phosphine, ethyldiphenylphosphine, trimethylphosphine, tripropylphosphine, triphenylphosphine, tri(o-tolyl)phosphine, tri(p-tolyl)phosphine, tris(2,4,6-trimethylphenyl)-phosphine, tris(3,5-dimethylphenyl)phosphine, dicyclohexyl-(2,6-diisopropylphenyl)phosphine, and tris(hydroxymethyl)phosphine. In some embodiments, the phosphine is dimethylphenylphosphine.

In some embodiments, the amine is selected from the group consisting of di-n-propylamine, dimethylphenylphosphine, and trimethylamine.

In some embodiments, the amount of the catalyst is about 1 mol % to about 100 mol % relative to the monomer. In some embodiments, the amount of the catalyst is selected from the group consisting of about 1 mol %, about 2 mol %, about 3 mol %, about 4 mol %, about 5 mol %, about 6 mol %, about 7 mol %, about 8 mol %, about 9 mol %, about 10 mol %, 11 mol %, about 12 mol %, about 13 mol %, about 14 mol %, about 15 mol %, about 16 mol %, about 17 mol %, about 18 mol %, about 19 mol %, about 20 mol %, 21 mol %, about 22 mol %, about 23 mol %, about 24 mol %, about 25 mol %, about 26 mol %, about 27 mol %, about 28 mol %, about 29 mol %, about 30 mol %, 31 mol %, about 32 mol %, about 33 mol %, about 34 mol %, about 35 mol %, about 36 mol %, about 37 mol %, about 38 mol %, about 39 mol %, about 40 mol %, 41 mol %, about 42 mol %, about 43 mol %, about 44 mol %, about 45 mol %, about 46 mol %, about 47 mol %, about 48 mol %, about 49 mol %, about 50 mol %, 51 mol %, about 52 mol %, about 53 mol %, about 54 mol %, about 55 mol %, about 56 mol %, about 57 mol %, about 58 mol %, about 59 mol %, about 60 mol %, 61 mol %, about 62 mol %, about 63 mol %, about 64 mol %, about 65 mol %, about 66 mol %, about 67 mol %, about 68 mol %, about 69 mol %, about 70 mol %, 71 mol %, about 72 mol %, about 73 mol %, about 74 mol %, about 75 mol %, about 76 mol %, about 77 mol %, about 78 mol %, about 79 mol %, about 80 mol %, 81 mol %, about 82 mol %, about 83 mol %, about 84 mol %, about 85 mol %, about 86 mol %, about 87 mol %, about 88 mol %, about 89 mol %, about 90 mol %, 91 mol %, about 92 mol %, about 93 mol %, about 94 mol %, about 95 mol %, about 96 mol %, about 97 mol %, about 98 mol %, about 99 mol %, and about 100 mol %. In some embodiments, the amount of the catalyst is about 10 mol % to about 60 mol % relative to the monomer. In some embodiments, the amount of the catalyst is about 20 mol % to about 50 mol % relative to the monomer. In some embodiments, the amount of the catalyst is about 40 mol % relative to the monomer.

In some embodiments, the concentration of the catalyst is about 0.1% by weight to about 15% by weight. In some embodiments, the concentration of the catalyst is selected from the group consisting of about 0.1%, about 0.2%, about 0.3%, about 0.4%, about 0.5%, about 0.6%, about 0.7%, about 0.8%, about 0.9%, about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, about 5%, about 5.25%, about 5.5%, about 5.75%, about 6%, about 6.25%, about 6.5%, about 6.75%, about 7%, about 7.25%, about 7.5%, about 7.75%, about 8%, about 8.25%, about 8.5%, about 8.75%, about 9%, about 9.25%, about 9.5%, about 9.75%, about 10%, about 10.25%, about 10.5%, about 10.75%, about 11%, about 11.25%, about 11.5%, about 11.75%, about 12%, about 12.25%, about 12.5%, about 12.75%, about 13%, about 13.25%, about 13.5%, about 13.75%, about 14%, about 14.25%, about 14.5%, about 14.75%, and about 15% by weight. In some embodiments, the concentration of the catalyst is about 0.1% by weight to about 10% by weight. In some embodiments, the concentration of the catalyst is about 1% by weight to about 9% by weight. In some embodiments, the concentration of the catalyst is about 0.1% by weight to about 5% by weight. In some embodiments, the concentration of the catalyst is about 1% by weight to about 9% by weight.

In some embodiments of the methods disclosed herein, the catalyst is a radical initiator. In some embodiments, the radical initiator is selected from the group consisting of a peroxide, an azo compound, a photoinitiator. In some embodiments, the radical initiator is a peroxide. In some embodiments, the peroxide is selected from the group consisting of hydrogen peroxide, tert-butyl hydroperoxide, tert-butyl peracetate, cumene hydroperoxide, dicumyl peroxide, benzoyl peroxide, and tert-butyl peroxide. In some embodiments, the peroxide is hydrogen peroxide.

In some embodiments, the radical initiator is an azo compound. In some embodiments, the azo compound is selected from the group consisting of 4,4'-azobis(4-cyanovaleric acid), 4,4'-azobis(4-cyanovaleric acid), 1,1'-azobis(cyclohexanecarbonitrile), 2,2'-azobis(2-methylpropionamidine) dihydrochloride, 2,2'-azobis(2-methylpropionitrile), and 2,2'-azobis(2-methylpropionitrile).

In some embodiments, the radical initiator is a photoinitiator. In some embodiments, the photoinitiator is an aryl ketone. In some embodiments, the photoinitiator is selected from the group consisting of acetophenone; anisoin; anthraquinone; anthroquinone-2-sulfonic acid; benzil; bezoin; benzoin ethyl ether; bezoin isobutyl ether; benzoin methyl ether; benzophenone; 3,3',4,4'-benzophenonetetracarboxylic dianhydride; 4-benzoylbiphenyl; 2-benzyl-2-(dimethylamino)-4'-morpholinobutyrophenone; 4,4'-bis(diethylamino)benzophenone; 4,4'-bis(dimethylamino)benzophenone; camphorquinone; 2-chlorothioxanthen-2-one; dibenzosuberenone; 2,2'-diethoxyacetophenone; 4,4'-dihydroxybenzophenone; 2,2'-dimethoxy-2-phenylacetophenone; 4-(dimethylamino)benzophenone; 4,4'-dimethylbenzil; 2,5-dimethylbenzophenone; 3,4-dimethylbenzophenone; 2-hydroxy-2-methylpropiophenone; 4'-ethoxyacetophenone; 2-ethylanthraquinone; 3'-hydroxyacetophenone; 4'-hydroxyacetophenone; 3-hydroxyacetophenone; 4-hydroxyacetophenone; 1-hydroxycyclohexyl phenyl ketone; 2-hydroxy-2-methylpropiophenone; 2-methylbenzophenone; 3-methylbenzophenone; methylbenzoylformate; 2-methyl-4'-(methylthio)2-morpholinopropiophenone; phenantrenequinone; 4'-phenoxyacetophenone; thioxanthen-9-one; and diphenyl(2,4,6-trimethylbenzoyl)phosphine oxide. In some embodiments, the photoinitiator is 2,2'-diethoxyacetophenone.

In some embodiments of the methods disclosed herein, the method further comprises applying to the keratin-containing material sample for a period of time an additive. In some embodiments, the additive is applied to the keratin-containing material sample between steps i) and ii). In some embodiments, the additive is applied to the keratin-containing material sample as a pre-treatment. In some embodiments of the methods disclosed herein, the mixture further comprises an additive. In some embodiments, the mixture of step ii) further comprises an additive. In some embodiments, the additive is applied to the keratin-containing material sample after step ii). In some embodiments, the mixture of step iii) further comprises an additive. In some embodiments, the additive is applied to the keratin-containing material sample after step iii). In some embodiments, the additive is applied to the keratin-containing material sample as a post-treatment.

In some embodiments, the additive is selected from the group consisting of a fatty acid, a fatty alcohol, a fatty acid ester, an amino acid mixture, a peptide mixture, an acidifier, a polycarboxylic acid, or a mixture thereof.

In some embodiments, the additive is a fatty acid, a fatty alcohol, a fatty acid ester, or a mixture thereof. In some embodiments, the fatty acid, the fatty alcohol, or the fatty acid alcohol is selected from the group consisting of butyric acid, caproic acid, caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, linolenic acid, arachidonic acid, eicosapentaenoic acid, erucic acid, docosahexaenoic acid, argan oil, coconut oil, jojoba oil, olive oil, palm oil, capryl alcohol, pelargonic alcohol, capric alcohol, undecyl alcohol, lauryl alcohol, tridecyl alcohol, myristyl alcohol, pentadecyl alcohol, cetyl alcohol, palmitoleyl alcohol, heptadecyl alcohol, stearyl alcohol, oleyl alcohol, nonadecyl alcohol, arachidyl alcohol, heneicosyl alcohol, behenyl alcohol, erucyl alcohol, lignoceryl alcohol, ceryl alcohol, ascorbyl palmitate, ascorbyl stearate, cetyl myristoleate, cetyl palmitate, a diglyceride, ethyl decanoate, ethyl macadmiate, ethyl octanoate, ethyl palmitate, ethylhexyl palmitate, glyceryl monostearate, glyceryl hydroxystearate, glycol distearate, glycol stearate, glycerol monolaurate, isopropyl palmitate, a monoglyceride, 2-oleoylglycerol, and a mixture thereof. In some embodiments, the fatty acid is selected from the group consisting of butyric acid, caproic acid, caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, linolenic acid, arachidonic acid, eicosapentaenoic acid, erucic acid, docosahexaenoic acid, jojoba oil, argan oil, coconut oil, jojoba oil, olive oil, palm oil, and a mixture thereof. In some embodiments, the fatty acid is selected from the group consisting of oleic acid, linoleic acid, jojoba oil, and a mixture thereof. In some embodiments, the fatty alcohol is selected from the group consisting of capryl alcohol, pelargonic alcohol, capric alcohol, undecyl alcohol, lauryl alcohol, tridecyl alcohol, myristyl alcohol, pentadecyl alcohol, cetyl alcohol, palmitoleyl alcohol, heptadecyl alcohol, stearyl alcohol, oleyl alcohol, nonadecyl alcohol, arachidyl alcohol, heneicosyl alcohol, behenyl alcohol, erucyl alcohol, lignoceryl alcohol, ceryl alcohol, and a mixture thereof. In some embodiments, the fatty alcohol is cetyl alcohol or cetearyl alcohol. In some embodiments, the fatty acid ester is selected from the group consisting of ascorbyl palmitate, ascorbyl stearate, cetyl myristoleate, cetyl palmitate, a diglyceride, ethyl decanoate, ethyl macadmiate, ethyl octanoate, ethyl palmitate, ethylhexyl palmitate, glyceryl monostearate, glyceryl hydroxystearate, glycol distearate, glycol stearate, glycerol monolaurate, isopropyl palmitate, a monoglyceride, 2-oleoylglycerol, and a mixture thereof.

In some embodiments, the additive is an amino acid mixture or a peptide mixture. In some embodiments, the additive is an amino acid mixture comprising one or more amino acids (naturally occurring L-form or D-form), which may be identified by the conventional three-letter abbreviations indicated in the below table.

TABLE 1

| (Amino acid codes) | |
| --- | --- |
| Name | 3-letter code |
| Alanine | Ala |
| Arginine | Arg |
| Asparagine | Asn |
| Aspartic acid | Asp |
| Cysteine | Cys |
| Glutamic acid | Glu |
| Glutamine | Gln |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

In some embodiments, the additive is an amino acid mixture comprising one or more amino acids or an N-acetylated amino acid (e.g., N-acetyl alanine, Ac-Ala). In some embodiments, the additive comprises an amino acid mixture selected from the group consisting of glycine (Gly), L-alanine (L-Ala), L-serine (L-Ser), L-cysteine (L-Cys), N-acetyl glycine (Ac-Gly), N-acetyl alanine (Ac-Ala), and N-acetyl serine (Ac-Ser). In some embodiments, the additive comprises an amino acid mixture selected from the group consisting of Ac-Gly, Ac-Ala, and Ac-Ser. In some embodiments, the additive comprises an amino acid mixture or a peptide mixture used in personal care industries. In some embodiments, the additive comprises an amino acid mixture or peptide mixture selected from the group consisting of blend of vegetable amino acids (sold under the trademark PISTON® KeraVeg 18), amino acid blend (sold under the trademark PRODEW® 500), cetearamidoethyldiethonium succinoyl hydrolyzed pea protein (sold under the trademark Vegetamide 18MEA-NJ), cetearamidoethyl diethonium hydrolyzed rice protein (sold under the trademark Vegetamide 18MEA-MR), rice peptides and amino acids (sold under the trademark KERARICE™), carob tree hydrolysate (sold under the trademark KERATRIX™), hydrolyzed keratin (sold under the trademark Promois WK-PD), and low molecular weight vegetable peptides (sold under the trademark GLUADIN® Kera-P LM). In some embodiments, the additive is carob tree hydrolysate (sold under the trademark KERATRIX™).

In some embodiments, the additive comprises an acidifier, a polycarboxylic acid, or a mixture thereof. In some embodiments, the additive comprises an acidifier or a polycarboxylic acid selected from the group consisting of aldobionic acid, azelaic acid, citric acid, ethylenediaminetetra-acetic acid, ethylenediamine-N,N'-disuccinic acid, gluconolactone, glutamic acid N,N-diacetic acid, lactic acid, methylglycinediacetic acid, tartaric acid, and a mixture thereof. In some embodiments, the additive comprises an acidifier or a polycarboxylic acid selected from the group consisting of citric acid, gluconolactone, glutamic acid N,N-diacetic acid, tartaric acid, tartronic acid, gluconic acid, succinic acid, itaconic acid, acetic acid, malonic acid, malic acid, 1,2,3,4-butanetetracarboxylic acid, and mixtures thereof. In some embodiments, the additive comprises citric acid and gluconolactone.

In some embodiments, the concentration of the additive is about 0.1% by weight to about 15% by weight. In some embodiments, the concentration of the additive is selected from the group consisting of about 0.1%, about 0.2%, about 0.3%, about 0.4%, about 0.5%, about 0.6%, about 0.7%, about 0.8%, about 0.9%, about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, about 5%, about 5.25%, about 5.5%, about 5.75%, about 6%, about 6.25%, about 6.5%, about 6.75%, about 7%, about 7.25%, about 7.5%, about 7.75%, about 8%, about 8.25%, about 8.5%, about 8.75%, about 9%, about 9.25%, about 9.5%, about 9.75%, about 10%, about 10.25%, about 10.5%, about 10.75%, about 11%, about 11.25%, about 11.5%, about 11.75%, about 12%, about 12.25%, about 12.5%, about 12.75%, about 13%, about 13.25%, about 13.5%, about 13.75%, about 14%, about 14.25%, about 14.5%, about 14.75%, and about 15% by weight. In some embodiments, the concentration of the additive is about 0.1% by weight to about 10% by weight. In some embodiments, the concentration of the additive is about 0.1% by weight to about 8% by weight. In some embodiments, the concentration of the additive is about 0.1% by weight to about 5% by weight. In some embodiments, the concentration of the additive is about 2% by weight. In some embodiments, the concentration of each additive is about 2% by weight.

In some embodiments of the methods disclosed herein, the mixture further comprises a solvent. In some embodiments, the solvent comprises dimethyl sulfoxide, water, acetone, buffer, or a mixture thereof. In some embodiments, the solvent is benign. In some embodiments, the solvent is not an organic solvent. In some embodiments, the solvent comprises water. In some embodiments, the solvent is water.

In some embodiments, the thiol-Michael addition grafting reactions on a keratin-containing material proceed faster and with better overall conversion in water, as compared to grafting in organic solvent. This behavior is consistent with a type of biphasic reaction known as "on-water." Certain organic reactions perform optimally on water, even when the organic reactants are insoluble in the aqueous phase.

Figure 3:
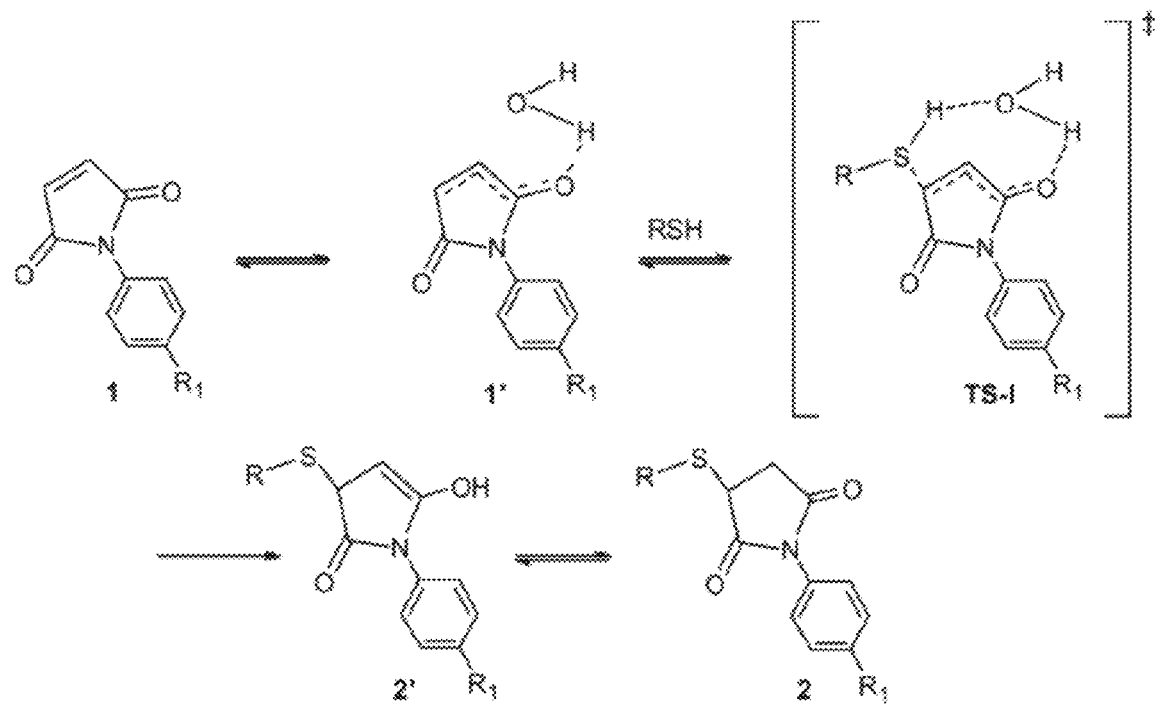
FIG. 3 is a schematic representation of the proposed mechanism for on-water activation in the thiol-Michael system.

Without being bound by any theory, this phenomenon may arise from water's ability to activate both the electrophile and nucleophile through hydrogen bonding. In some embodiments, the proposed mechanism for on-water activation in the thiol-Michael system is shown in FIG. 3.

In some embodiments, the mixture is an emulsion. In some embodiments, the mixture further comprises a surfactant.

Exemplary Properties of a Keratin-Containing Material

In some embodiments, a keratin-containing material is damaged in response to one or more stresses. In some embodiments, the one or more stresses are selected from the group consisting of washing, drying, brushing, combing, rubbing, styling, bleaching, dyeing, sun exposure, and heat treatment.

In another aspect, the disclosure provides a method for treating a keratin-containing material, wherein hydrophobicity of the keratin-containing material is improved, comprising:
  i) providing a keratin-containing material sample comprising a plurality of disulfide bonds;
  ii) applying to the keratin-containing material sample for a period of time a mixture, comprising a reducing agent, wherein the keratin-containing material sample comprises a plurality of free thiol groups; and
  iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;
thereby improving the hydrophobicity of the keratin-containing material.

In another aspect, the disclosure provides a method for treating a keratin-containing material, wherein hydrophobicity of the keratin-containing material is improved, comprising:
  i) providing a keratin-containing material sample comprising a plurality of disulfide bonds;
  ii) applying to the keratin-containing material sample for a period of time a mixture, comprising a reducing agent and a catalyst, wherein the keratin-containing material sample comprises a plurality of free thiol groups; and
  iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;
thereby improving the hydrophobicity of the keratin-containing material.

In another aspect, the disclosure provides a method for treating a keratin-containing material, wherein hydrophobicity of the keratin-containing material is improved, comprising:
  i) providing a keratin-containing material sample comprising a plurality of disulfide bonds; and
  ii) applying to the keratin-containing material sample for a period of time a mixture, comprising a reducing agent and a monomer; wherein the monomer is selected from the group consisting of an acrylate, a methacrylate, a monomer comprising a vinyl group, a monomer comprising an alkyne group, and a monomer comprising a maleimide group, thereby forming a plurality of free thiol groups which react with the monomer to form a plurality of covalent bonds between the free thiol groups and the monomers;
thereby improving the hydrophobicity of the keratin-containing material.

In some embodiments, the advancing water contact angle is greater than about 70°. In some embodiments, the advancing water contact angle is greater than about 80°. In some embodiments, the advancing water contact angle is greater than about 90°. In some embodiments, the advancing water contact angle is greater than about 100°.

In some embodiments, the advancing water contact angle is selected from the group consisting of about 70°, about 71°, about 72°, about 73°, about 74°, about 75°, about 76°, about 77°, about 78°, about 79°, about 80°, about 81°, about 82°, about 83°, about 84°, about 85°, about 86°, about 87°, about 88°, about 89°, about 90°, about 91°, about 92°, about 93°, about 94°, about 95°, about 96°, about 97°, about 98°, about 99°, about 100°, about 101°, about 102°, about 103°, about 104°, about 105°, about 106°, about 107°, about 108°, about 109°, and about 110°. In some embodiments, the advancing water contact angle is about 100°.

In another aspect, the disclosure provides a method for treating a keratin-containing material, wherein elongation at break of the keratin-containing material is improved, comprising:
  i) providing a keratin-containing material sample comprising a plurality of disulfide bonds;
  ii) applying to the keratin-containing material sample for a period of time a mixture, comprising a reducing agent, wherein the keratin-containing material sample comprises a plurality of free thiol groups; and
  iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;
thereby improving the elongation at break of the keratin-containing material.

In another aspect, the disclosure provides a method for treating a keratin-containing material, wherein elongation at break of the keratin-containing material is improved, comprising:
  i) providing a keratin-containing material sample comprising a plurality of disulfide bonds;
  ii) applying to the keratin-containing material sample for a period of time a mixture, comprising a reducing agent and a catalyst, wherein the keratin-containing material sample comprises a plurality of free thiol groups; and
  iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;
thereby improving the elongation at break of the keratin-containing material.

In another aspect, the disclosure provides a method for treating keratin-containing material, wherein elongation at break of the keratin-containing material is improved, comprising:
  i) providing a keratin-containing material sample comprising a plurality of disulfide bonds; and
  ii) applying to the keratin-containing material sample for a period of time a mixture, comprising a reducing agent and a monomer; wherein the monomer is selected from the group consisting of an acrylate, a methacrylate, a monomer comprising a vinyl group, a monomer comprising an alkyne group, and a monomer comprising a maleimide group, thereby forming a plurality of free thiol groups which react with the monomer to form a plurality of covalent bonds between the free thiol groups and the monomers;
thereby improving the elongation at break of the keratin-containing material.

In some embodiments, the elongation at break of the keratin-containing material is used to evaluate the strength of the material. Stronger materials can withstand more stress and strain. Stronger materials can be elongated further before breaking.

In another aspect, the disclosure provides a method for treating a keratin-containing material, wherein a Young's modulus of the keratin-containing material is improved, comprising:
  i) providing a keratin-containing material sample comprising a plurality of disulfide bonds;
  ii) applying to the keratin-containing material sample for a period of time a mixture, comprising a reducing agent, wherein the keratin-containing material sample comprises a plurality of free thiol groups; and
  iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;
thereby improving the Young's modulus of the keratin-containing material.

In another aspect, the disclosure provides a method for treating a keratin-containing material, wherein a Young's modulus of the keratin-containing material is improved, comprising:
  i) providing a keratin-containing material sample comprising a plurality of disulfide bonds;
  ii) applying to the keratin-containing material sample for a period of time a mixture, comprising a reducing agent and a catalyst, wherein the keratin-containing material sample comprises a plurality of free thiol groups; and
  iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the Young's modulus of the keratin-containing material.

In another aspect, the disclosure provides a method for treating a keratin-containing material, wherein a Young's modulus of the keratin-containing material is improved, comprising:

i) providing a keratin-containing material sample comprising a plurality of disulfide bonds; and ii) applying to the keratin-containing material sample for a period of time a mixture, comprising a reducing agent and a monomer; wherein the monomer is selected from the group consisting of an acrylate, a methacrylate, a monomer comprising a vinyl group, a monomer comprising an alkyne group, and a monomer comprising a maleimide group, thereby forming a plurality of free thiol groups which react with the monomer to form a plurality of covalent bonds between the free thiol groups and the monomers;

thereby improving the Young's modulus of the keratin-containing material.

In another aspect, the disclosure provides a method for treating a keratin-containing material, wherein an ultimate tensile strength of the keratin-containing material is improved, comprising:

i) providing a keratin-containing material sample comprising a plurality of disulfide bonds;

ii) applying to the keratin-containing material sample for a period of time a mixture, comprising a reducing agent, wherein the keratin-containing material sample comprises a plurality of free thiol groups; and iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the ultimate tensile strength of the keratin-containing material.

In another aspect, the disclosure provides a method for treating a keratin-containing material, wherein an ultimate tensile strength of the keratin-containing material is improved, comprising:

i) providing a keratin-containing material sample comprising a plurality of disulfide bonds;

ii) applying to the keratin-containing material sample for a period of time a mixture, comprising a reducing agent and a catalyst, wherein the keratin-containing material sample comprises a plurality of free thiol groups; and iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the ultimate tensile strength of the keratin-containing material.

In another aspect, the disclosure provides a method for treating a keratin-containing material, wherein an ultimate tensile strength of the keratin-containing material is improved, comprising:

i) providing a keratin-containing material sample comprising a plurality of disulfide bonds; and ii) applying to the keratin-containing material sample for a period of time a mixture, comprising a reducing agent and a monomer; wherein the monomer is selected from the group consisting of an acrylate, a methacrylate, a monomer comprising a vinyl group, a monomer comprising an alkyne group, and a monomer comprising a maleimide group, thereby forming a plurality of free thiol groups which react with the monomer to form a plurality of covalent bonds between the free thiol groups and the monomers;

thereby improving the ultimate tensile strength of the keratin-containing material.

In some embodiments, the ultimate tensile strength of the keratin-containing material is used to evaluate the structural integrity of the material. Ultimate tensile strength is the capacity of a material to withstand loads tending to elongate the material.

In another aspect, the disclosure provides a method for treating a keratin-containing material, wherein a protein loss value of the keratin-containing material is improved, comprising:

i) providing a keratin-containing material sample comprising a plurality of disulfide bonds;

ii) applying to the keratin-containing material sample for a period of time a mixture, comprising a reducing agent, wherein the keratin-containing material sample comprises a plurality of free thiol groups; and iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the protein loss value of the keratin-containing material.

In another aspect, the disclosure provides a method for treating a keratin-containing material, wherein a protein loss value of the keratin-containing material is improved, comprising:

i) providing a keratin-containing material sample comprising a plurality of disulfide bonds;

ii) applying to the keratin-containing material sample for a period of time a mixture, comprising a reducing agent and a catalyst, wherein the keratin-containing material sample comprises a plurality of free thiol groups; and iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;

thereby improving the protein loss value of the keratin-containing material.

In another aspect, the disclosure provides a method for treating keratin-containing material, wherein a protein loss value of the keratin-containing material is improved, comprising:
  i) providing a keratin-containing material sample comprising a plurality of disulfide bonds; and
  ii) applying to the keratin-containing material sample for a period of time a mixture, comprising a reducing agent and a monomer; wherein the monomer is selected from the group consisting of an acrylate, a methacrylate, a monomer comprising a vinyl group, a monomer comprising an alkyne group, and a monomer comprising a maleimide group, thereby forming a plurality of free thiol groups which react with the monomer to form a plurality of covalent bonds between the free thiol groups and the monomers;
thereby improving the protein loss value of the keratin-containing material.

In some embodiments, the protein loss value of the keratin-containing material is used to evaluate the strength and the structural integrity of the material. For example, after chemical treatments such as bleaching, perming, or straightening, keratin-containing materials become damaged, which results in higher protein loss. A higher protein loss value is correlated with more damage and less structural integrity.

In another aspect, the disclosure provides a method for treating a keratin-containing material, wherein a denaturation temperature of the keratin-containing material is improved, comprising:
  i) providing a keratin-containing material sample comprising a plurality of disulfide bonds;
  ii) applying to the keratin-containing material sample for a period of time a mixture, comprising a reducing agent, wherein the keratin-containing material sample comprises a plurality of free thiol groups; and
  iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;
thereby improving the denaturation temperature of the keratin-containing material.

In another aspect, the disclosure provides a method for treating a keratin-containing material, wherein a denaturation temperature of the keratin-containing material is improved, comprising:
  i) providing a keratin-containing material sample comprising a plurality of disulfide bonds;
  ii) applying to the keratin-containing material sample for a period of time a mixture, comprising a reducing agent and a catalyst, wherein the keratin-containing material sample comprises a plurality of free thiol groups; and
  iii) applying a monomer to the keratin-containing material sample, wherein the monomer is selected from the group consisting of an acrylate, a methacrylate, a monomer comprising a vinyl group, a monomer comprising an alkyne group, and a monomer comprising a maleimide group, thereby forming a plurality of covalent bonds between the free thiol groups and the monomers;
thereby improving the denaturation temperature of the keratin-containing material.

In another aspect, the disclosure provides a method for treating keratin-containing material, wherein a denaturation temperature of the keratin-containing material is improved, comprising:
  i) providing a keratin-containing material sample comprising a plurality of disulfide bonds; and
  ii) applying to the keratin-containing material sample for a period of time a mixture, comprising a reducing agent and a monomer; wherein the monomer is selected from the group consisting of an acrylate, a methacrylate, a monomer comprising a vinyl group, a monomer comprising an alkyne group, and a monomer comprising a maleimide group, thereby forming a plurality of free thiol groups which react with the monomer to form a plurality of covalent bonds between the free thiol groups and the monomers;
thereby improving the denaturation temperature of the keratin-containing material.

In some embodiments, the denaturation temperature of the keratin-containing material is used to evaluate the strength and the structural integrity of the material. For example, after chemical treatments such as bleaching, perming, or straightening, keratin-containing materials become damaged. Damaged materials are correlated with decreased denaturation temperatures.

In some embodiments of the methods disclosed herein, the treated keratin-containing material is evaluated by sensory evaluation. In some embodiments, the sensory evaluation is blinded. In some embodiments, the results of the sensory evaluation are categorized as nothing, moderately conditioned, or very product-y. In some embodiments, substantial grafting efficiency correlates to very product-y sensory evaluation results.

In some embodiments, the treated keratin-containing material mimics virgin keratin-containing material. In some embodiments, the treated keratin-containing material has similar characteristics to virgin keratin-containing material.

In some embodiments, the keratin-containing material treatment provides a wash-resistant functional (i.e. hydrophobic) layer.

In some embodiments, the treated keratin-containing material is treated hair. In some embodiments, the treated hair mimics the 18-MEA conditioning layer of virgin hair. In some embodiments, the monomer on the treated hair reinstalls a hydrophobic "healthy hair" layer.

In some embodiments, the hair treatment provides a wash-resistant functional (i.e. hydrophobic) layer. In some embodiments, the treated hair has improved alignment. In some embodiments, the treated hair has long-lasting smoothness. In some embodiments, the treated hair has improved shine. For example, hair health can be assessed based on one or more of an elongation at break, a Young's modulus, an ultimate tensile strength, a protein loss value, and a denaturation temperature.

In some embodiments, the treated keratin-containing material is treated nails. In some embodiments, the nails are fingernails or toenails. In some embodiments, the treated nails mimic virgin or new nails. In some embodiments, the treated nails improve flexibility. In some embodiments, the treated nails are less brittle. For example, brittleness can be assessed based on one or more of an elongation at break, a Young's modulus, an ultimate tensile strength, a protein loss value, and a denaturation temperature.

Exemplary Kits

One aspect of the disclosure provides a kit comprising a reducing composition comprising a reducing agent; a monomer composition comprising a monomer; and instructions for use.

In some embodiments, the reducing composition comprises a reducing agent; and a solvent.

In some embodiments, the monomer composition comprises a monomer; and a solvent.

In some embodiments, the solvent comprises dimethyl sulfoxide, water, acetone, buffer, or a mixture thereof. In some embodiments, the solvent comprises water. In some embodiments, the solvent is water.

Another aspect of the disclosure provides a kit comprising a mixture comprising a reducing agent and a catalyst; a monomer composition comprising a monomer; and instructions for use.

Another aspect of the disclosure provides a kit comprising a mixture comprising a reducing agent and a monomer; and instructions for use.

In some embodiments of the kits disclosed herein, the reducing agent is in a concentration of about 0.1% by weight to about 15% by weight.

In some embodiments of the kits disclosed herein, the monomer is selected from the group consisting of an acrylate, a methacrylate, a monomer comprising a vinyl group, a monomer comprising an alkyne group, and a monomer comprising a maleimide group.

EXEMPLIFICATION

The invention now being generally described, it will be more readily understood by reference to the following, which is included merely for purposes of illustration of certain aspects and embodiments of the present invention, and is not intended to limit the invention.

Example 1—Hair Reduction

In order to convert hair keratin disulfide bonds to free thiols a hair fiber must be exposed to and allowed to react with a reducing agent. Although this reduction process has been well-studied in the context of permanent waving (See, e.g., Wickett, R. R. J. Soc. Cosmet. Sci. 1983, 34, 301-316; Yu, D.; Cal, J. Y.; Church, J. S.; Wang, L. Int. J. Biol. Macromol. 2015, 78, 32-38; Tian, W.; Hu, Y.; Wang, W.; Yu, D. RSC Adv. 2015, 5, 91932-91936), conditions for reducing hair with minimal damage have yet to be found. Reduction throughout the entire hair fiber was accomplished using ammonium thioglycolate (ATG), and Table 2 shows the ATG reduction parameters adjusted to provide sufficient thiol content while minimizing hair damage. Similar information is given in Table 3 for L-cysteine, which is a reducing agent only active at hair's surface.

TABLE 2

Bulk reduction parameters for sufficient thiol content and minimal damage.

| Parameter | Useful Range | Range Investigated | Preferred Level |
| --- | --- | --- | --- |
| Conc. of ATG | 1%-11% by wt | 5%-30% by wt | 5% by wt |
| Liquor Ratio | 3:1 to 10:1 | 2:1 to 100:1 | 5:1 |
| Time | 15-30 minutes | 2-25 minutes | 15 minutes |
| pH | 7-10 | 7.5-10.5 | 9.5 |

TABLE 3

Surface reduction parameters for sufficient thiol content and minimal damage.

| Parameter | Useful Range | Range Investigated | Preferred Level |
| --- | --- | --- | --- |
| Conc. of L-cysteine | 1%-11% by wt | 5%-30% by wt | 5%-10% by wt |
| Liquor Ratio | 3:1 to 10:1 | 2:1 to 10:1 | 5:1 |
| Time | 15-30 minutes | 2-25 minutes | 15 minutes |
| pH | 7-10 | 7.5-10.5 | 9.5 |

Ellman's Method

Figure 4:
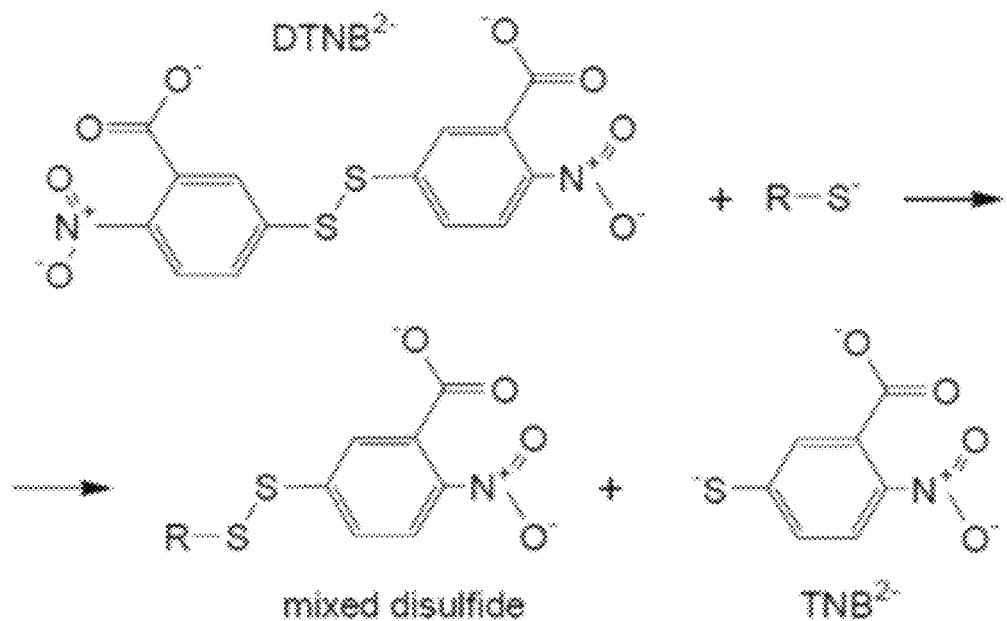
FIG. 4 is a schematic representation of the reaction of DTNB with a free thiol to form a mixed disulfide and the UV-active molecule TNB.

The reduction of disulfide bonds to free thiols was monitored with Ellman's method, which consists of thiol derivatization and subsequent spectroscopy. See, e.g., Fernandes, M.; Cavaco-Paulo, A. Biocatal. Biotransfor. 2012, 30, 10. First, a known concentration of the molecule 5,5'-dithiobis-(2-nitrobenzoic acid) (DTNB, Ellman's reagent) was stirred in solution with hair fibers. The DTNB reacted with the thiols to form an equimolar mixture of a mixed disulfide and the UV-active TNB moiety (FIG. 4), which was then detected with UV-VIS spectroscopy and compared with a calibration curve obtained using L-cysteine standards. The TNB intensity was quantified at 407 nm. This method allowed for the µmol/mg quantification of free thiol present on hair.

This method also allows for the µmol/mg quantification of free thiol present on other a keratin-containing material.

Concentration of the Reducing Agent

As the concentration of ATG decreased, the conversion of disulfide bonds to free thiols increased (Table 4). Experiments were conducted at a pH of 9.5 and a liquor ratio of 10:1 (ratio by weight of the mixture to the hair sample) for 15 minutes. Therefore, 5% by weight was a preferred concentration of ATG for grafting.

TABLE 4

Free thiol content achieved using different concentrations of ATG

| ATG Concentration (wt %) | Free Thiol (µmol/g of hair) |
| --- | --- |
| 5 | 38 ± 3 |
| 10 | 41 ± 2 |
| 20 | 24 ± 1 |
| 30 | 17 ± 1 |

Liquor Ratio

Figure 5:
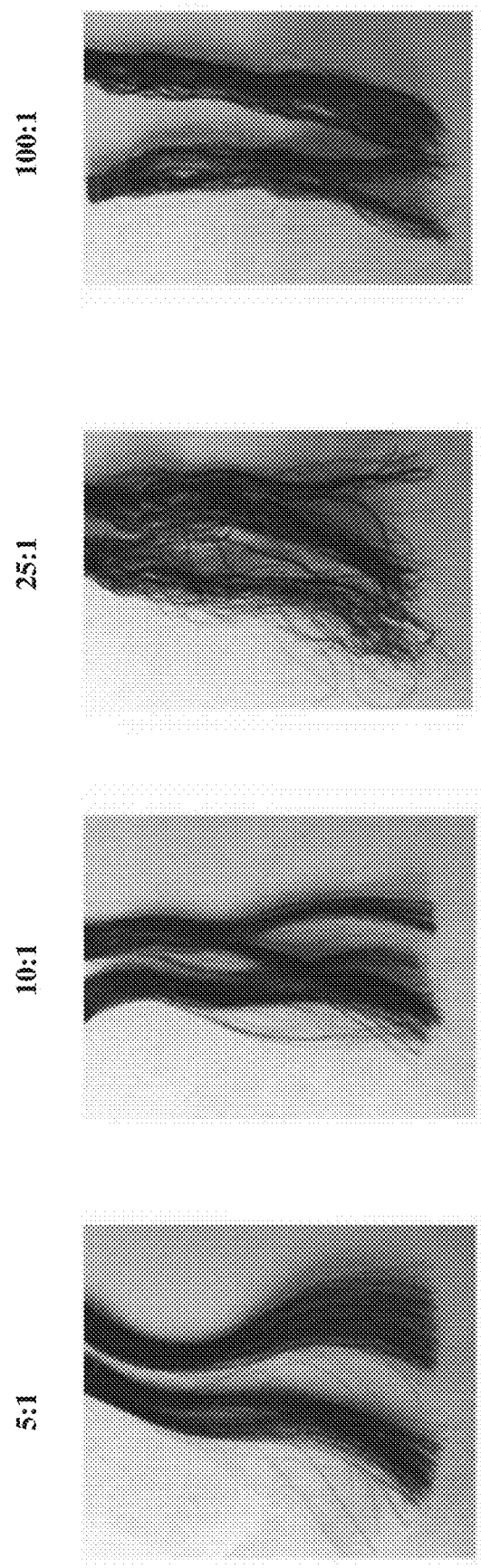
FIG. 5 depicts the visual appearance of hair fibers reduced under various liquor ratios.

The weight ratio of the reducing solution to the hair fiber, known in the textile industry as the "liquor ratio," has proven to be an important parameter. As the liquor ratio decreased, the free thiol content after reduction increased (Table 5). Experiments were conducted at a pH of 9.5 with 5% by weight of ATG for 15 minutes. This effect was likely due to the pseudo-first order nature of disulfide bond reduction, in which ATG was in large excess. The rate of disulfide bond breaking therefore increased as the disulfide bond concentration effectively increased (Equation 1). See, e.g., Manuszak, M. A.; Borish, E. T.; Wickett, R. R. J. Soc. Cosmet. Sci. 1996, 47, 49-58; Wickett, R. R. J. Soc. Cosmet. Sci. 1983, 34, 301-316. The level of hair fiber damage observed visually was less with lower liquor ratios (FIG. 5). In other words, as the liquor ratio increases fibers show more visible damage. For these two reasons, of the range of ratios studied a preferred liquor ratio for grafting was 5:1.

TABLE 5

Thiol content determined by Ellman's reagent using different liquor ratios during reduction

| Ratio | Free Thiol (μmol/g of hair) |
|---|---|
| 2:1 | 35 ± 6 |
| 5:1 | 51 ± 4 |
| 10:1 | 36 ± 3 |
| 25:1 | 32 ± 3 |
| 100:1 | 23 ± 3 |

$$\frac{-dC_{s-s}}{dt} = k * C_{s-s} \quad \text{Equation 1}$$

Rate equation for disulfide bond reduction.

Reduction Time

Figure 6:
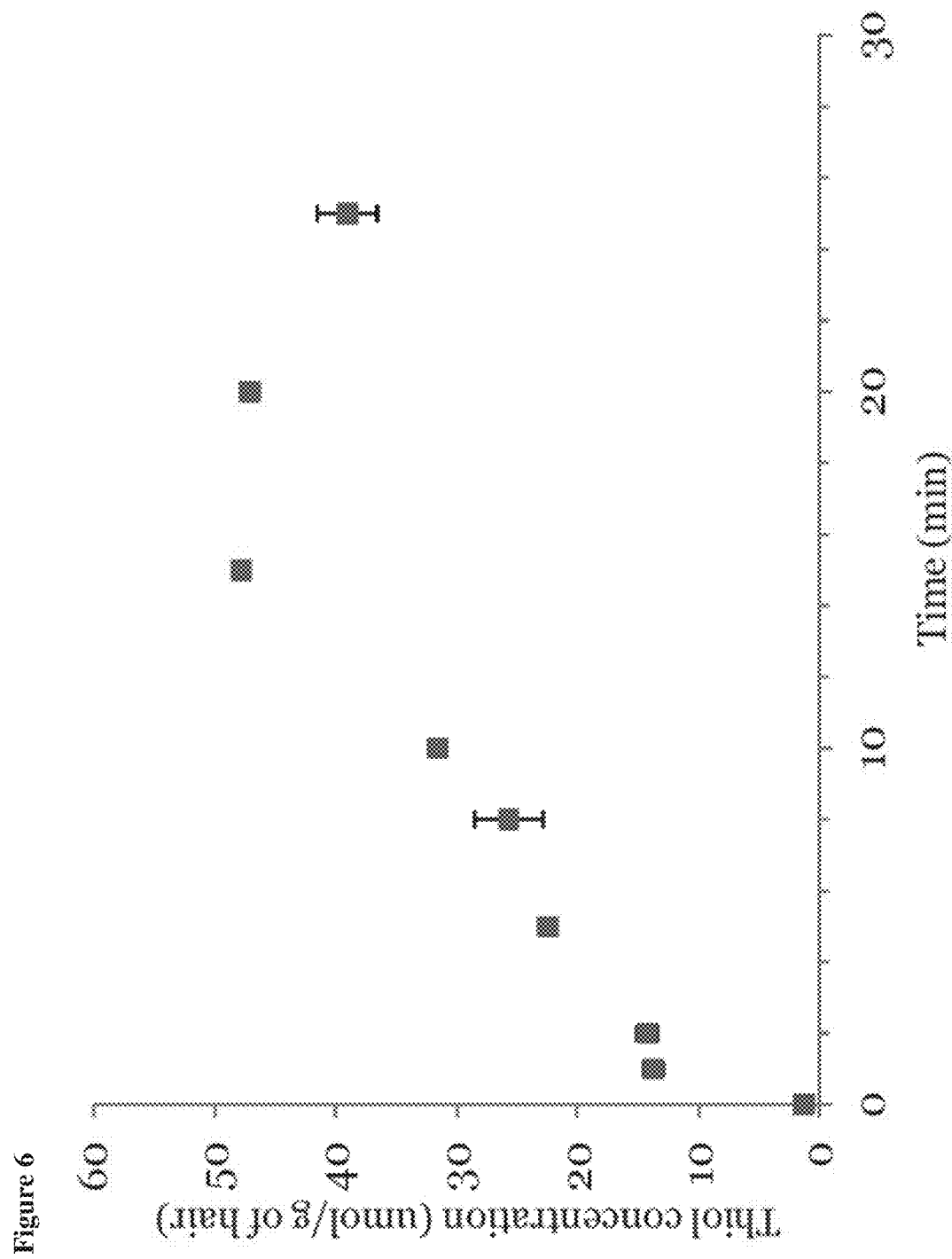
FIG. 6 depicts a kinetic study of hair reduction with a reducing agent.

The reduction step timing was varied in order to yield sufficient conversion of disulfide bonds to free thiols without exposing hair to the damaging reducing solution any longer than necessary. A kinetic study of the reduction process showed that 15 minutes was sufficient to achieve maximum hair reduction (FIG. 6). Experiment was conducted at a pH of 9.5 with 5% by weight of ATG for at a liquor ratio of 5:1. It should be noted that the maximum thiol content as determined by the Ellman's method is much lower than that obtained using amino acid analysis, 800 μmol/g of hair. See, e.g., Manuszak, M. A.; Borish, E. T.; Wickett, R. R. J. Soc. Cosmet. Sci. 1996, 47, 49-58. It is possible that the measurement using Ellman's method was mainly limited on hair surface, likely due to its relatively large molecular size.

N-Ethylmaleimide Assay

Figure 7:
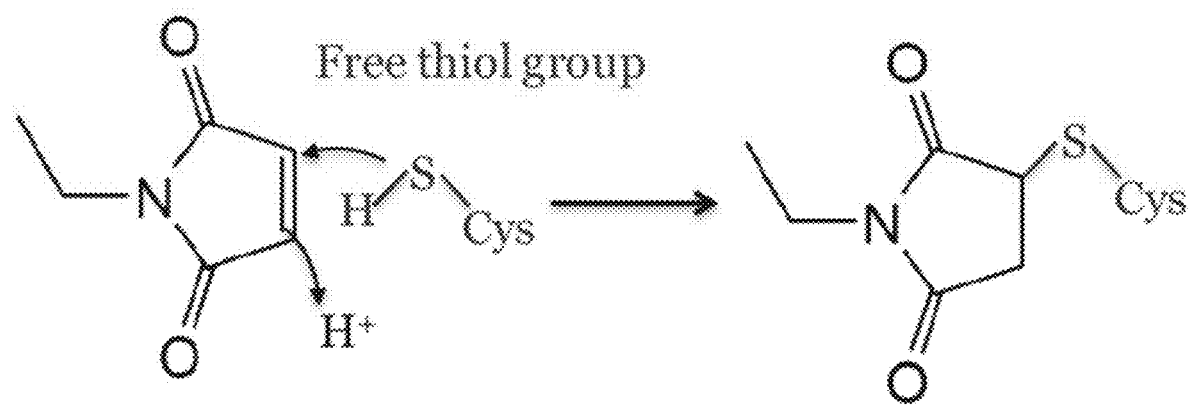
FIG. 7 is a schematic representation of reaction of NEM with free thiol groups to form a stable thioether.

N-ethylmaleimide (NEM) is another reagent that reacts specifically with thiol groups at pH 6.5-7.5 to form stable thioether groups (FIG. 7). Since NEM has a characteristic absorbance peak at 300 nm in its UV-vis spectrum, the reaction was monitored by the decrease in absorbance at 300 nm. Compared to the Ellman's reagent, NEM is a much smaller molecule and thus able to penetrate through the cuticle into the cortex region. It was expected that NEM assay would provide bulk measurement of thiol content in hair samples. In a typical experiment, a known concentration of NEM was mixed with hair fibers in a phosphate buffered saline (PBS) solution containing 0.1 M phosphate, 0.15 M sodium chloride, at pH 7.2. The level of decrease in NEM concentration was used to quantify free thiol content on hair.

When an experiment was conducted at a pH of 9.5 with 5% by weight of ATG for at a liquor ratio of 5:1, the thiol content was determined to be in the range of 600-800 μmol/g of hair by the NEM assay. This result was very similar to the results obtained using amino acid analysis. See e.g., Manuszak, M. A.; Borish, E. T.; Wickett, R. R. J. Soc. Cosmet. Sci. 1996, 47, 49-58. The results suggest that the NEM assay could be used a bulk measurement method for thiol quantification in hair samples whereas the Ellman's method was more useful for surface thiol content measurement.

This method also allows for the μmol/mg quantification of free thiol present on other a keratin-containing material.

Example 2—Grafting Monomers to Hair

Radical Thiol-Ene Grafting

Synthetic Procedure

Figure 8:
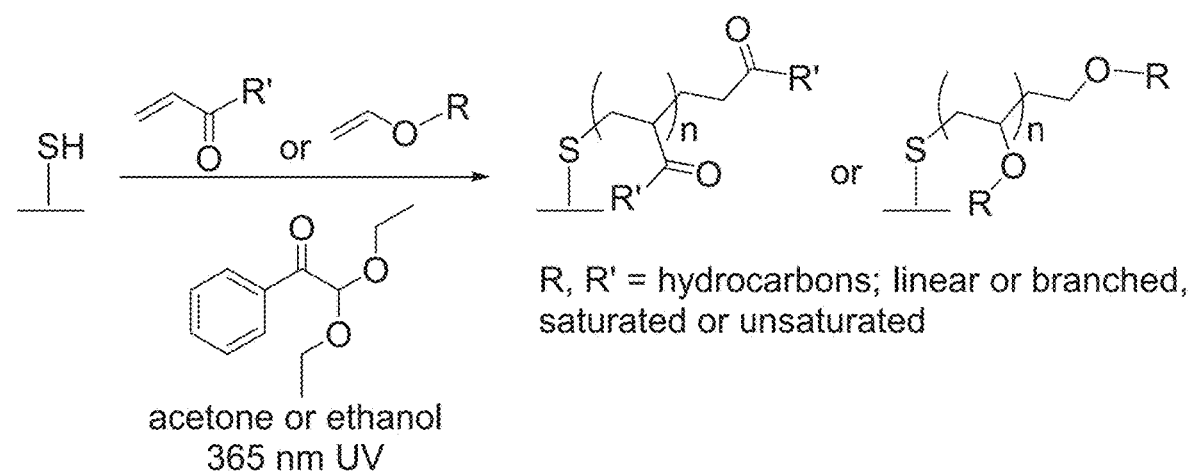
FIG. 8 is a schematic representation of the UV-mediated radical thiol-ene coupling with hydrophobic acrylates or vinyl ethers.

One possible route for the covalent attachment of monomers is the radical thiol-ene grafting process, in which ene-functional monomers are polymerized off of thiol functional groups when irradiated with UV light. 365 nm light and the initiator 2,2'-diethoxyacetophenone (DEAP) were used to initiate the grafting of acrylates and vinyl ethers from reduced hair's surface thiols in acetone or ethanol (FIG. 8).

Hydrophobic Monomer Selection

Figure 9:
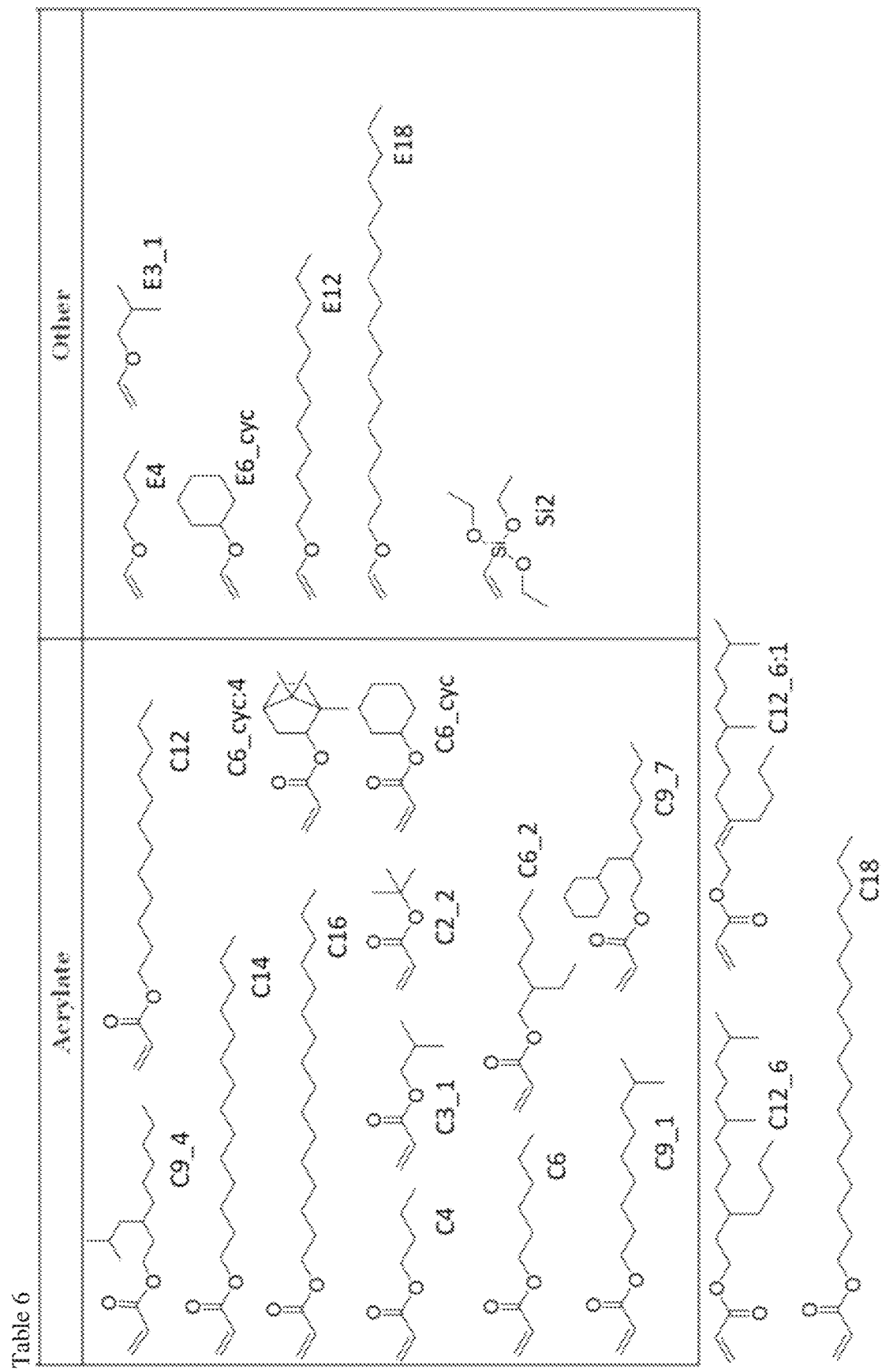
FIG. 9 depicts exemplary monomers useful in the disclosed methods of treating a keratin-containing material.

A variety of hydrophobic acrylates, vinyl ethers, and vinyl silanes have been investigated (Table 6, FIG. 9). Exemplary structure-activity testing was conducted in which monomers were grafted to reduced hair tresses and then evaluated using Fourier transform infrared (FTIR) spectroscopy and sensory assessments.

Thiol-Michael Grafting

Synthetic Procedure

The thiol-Michael addition of small molecule enes (olefin-containing small molecules) has also been used as a grafting pathway for covalent attachment of small molecules to hair. Without being bound by any theory, it is proposed that based on the initiating agent (catalyst), the reaction could proceed via either one of the two pathways: nucleophilic initiation and base catalysis, or both. See, e.g., Desmet, G. B.; Sabbe, M. K.; D'hooge, R.; Espeel, P.; Celasun, S.; Marin, G. B.; Du Prez, F. E.; Reyniers, M-F. Polym. Chem. 2017, 8, 1341-1352. Both reaction pathways were investigated using different initiating agents: amine-based catalysts which could undergo both base-catalyzed and nucleophile initiated pathways and tertiary phosphine-based catalyst which are primarily responsible for nucleophilic initiation. See, e.g., Desmet, G. B.; Sabbe, M. K.; D'hooge, R.; Espeel, P.; Celasun, S.; Marin, G. B.; Du Prez, F. E.; Reyniers, M-F. Polym. Chem. 2017, 8, 1341-1352. For all thiol-Michael addition reaction studies, hexyl acrylate and N-ethyl maleimide (NEM) molecules were used as model monomers and either dimethyl sulfoxide (DMSO), acetone, water, or mixtures thereof were used as solvent system. Important parameters such as monomer-to-thiol ratios, choice of solvent, catalyst concentration, and liquor ratio that dictate reaction efficiency were optimized.

Nucleophile-Catalyzed Thiol-Michael Grafting (Phosphine Catalysts)

The thiol-Michael reaction is an addition mechanism that may occur between a thiol and an activated (electron-withdrawing) ene in the presence of a base or nucleophile catalyst. The nucleophilic reaction is generally mediated by a phosphine catalyst, or by a primary or secondary amine. See, e.g., Chan, J. W.; Hoyle, C. E.; Lowe, A. B.; Bowman, M. Macromolecules 2010, 43, 6381-6388.

Figure 10:
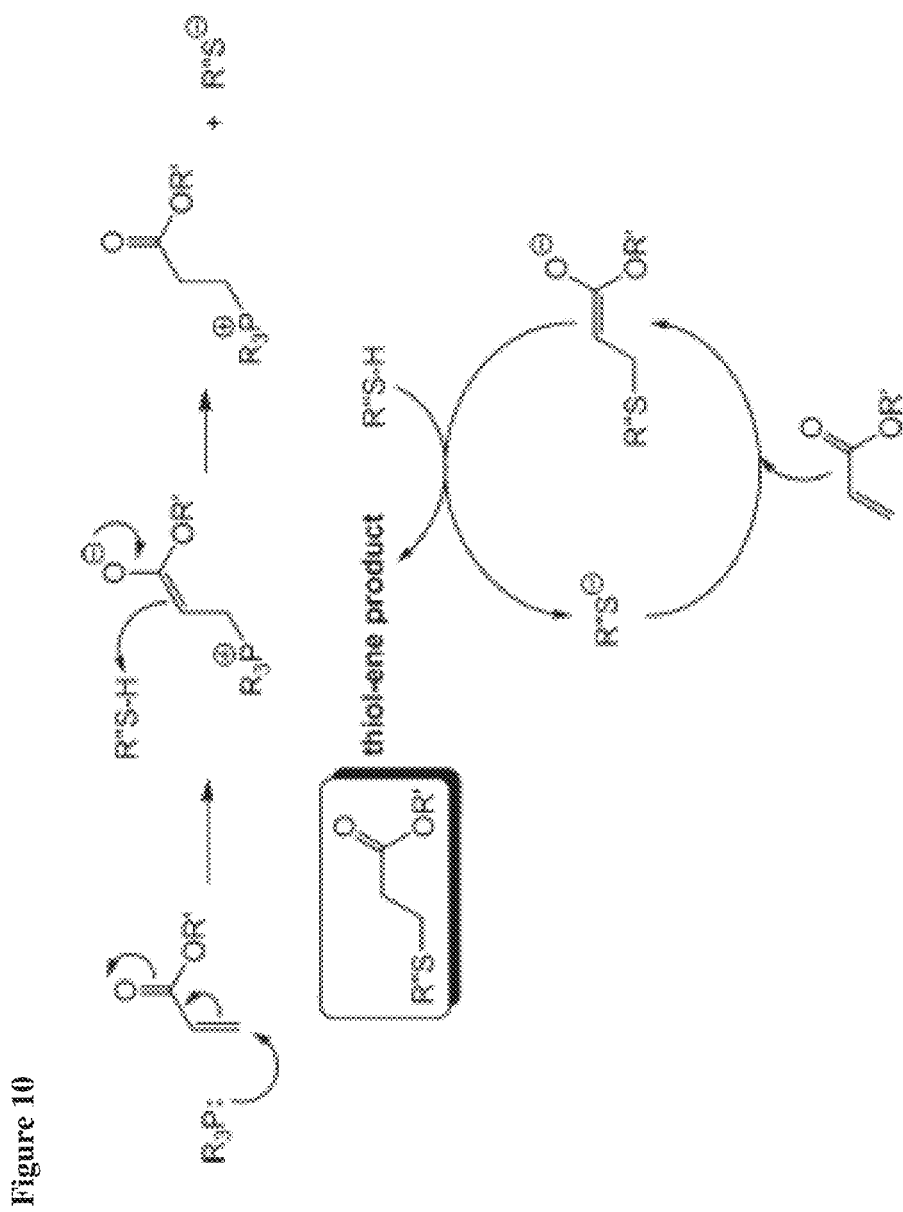
FIG. 10 is a schematic representation of thiol-Michael addition reaction via a nucleophile-initiated pathway.

Nucleophile-initiated thiol-Michael addition reactions were studied using tertiary phosphine as a catalyst and hexyl acrylate as a model monomer. Without being bound by any theory, as proposed in FIG. 10, the reaction starts with a nucleophilic attack of a catalyst on the double bond of the monomer resulting in a formation of a basic carbanion, which further reacts with a free thiol to form desired thiolate anion. In an addition step, the thiolate anion reacts with another molecule of a monomer to result in an anionic form of the product which further undergoes deprotonation in the presence of another free thiol. As a result the final product and another thiolate anion are formed. The newly formed thiolate anion then undergoes the same chain transfer process described above leading to very fast reaction rates. See, e.g., Desmet, G. B.; Sabbe, M. K.; D'hooge, R.; Espeel, P.; Celasun, S.; Marin, G. B.; Du Prez, F. E.; Reyniers, M-F. Polym. Chem. 2017, 8, 1341-1352.

Preferred Grafting Parameters

There are four main parameters that were varied for each system to achieve preferred grafting conditions. Table 7 showed preferred parameters for grafting with hexyl acrylate in the presence of a tertiary phosphine catalyst.

TABLE 7

Preferred grafting parameters for hexyl acrylate grafting with the tertiary phosphine catalyst dimethylphenylphosphine.

| Parameter | Range Investigated | Preferred Conditions |
| --- | --- | --- |
| Liquor Ratio | 5:1 to 20:1 | 5:1 |
| Monomer-to-Thiol Ratio | 1:1 to 10:1 | 2.5:1 |
| Catalyst Concentration (with respect to monomer) | 20 mol %-50 mol % | 40 mol % |
| Solvent System | DMSO, H$_2$O, H$_2$O/DMSO mixture | H$_2$O/DMSO mixture 90% H$_2$O/10% DMSO |

Liquor Ratio

Similar to the reduction process, "liquor ratio" in grafting process, refers to the weight ratio of the total grafting solution to the hair fiber. For grafting, it was important that just enough liquid was supplied to saturate the entire hair tress. Any additional liquor only served to dilute the concentration of hair thiols in the reduction system. Liquor ratios between 20:1 and 5:1 were studied. The balance was found at the preferred grafting liquor ratio of 5:1.

Monomer-To-Thiol Ratio

The reaction efficiency was studied at different monomer-to-thiol ratios. For each experimental condition, catalyst concentrations were kept constant at 30 mol % with respect to the monomer concentration. Based on the empirical data obtained from NEM assay, free thiol concentration of the reduced hair sample was assumed to be 800 μmol free thiol/g hair. All further monomer-to-thiol ratio calculations were performed based on this assumption.

Figure 11:
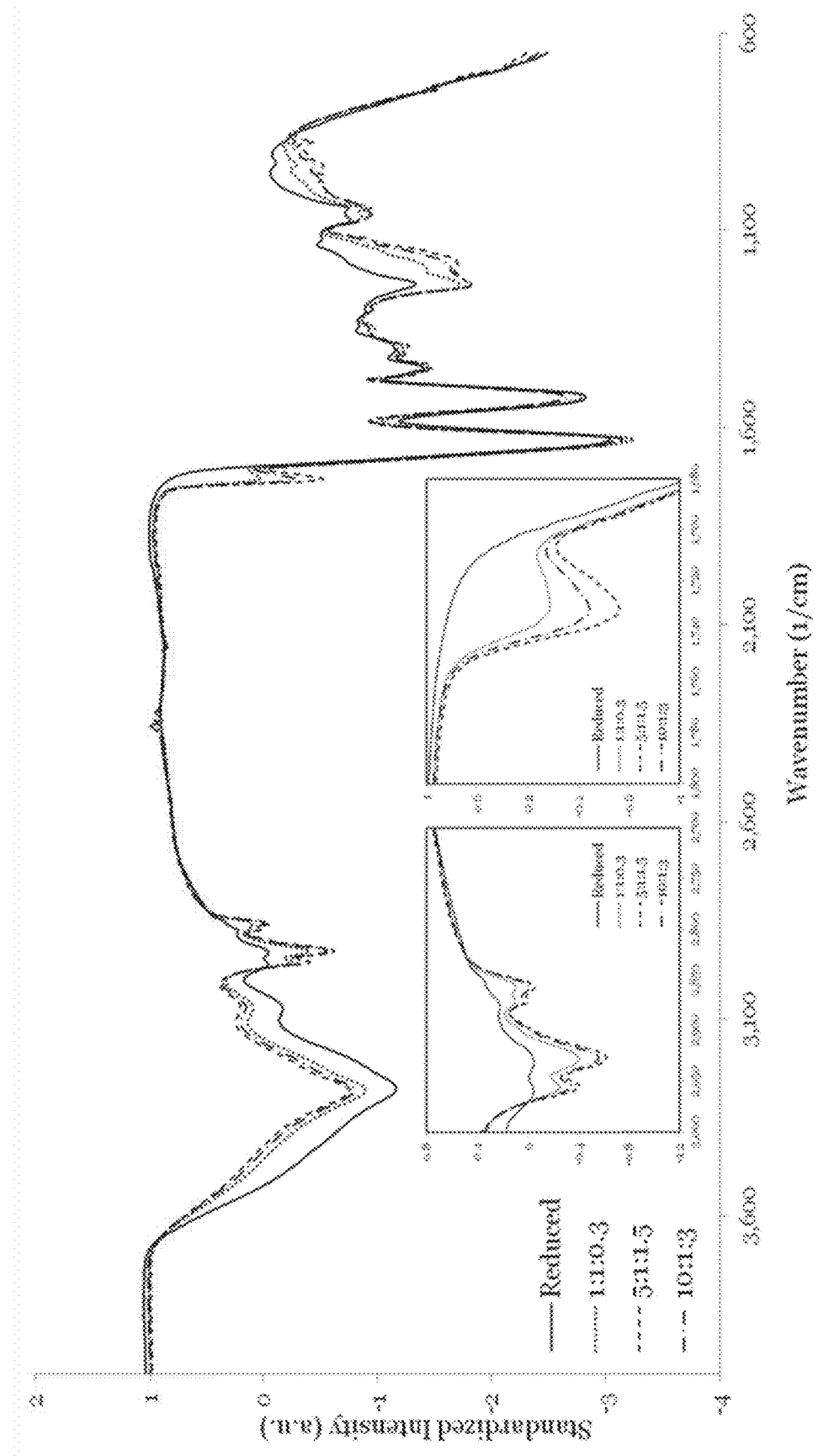
FIG. 11 depicts FTIR spectra of hair after grafting with an exemplary acrylate monomer at various monomer-to-thiol ratios for 3 h.

The wide range from 1:1 to 10:1 of monomer-to-thiol ratios was investigated. From the first series of experiments it was found that monomer-to-thiol ratio of 5:1 resulted in the strongest peaks on the FTIR spectra in the carbonyl peak region (about 1730 cm$^{-1}$) corresponding to the presence of carbonyl groups of hexyl acrylate on hair. In addition, the alkyl peaks region (ca. 3000-2800 cm$^{-1}$) on the FTIR also showed the strongest signals for the 5:1 ratio (FIG. 11). The tertiary phosphine catalyst was kept constant at 30 mol % concentration with respect to acrylate. All spectra shown are of hair tresses after thorough washing with sodium laureth sulfate (SLES).

Figure 12:
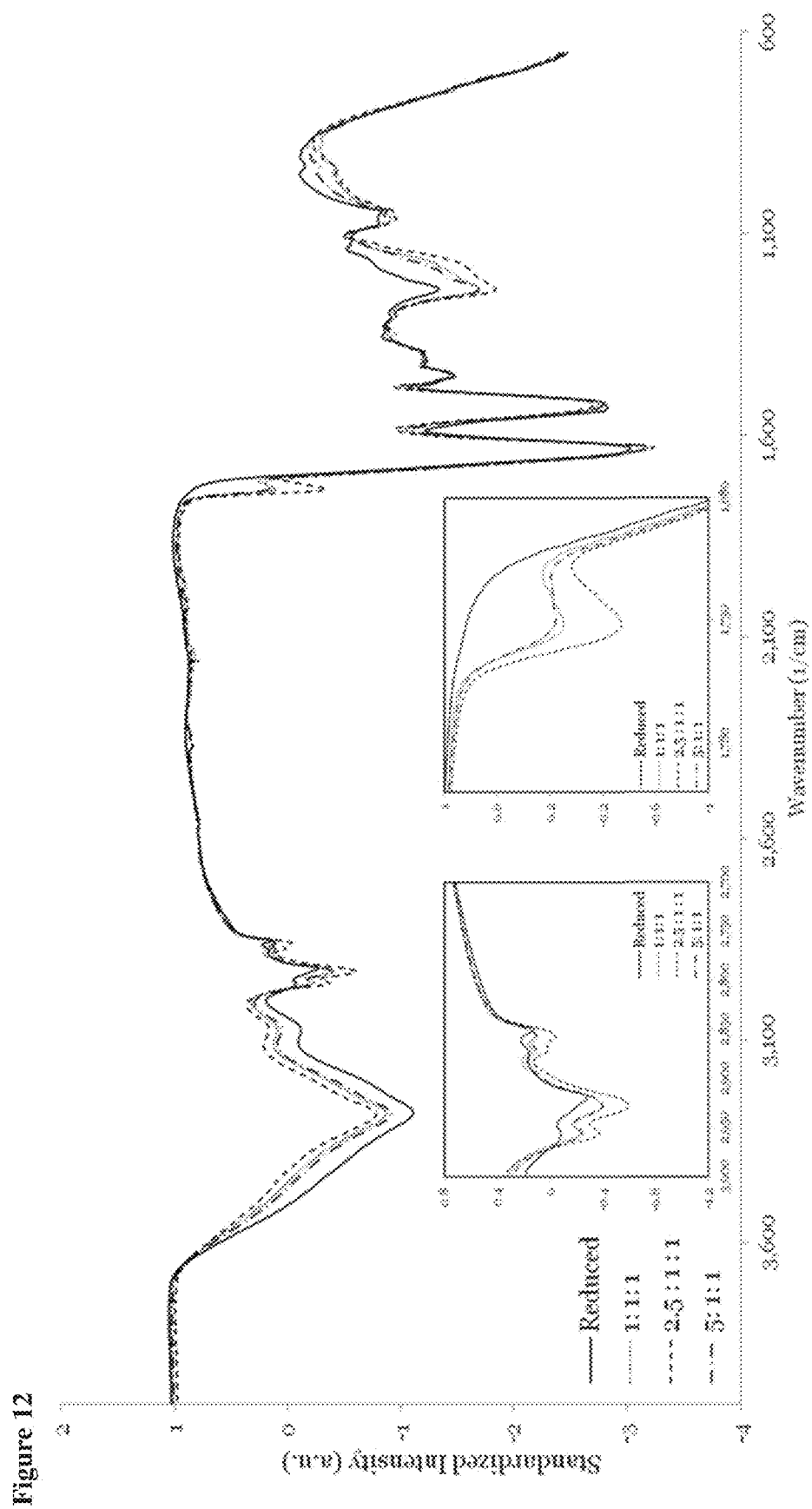
FIG. 12 depicts FTIR spectra of hair after grafting with an exemplary acrylate monomer at various monomer-to-thiol ratios for 3 h.

In the next set of experiments, lower monomer-to-thiol ratios were used, below 5:1, while keeping catalyst concentration constant for all conditions to truly study effect of the monomer concentration with respect to thiol groups on hair. As can be seen in FIG. 12, 1:1, 2.5:1 and repeat of 5:1 monomer-to-thiol ratios were explored. The preferred monomer-to-thiol ratio was found to be at 2.5:1. Both alkyl peaks region (about 3000-2800 cm$^{-1}$) and carbonyl peak region (about 1730 cm$^{-1}$) showed the strongest peak intensities for 2.5:1:1 monomer-to-thiol-to-catalyst ratio. All spectra shown are of hair tresses after thorough SLES washing.

Catalyst Concentration

Figure 13:
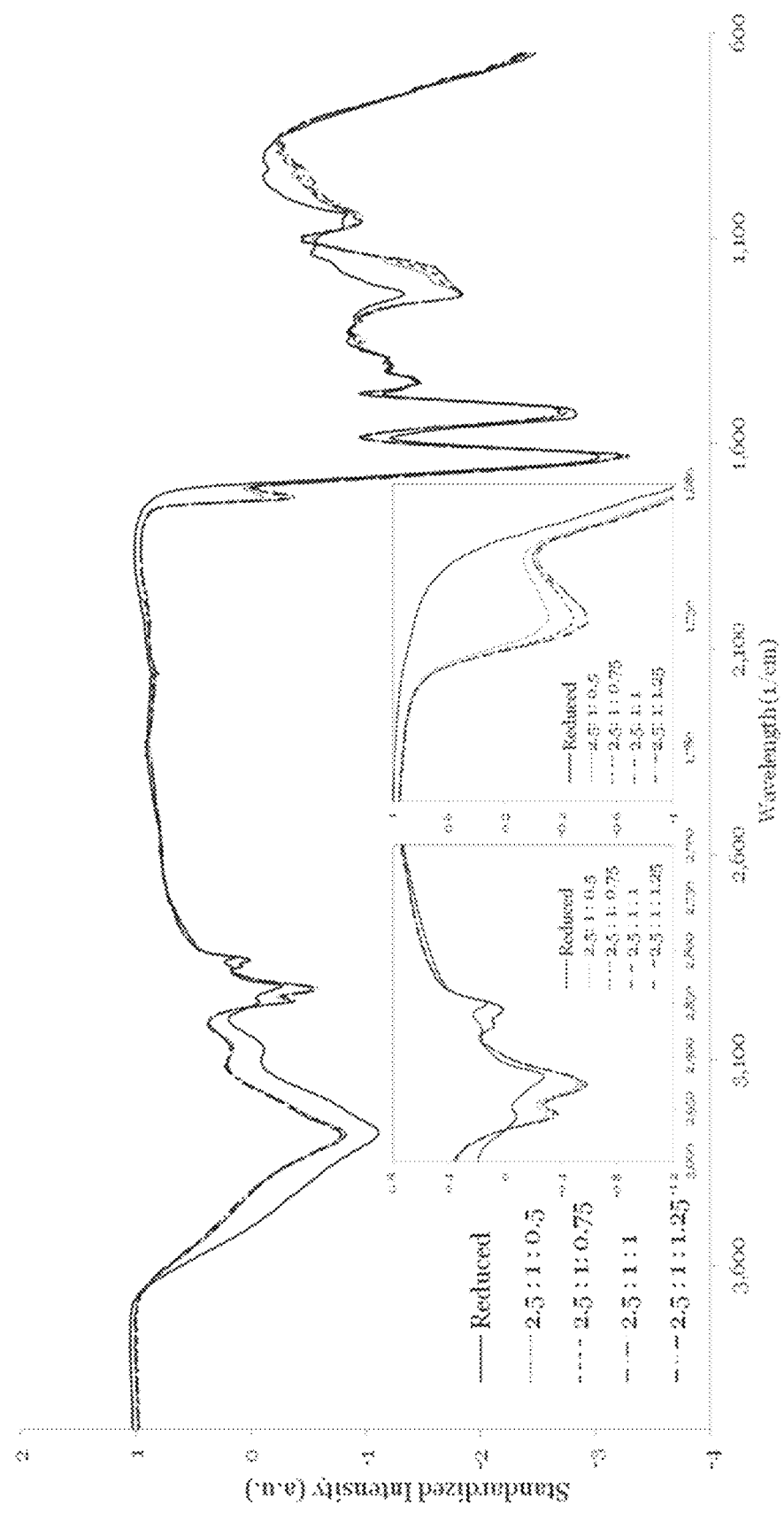
FIG. 13 depicts FTIR spectra of hair after grafting with an exemplary acrylate monomer at various catalyst concentrations for 1 h.

Once a preferred monomer-to-thiol ratio was identified, the effect of catalyst concentrations was studied. The previous results showed that 2.5:1 monomer-to-thiol ratio is preferred. In the study, 40 mol % of tertiary phosphine catalyst was used. A systematic study was performed to cover catalyst concentrations from 20 mol % to 50 mol % with respect to acrylate concentration for the preferred 2.5:1 monomer-to-thiol ratio. It was found that at 2.5:1:1 and 2.5:1:1.25 monomer-to-thiol-to-catalyst ratios, corresponding to catalyst concentrations of 40 mol % and 50 mol %, with respect to acrylate, resulted in the most intense peaks in the carbonyl peak region (about 1730 cm$^{-1}$) on the FTIR spectra (FIG. 13). All spectra shown are of hair tresses after thorough SLES washing. Since no significant advantages of using high catalyst concentration of 50 mol % were observed, the catalyst concentration was fixed at 40 mol % for the following experiments.

Solvent System

In all initial experiments, dimethyl sulfoxide (DMSO) was used as the only solvent. However due to potential high rate of penetration of DMSO through the biological systems, experiments were initiated to test other more benign solvents. As a starting point, the mixed solvent system was explored where DMSO was mixed with water at various weight ratios. At the preferred grafting conditions found using DMSO as a solvent (2.5:1:1 of monomer-to-thiol-to-catalyst ratio), water was introduced to replace DMSO by 50%, 75%, 90%, and by 100%.

Figure 14:
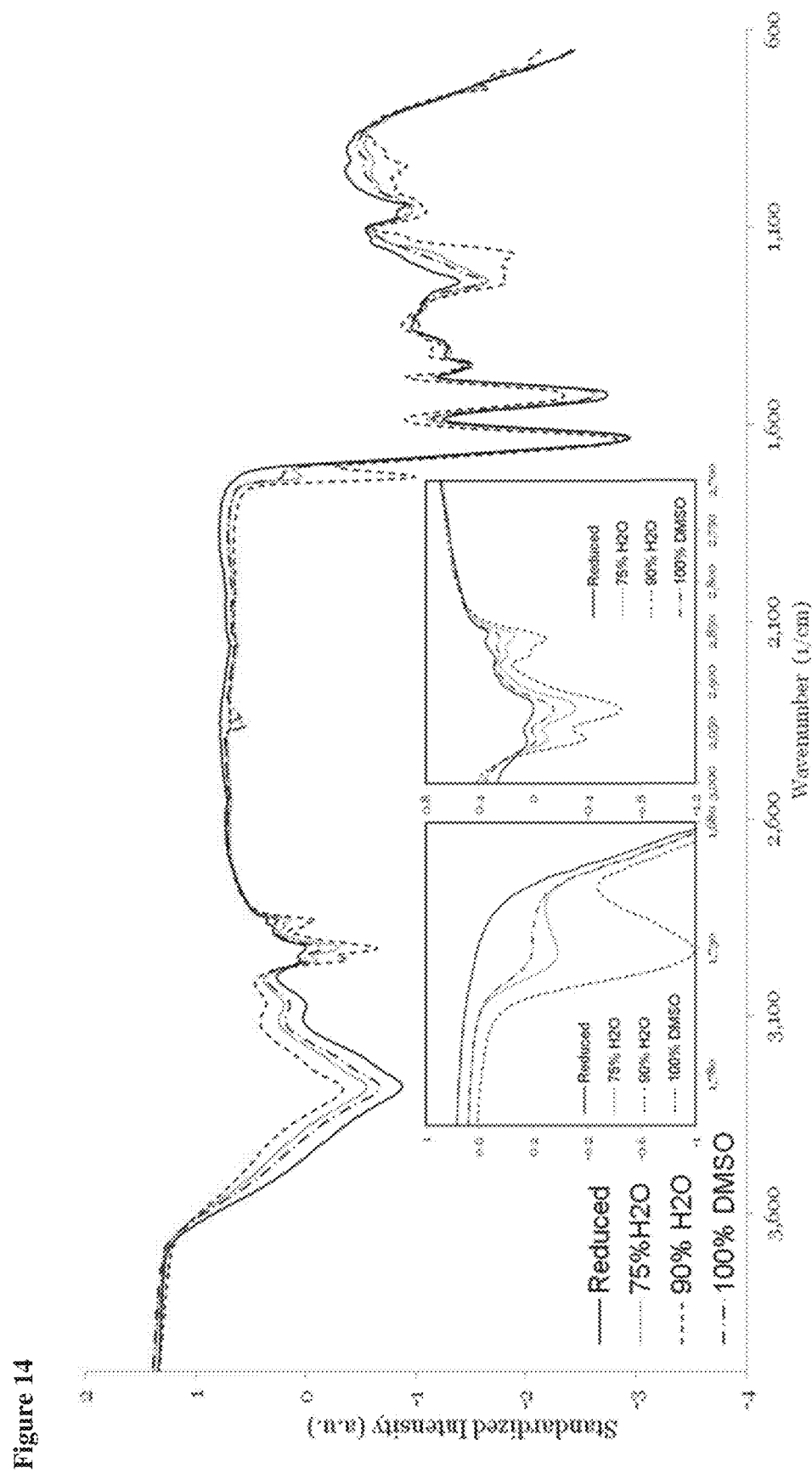
FIG. 14 depicts FTIR spectra of hair after grafting with an exemplary acrylate monomer in mixed aqueous solvent systems for 1 h.

As can be seen from FIG. 14, the mixed solvent systems where water replaced DMSO by 90% showed the best results outperforming DMSO only or water only solvent systems. Without being bound by theory, this result may be attributed to the highly concentrated localized delivery of reagents to the reactive thiol groups on hair. The carbonyl peak region (about 1730 cm$^{-1}$) and alkyl peak region (about 3000-2800 cm$^{-1}$) of the spectra showed the strongest peak intensities for system with mixed DMSO/H$_2$O solvent system at 90% H$_2$O-10% DMSO concentration. All spectra shown are of hair tresses after thorough SLES washing.

The model monomer of hexyl acrylate was successfully grafted onto thiol groups of hair via thiol-Michael addition using tertiary phosphine as an initiating agent. After systematically varying the parameters, preferred conditions produced efficient grafting based on the FTIR spectra included 2.5:1 monomer-to-thiol ratio, 40 mol % catalyst concentration with respect to monomer concentration, liquor ratio of 5:1, and in the H$_2$O/DMSO solvent system at 90% H$_2$O and 10% DMSO concentration. The phosphine catalyst was found to be very reactive. In the H$_2$O/DMSO solvent system, reactions were complete in 1 hour.

Nucleophile and Base-Catalyzed Thiol-Michael Grafting (Amine Catalysts)

Figure 15:
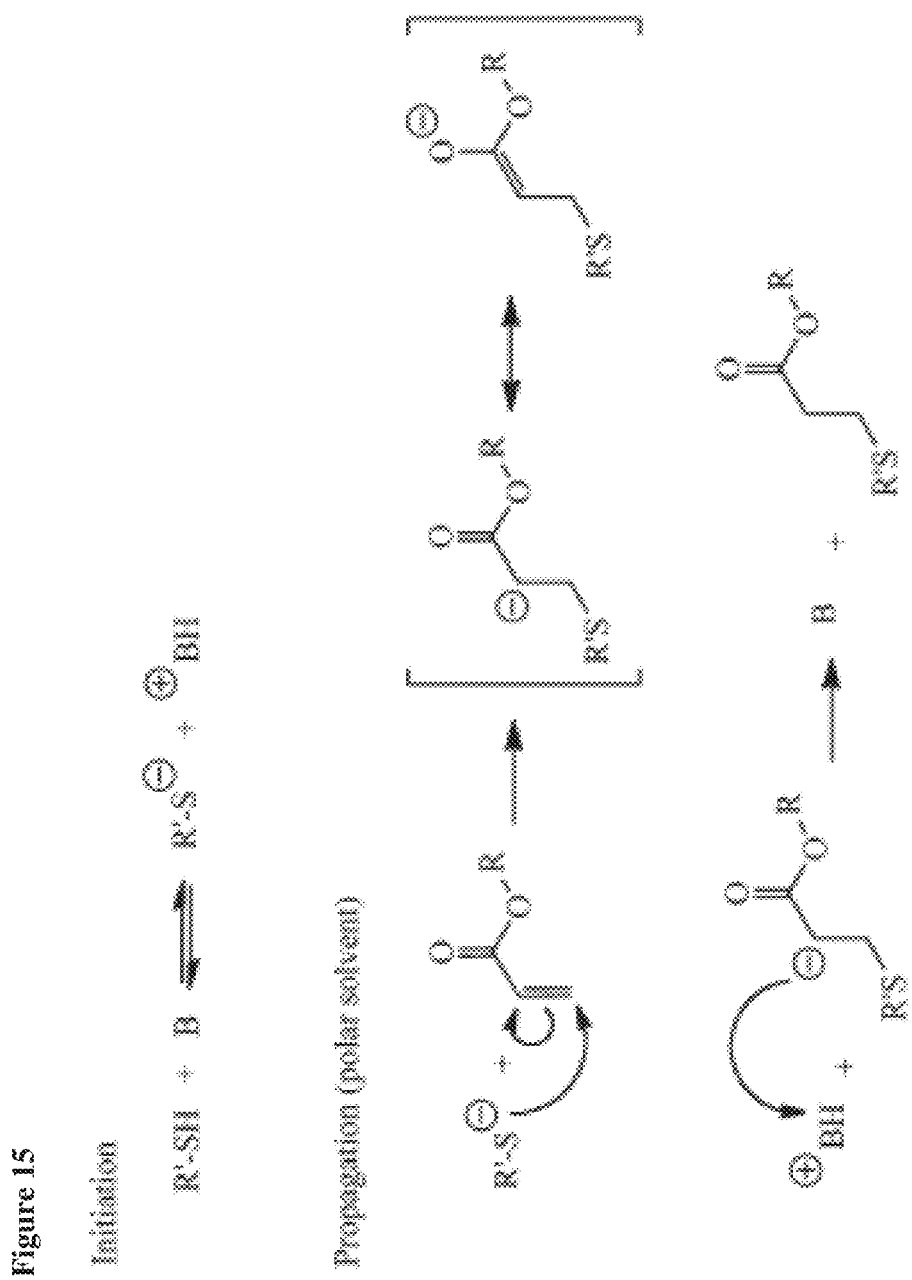
FIG. 15 is a schematic representation of the thiol-Michael addition reaction via a base-initiated pathway.

Thiol-Michael grafting may also be mediated by amine catalysts, which may proceed through a combination of basic and nucleophilic pathways depending on the structure of the amine. Without being bound by any theory, it is proposed that primary and secondary amines are generally assumed to proceed through both mechanisms, while tertiary amines serve as base catalysts only. See, e.g., Desmet, G. B.; Sabbe, M. K.; D'hooge, R.; Espeel, P.; Celasun, S.; Marin, G. B.; Du Prez, F. E.; Reyniers, M-F. Polym. Chem. 2017, 8, 1341-1352. Without being bound by any theory, FIG. 15 shows the proposed mechanism for the base-mediated pathway, which begins with the deprotonation of the thiol by the base in order to form a thiolate anion. See, e.g., Desmet, G. B.; Sabbe, M. K.; D'hooge, R.; Espeel, P.; Celasun, S.; Marin, G. B.; Du Prez, F. E.; Reyniers, M-F. Polym. Chem. 2017, 8, 1341-1352. Propagation occurs by (3-addition of the thiolate anion to an activated carbonyl, and subsequent proton transfer from the protonated base to yield thiol-Michael adduct.

Preferred Grafting Parameters

There are four main parameters that were varied for the amine-catalyzed system to achieve preferred grafting conditions. Table 8 showed preferred parameters for grafting with hexyl acrylate in the presence of a secondary amine catalyst.

TABLE 8

Preferred grafting parameters for hexyl acrylate grafting with the secondary amine catalyst di-n-propylamine (DNPA).

| Parameter | Range Investigated | Preferred Conditions |
| --- | --- | --- |
| Liquor Ratio | 5:1 to 20:1 | 5:1 |
| Monomer-to-Thiol Ratio | 1:1 to 30:1 | 10:1 or 30:1 |
| Catalyst Concentration (with respect to monomer) | 30 mol %-90 mol % | 30 mol % |
| Solvent System | DMSO, acetone, H$_2$O, H$_2$O/DMSO mixture | H$_2$O |

Table 9 showed preferred parameters for grafting of monomers to hair thiols after reduction for exemplary embodiments.

TABLE 9

Preferred grafting parameters for grafting of exemplary monomers with a catalyst.

| Component | Reagents Investigated | Preferred Reagents | Preferred Conditions |
| --- | --- | --- | --- |
| Monomer | Acrylates, maleimides | Hexyl acrylate Dodecyl acrylate N-ethylmaleimide (NEM) PEG-maleimide | 2 wt %-60 wt % |
| Catalyst | Amines, phosphines, radical initiators | Di-n-propylamine Dimethylphenyl-phosphine Triethylamine | 1 wt %-9 wt % |
| Solvent System | DMSO, acetone, H$_2$O, mixtures thereof | H$_2$O | 100% H$_2$O |

Liquor Ratio

As in the disclosed reduction process and phosphine-mediated grafting process, for the secondary amine grafting system a 5:1 liquor ratio was found to be preferred for ensuring total hair saturation with concentrated actives.

Catalyst

The effect of catalyst concentrations was also studied. In the study, the mol % of the secondary amine catalyst DNPA with respect to monomer was investigated, at values of 30 mol %, 60 mol %, and 90 mol %.

Figure 16:
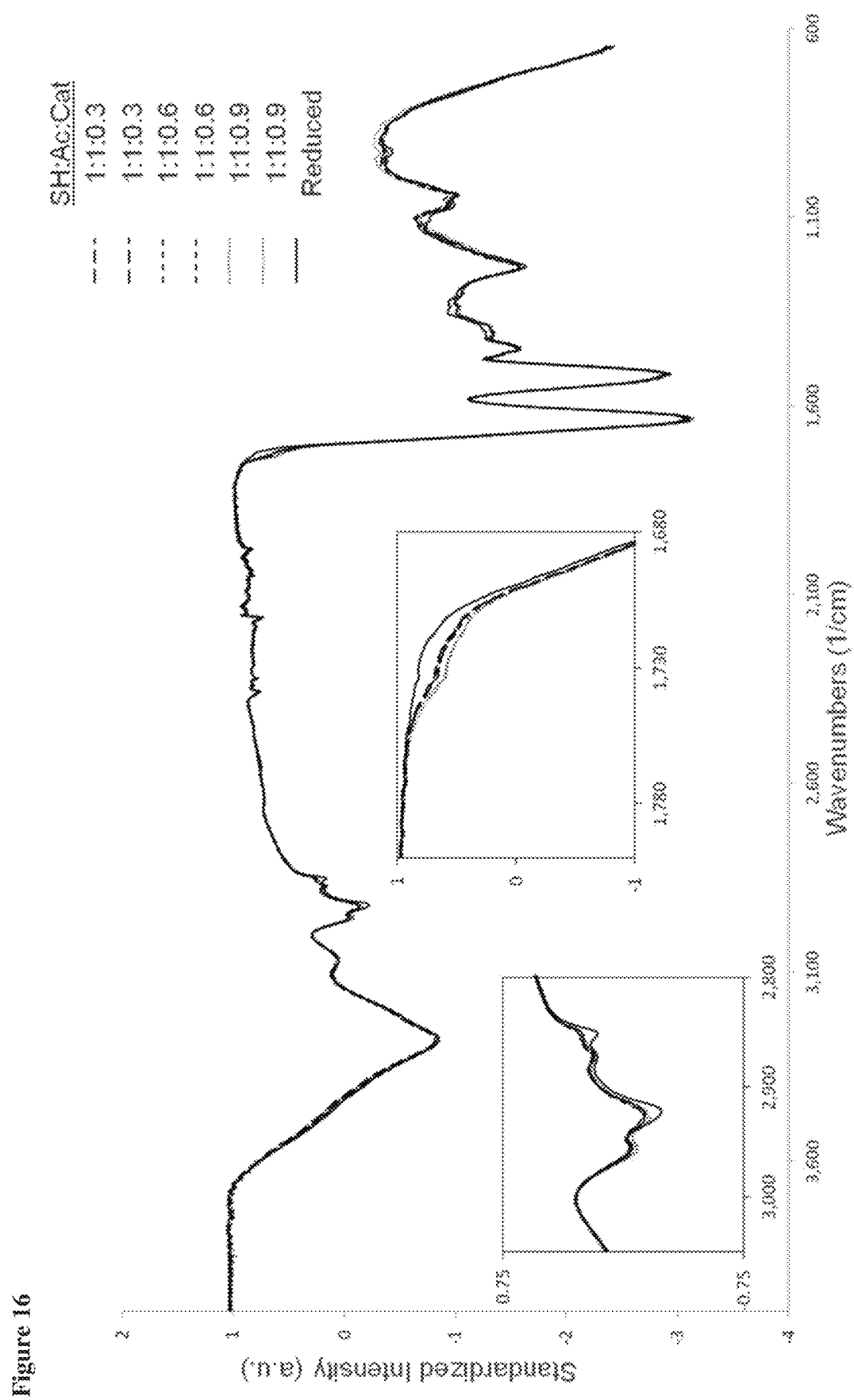
FIG. 16 depicts FTIR spectra of hair after grafting with an exemplary acrylate monomer at various secondary amine catalyst ratios for 3 h.

In this systematic study, it was found that at 1:1 monomer-to-thiol ratio the carbonyl peak intensity did not vary appreciably with the amount of catalyst used (FIG. 16). The carbonyl peak region (about 1730 cm$^{-1}$) showed a modest dose response. As the mol % of catalyst increased, the peak intensity increased slightly. All spectra shown are of hair tresses after thorough SLES washing. Therefore, additional studies were conducted using a catalyst concentration of 30 mol %.

Monomer-To-Thiol Ratio

The reaction efficiency was studied at different monomer-to-thiol ratios. For each experimental condition, catalyst concentrations were kept constant at 30 mol % with respect to the monomer concentration. Based on the empirical data obtained from NEM assay, free thiol concentration of the reduced hair sample was assumed to be 800 µmol free thiol/g hair. All further monomer-to-thiol ratio calculations were performed based on this assumption.

Figure 17:
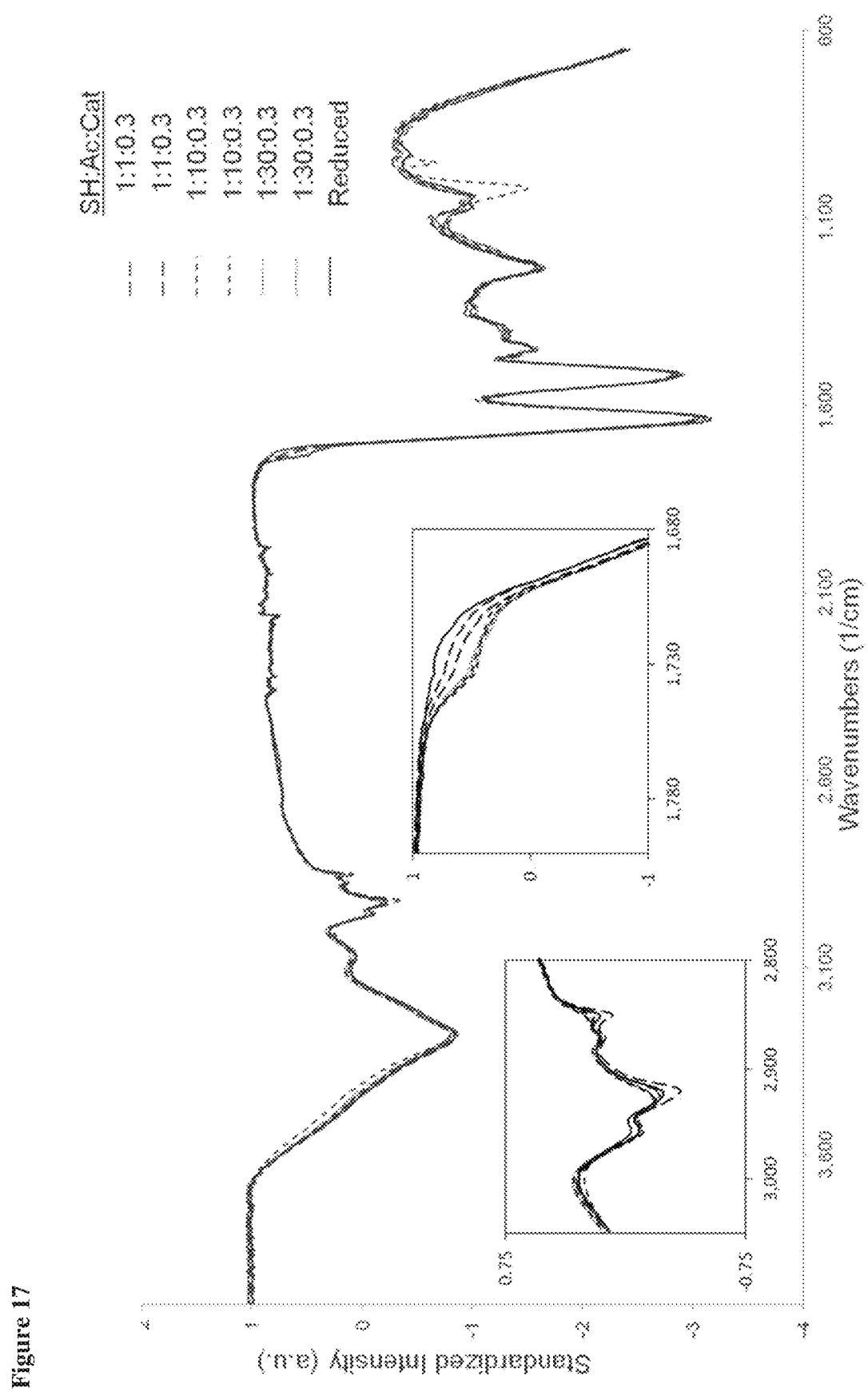
FIG. 17 depicts FTIR spectra of hair after grafting with an exemplary acrylate monomer at various monomer-to-thiol ratios for 3 h.

The wide range from 1:1 to 30:1 of monomer-to-thiol ratios was investigated. From this series of experiments, it was found that the intensity of the carbonyl peak for the 10:1 ratio was equally strong as the peak observed for the 30:1 ratio (FIG. 17).

Solvent System

Dimethyl sulfoxide (DMSO) was used as the solvent in all initial experiments, since it was known to facilitate efficient thiol-Michael addition reactions. See, e.g., Li, G.-Z.; Randev, R. K.; Soeriyadi, A. H.; Rees, G.; Boyer, C.; Tong, Z.; Davis, T. P.; Becer, C. R.; Haddleton, D. M. Polym. Chem. 2010, 1, 1196-1204. However due to potential high rate of penetration of DMSO through the biological systems, experiments were initiated to test other solvents.

Figure 18:
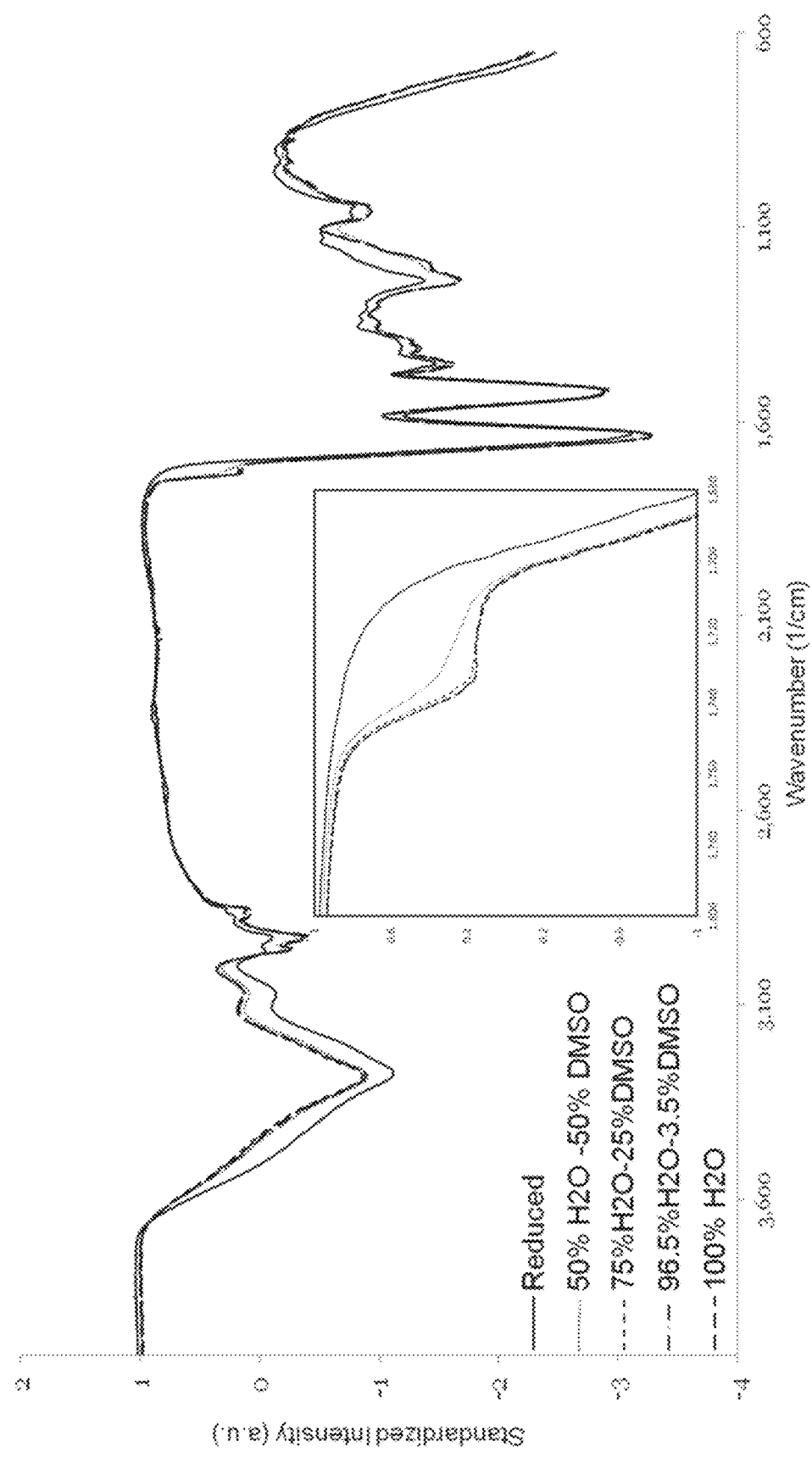
FIG. 18 depicts FTIR spectra of hair after grafting with an exemplary acrylate monomer in aqueous solvent systems for 1 h.

Experiments were conducted to investigate the effect of water as a solvent or co-solvent for hexyl acrylate grafting to hair with a secondary amine catalyst. Here, hexyl acrylate was grafted to hair at a 1:10:3 thiol-to-monomer-to-catalyst ratio in various solvent compositions, containing water at a concentration from 50 wt % to 100 wt %. FIG. 18 showed that in general, as the proportion of water in the solvent mixture increased, the carbonyl peak intensity also increased.

It was worth noting that although the carbonyl peak intensity tended to increase with the amount of water in the solvent mixture, the peaks observed within each sample were more heterogeneous compared to carbonyl peaks observed when grafting entirely in DMSO. Without being bound by any theory, it was hypothesized that the micellization of the organic materials (monomer, catalyst, optional DMSO) in water caused significant grafting on hair in some concentrated regions but not others.

Thiol-Michael Grafting of Maleimides (No Catalyst)

Compared to acrylates, maleimides are much more reactive due to their highly electron-deficient ene groups. See, e.g., Desmet, G. B.; Sabbe, M. K.; D'hooge, R.; Espeel, P.; Celasun, S.; Marin, G. B.; Du Prez, F. E.; Reyniers, M-F. Polym. Chem. 2017, 8, 1341-1352. In this study, all maleimide grafting experiments were carried out in PBS solution (0.1 M phosphate and 0.15 M sodium chloride at pH 7.2) without any catalyst. The main parameters including liquor ratio, monomer-to-thiol ratio, and reaction time were varied to achieve preferred grafting conditions. Table 10 shows the preferred parameters for grafting with NEM.

TABLE 10

Preferred grafting parameters for NEM grafting in PBS buffer.

| Parameter | Range Investigated | Preferred Conditions |
| --- | --- | --- |
| Liquor Ratio | 5:1 to 20:1 | 5:1 |
| Monomer-to-Thiol Ratio | 0.5:1 to 3:1 | 1.5:1 |
| Reaction Time | 0-120 min | 30 min |

Liquor Ratio

Similar to the disclosed hexyl acrylate grafting systems, a 5:1 liquor ratio was found to be preferred for ensuring total hair saturation with concentrated actives.

Monomer-To-Thiol Ratio

The grafting efficiency was evaluated at different NEM-to-thiol ratios. All experiments were carried out for 1 h at the preferred liquor ratio of 5:1. The amount of thiols grafted by NEM was determined using the NEM assay described in Example 1. Table 11 shows that the maximum amount of thiols was consumed at an NEM-to-thiol ratio of 1.5:1, suggesting the maximum NEM grafting under this condition.

TABLE 11

NEM-to-thiol ratio optimization to achieve maximum thiol consumption and thus optimum NEM grafting

| | Thiols Consumed at Various NEM-to-Thiol Ratios ($\mu$mol/g of hair) | | | |
|---|---|---|---|---|
| Time (h) | 0.5:1 | 1.0:1 | 1.5:1 | 3.0:1 |
| 0 | 0 | 0 | 0 | 0 |
| 1 | 210 | 283 | 621 | 551 |
| 2 | 373 | 533 | 604 | 587 |

Reaction Time

Figure 19:
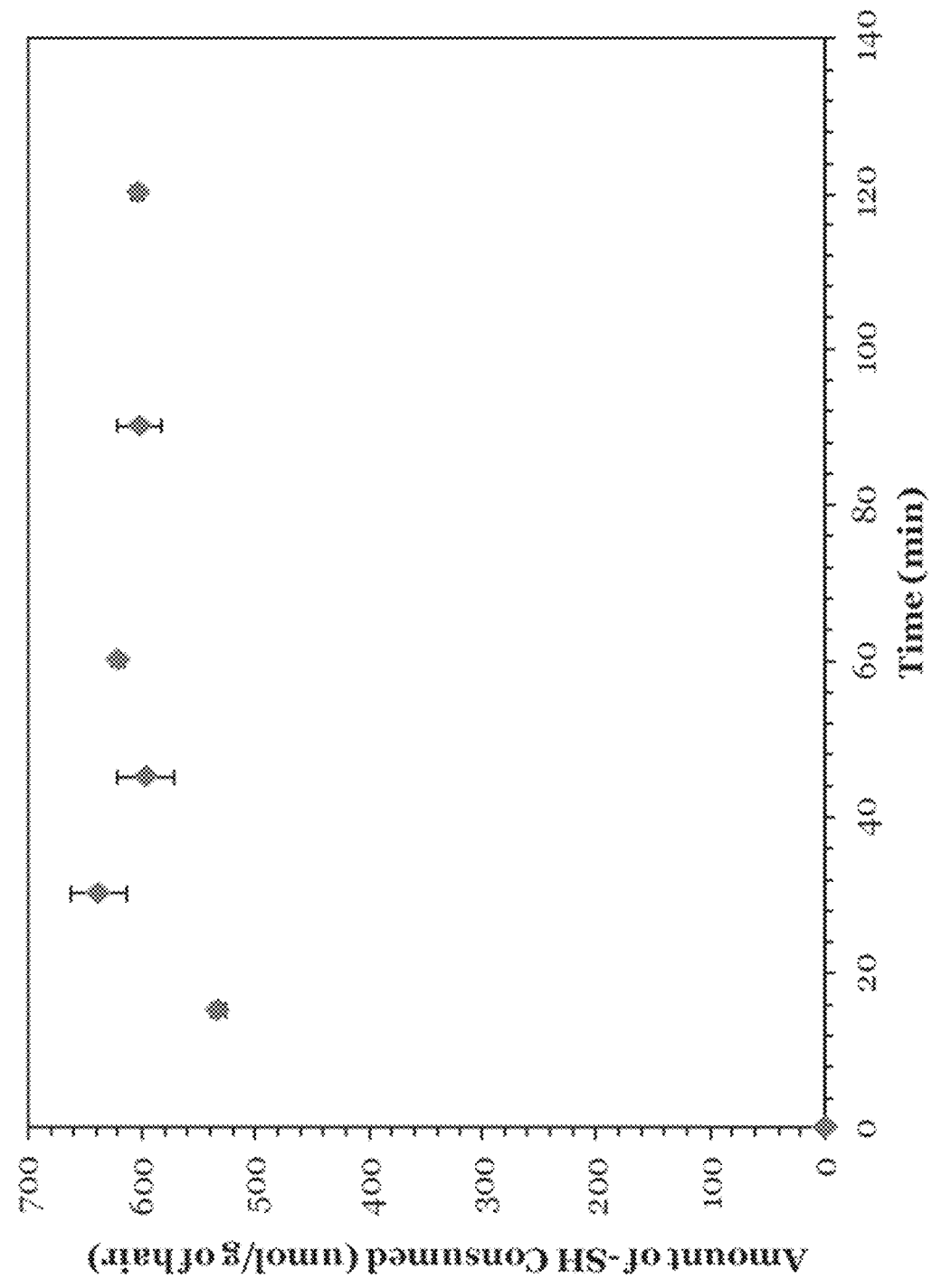
FIG. 19 depicts the amount of thiol groups consumed at different time points during grafting with an exemplary maleimide monomer.

Different reaction times were also explored to determine the preferred reaction time. FIG. 19 shows the amount of thiols consumed during the course of 2 hr NEM grafting process. Within the first 30 min, the maximum amount of grafting had already been achieved. These results clearly demonstrated the high reactivity of NEM as compared to hexyl acrylate, which usually required a minimum 1 h reaction time to achieve significant grafting.

Grafting with Other Maleimides

Figure 20A:
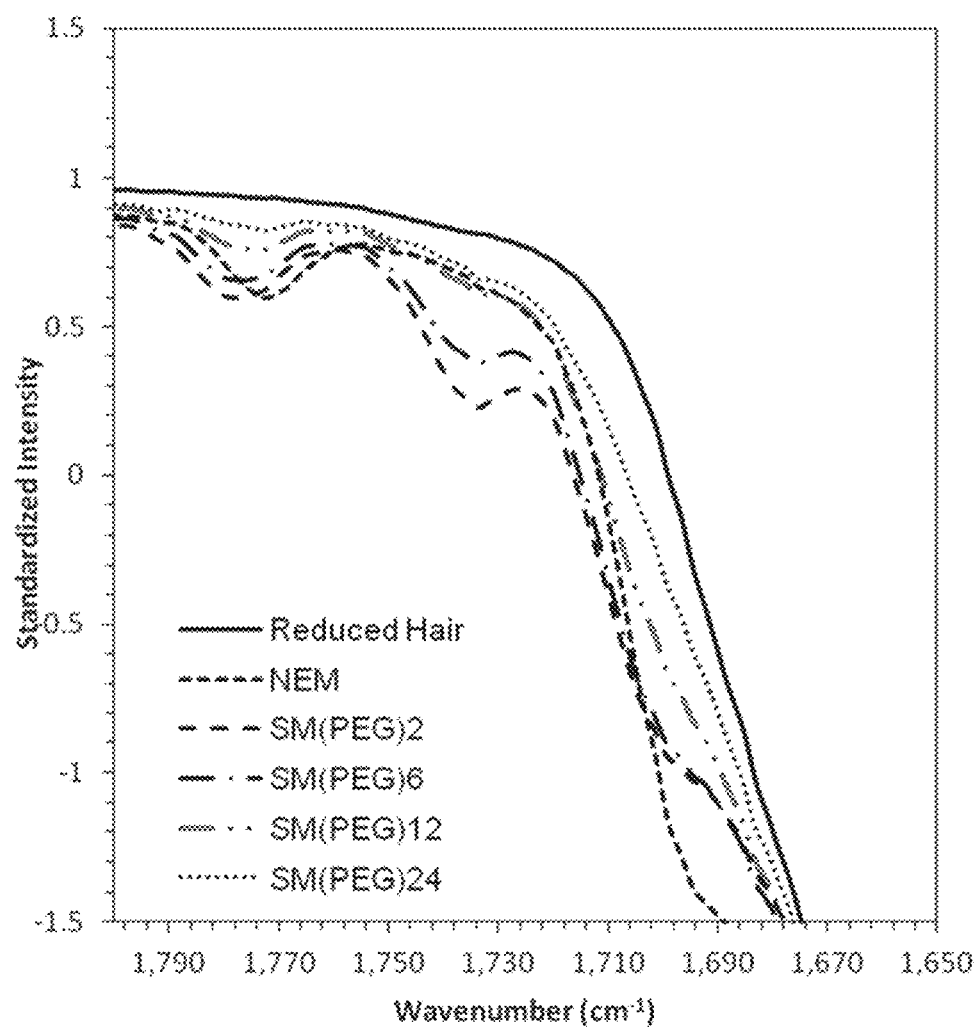
FIG. 20A depicts carbonyl peak region of FTIR spectra of hair after grafting with exemplary maleimide monomers in aqueous solvent systems for 1 h.
Figure 20B:
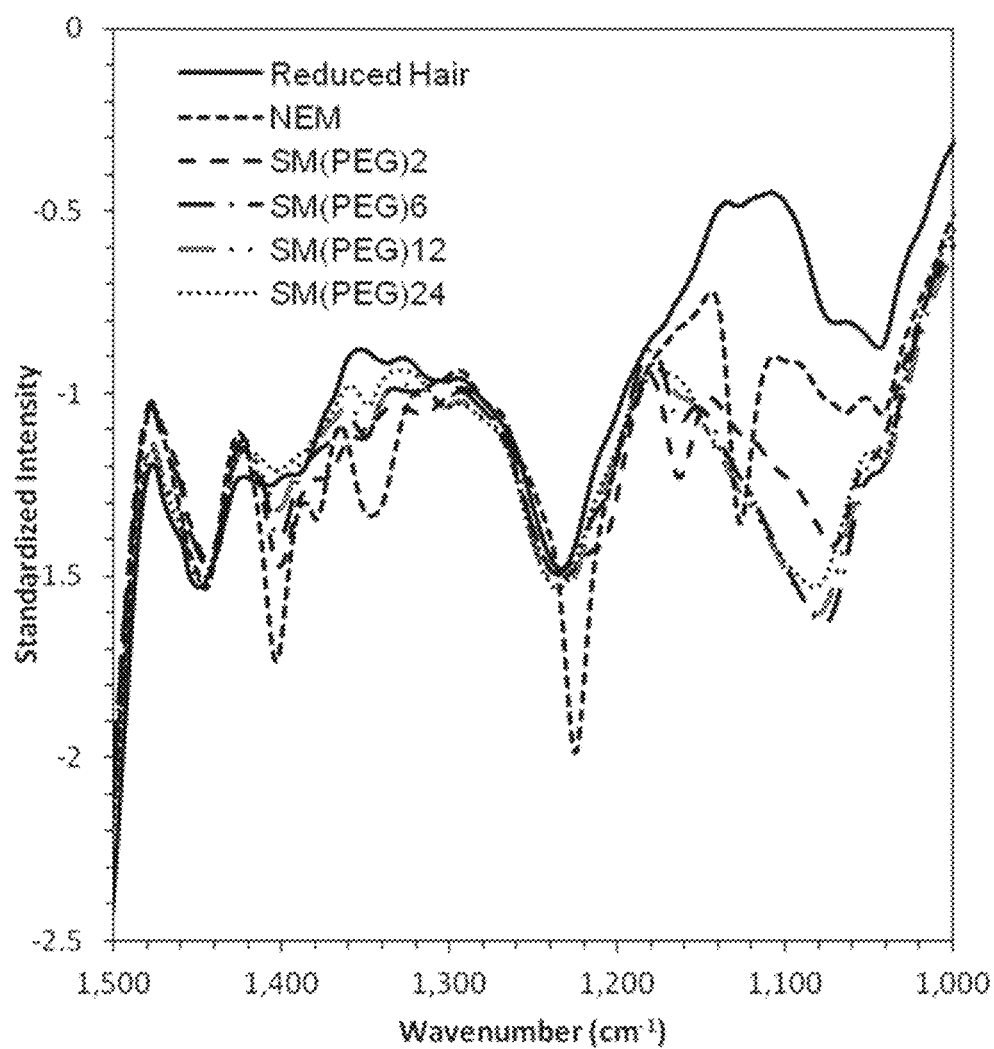
FIG. 20B depicts alkyl peak region of FTIR spectra of hair after grafting with exemplary maleimide monomers in aqueous solvent systems for 1 h.

To further explore other maleimides, a series of succinimidyl-[(N-maleimidopropionamido)-diethyleneglycol] esters (NHS-PEG$_n$-Maleimides) were acquired, each having the same heterobifunctional structure but differing in the number of discrete ethylene glycol units (n=2, 6, 12, 24). In this case, besides the maleimide group that reacts with thiol groups on hair, the N-hydroxysuccinimide ester (NHS) group can also react with amine groups on hair to further enhance the grafting efficiency. The preliminary screening study showed that all NHS-PEG$_n$-Maleimides were successfully grafted, confirmed by the prominent signature peaks in their FTIR spectra (FIGS. 20A and 20B).

Simultaneous Reduction and Grafting

A "one-step process" of simultaneous reduction and grafting also was developed as a more effective method for covalent attachment of molecules to hair. This method has the benefit of significantly reducing the processing time and reducing overall hair damage. Reducing solutions with ammonium thioglycolate (ATG), L-cysteine, and glutathione were explored as solvent media. Due to regulatory limits on the use of di-n-propylamine (DNPA), a tertiary amine, triethylamine, also was explored as an alternative catalyst. Hexyl acrylate was used as a model monomer, yet simultaneous grafting was also demonstrated using other acrylated monomers. Important parameters such as monomer-to-thiol ratio, choice of reducing media, reducing agent concentration, and catalyst concentrations were varied.

Preferred Grafting Parameters

Grafting parameters specific to simultaneous grafting included five different parameters. The liquor ratio for all studies was set at 5:1 as it resulted in the highest grafting efficiency based on the two-step grafting. Table 12 showed preferred parameters for grafting with hexyl acrylate in the presence of a tertiary amine catalyst.

TABLE 12

Preferred simultaneous grafting parameters for hexyl acrylate grafting with the tertiary amine catalyst, trimethylamine

| Parameter | Range Investigated | Preferred Conditions |
|---|---|---|
| Liquor Ratio | 5:1 | 5:1 |
| Monomer-to-Thiol Ratio | 1:1 to 10:1 | 1:1 to 10:1 |
| Catalyst Concentration (with respect to monomer) | 10 mol %-100 mol % | 10 mol %-30 mol % |
| Reaction Time | 15 min to 3 h | 15 min to 1 h |
| Reducing Solution | ATG, L-cysteine, glutathione | ATG or L-cysteine at 2.5 wt % to 3.5 wt % wrt total solution |

Table 13 showed preferred parameters for simultaneous reduction and grafting of monomers to hair thiols for exemplary embodiments.

TABLE 13

Preferred grafting parameters for simultaneous reduction and grafting of exemplary monomers with a catalyst.

| Component | Reagents Investigated | Preferred Reagents | Preferred Conditions |
|---|---|---|---|
| Monomer | Acrylates | Hexyl acrylate Dodecyl acrylate | 2 wt %-30 wt % |
| Catalyst | Amines | Triethylamine | 0.1 wt %-5 wt % |
| Solvent System | H$_2$O | H$_2$O | 100% H$_2$O |
| Reducing Agent | ATG, L-cysteine, and glutathione | ATG and L-cysteine | 5 wt % |

Reducing Agent Type

Figure 21:
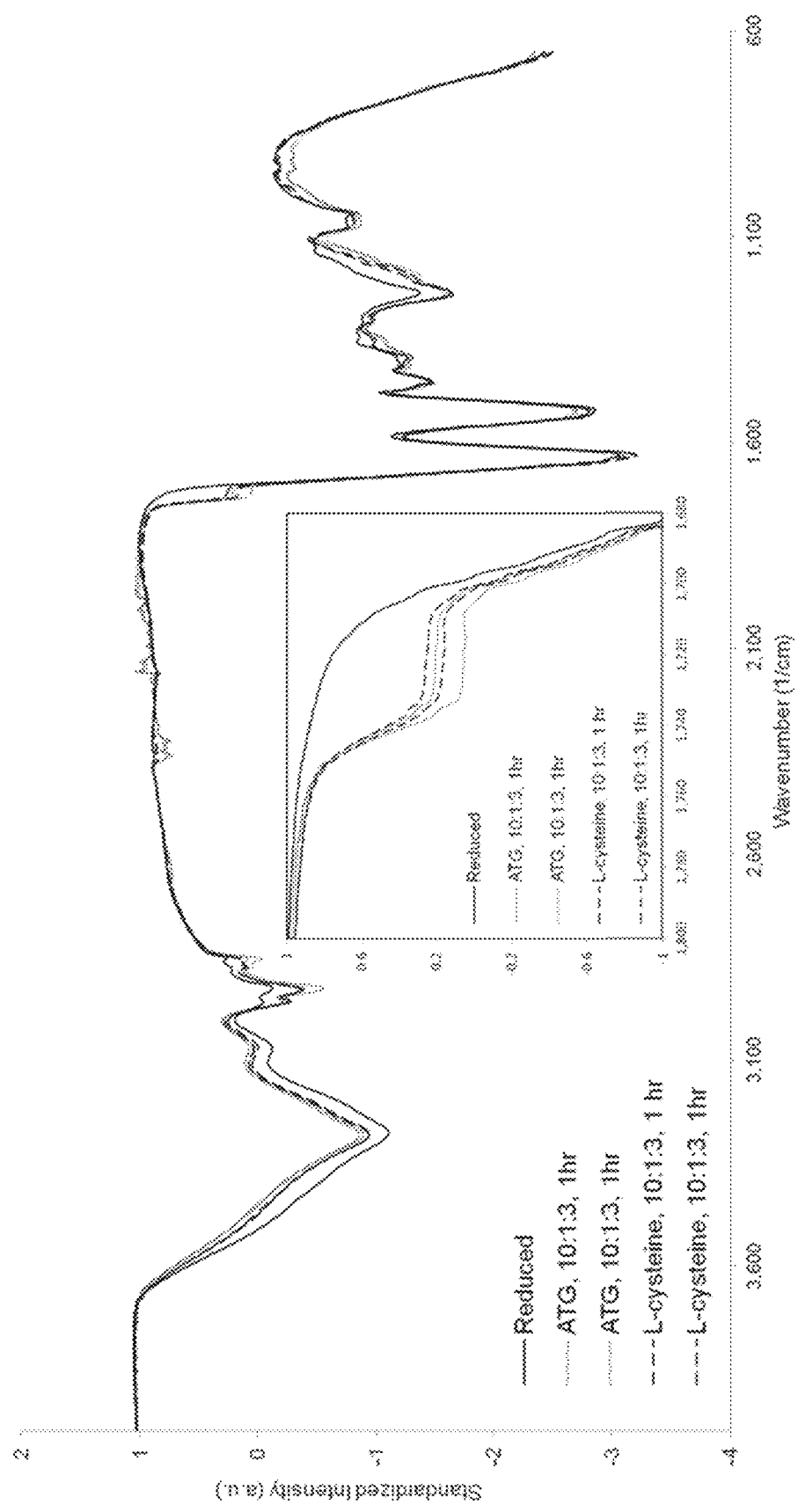
FIG. 21 depicts FTIR spectra of hair after simultaneous grafting with an exemplary acrylate monomer with an amine and a reducing agent for 1 h.

The most important difference between two-step grafting and one-step simultaneous grafting is the use of reducing agent solution as a solvent system for grafting. Previously, in a two-step reduction grafting disclosed herein, either water, organic solvents, or mixtures of thereof were used as solvent systems. The stock reducing agent solutions for simultaneous grafting were prepared in water at 5 wt % concentration. Three different reducing agents were explored in this study: ammonium thioglycolate (ATG), L-cysteine, and glutathione. Previous results from the two-step grafting process using amine catalyst of di-n-propylamine showed that the preferred monomer-to-thiol ratio was 10:1 with 30 mol % of catalyst with respect to monomer. Hence, all experiments here were carried out at the same conditions. FIG. 21 shows that the one-step process of simultaneous reduction and grafting in the presence of either ATG or L-cysteine at 3.5 wt % concentration with respect to the total mixture resulted in similar grafting after 1 h of reaction where strong prominent carbonyl peaks around 1730 cm$^{-1}$ were observed for both conditions. These peaks indicated substantial grafting efficiency for both solutions. All spectra shown are of hair tresses after thorough SLES washing.

Reducing Agent Concentration

Figure 22:
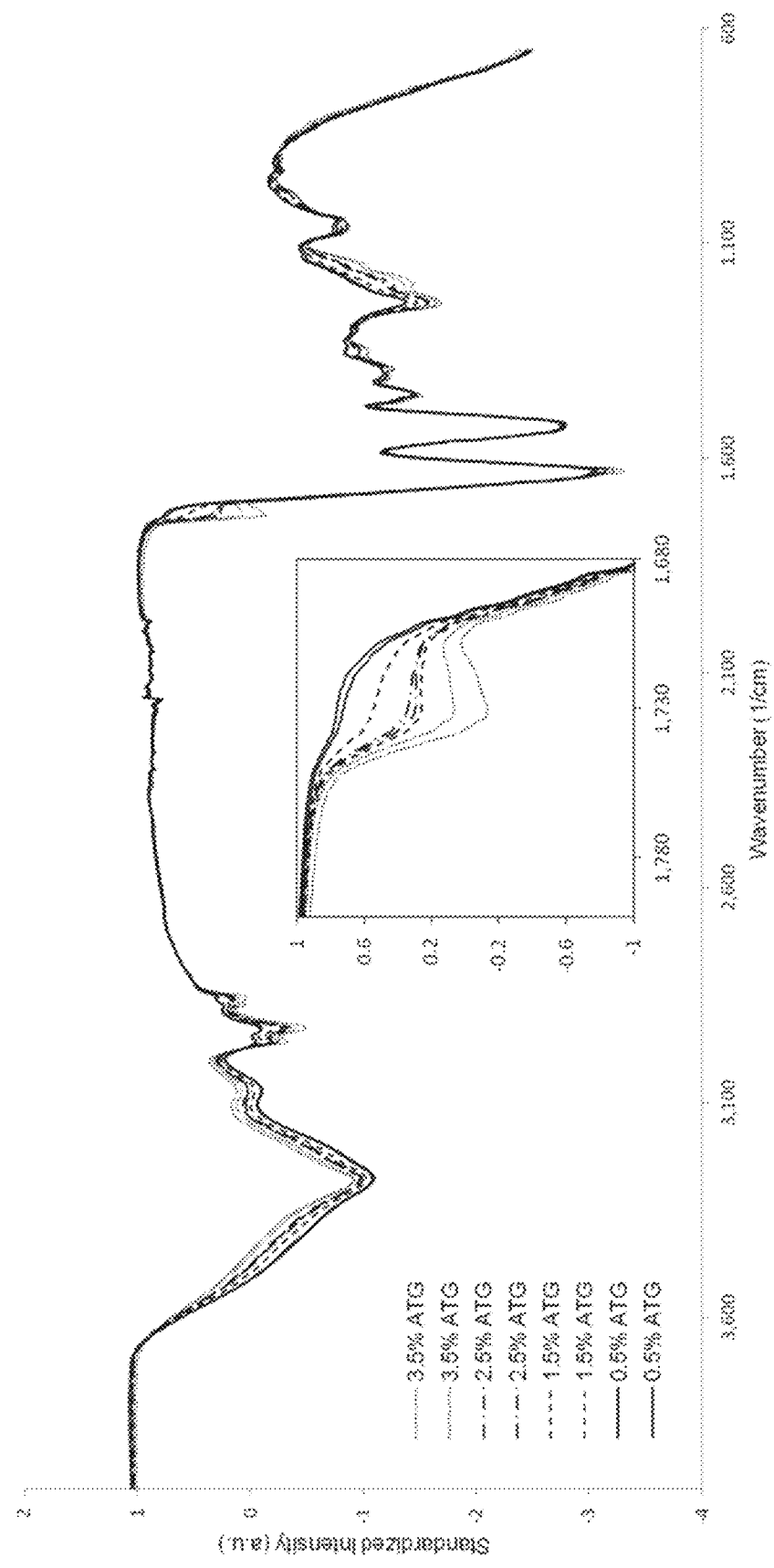
FIG. 22 depicts FTIR spectra of hair after simultaneous grafting with an exemplary acrylate monomer with an amine and various concentrations of a reducing agent for 1 h.

A wide range of concentrations between 0.5 wt % and 3.5 wt % of reducing agent, ATG, was explored. In the study, the monomer-to-thiol ratio was kept at 10:1 and catalyst concentration was kept at 30 mol % of DNPA with respect to monomer. A clear positive dose response was observed with increasing concentration of ATG indicating higher grafting efficiency (FIG. 22). All spectra shown are of hair tresses after thorough SLES washing. While 3.5 wt % of ATG resulted in the strongest carbonyl peaks around 1730 cm$^{-1}$, prominent peaks were also observed when 1.5 wt % and 2.5 wt % ATG concentrations were used. This indicated that lower preferred ATG concentrations might be used to mitigate the overall hair damage.

Monomer-To-Thiol Ratio

Figure 23A:
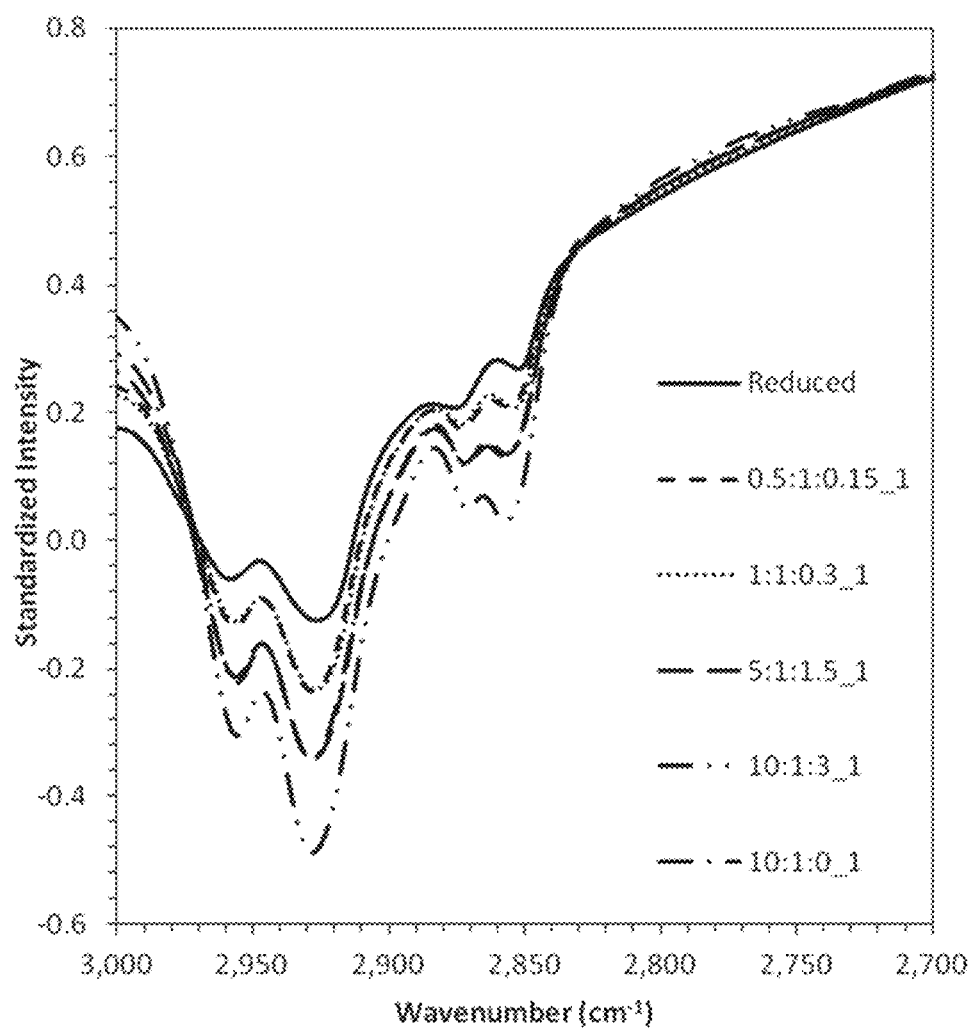
FIG. 23A depicts alkyl peak region of FTIR spectra after grafting with an exemplary acrylate monomer at various monomer-to-thiol ratios for 30 min.
Figure 23B:
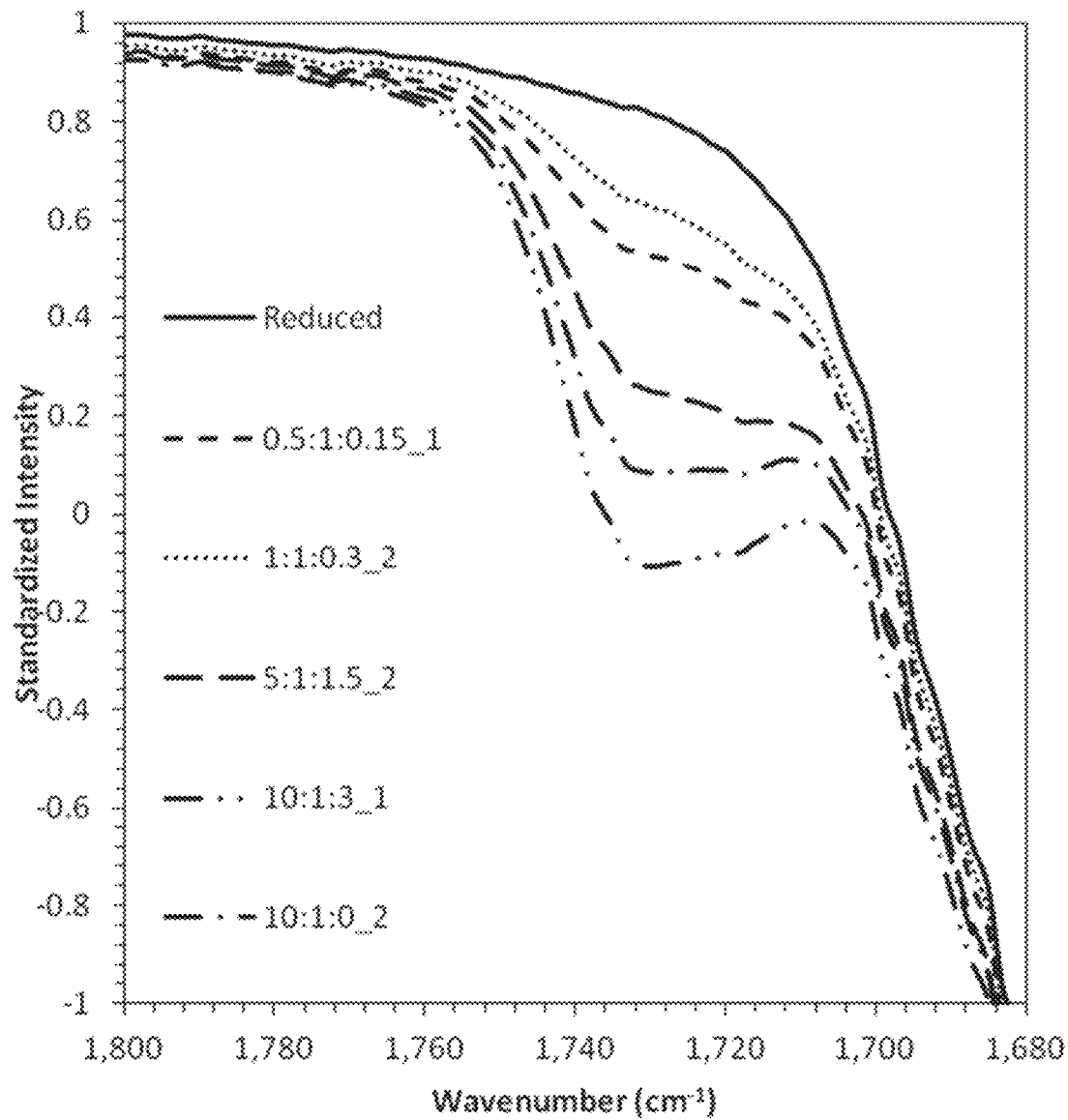
FIG. 23B depicts carbonyl peak region of FTIR spectra of hair after grafting with an exemplary acrylate monomer at various monomer-to-thiol ratios for 30 min.

As 10:1 monomer-to-thiol ratio was found to result in high grafting efficiency, a range of ratios from 0.5:1 to 10:1 was explored where catalyst concentration was kept at 30 mol % with respect to monomer. FIGS. 23A and 23B show a clear positive dose response with increased in monomer-to-thiol ratio obtained after 30 minutes of simultaneous grafting.

Choice of Catalyst

Secondary amine catalyst, di-n-propylamine (DNPA), was previously identified as a lead catalyst in a two-step reduction and grafting process. It was also demonstrated that DNPA could be used in a one-step simultaneous reduction and grafting process, which resulted in high grafting efficiency. However, due to the regulatory and safety constraints of using DNPA catalyst in personal care, a tertiary amine of triethylamine (TEA) was explored. TEA was added at 30 mol % with respect to monomer and monomer-to-thiol ratio was kept at 10:1.

Figure 24:
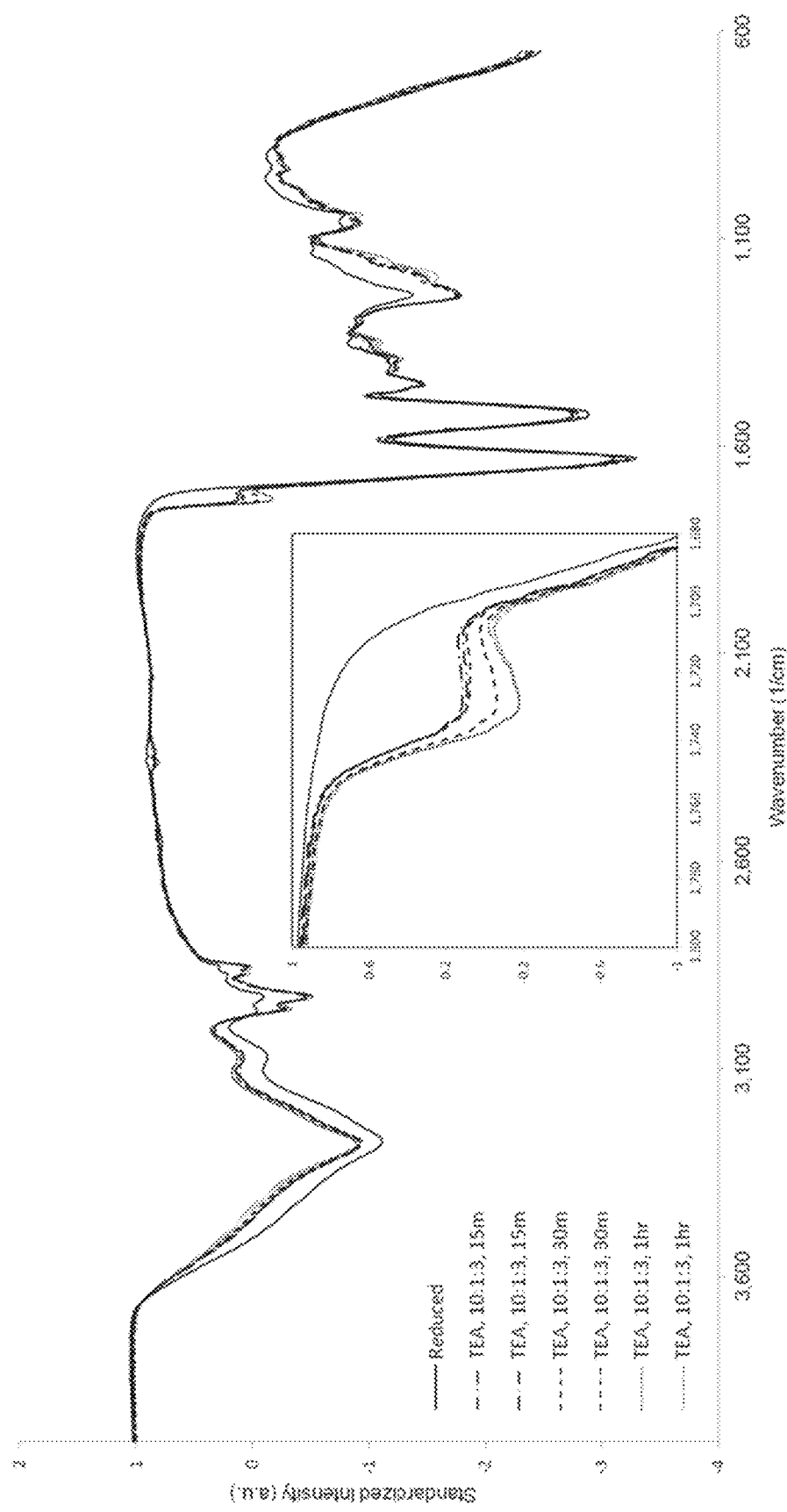
FIG. 24 depicts FTIR spectra of hair after simultaneous grafting with an exemplary acrylate monomer with an amine and a reducing agent for various reaction times.

FTIR spectra of hair tresses after 15 min, 30 min, and 1 h of simultaneous grafting with hexyl acrylate where TEA was used as a catalyst and ATG reducing solution as a solvent media. All spectra shown are of hair tresses after thorough SLES washing. Strong carbonyl peak intensities around 1730 cm$^{-1}$ were observed after just 15 minutes of simultaneous grafting. The reaction seemed to further progress with time and showed stronger peak intensities after 1 h (FIG. 24). Such a short time frame of 15 minutes for simultaneous reduction and grafting as opposed to conventional chemistry (2-step process: 15 minutes of reduction and up to 1 hr of grafting), would be an advantage with the grafting process. Moreover, the time frame for such grafting could be optimized based on the reaction kinetics observed here to achieve desired level of grafting.

Figure 25:
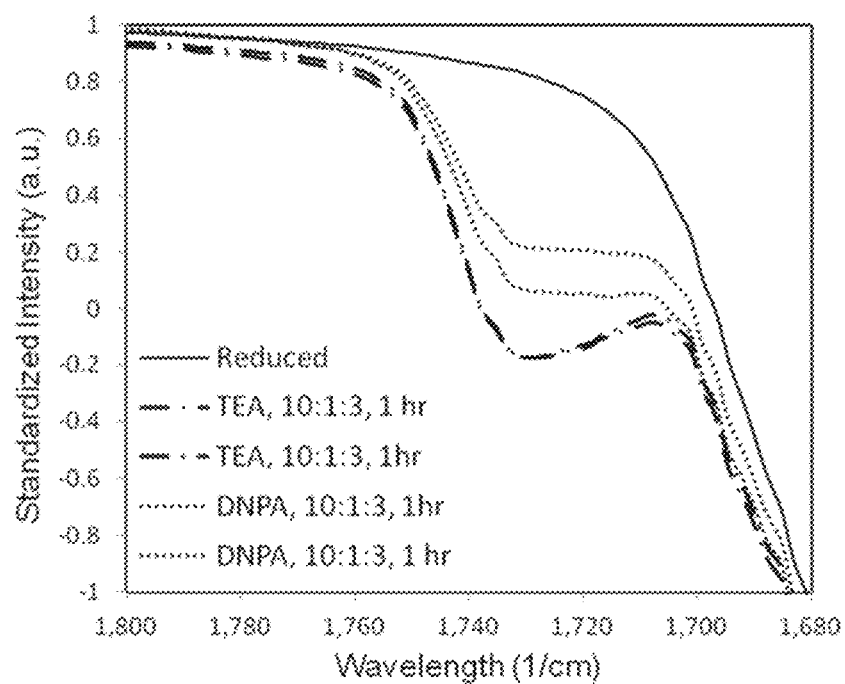
FIG. 25 depicts carbonyl peak region of FTIR spectra of hair after a two-step grafting process with an exemplary acrylate monomer with either a secondary amine or a tertiary amine and a reducing agent.

The efficiency achieved using tertiary amine as a catalyst was unexpected as from literature it is known that tertiary amines correlate to slower reaction rates than secondary amines. As can be seen in FIG. 25, much higher grafting efficiency was achieved with TEA initiated reaction in simultaneous grafting (FIG. 25). Without being bound by any theory, it is hypothesized that unique basic conditions under which simultaneous grafting occurs facilitates a base-catalyzed reaction pathway in the presence of triethylamine.

Catalyst Concentration

The grafting efficiency was further evaluated based on the varying concentrations of triethylamine. Due to the regulatory constraints on the use of hexyl acrylate as a monomer in personal care, it is of interest to minimize the monomer-to-thiol ratio. Hence, a systematic study with varying concentrations of TEA from 10 mol % to 100 mol % was performed where monomer-to-thiol ratio was lowered to 1:1.

Figure 26A:
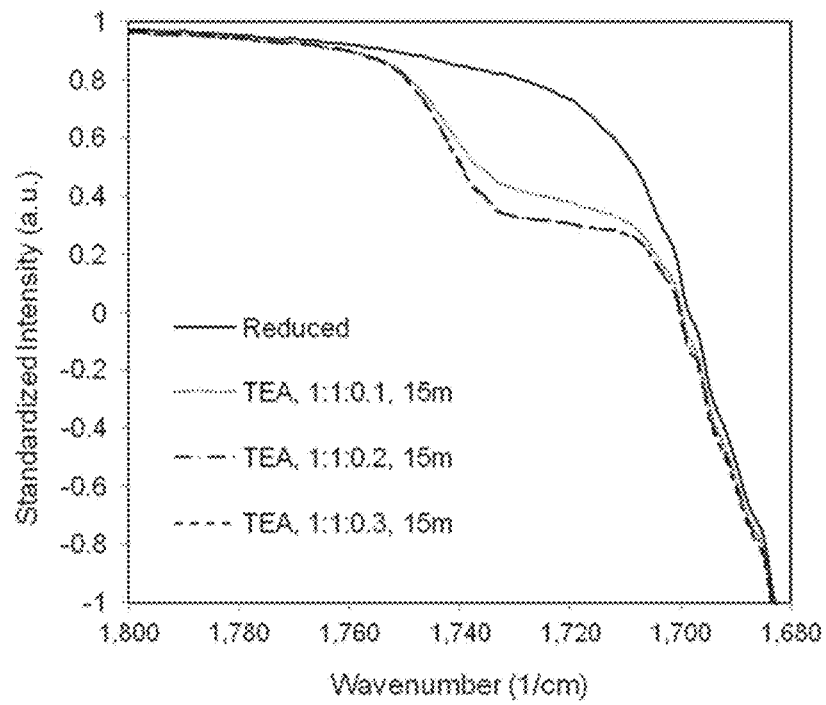
FIG. 26A depicts carbonyl peak region of FTIR spectra of hair after simultaneous grafting with an exemplary acrylate monomer with varying concentrations of a tertiary amine and a reducing agent for 15 min.
Figure 26B:
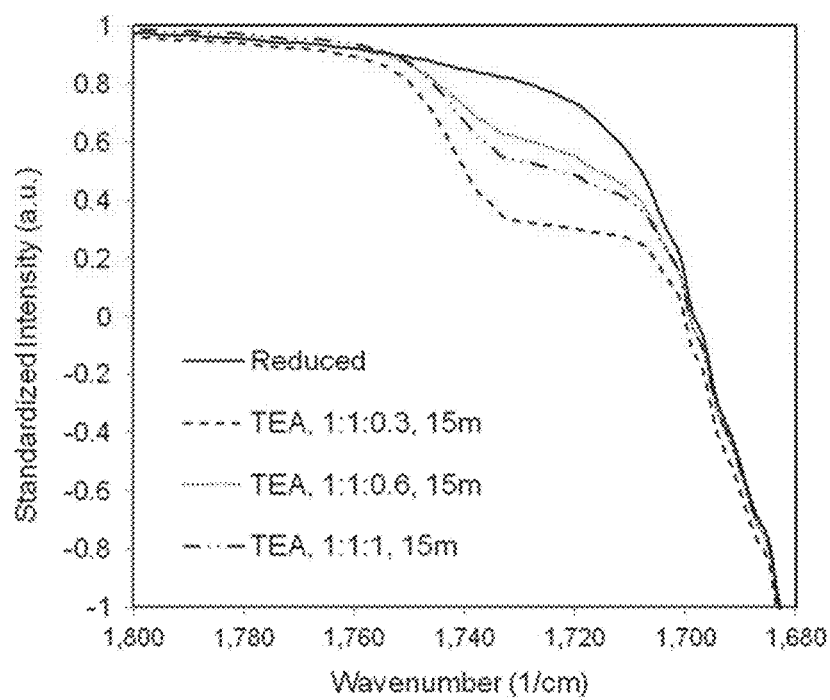
FIG. 26B depicts carbonyl peak region of FTIR spectra of hair after simultaneous grafting with an exemplary acrylate monomer with higher concentrations of a tertiary amine and a reducing agent for 15 min.
Figure 26C:
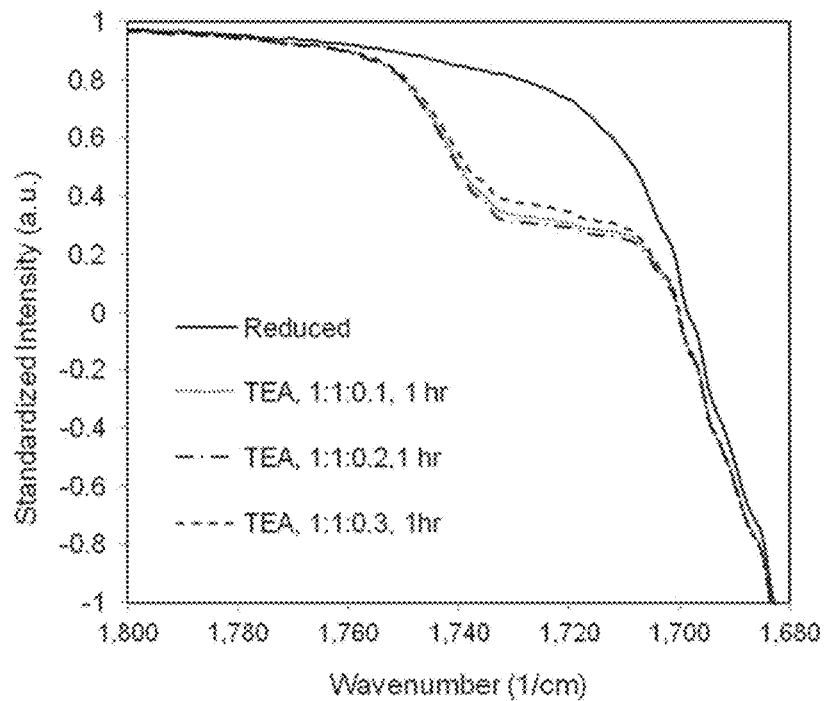
FIG. 26C depicts carbonyl peak region of FTIR spectra of hair after simultaneous grafting with an exemplary acrylate monomer with varying concentrations of a tertiary amine and a reducing agent for 1 h.
Figure 26D:
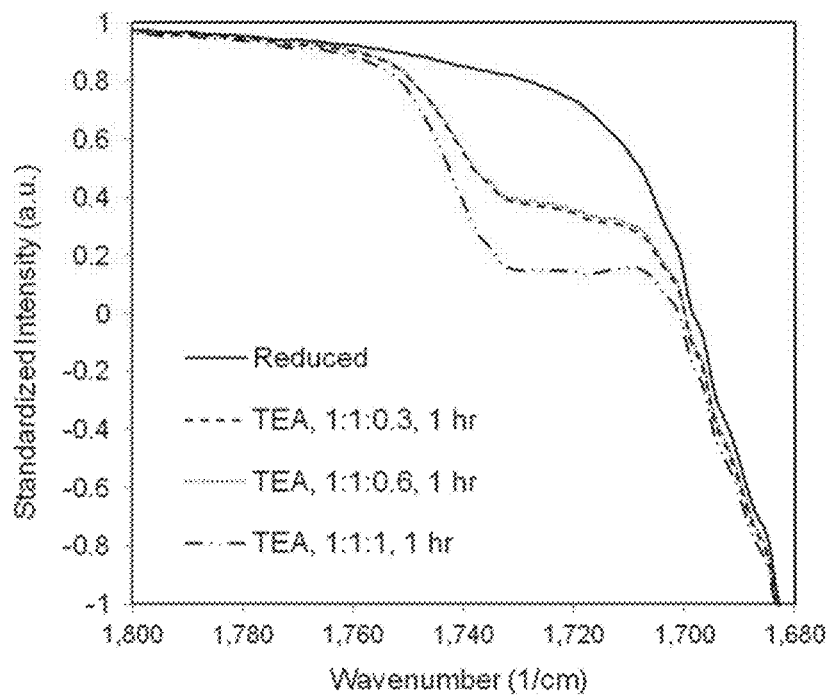
FIG. 26D depicts carbonyl peak region of FTIR spectra of hair after simultaneous grafting with an exemplary acrylate monomer with higher concentrations of a tertiary amine and a reducing agent for 1 h.

At TEA concentrations of 10 mol %, 20 mol %, and 30 mol % after 15 minutes of simultaneous grafting similar carbonyl peak intensities were observed (FIG. 26A), and reactions did not progress with time (FIG. 26B). However, as TEA concentration increased to 60 mol % and 100 mol %, the grafting efficiency was lower after 15 minutes (FIG. 26C), but reactions progressed after 1 h resulting in strong peak intensities (FIG. 26D). Without being bound by any theory, it is hypothesized that at high catalyst concentrations, the reaction is diffusion limited, and, hence, progresses slowly while reaching high grafting efficiency after 1 h.

Grafting on Damaged Hair

A main goal of grafting process was to restore a healthy layer on the hair surface, specifically targeting hair that was severely damaged by bleaching and heat treatments. This hydrophobic layer mimics the 18-MEA layer of healthy hair. For example, as a result of chemical bleaching, disulfide bonds of cysteine residues in hair undergo oxidation to form cysteic acid groups. Since disulfide bonds provide mechanical linkages within proteins hair is composed of, degradation of disulfide bonds could lead to degradation of hair proteins and hair damage. In addition, during the bleaching process the thioester bonds binding 18-methyl eicosanoic acid to hair may be attacked by the alkaline bleaching reagents resulting in partial removal of this hydrophobic layer rendering hair hydrophilic. See, e.g., Finlay, A. Y.; Frost, P.; Keith, A. D.; Snipes, W. Br. J. Dermatol. 1980, 103, 357-365. Another common way to damage hair is through continuous heat treatments, such as straightening and curling at high temperatures. It is known that in the temperature range commonly used in such hair styling treatments, up to 230° C. (450° F.), keratinious structures of hair start to denature, especially above 200° C. and in the presence of water. See, e.g., Evans, T.; Wickett, R. R. Practical Modern Hair Science. 2012.

Grafting on Hair Damaged by Bleaching

Based on the encouraging results of grafting on virgin (non-damaged) hair via simultaneous grafting, simultaneous grafting on bleached hair was explored. Experiments were performed at 10:1 monomer-to-thiol ratio with 30 mol % of TEA catalyst with respect to the monomer, and in both L-cysteine and ATG reducing solutions at 3.5 wt % concentrations.

Figure 27A:
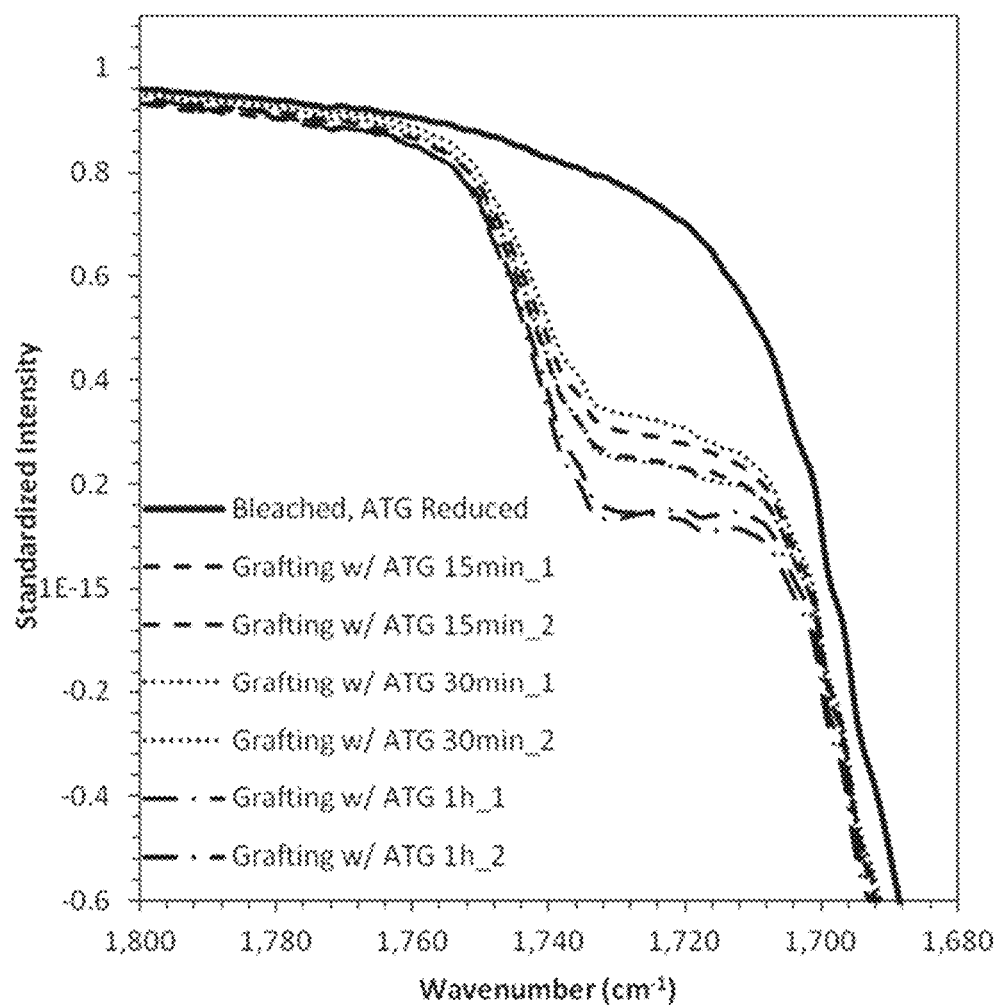
FIG. 27A depicts carbonyl peak region of FTIR spectra of hair after simultaneous grafting on bleached hair with an exemplary acrylate monomer with an exemplary reducing agent for various reaction times.
Figure 27B:
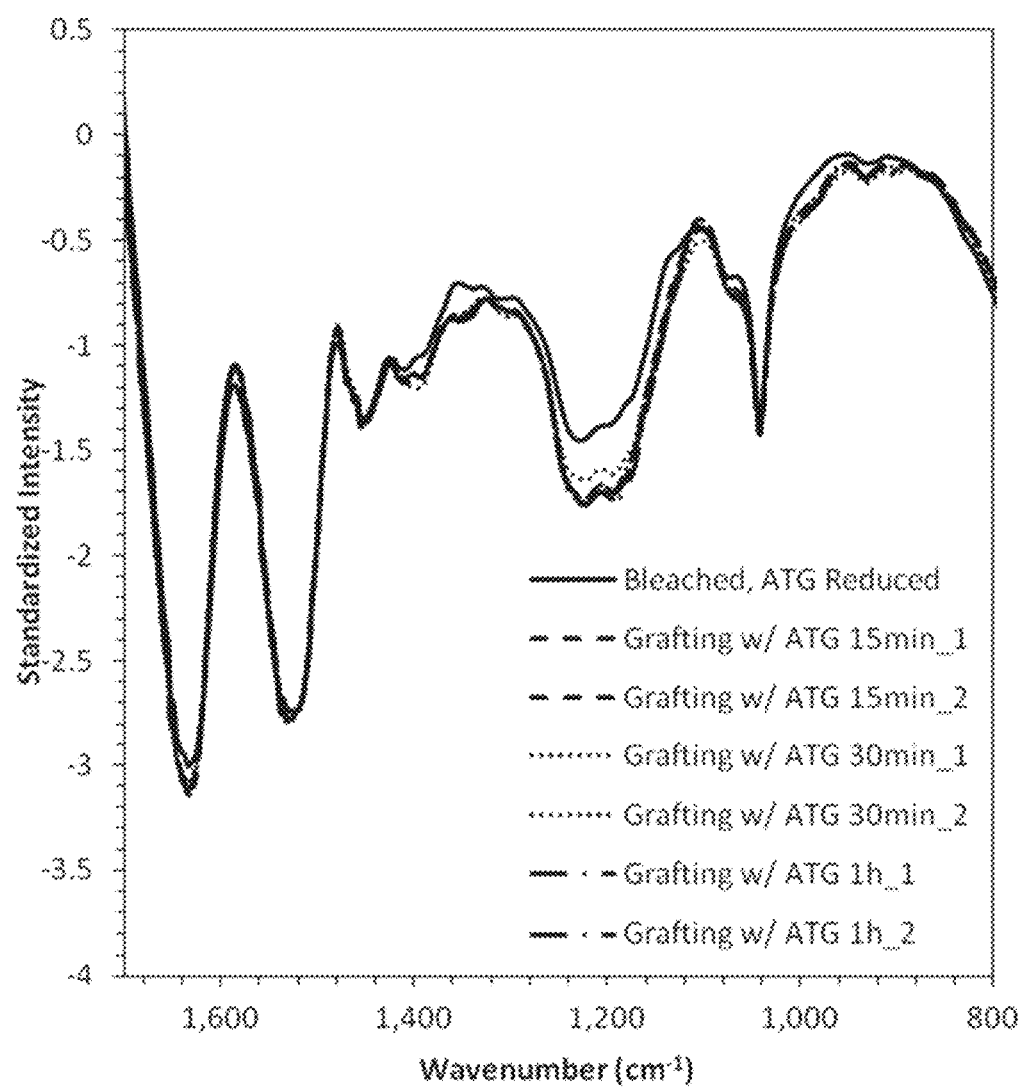
FIG. 27B depicts alkyl peak region of FTIR spectra of hair after simultaneous grafting on bleached hair with an exemplary acrylate monomer with an exemplary reducing agent for various reaction times.

Substantial grafting was achieved on bleached hair in simultaneous grafting conditions in ATG reducing media after only 15 minutes (FIG. 27A). The reaction progressed with time showing stronger carbonyl peaks after 30 minutes and 1 h. It should be noted that peaks corresponding to cysteic acid groups appeared as expected after bleaching indicating sulfur oxidation levels and remained after grafting (FIG. 27B). It seems that while some disulfide bonds converted to cysteic acid groups after bleaching, the remaining disulfide bonds were utilized in simultaneous reduction and grafting.

Figure 28A:
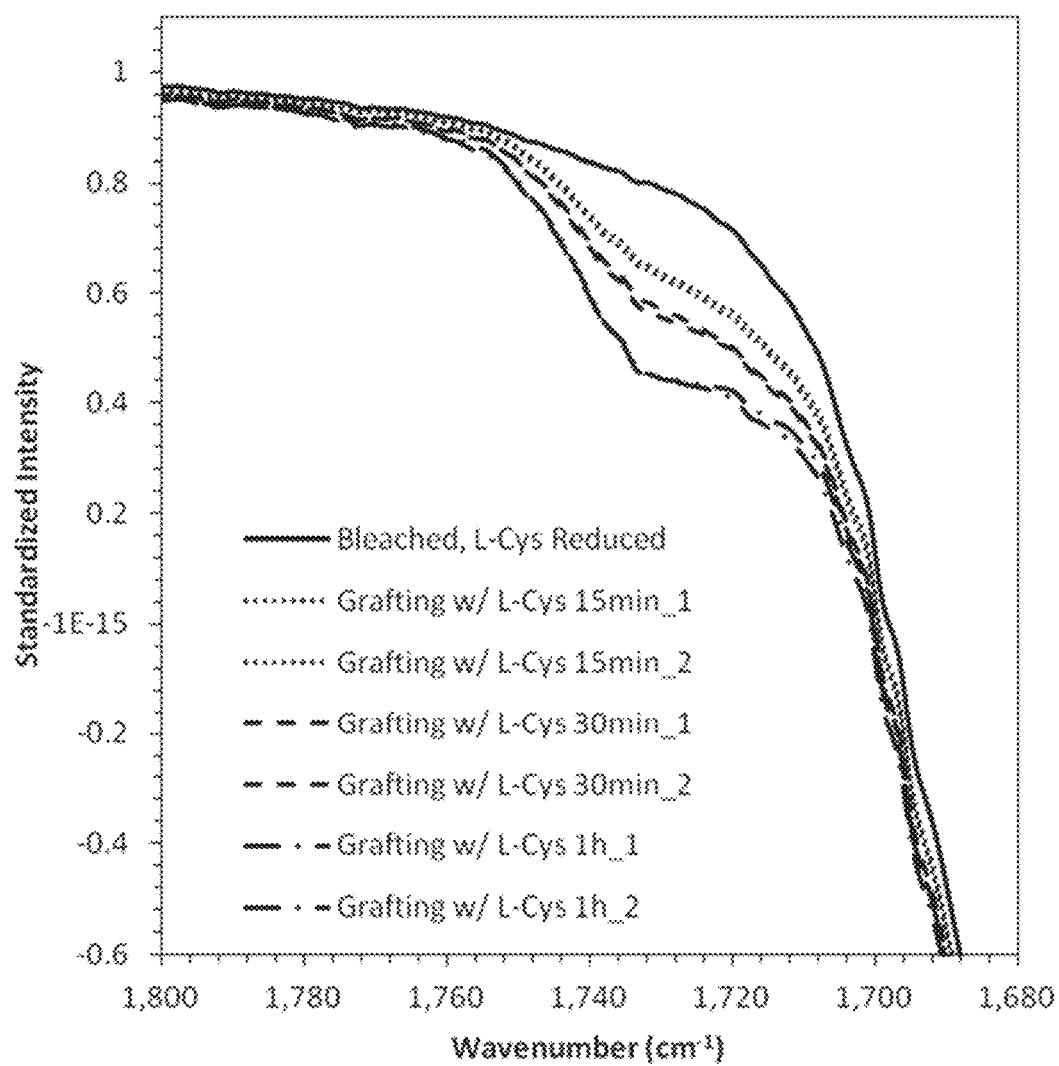
FIG. 28A depicts carbonyl peak region of FTIR spectra of hair after simultaneous grafting on bleached hair with an exemplary acrylate monomer with an exemplary reducing agent for various reaction times.
Figure 28B:
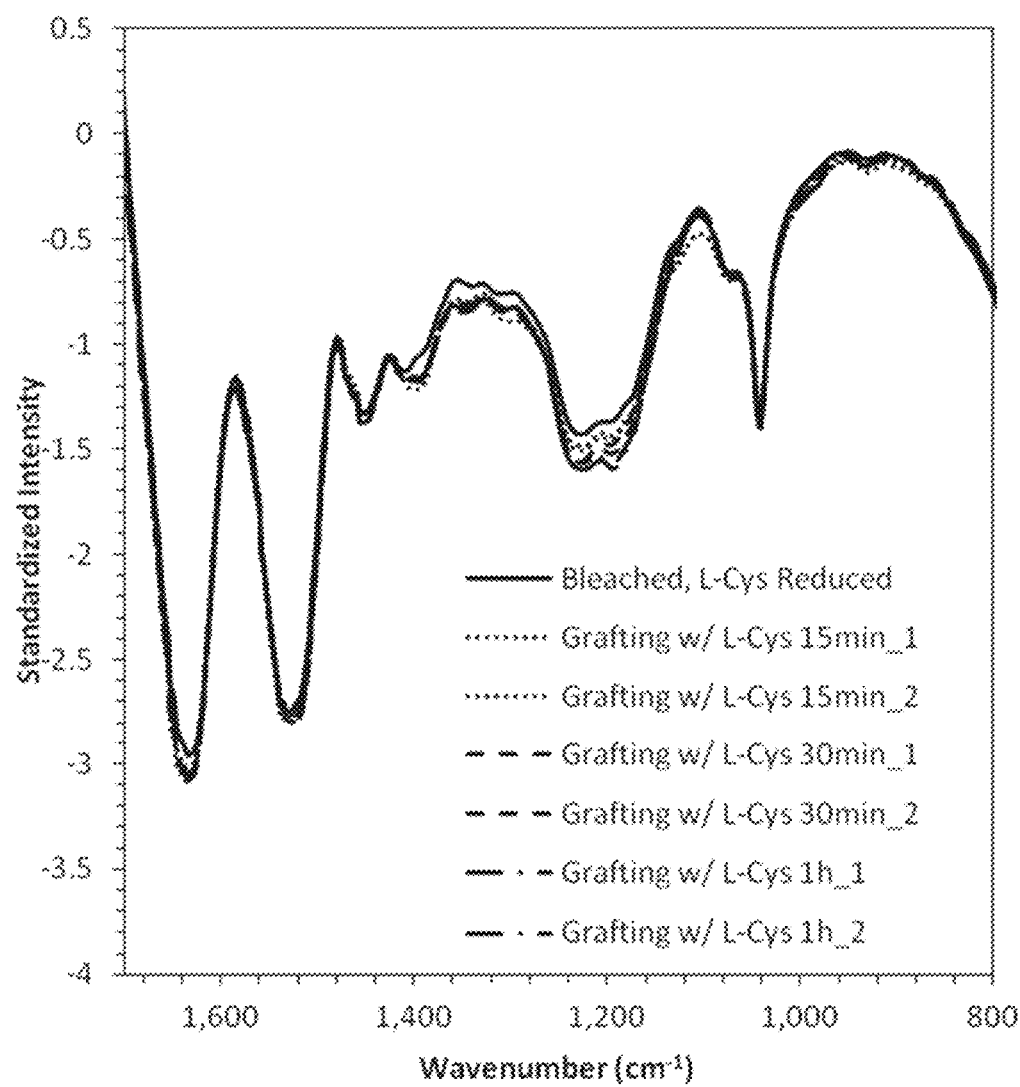
FIG. 28B depicts alkyl peak region of FTIR spectra of hair after simultaneous grafting on bleached hair with an exemplary acrylate monomer with an exemplary reducing agent for various reaction times.

Slightly lower grafting efficiencies were observed when L-cysteine reducing solution was used, yet a clear reaction progression with time was observed after 15 min, 30 min, and 1 h (FIGS. 28A and 28B). Without being bound by any theory, the lower grafting efficiency obtained could be explained by the fact that L-cysteine is a milder reducing agent than ATG and hence results in reduction and grafting on the hair surface only. The data suggested that by utilizing L-cysteine, a mild reducing agent, the hair surface was targeted for grafting reactions and hence minimized damage within the hair cortex. Damage within the hair cortex could occur when strong reducing agents are used.

Grafting on Hair Damaged by Heat

Figure 29:
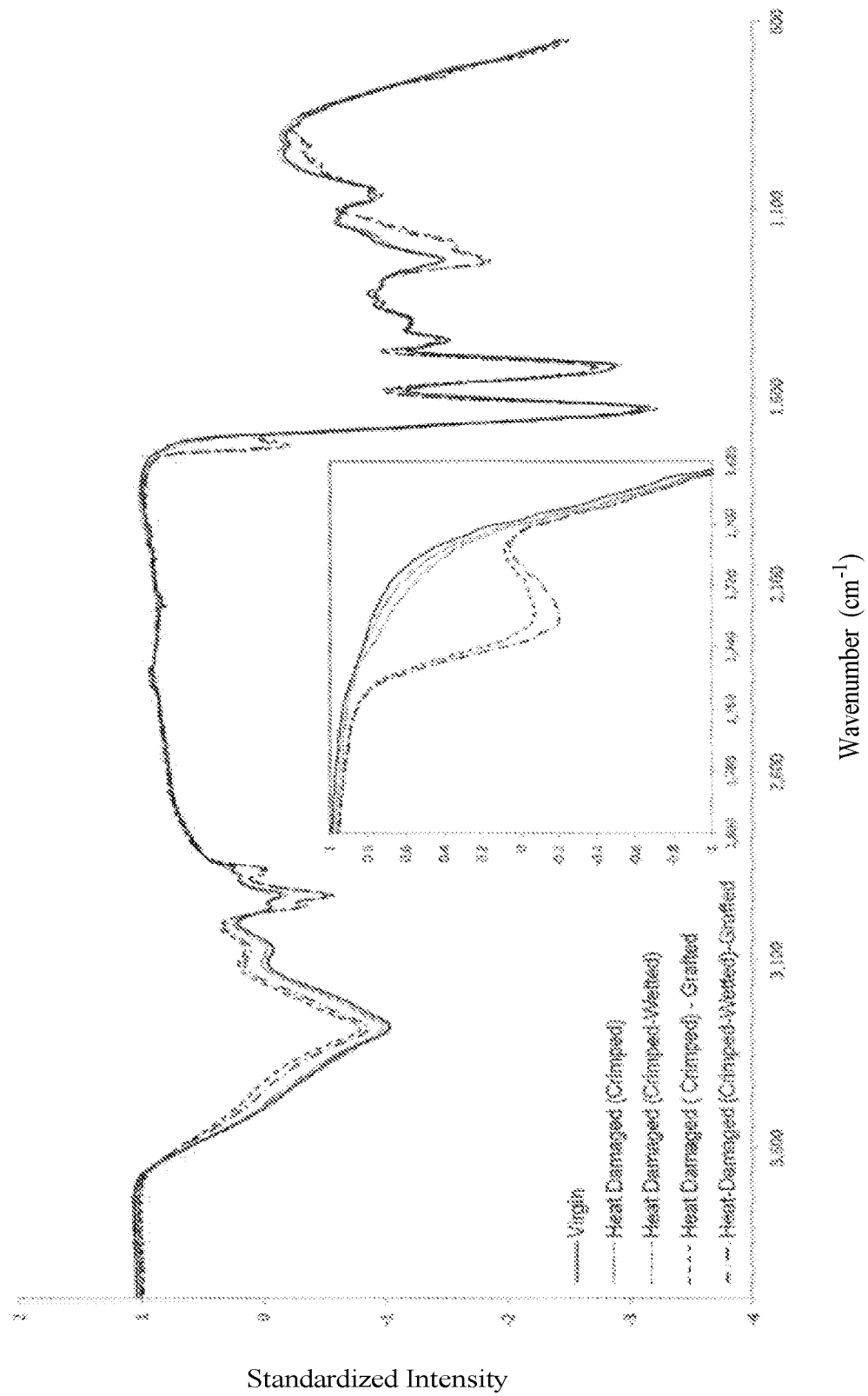
FIG. 29 depicts FTIR spectra of hair after grafting on heat damage hair with an exemplary acrylate monomer.

To mimic hair damage by heat, for example, by using heat tools such as a blow dryer, a curling iron, a flat iron or other heat treatments, brown hair tresses were exposed to 26 applications of a styling iron at 400° F. Additionally, to exaggerate the damage further, some hair tresses were subjected to water spritzing in between heat applications. To study the effects of grafting, hair was then reduced and grafted with hexyl acrylate in water at 10:1 monomer-to-thiol ratio with 30 mol % of DNPA catalyst with respect to monomer. As can be seen in FIG. 29, strong carbonyl peak intensities indicate that grafting was possible using hair severely damaged by heat treatments.

Additional Monomer Screening

Figure 31:
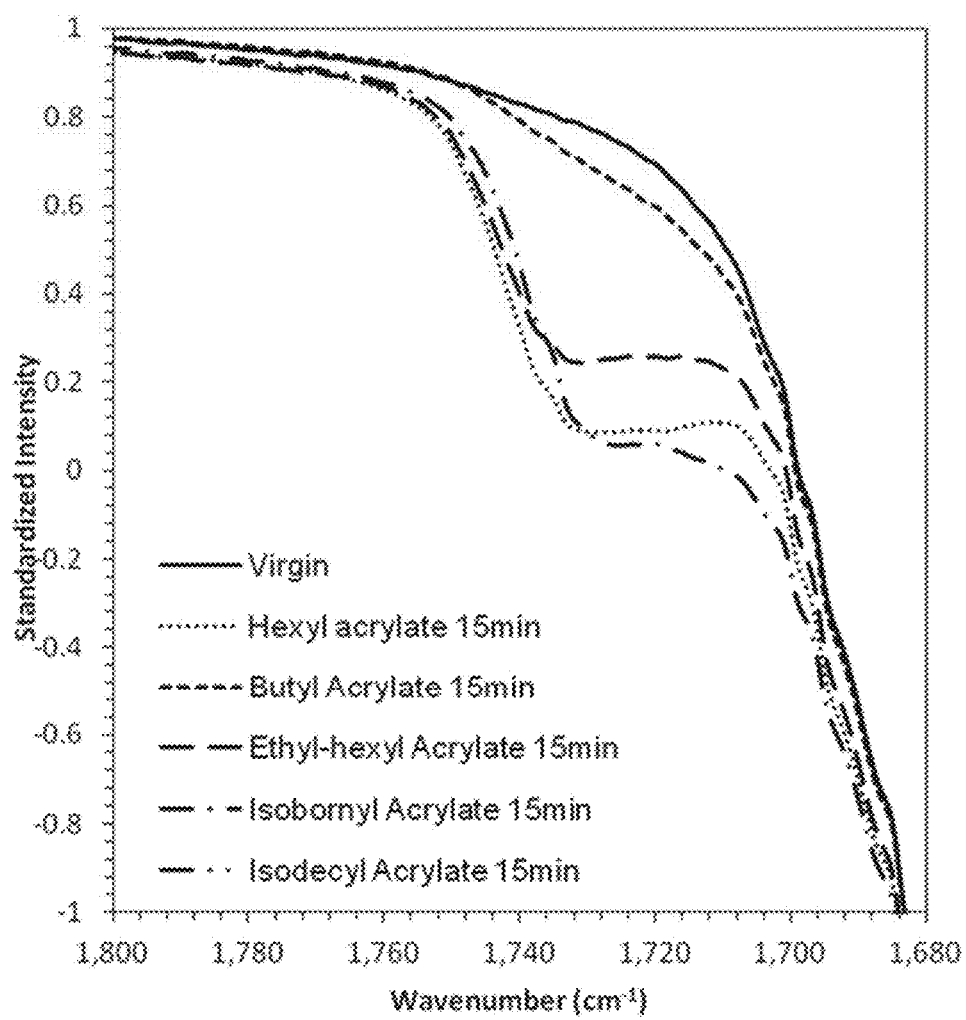
FIG. 31 depicts carbonyl peak region of FTIR spectra of hair after simultaneous grafting with different exemplary acrylate monomers, a tertiary amine, and a reducing agent for 15 min.

Due to regulatory constraints imposed on the use of hexyl acrylate in personal care, other acrylated monomers were explored for simultaneous grafting. As a first round of such monomer screening, eight different acrylated monomers were studied (Table 14, FIG. 30). For all experiments, monomer-to-thiol ratio was kept at 10:1 in the presence of TEA catalyst at 30 mol %, and ATG reducing solution was used. After 15 minutes of reaction, prominent carbonyl peaks around 1730 $cm^{-1}$ were observed indicating grafting (FIG. 31). All spectra shown are of hair tresses after thorough SLES washing. The grafting efficiencies were extensive among the four monomers tested from Table 14.

Semi-Simultaneous Reduction and Grafting

A semi-simultaneous grafting method, where the reducing agent was applied immediately followed by the grafting monomer solution. No wash or rinse was used in between two applications. PEG-diacrylates were used as monomers.

Preferred Grafting Parameters

Since simultaneous grafting studies showed tresses grafted with PEG-diacrylate led to favorable sensory attributes, PEG-diacrylates were selected as monomers for semi-simultaneous grafting studies. Grafting parameters specific to semi-simultaneous grafting included 6 different parameters: liquor ratio, monomer-to-thiol ratio, catalyst concentration, reaction time, reducing agent concentration, and pH. Table 15 showed preferred parameters for semi-simultaneous grafting with a PEG diacrylate with a molecular weight of about 700 g/moL (PEG-DA 700). It is of interest to minimize the use of all chemicals and to carry out grafting under mild conditions, e.g., low reducing agent concentrations, weak alkaline pH, shorter reaction time, etc.

TABLE 15

Preferred semi-simultaneous grafting parameters for PEG-diacrylate grafting.

| Parameter | Range Investigated | Preferred Conditions |
| --- | --- | --- |
| Liquor Ratio | 1:1 to 5:1 | 1.1:1 |
| Monomer-to-Thiol Ratio | 0.1:1 to 2.5:1 | 0.38:1 |
| Catalyst Concentration (with respect to monomer) | 0 mol %-30 mol % | 0 mol % |
| Reaction Time | 15 min to 1 h | 15 min |
| Reducing Solution | ATG or L-cysteine | ATG at 2.5 wt % wrt total solution |
| pH | 7.0-9.5 | 8.5 |

Liquor Ratio

Figure 32A:
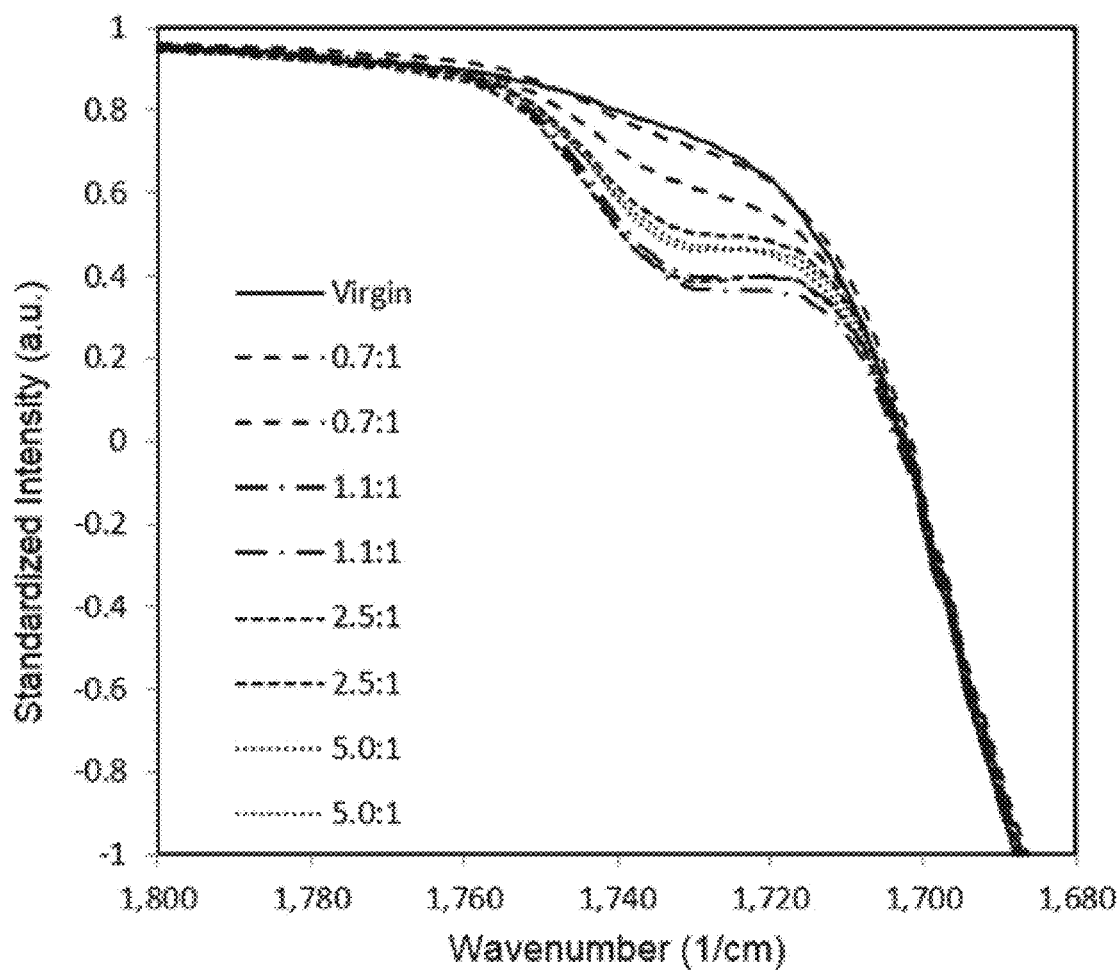
FIG. 32A depicts carbonyl peak region of FTIR spectra of virgin hair after semi-simultaneous grafting with an exemplary PEG-diacrylate monomer at various ratios by weight of the mixture to the hair sample.
Figure 32B:
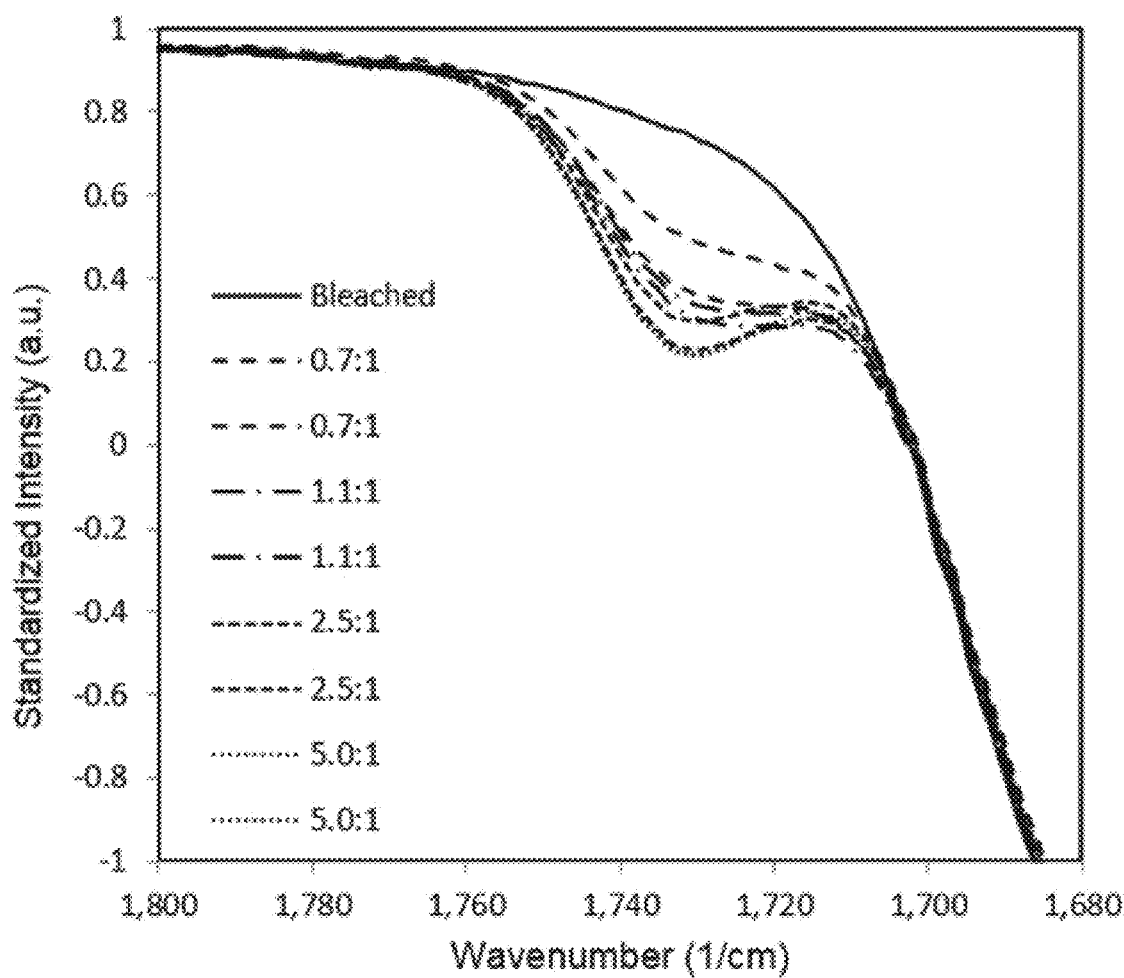
FIG. 32B depicts carbonyl peak region of FTIR spectra of bleached hair after semi-simultaneous grafting with an exemplary PEG-diacrylate monomer at various ratios by weight of the mixture to the hair sample.

To reduce the use of chemicals, grafting at lower liquor ratios was also explored. The liquor ratio is the ratio by weight of the mixture to the hair sample. FTIR spectra of virgin (FIG. 32A) or bleached (FIG. 32B) hair tresses grafted with PEG-DA 700 at liquor ratios varying from 0.7:1 to 5:1 are shown. In both systems, very similar grafting was achieved when a liquor ratio of 1.1:1 or above was used; only at the liquor ratio of 0.7:1 more heterogeneous grafting was observed. Blinded sensory evaluation showed that hair tresses grafted at any liquor ratio between 0.7:1 and 2.5:1 showed similar sensory properties with all ratios demonstrating desired sensory properties. Based on both FTIR and sensory evaluation results, a ratio of 1.1:1 was then selected as a preferred liquor ratio to achieve high grafting efficiency as well as the desired sensory properties.

Catalyst Concentration

Figure 33:
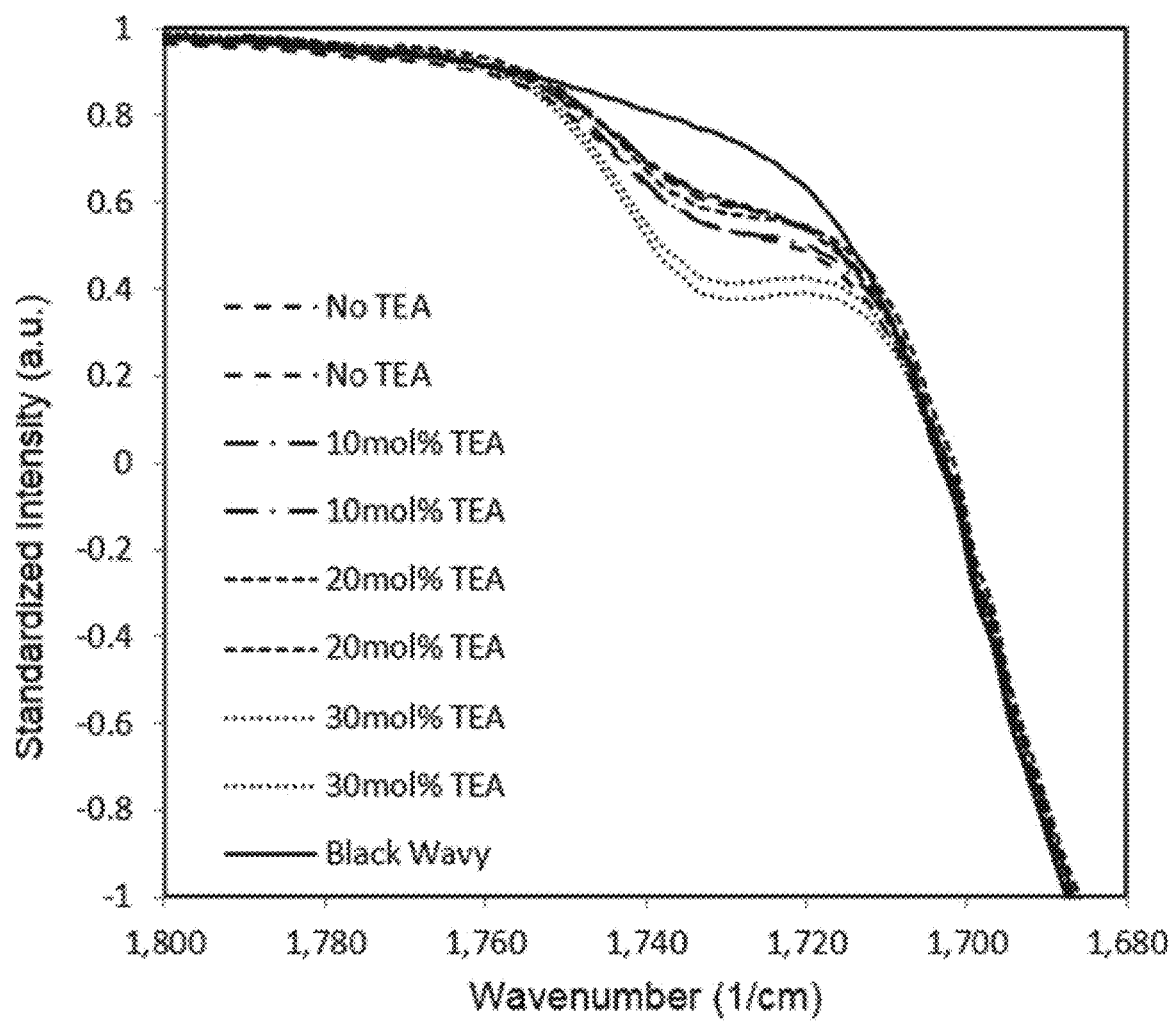
FIG. 33 depicts carbonyl peak region of FTIR spectra of hair after semi-simultaneous grafting with an exemplary PEG-diacrylate monomer with various concentrations of a catalyst.

Due to the regulatory and safety constraints of using triethylamine (TEA) catalyst in personal care, it is of interest to minimize the TEA concentration. FIG. 33 shows FTIR spectra of hair tresses grafted with PEG-DA 700 in the presence of 0-30 mol % of TEA (wrt PEG-DA 700 concentration). Although maximal grafting was achieved at 30 mol % TEA, significant grafting was observed at all TEA concentrations and no noticeable difference was observed between no TEA and lower TEA concentrations (10-20 mol %). Blinded sensory evaluation also showed that the feel of hair tresses was more favorable when no TEA was used. More specifically, hair felt smoother, softer, and more conditioned when no TEA was used. Based on both FTIR and sensory evaluations results, all later grafting experiments were performed without any TEA catalyst.

Reducing Agent Concentration

Figure 34:
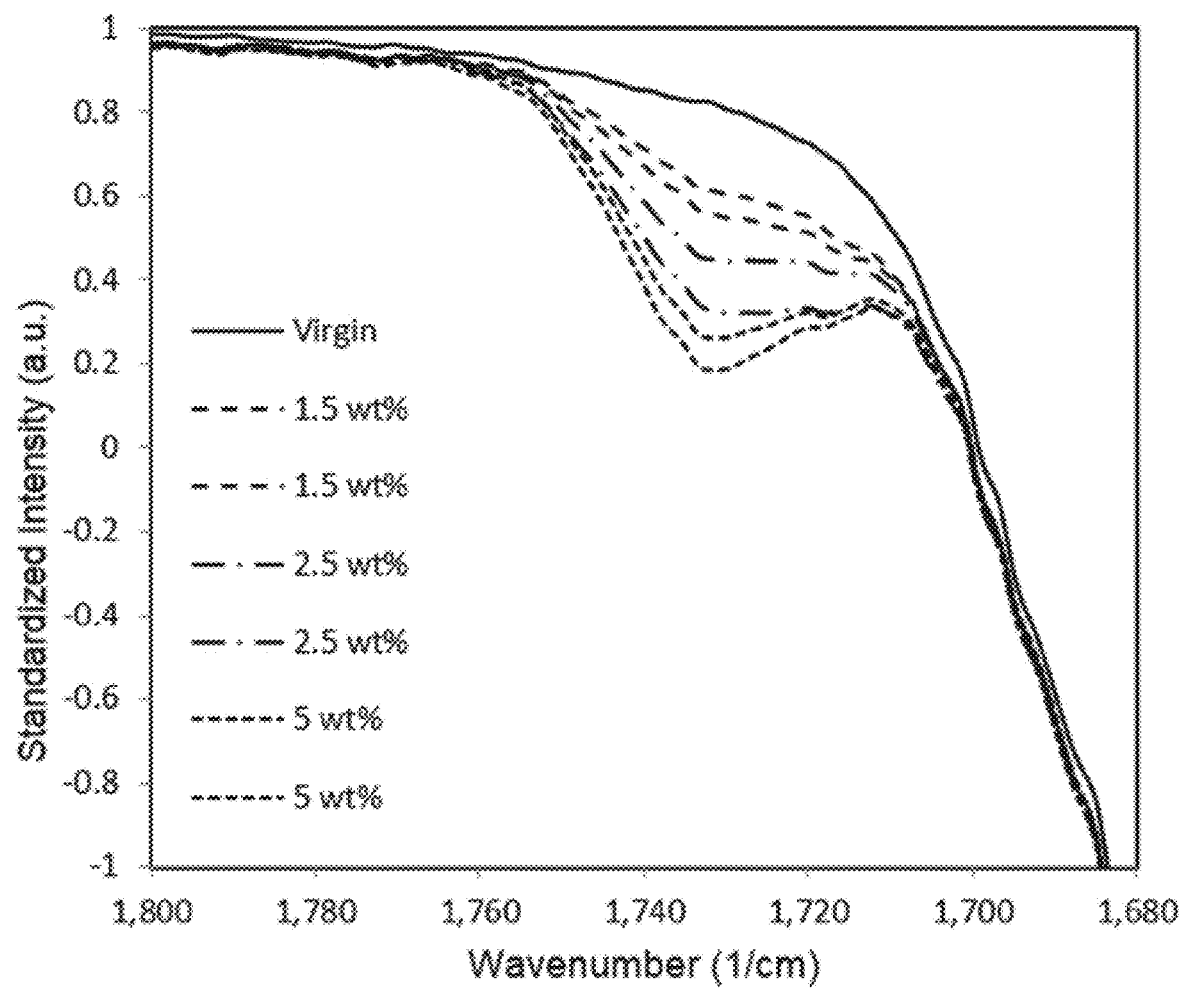
FIG. 34 depicts carbonyl peak region of FTIR spectra of hair after semi-simultaneous grafting with an exemplary PEG-diacrylate monomer after applying various concentrations of a reducing agent.

Different reducing agent concentrations were explored. FIG. 34 shows FTIR spectra of hair tresses grafted with PEG-DA 700 at ATG concentrations of 1.5, 2.5, and 5 wt %. Although the grafting efficiency was reduced at the lowest ATG concentration of 1.5 wt %, the grafting efficiency at 2.5 wt % was only slightly lower than that at 5 wt %. Therefore, 2.5 wt % was considered a preferred ATG concentration.

pH

Figure 35:
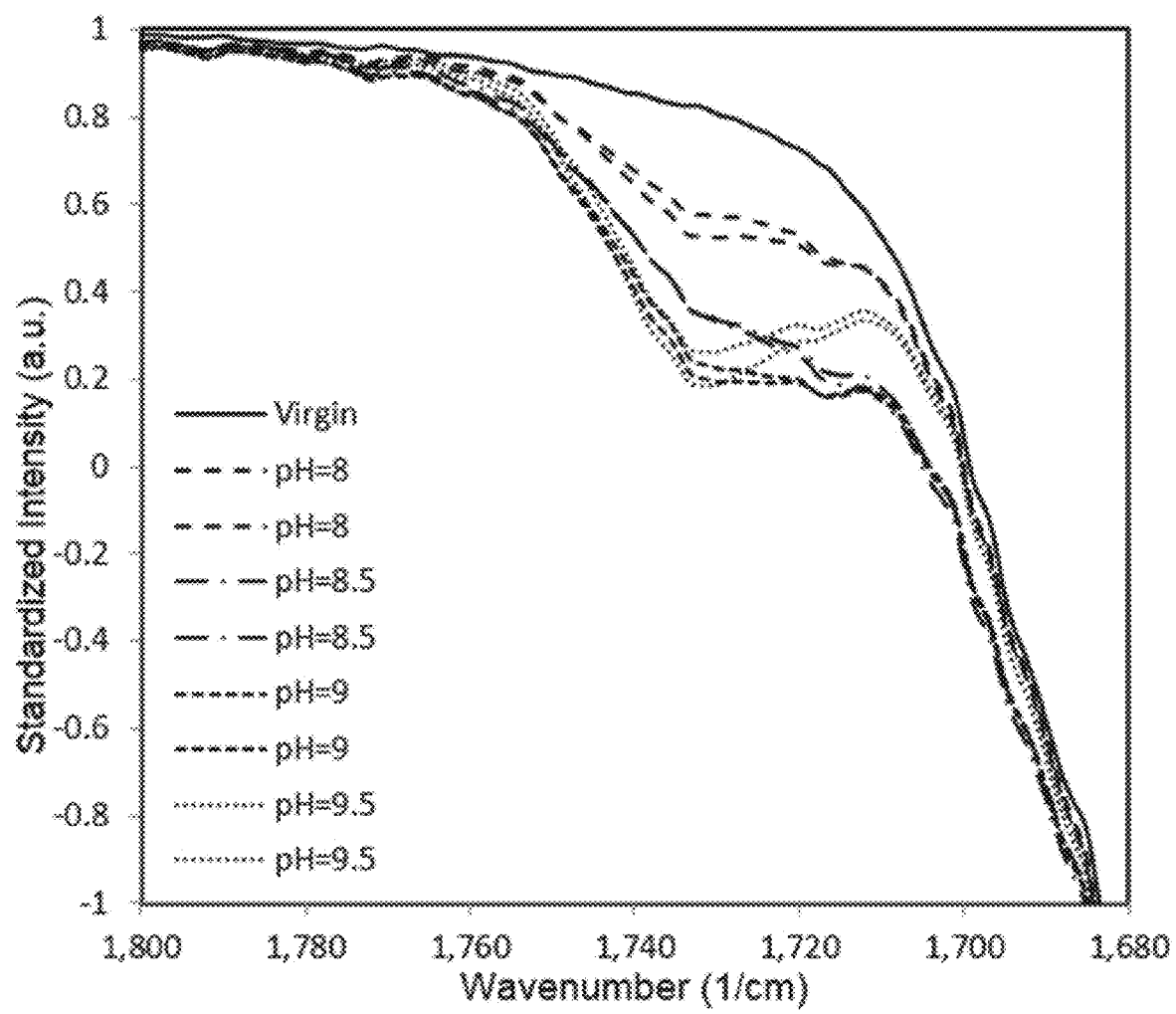
FIG. 35 depicts carbonyl peak region of FTIR spectra of hair after semi-simultaneous grafting with an exemplary PEG-diacrylate monomer at various pH values.

Grafting at a pH lower than 9.5 was also explored. FIG. 35 shows FTIR spectra of hair tresses grafted with PEG-DA 700 at pH values varying from about 8.0 to about 9.5. Very similar carbonyl peak intensities were observed for all pH values in the range of 8.5-9.5, suggesting that grafting can be achieved at any pH between 8.5 and 9.5. Therefore, pH 8.5 was considered as the preferred pH for grafting at mild conditions.

PEG-Diacrylate Size Screening

Figure 36A:
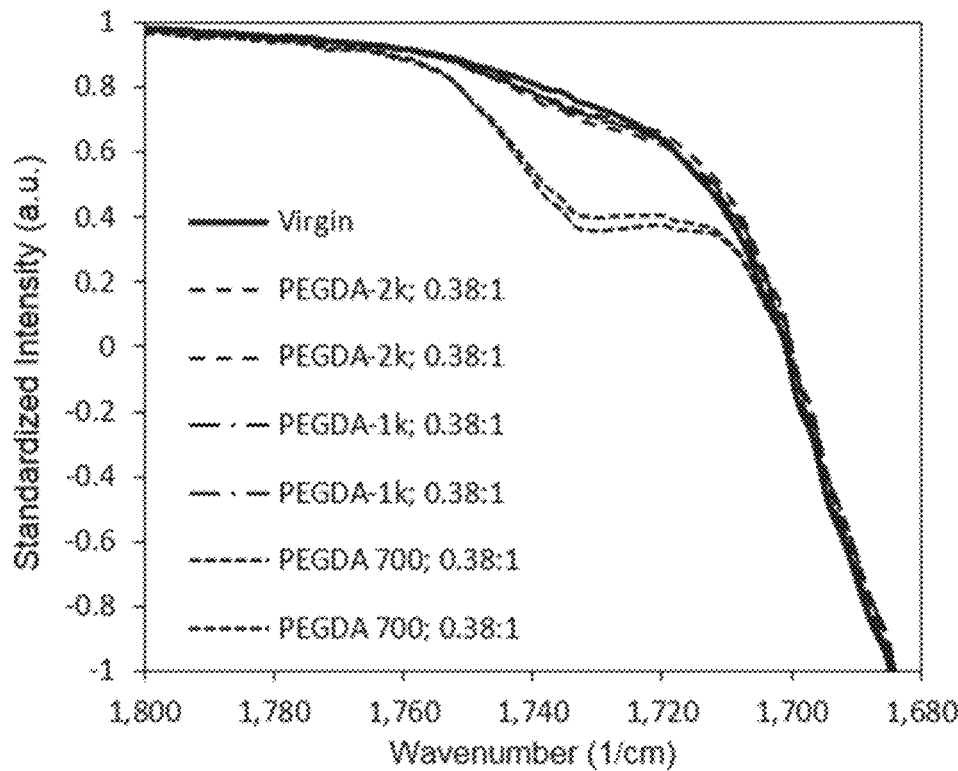
FIG. 36A depicts carbonyl peak region of FTIR spectra of virgin hair after semi-simultaneous grafting with various PEG-diacrylate monomers.
Figure 36B:
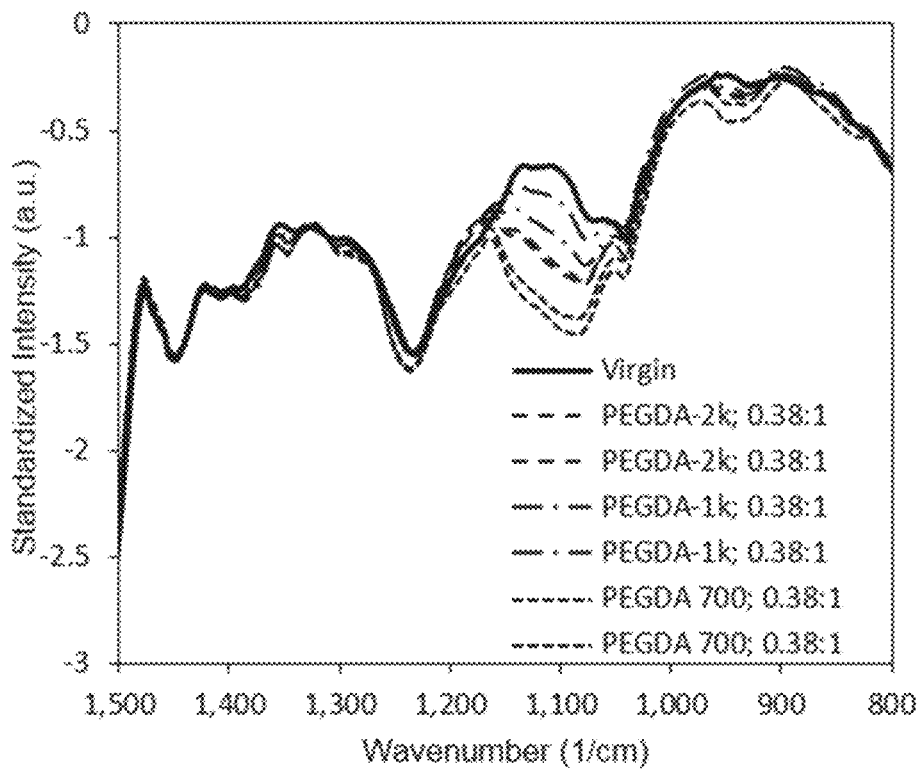
FIG. 36B depicts alkyl peak region of FTIR spectra of virgin hair after semi-simultaneous grafting with various PEG-diacrylate monomers.
Figure 37A:
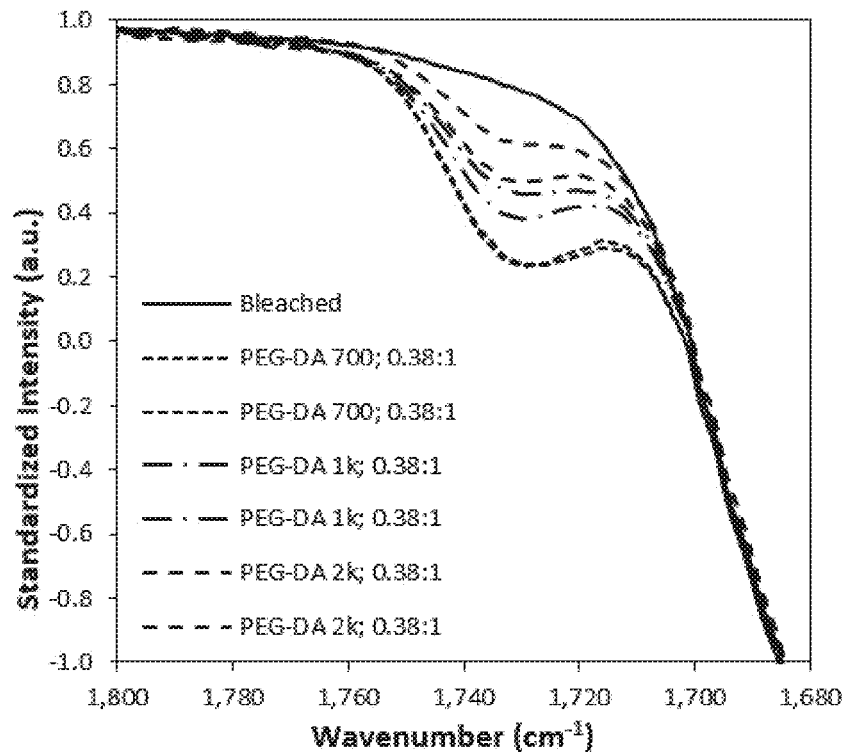
FIG. 37A depicts carbonyl peak region of FTIR spectra of bleached hair after semi-simultaneous grafting with various PEG-diacrylate monomers.
Figure 37B:
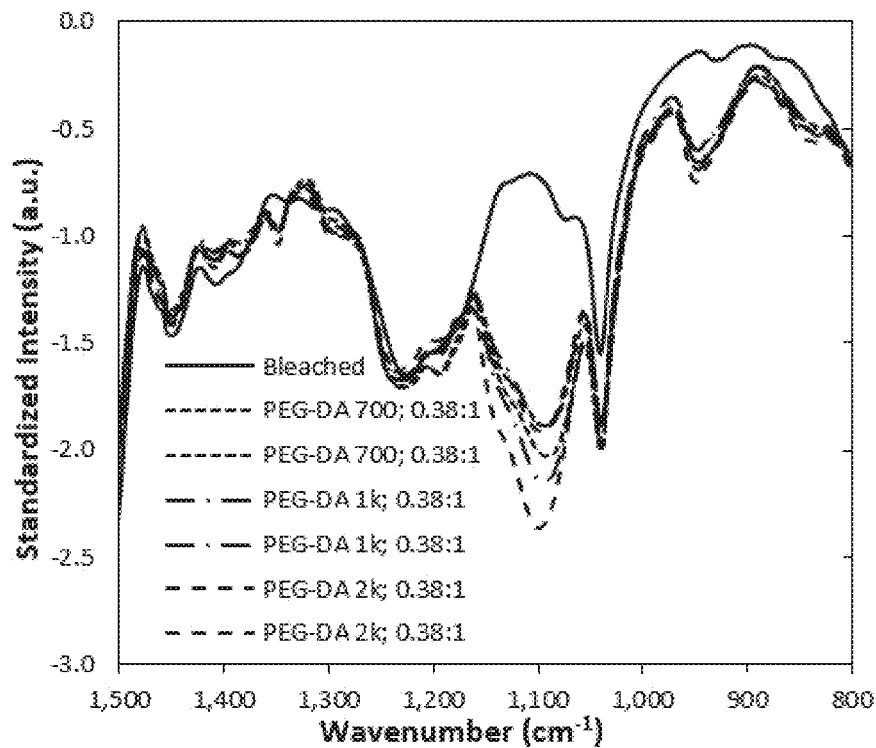
FIG. 37B depicts alkyl peak region of FTIR spectra of bleached hair after semi-simultaneous grafting with various PEG-diacrylate monomers.

Previously, although only some grafting of PEG-diacrylates with different molecular weights was obtained when using the simultaneous grafting method, sensory evaluation did reveal a clear dose response where more favorable feel of hair tresses was achieved with an increase in molecular weights of the grafted PEG-diacrylates. Effective grafting of PEG-diacrylates was achieved using the semi-simultaneous grafting method. Therefore, size screening of PEG-diacrylates using semi-simultaneous grafting was performed. FIG. 36 shows FTIR spectra of hair samples grafted with PEG-diacrylate with molecular weights of 700, 1 k, and 2 k Da (i.e., PEG-DA 700, 1 k, and 2 k) at the same molar concentration (FIGS. 36A and 36B). The grafting efficiencies are relatively lower for the two PEG-diacrylates with higher molecular weights, i.e., 1 k and 2 k Da. However, detectable PEG signature peaks in the alkyl peak region (800-1500 $cm^{-1}$) were still observed, which confirmed the successful grafting of the PEG-diacrylates. Blinded sensory evaluation showed that hair tresses grafted with PEG-DA 2 k felt smoother, softer, and more conditioned than hair tresses grafted with lower molecular weight PEG-diacrylates. This was consistent with sensory results on the tresses grafted with PEG-diacrylates using the simultaneous grafting method. The sensory benefits of grafting with PEG-DA 2 k were clear on bleached hair tresses. Without being bound by any theory, this could be due to the much higher grafting efficiency achieved on the bleached tresses (FIGS. 37A and 37B) as compared to the grafting on virgin hair tresses (FIGS. 36A and 36B).

Grafting of Multi-Arm PEG-Acrylates

Other multi-arm PEG-acrylates (PEG-AA) with high molecular weights were explored. These include 4-arm PEG-AA with molecular weights of 2 k, 5 k, and 10 k as well as 8-arm PEG-AA with molecular weights of 5 k and 20 k.

For all experiments, the monomer-to-thiol ratio was kept the same as that for PEG-DA 700 and 2 k (0.38:1). Unfortunately, no grafting was detectable by FTIR for any multi-arm PEG-AAs. However, 4-arm PEG-AA 5 k consistently showed preferred sensory properties in both wet and dry states. The sensory properties with 4-arm PEG-AA 5 k indicated some grafting occurred.

TABLE 16

Screening of exemplary large multi-arm PEG-acrylates by semi-simultaneous grafting.

| Experiment | Monomers | FTIR Results | Preferred Sensory Properties |
|---|---|---|---|
| I | PEG-DA 2k<br>4-arm PEG-AA 2k<br>4-arm PEG-AA 5k<br>4-arm PEG-AA 10k | No grafting detected for multi-arm monomers | 4-arm PEG-AA 5k |
| II | PEG-DA 2k<br>8-arm PEG-AA 5k<br>8-arm PEG-AA 20k<br>4-arm PEG-AA 5k | No grafting detected for multi-arm monomers | 4-arm PEG-AA 5k<br>8-arm PEG-AA 20k |
| III | PEG-DA 700<br>PEG-DA 2k<br>4-arm PEG-AA 5k<br>8-arm PEG-AA 5k | No grafting detected for multi-arm monomers | 4-arm PEG-AA 5k |

Example 2—Covalent Bonding Analysis

Fourier Transform Infrared (FTIR) Spectroscopy

Figure 38:
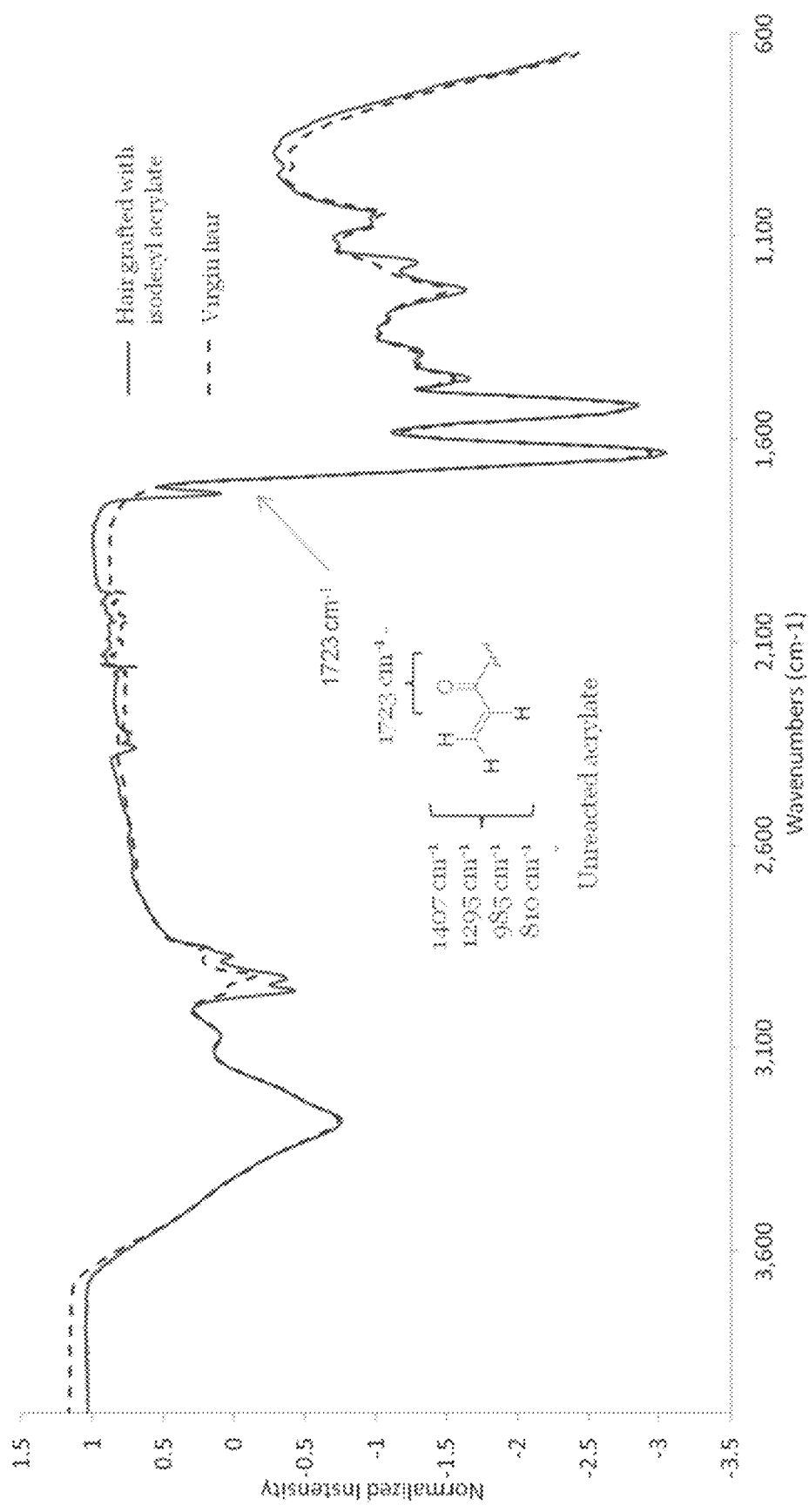
FIG. 38 depicts FTIR spectrum showing virgin hair (dashed line) and treated hair grafted with an exemplary monomer (solid line).

The presence of grafted vinyl acrylate polymers was detected qualitatively with FTIR spectroscopy, via the presence of the carboxylate stretch at about 1730 cm$^{-1}$. If this peak was present without any accompanying "ene" peaks at about 1407, 1295, 985, or 810 cm$^{-1}$, the presence of adsorbed (not covalently bound) monomer was ruled out. See, e.g., Wickett, R. R. J. Soc. Cosmet. Sci. 1983, 34, 301-316; and Yu, D.; Cal, J. Y.; Church, J. S.; Wang, L. Int. J. Biol. Macromol. 2015, 78, 32-38. The carboxylate stretch also remained intact after washing. FIG. 38 shows the FTIR spectrum for hair grafted with isodecyl acrylate (solid line) compared to virgin hair (dashed line). The FTIR spectrum for grafted hair showed a carbonyl peak at 1723 cm$^{-1}$, which indicated monomer/polymer present at the hair surface. The spectrum did not have any of the stretches indicative of unreacted acrylate (peaks at about 1407, 1295, 985, or 810 cm$^{-1}$). Hydrophobic vinyl ethers do not contain characteristic stretches that can be assessed via FTIR in the presence of hair.

Gravimetric Analysis

Figure 39A:
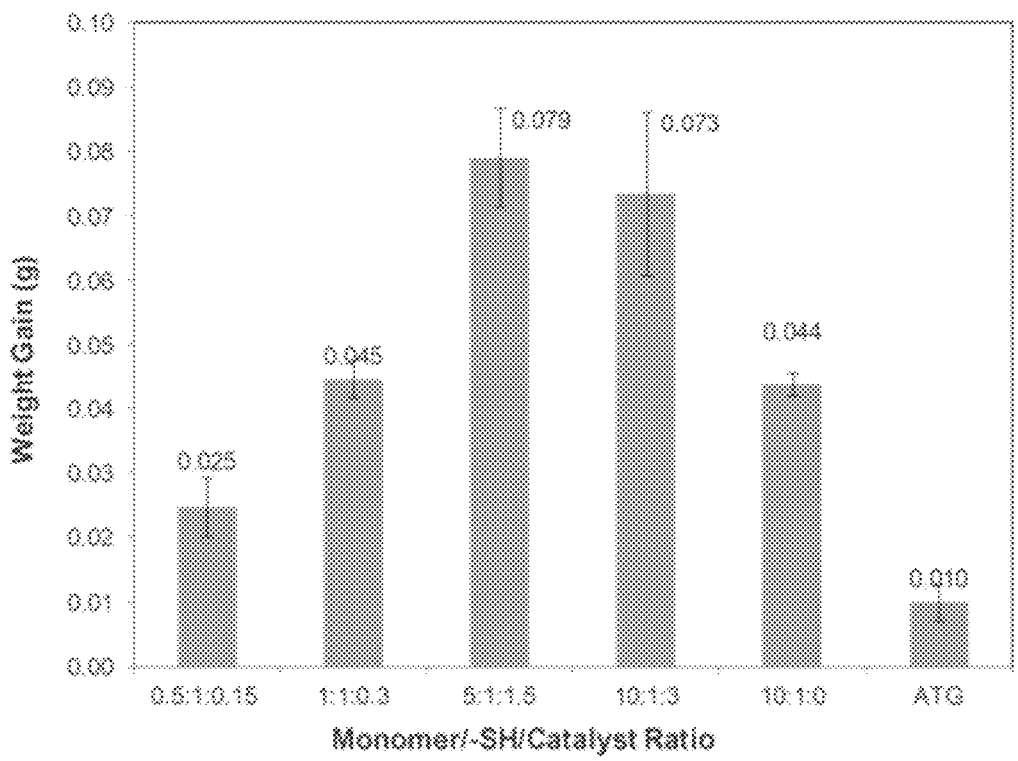
FIG. 39A depicts absolute weight gain for hair tresses treated with various monomer-to-thiol-to-catalyst ratios.
Figure 39B:
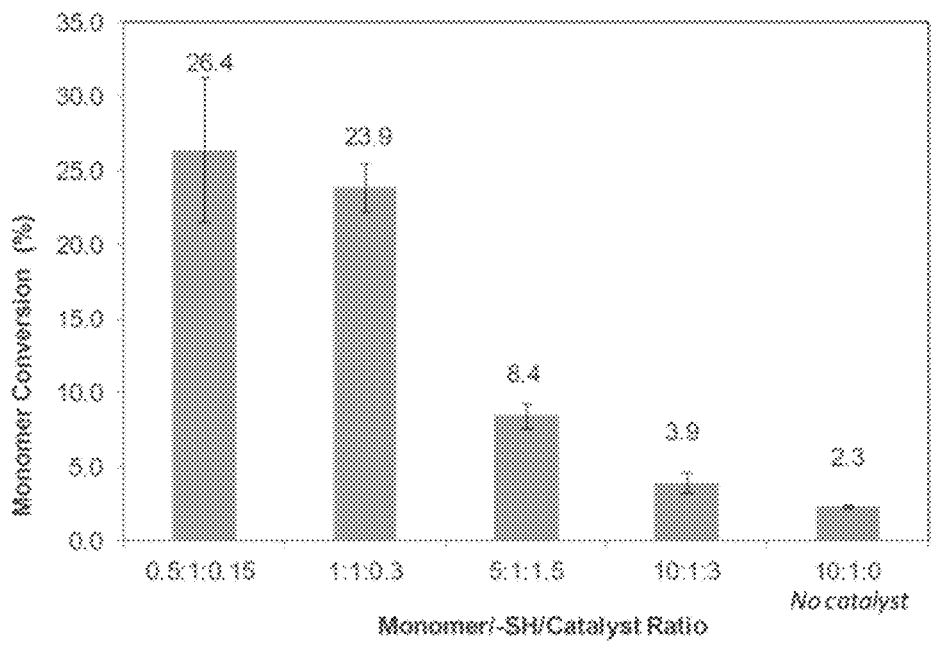
FIG. 39B depicts monomer conversion for hair tresses treated with various monomer-to-thiol-to-catalyst ratios.

To further confirm and quantify grafting efficiency, gravimetric analysis was performed. The absolute weight gain of tresses after grafting (FIG. 39A) and monomer conversion (FIG. 39B) were determined for each of the monomer-to-thiol ratio. As a control, reduced hair tress was used and treated with similar washing and drying steps as grafted samples. Significant increase in both weight gain and monomer conversion efficiency was found for all grafted samples as compared to reduced hair control, which further supports grafting had occurred.

Example 3—Characterization of a Keratin-Containing Material

Methods of treating a keratin-containing material to graft monomeric and polymeric materials to a keratin-containing material were disclosed herein.

Sensory Results

Radical Thiol-Ene Grafting

Figure 40:
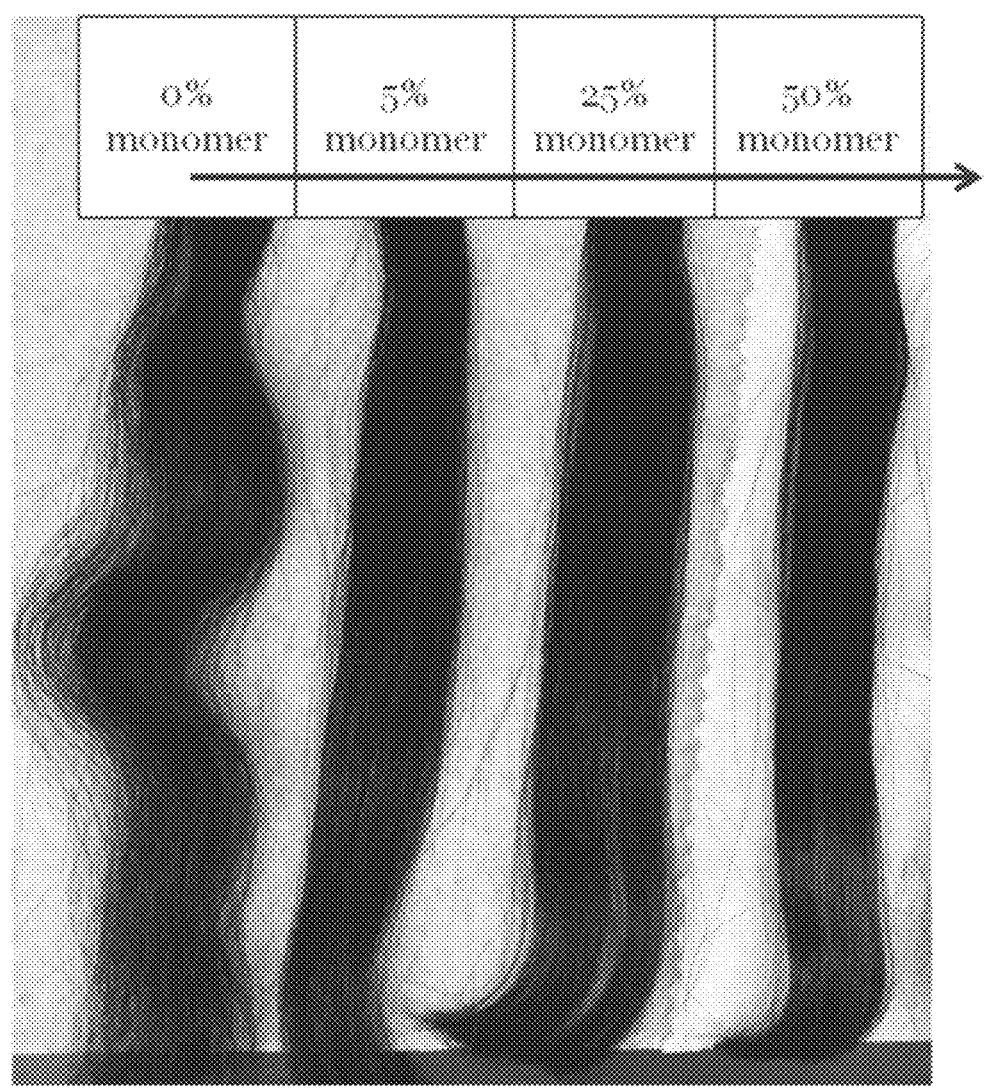
FIG. 40 depicts frizzy hair tresses grafted with solutions containing varying concentrations of an exemplary monomer based on the disclosed methods.

Blinded sensory testing was used to evaluate visual and tactile properties of tresses and mannequins grafted with hydrophobic acrylates or vinyl ethers. Overall, grafting provides hair with a smooth, conditioned feeling and good fiber alignment. In tresses, it was found that as the monomer weight % used for grafting increased, the tactile and sensory properties became more favorable (FIG. 40). In these experiments, the monomer dodecyl vinyl ether was grafted to wavy/frizzy black tresses in acetone at various concentrations for 1 hour under 365 nm light. A blinded evaluation by an experienced sensory evaluator showed that tresses grafted using a higher concentration of monomer were more preferred. Reduction conditions were with 5% ATG by weight at a pH of 9.5 with a 5:1 liquor ratio for 15 min. Note that reduced a reduced tress control (not pictured) was evaluated by a blinded sensory panel to be similar to the tress grafted with 5% monomer. That is, hair felt more conditioned and smooth to the touch after treating hair using the disclosed methods.

Figure 41:
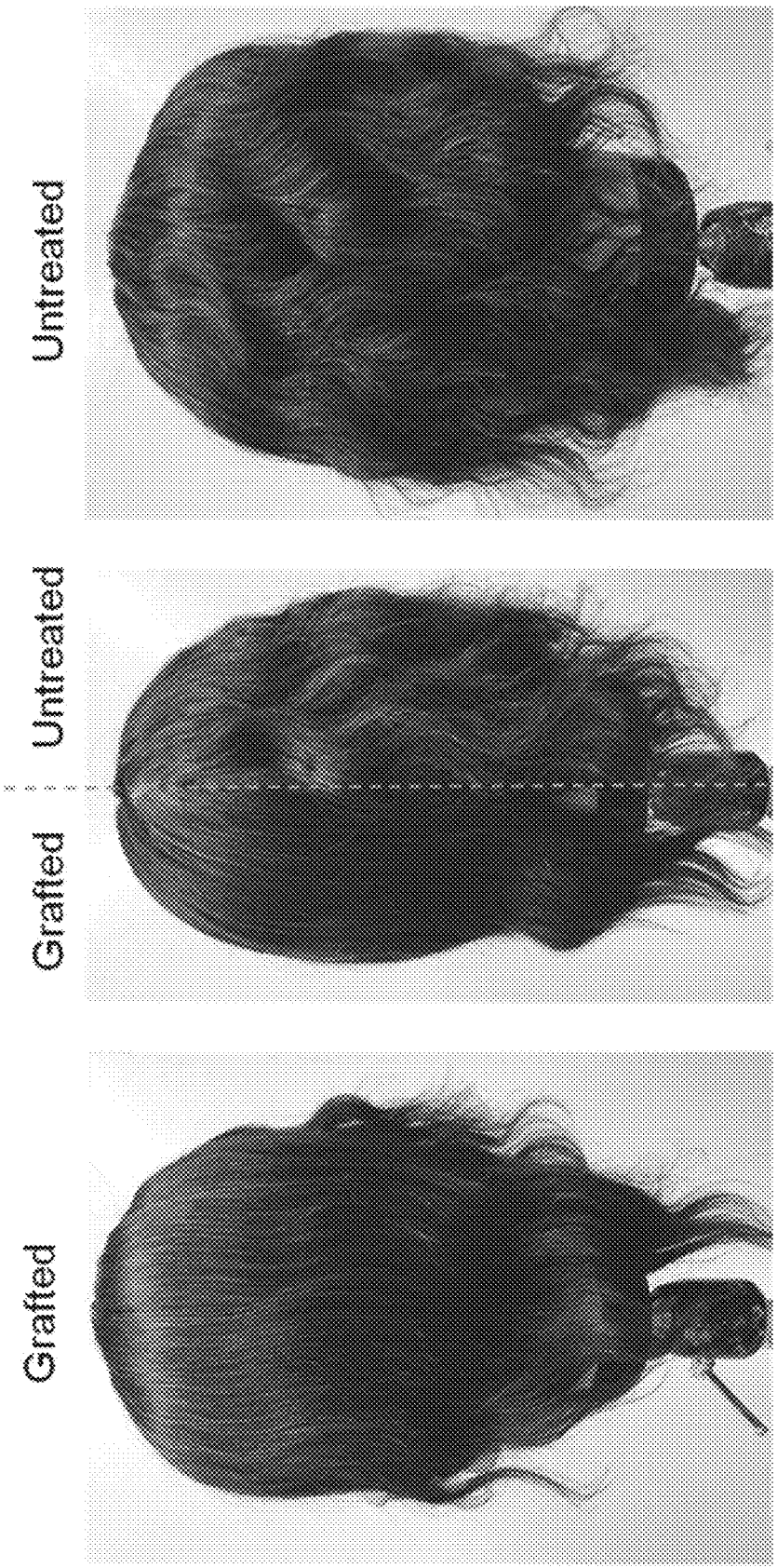
FIG. 41 depicts a mannequin with one side grafted with an exemplary acrylate monomer (left) and one side untreated (right).

When grafted onto a mannequin head, a PEG diacrylate provided noticeable tactile changes, improved fiber alignment, and induced straightening in comparison to hair that was untreated (FIG. 41). The grafted side (left) had favorable tactile properties compared to the untreated hair when evaluated by a blinded sensory panel.

Figure 42:
FIG. 42 depicts a mannequin with one side reduced only (left) and one side reduced and grafted with an exemplary acrylate monomer (right) and then curled and exposed to 90% relative humidity for 15 min.

After reducing or reducing and grafting the hair, the mannequin head was curled with a 1" barrel curling iron. The initial curls were noticeably tighter on the grafted side (right) of the mannequin according to a blinded sensory evaluation panel. After exposure to 90% relative humidity (RH) at 25° C. for 15 minutes, the grafted side also showed better curl retention according to a blinded sensory evaluation panel. Thus, data also suggested that grafting had a favorable effect on stylability (FIG. 42).

Various Grafting Methods Compared to Virgin a Keratin-Containing Material

Figure 43:
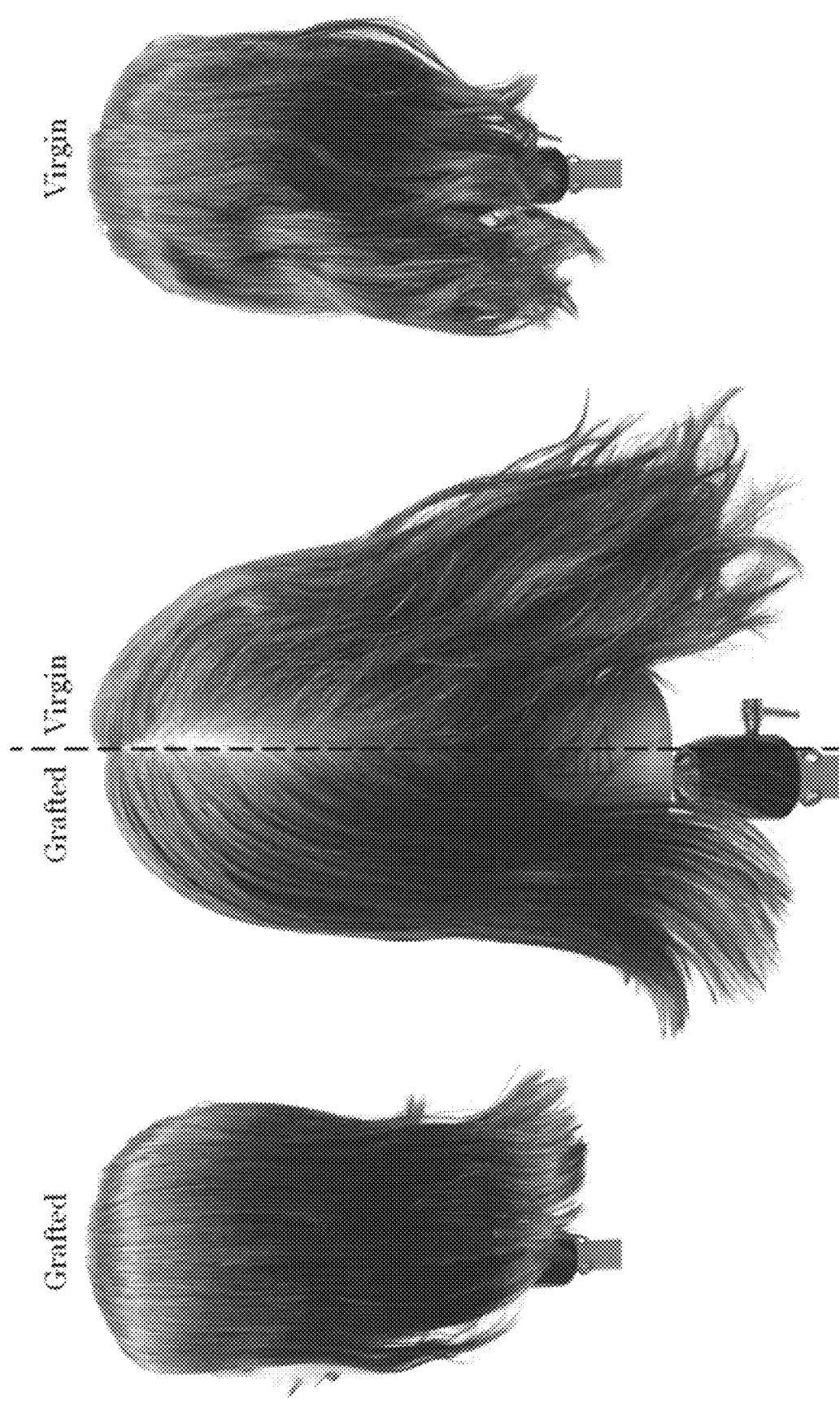
FIG. 43 depicts a mannequin with one side reduced and grafted with an exemplary acrylate monomer (left) compared to untreated hair (right).

Blinded sensory evaluation panels have evaluated the visual and tactile properties of mannequins grafted with hexyl acrylate using various grafting methods. Overall, grafting provided hair with a smooth, conditioned feeling and improved fiber alignment in comparison to un-treated hair (FIG. 43). FIG. 43 shows a mannequin with one side reduced and grafted with hexyl acrylate at a 1:30:9 thiol:acrylate:DNPA ratio (left) and one side untreated (right).

Blinded sensory testing is used to evaluate visual and tactile properties of other a keratin-containing material, including fingernails and toenails. The treated a keratin-containing material are compared to virgin a keratin-containing material.

Grafting on Hair Damaged by Heat

Heat damaged hair tresses (damaged using a styling iron-crimper) before and after grafting were evaluated by a blinded sensory panel. Grafted tresses were were found to have preferred sensory properties over non-grafted damaged hair. Grafted hair tresses felt smoother and were easier to comb.

Grafting with PEG-Diacrylates

Aside from the hexyl acrylate monomer, which possesses one acrylate group, diacrylate monomers with two acrylate groups were also explored for grafting. Without being bound by any theory, it was hypothesized that having two acrylate groups on one monomer would further increase the potential for binding to thiol groups and would also improve mechanical properties of a keratin-containing material.

For example, using diacrylate monomers could make hair stronger, which is of high interest for damaged hair. It was found that hair grafted with PEG diacrylates of varying molecular weights had favorable tactile properties as evaluated by a blinded sensory panel. Specifically, hair felt smooth, strong and well-conditioned.

Shine Band Testing

Figure 44:
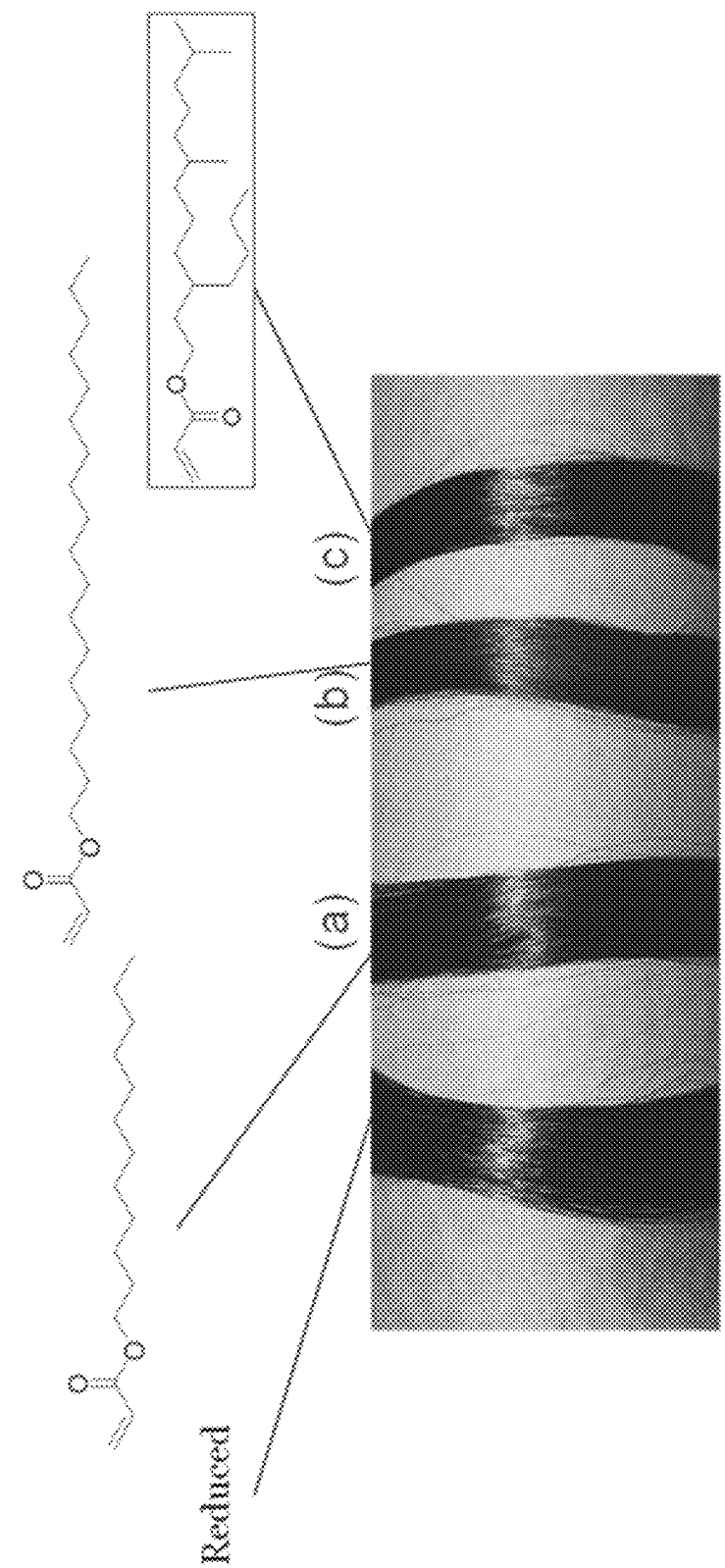
FIG. 44 depicts shine characteristics of tresses grafted with an exemplary vinyl ether monomer based on the disclosed methods.

FIG. 44 showed the shine characteristics of tresses grafted with either (a) dodecyl acrylate, (b) octadecyl acrylate, or (c) 3-butyl-7,11-dimethyldodecyl acrylate compared with a tress that was reduced only (not grafted). A blinded sensory evaluator determined that sample (c) exhibited the best shine, followed by samples (a) and (b), followed by the reduced tress control. It was also found that particularly high molecular weight, branched acrylates provided a noticeable increase in hair shine (FIG. 44).

Mechanical Testing

Mechanical characterization of keratin-containing material samples is carried out on the INSTRON® 3342 (Instron, Norwood Mass.) equipped with 100N load-cell (Instron #2519-103). Keratin-containing material samples are mounted onto the instrument via modified Instron 2710-101 grips, which prevent the sample from slipping from the grips during testing. The instrument grip distance was adjusted such that the sample was at neutral extension as indicated by the instrument force being close to zero (+0.01N). For example, single-fiber hair samples can be evaluated using an INSTRON®.

The extension pull test is preprogrammed into Bluehill Lite Software used to operate the instrument. The extension pull test is used to determine the stiffness, stretchiness, and strength of a keratin-containing material by measuring the Young's Modulus, elongation at break, and ultimate tensile strength. The Young's Modulus is utilized as a measure of material stiffness, while the elongation at break is used as a measure of material flexibility. The sample is mounted onto the instrument such that the hair sample is fixed within the instrument grips. The instrument grip distance is adjusted such that the sample was at neutral extension as indicated by the instrument force being close to zero (+0.01N). Subsequently, extension until sample failure is performed at 20 mm/min. The stress strain data recorded by instrument during the extension is exported to Excel where the reported mechanical properties are calculated.

An Excel template is used to automatically extract a number of parameters from the instrument generated data. The Young's modulus (YM) is calculated as the straight line slope of the stress-strain curve between 0.1% and 0.4%. The R squared value of the linear fit is above 0.98 or else the data point is discarded. The elongation at break is determined as the strain at which the sample, for example, a hair fiber, breaks. Ultimate stress is calculated as the maximum stress recorded during the experiment. Ultimate tensile strength is the capacity of a material to withstand loads tending to elongate. Ultimate tensile strength is the maximum stress that a material or sample can withstand while being pulled before breaking.

Water Uptake Testing

A hair sample was first dried in a desiccator for 16 hours. The sample was weighed and placed into a humidity chamber at 90% RH for 15 minutes. The sample was then removed and weighed again.

Water Contact Angle

Water contact angles (CA) are measured using a goniometer equipped with an automated dispenser (Model 500, Rame-Hart). Advancing and receding angles are measured with the sessile drop method by depositing a droplet of 1 µL on the surface, then increasing the volume to 4 µL, finally decreasing it. Advancing angles are considered as the maximum angles observed during the droplet growth. Receding contact angles are measured in correspondence of the drop profile just before the contact surface reduction. Each CA value is averaged from measurements of four drops with an estimated maximum error of 4°. The CA is measured using distilled water.

Differential Scanning Calorimetry

Figure 60A:
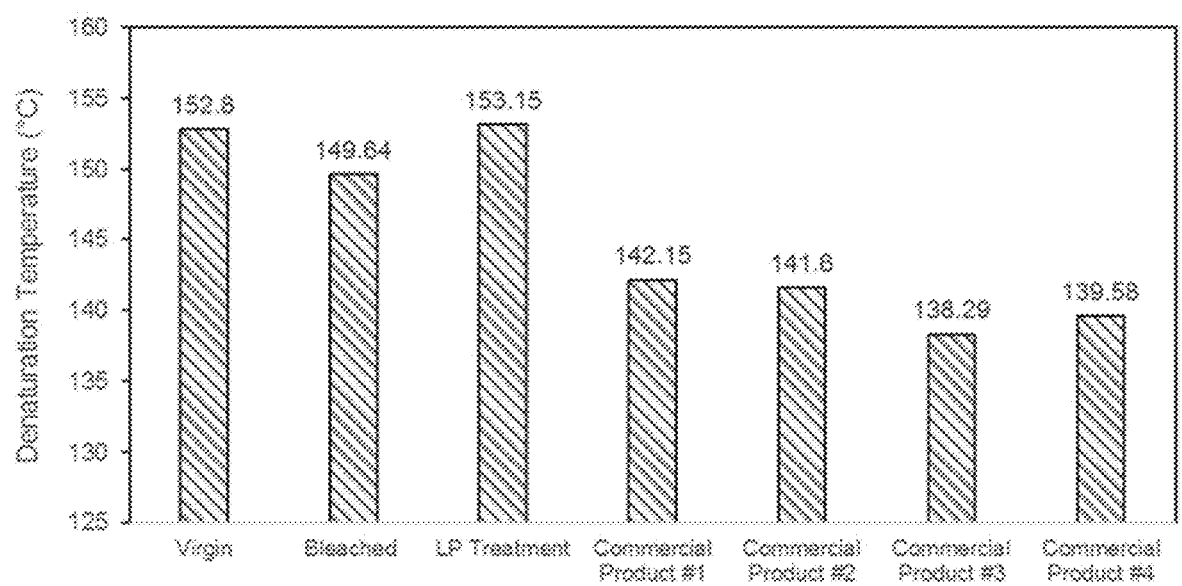
FIG. 60A depicts denaturation temperatures of untreated virgin hair, untreated bleached hair, bleached hair after semi-simultaneous grafting with an exemplary PEG-diacrylate monomer and post-treatment with gluconolactone and citric acid, and bleached hair treated with various commercial products.

Differential Scanning Calorimetry (DSC) analysis is performed on both wet and dry hair. For wet method DSC, about 5-10 mg of hair is weighed into stainless steel pressure resistant sample pan and 50 µl of water is added. The pan is then sealed and samples are equilibrated overnight before DSC analysis. Samples are then heated from 30 to 250° C. at 5° C./min heating rate. For dry method DSC, about 5-10 mg of hair is weighed into aluminium sample pan and sealed with a lid. The lid is later pierced to allow moisture to escape during analysis. The samples are also heated from 30 to 250° C. at 5° C./min heating rate. Using DSC analysis, denaturation temperature of the hair could be identified. Hair denaturation temperature is usually used to evaluate hair strength and structural integrity. It decreases after various chemical treatments such as bleaching, perming, or straightening treatments indicating hair damage. As expected, hair denaturation temperature decreased by about 4° C. after bleaching treatment and further decreased by 10-15° C. after commercial treatments indicating dramatic hair damage (FIG. 60A). However, after grafting and gluconolactone and citric acid post-treatment on bleached hair (damaged hair), denaturation temperature was brought back to the level of untreated hair (compare virgin to LP treatment in FIG. 60A) indicating improved hair strength.

Scanning Electron Microscopy (SEM)

Figure 45A:
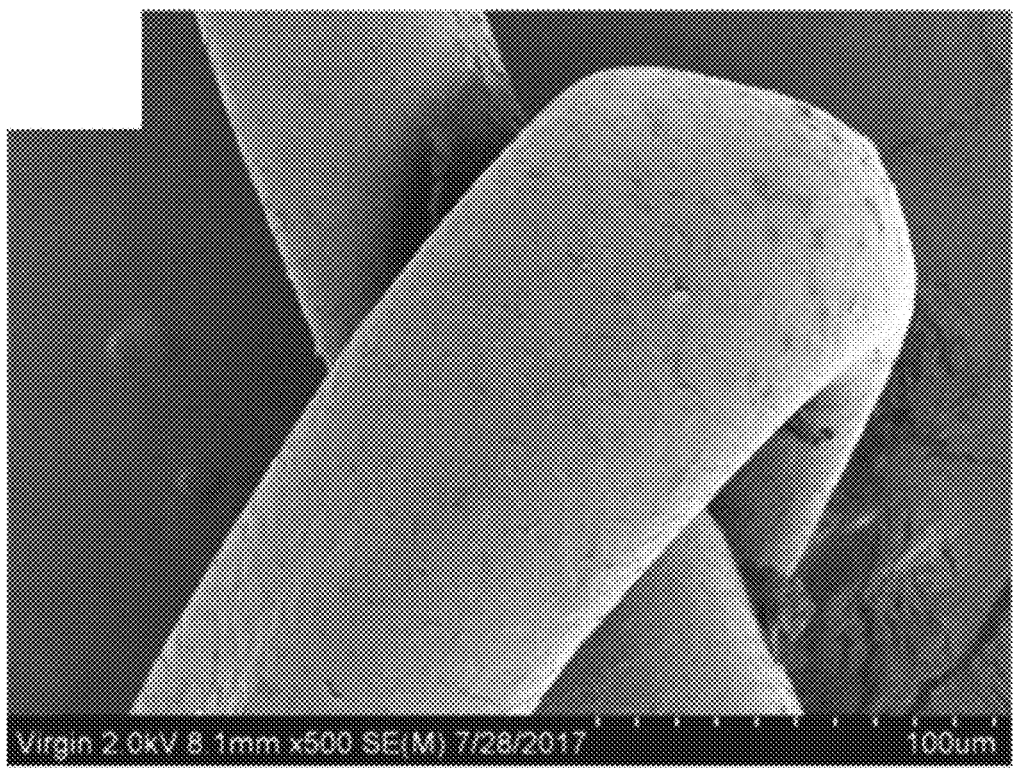
FIG. 45A depicts scanning electron micrograph (SEM) of knotted virgin hair.
Figure 45B:
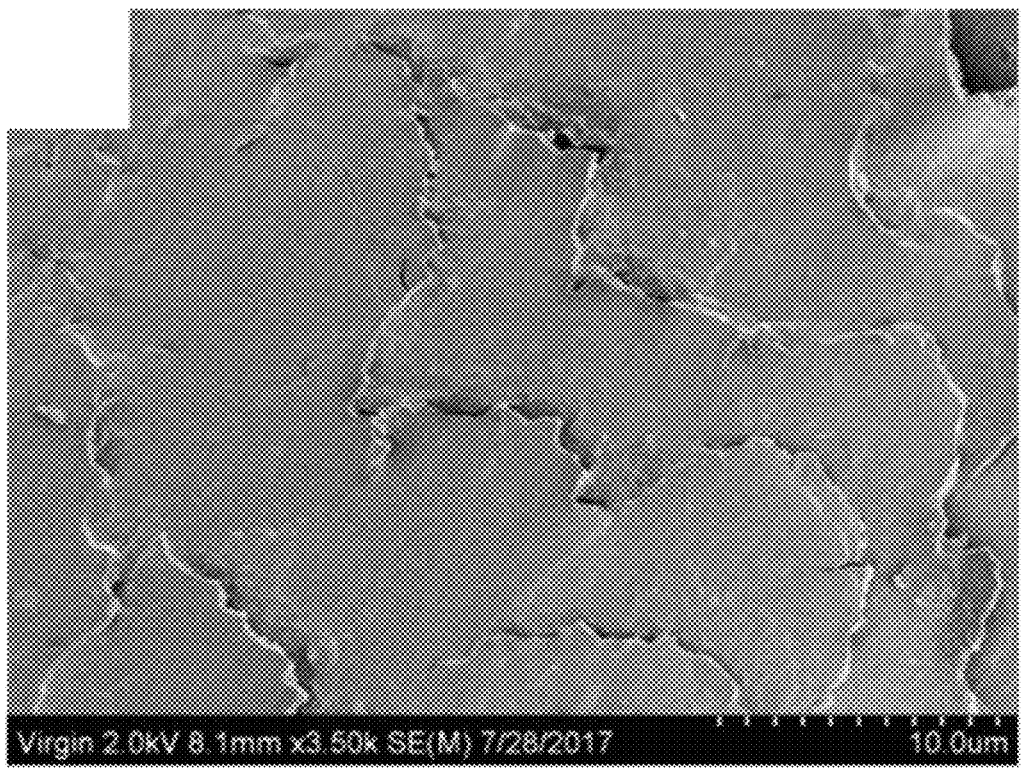
FIG. 45B depicts SEM of virgin hair cuticle.
Figure 45C:
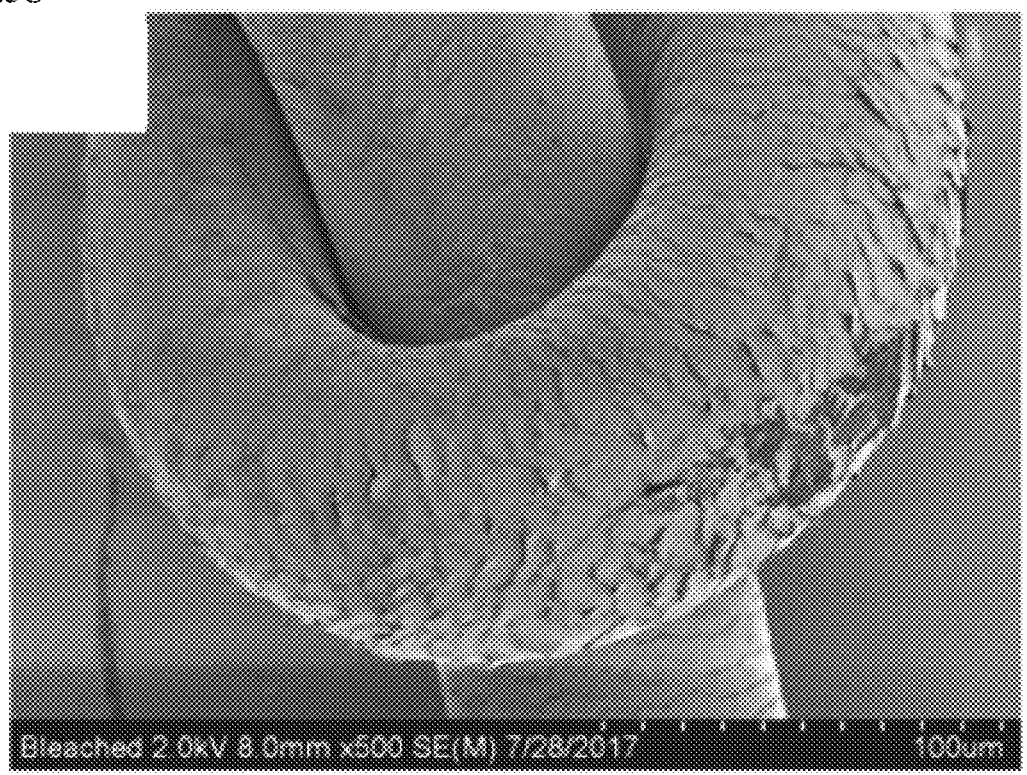
FIG. 45C depicts SEM of knotted bleached hair.
Figure 45D:
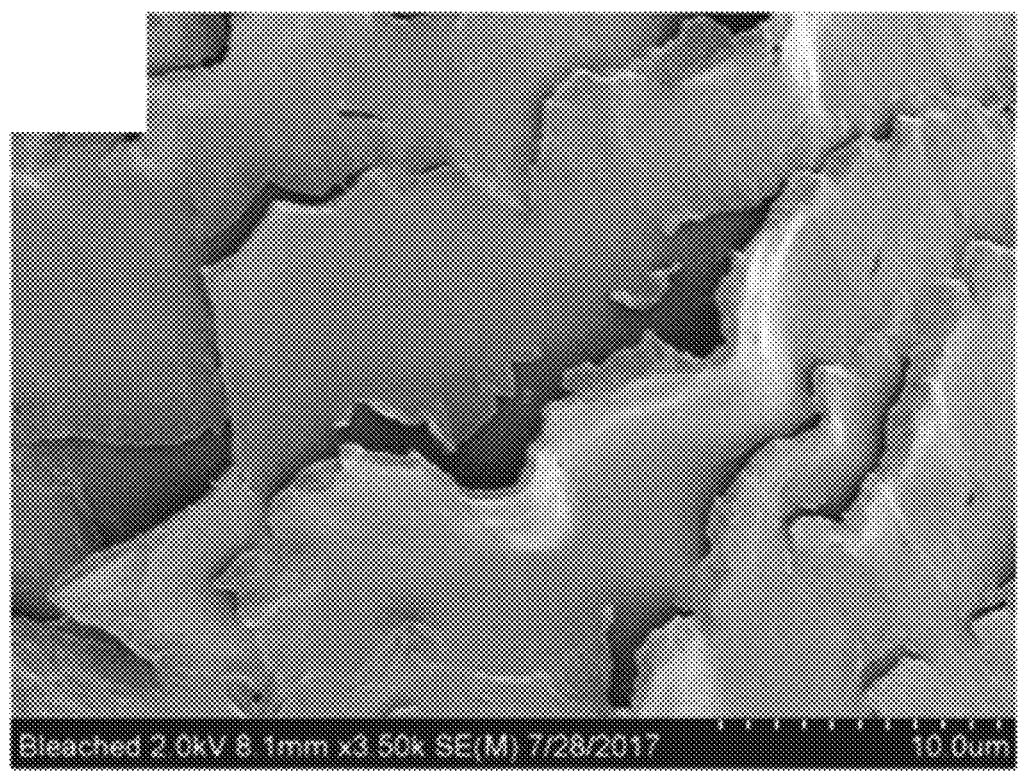
FIG. 45D depicts SEM of bleached hair cuticle.
Figure 45E:
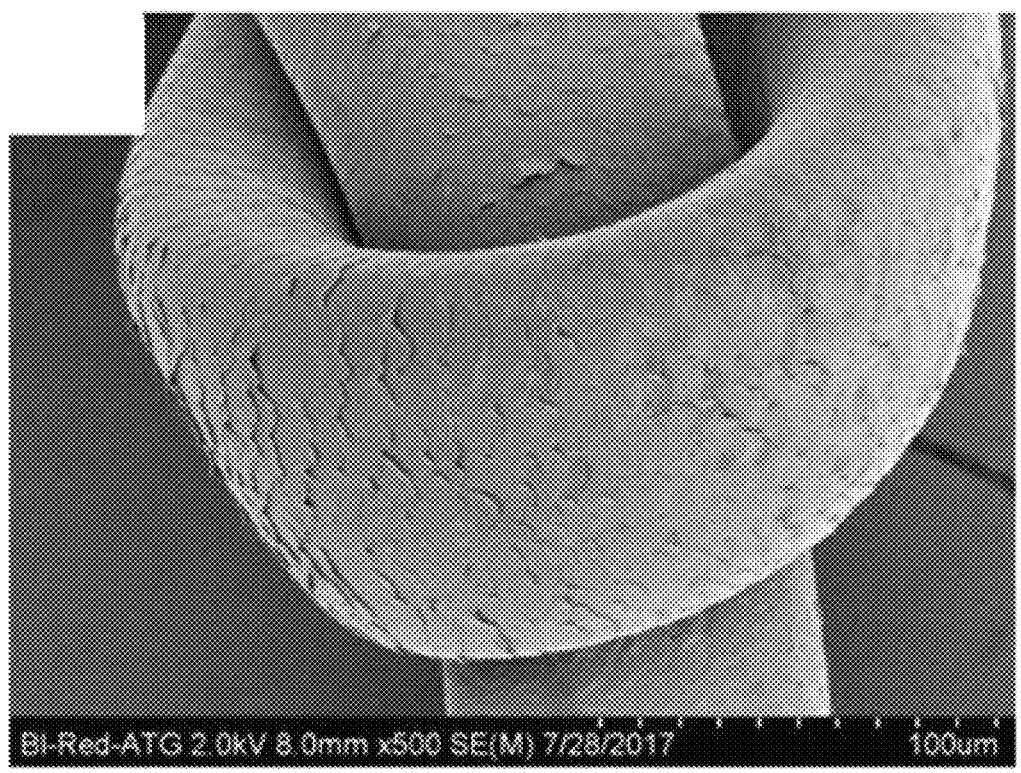
FIG. 45E depicts SEM of knotted reduced bleached hair.
Figure 45F:
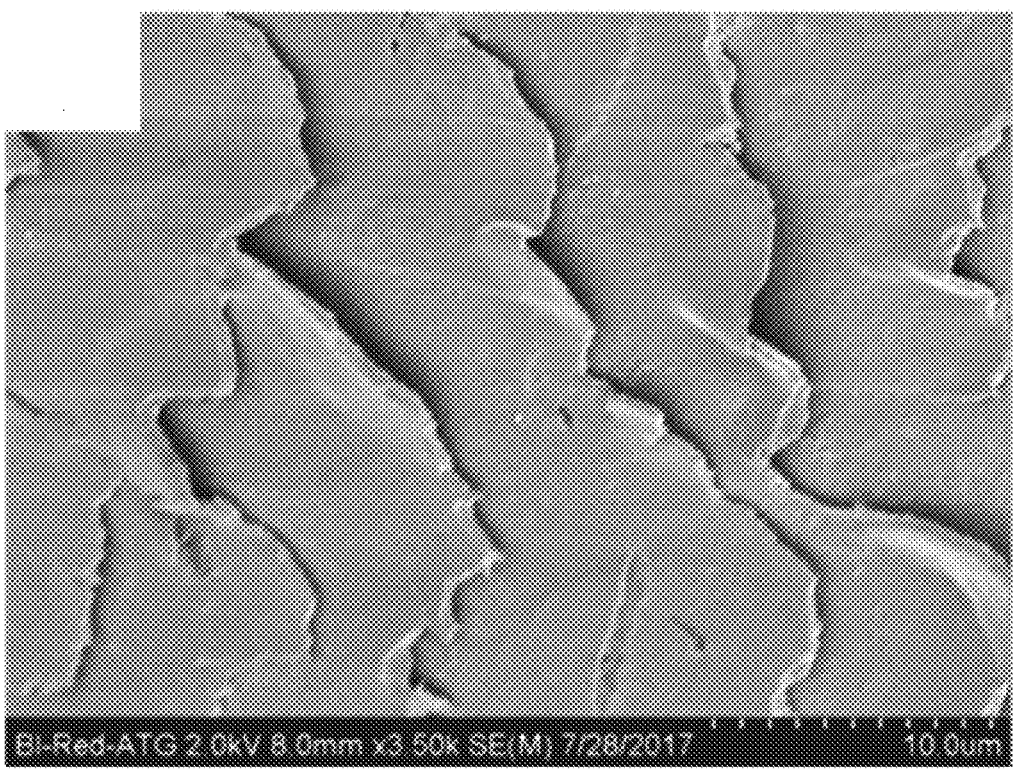
FIG. 45F depicts SEM of reduced bleached hair cuticle.
Figure 45G:
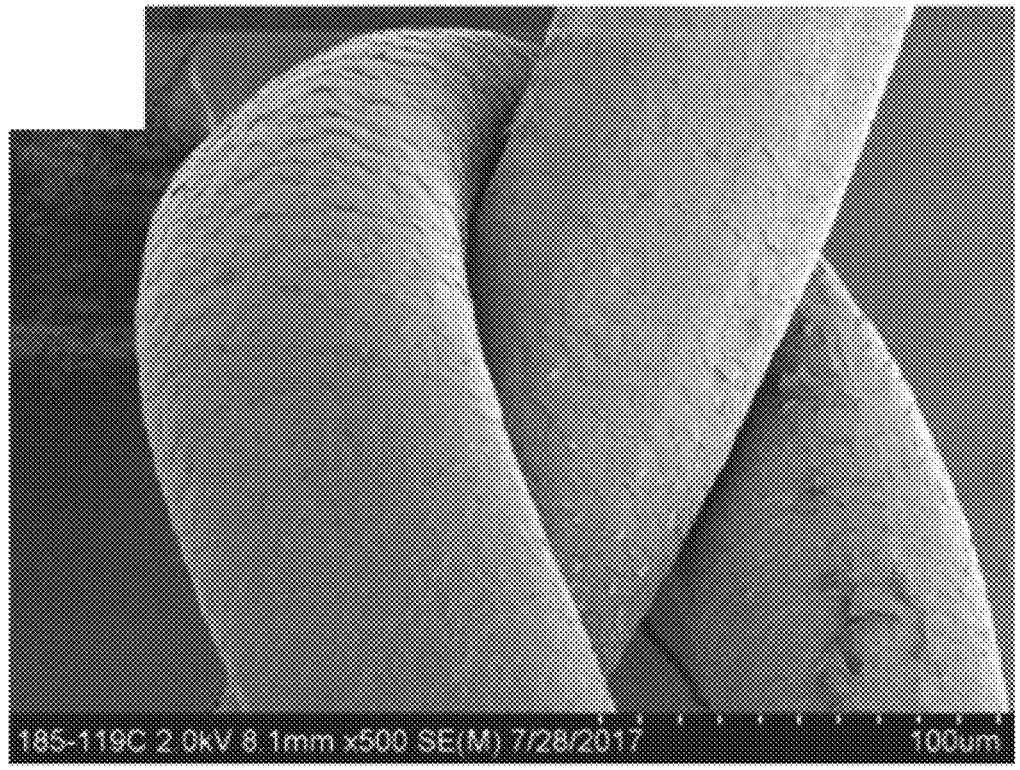
FIG. 45G depicts SEM of knotted reduced and grafted bleached hair.
Figure 45H:
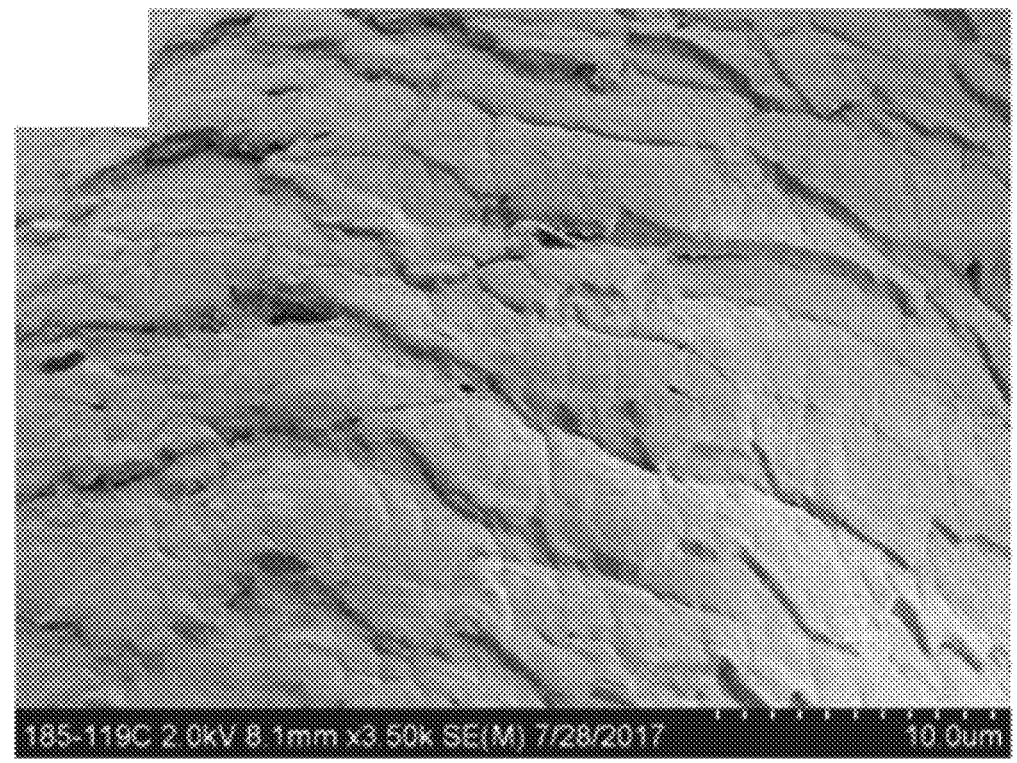
FIG. 45H depicts SEM of reduced and grafted bleached hair cuticle.

To study morphological changes of the damaged hair surface before and after grafting, scanning electron microscopy (SEM) analysis was employed. Hair was evaluated after bleaching, after reduction of bleached hair with ATG, and after simultaneous grafting of bleached hair with hexyl acrylate in ATG reducing solution. As expected, hair cuticles appeared dramatically lifted after bleaching (FIG. 45C and FIG. 45D) as compared to virgin hair (FIG. 45A and FIG. 45B). No noticeable differences were found after reduction of bleached hair in 5 wt % ATG reducing solution (FIG. 45E and FIG. 45F). Significant improvement in cuticle morphology was observed after simultaneous grafting with hexyl acrylate in ATG reducing solution (FIG. 45G and FIG. 45H). Cuticles no longer appeared lifted and hair cuticle surface appeared smooth resembling virgin hair.

Lowry Assay for Protein Loss

Figure 60B:
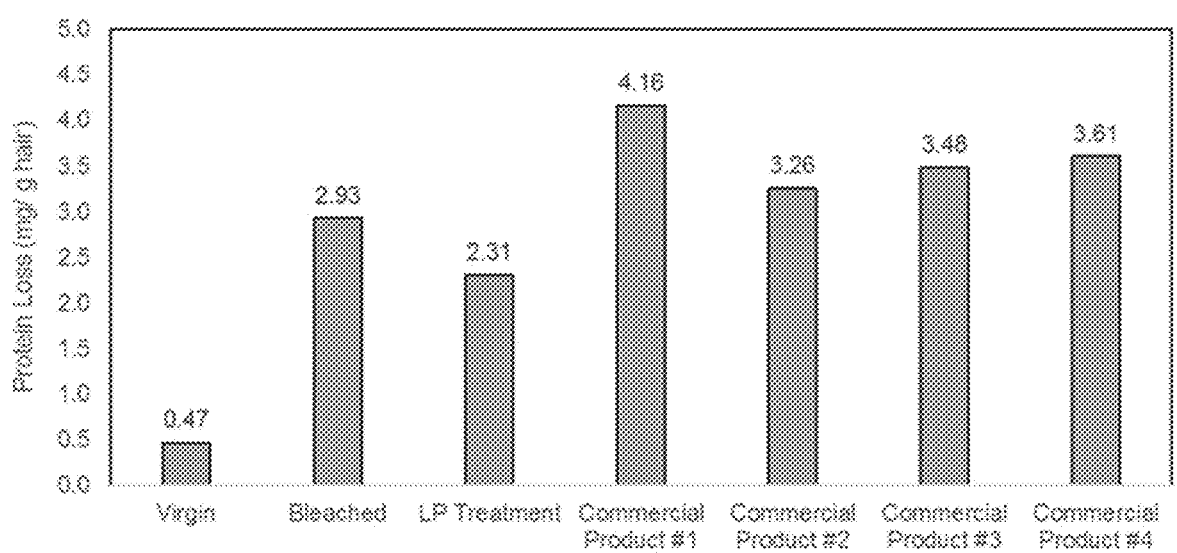
FIG. 60B depicts protein loss values of untreated virgin hair, untreated bleached hair, bleached hair after semi-simultaneous grafting with an exemplary PEG-diacrylate monomer and post-treatment with gluconolactone and citric acid, and bleached hair treated with various commercial products.

To study changes of the hair surface before and after grafting, a protein quantification assay was employed. After various chemical treatments such as bleaching, perming, or straightening treatments were applied, hair cuticles become damaged which resulted in higher protein loss. To quantify this loss before and after grafting, a Modified Lowry Protein Assay was employed. Hair fibers were first cut into ¼ inch pieces and about 250 mg of hair was submerged into 4 mLml of water in the scintillation vial. Vials were then placed on the automatic vortex machine for 4 hours. The supernatant was then collected and diluted with 0.2N NaOH solution at 1:1 ratio for each hair sample and left to sit for 30 minutes for solubilization. About 200 µL of solubilized protein solution was then added into a 2 mL Eppendorf tube and mixed with 1 mL of Modified Lowry Reagent at 20-seconds intervals. Each sample was run in triplicate. After about 10 minutes, 100 µL of Folin-Ciocalteu Reagent was added into each sample and vortexed. The solutions were then left to develop for another 30 minutes. After 30 minutes, solutions were transferred into cuvettes and their absorbance at about 750 nm was measured using UV-Vis spectrophotometer. As expected, after bleaching, proteins were more easily leached out of the hair fibers as indicated by a dramatic increase in protein loss from 0.47 mg/g hair for virgin hair to 2.93 mg/g hair for bleached hair. In addition, chemical treatments with commercial products led to a further increase in protein loss, while after grafting and a post-treatment with gluconolactone and citric acid, protein loss was reduced indicating less damage has been inflicted on the hair fibers (FIG. 60B).

Example 4—Grafting with Additives

To further improve hair sensory benefits, grafting with various additives has also been explored. These include emollients, fatty acids, fatty alcohols, fatty esters, peptides, and amino acids. The additive examples were performed using the following process: 5 wt % ammonium thioglycolate reducing solution at a pH of about 9.5 and a liquor ratio of 1.1:1 was applied to hair tresses followed by application of PEG-diacrylate 700 at a monomer-to-thiol ratio of about 0.38:1 with additives added to the monomer mixture. The treatment was carried out for 30 minutes.

Fatty Acids and Fatty Alcohols

Figure 46:
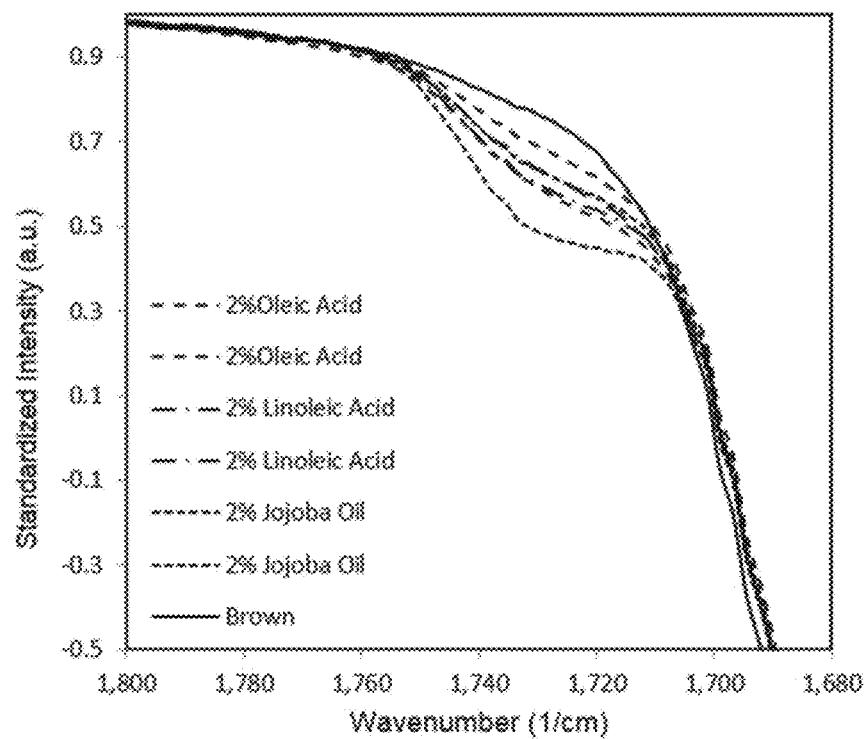
FIG. 46 depicts carbonyl peak region of FTIR spectra of hair after semi-simultaneous grafting with an exemplary PEG-diacrylate monomer with various fatty acid additives.
Figure 47:
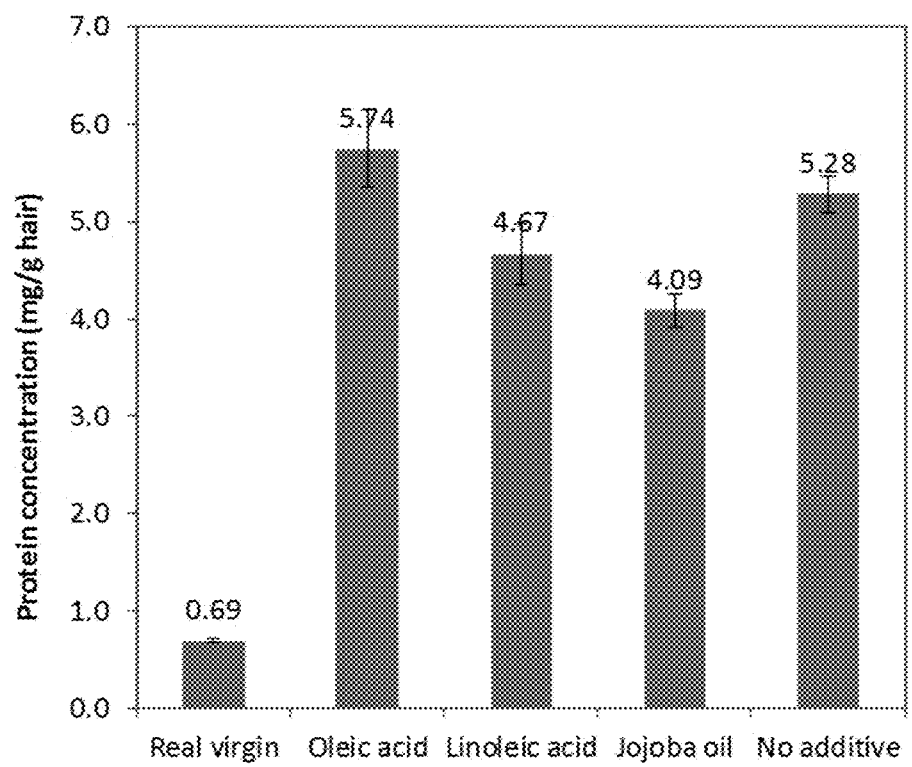
FIG. 47 depicts protein loss values of hair after semi-simultaneous grafting with an exemplary PEG-diacrylate monomer with various fatty acid additives.

The types of fatty acids, fatty alcohols screened in this study include oleic acid, linoleic acid, jojoba oil (a mixture of fatty acids), cetyl alcohol, and cetearyl alcohol. FIG. 46 shows grafting in the presence of 2 wt % (with respect to the total grafting mixture) of oleic acid, linoleic acid, or jojoba oil additive. The grafting efficiency was similar for all three fatty acids. It was noticed that all hair tresses grafted with fatty acids felt very soft and smooth in the wet state and the tress grafted with oleic acid additive showed most favorable sensory properties in the dry state. Using a Lowry assay, the protein loss values for hair samples treated with or without fatty acid additives were also determined. FIG. 47 shows that the protein loss concentrations for hair tresses grafted with linoleic acid or jojoba oil additive were slightly lower compared to the tresses grafted with no additive or oleic acid, suggesting that linoleic acid or jojoba oil may provide some protection over hair cuticles during grafting. Differential scanning calorimety (DSC) analysis also showed a slight increase in hair denaturation temperature ($T_d$) for the hair sample grafted with linoleic acid additive, suggesting some improvement in hair structural integrity by linoleic acid. Altogether, the results suggest that the use of fatty acids like oleic acid or linoleic acid as additives during grafting may lead to desired sensory properties or healthy benefits. In addition to fatty acids, selected fatty alcohols including cetyl alcohol and cetearyl alcohol were also explored. However no statistically significant benefits were observed.

Amino Acid Mixtures & Peptide Mixtures

Figure 48A:
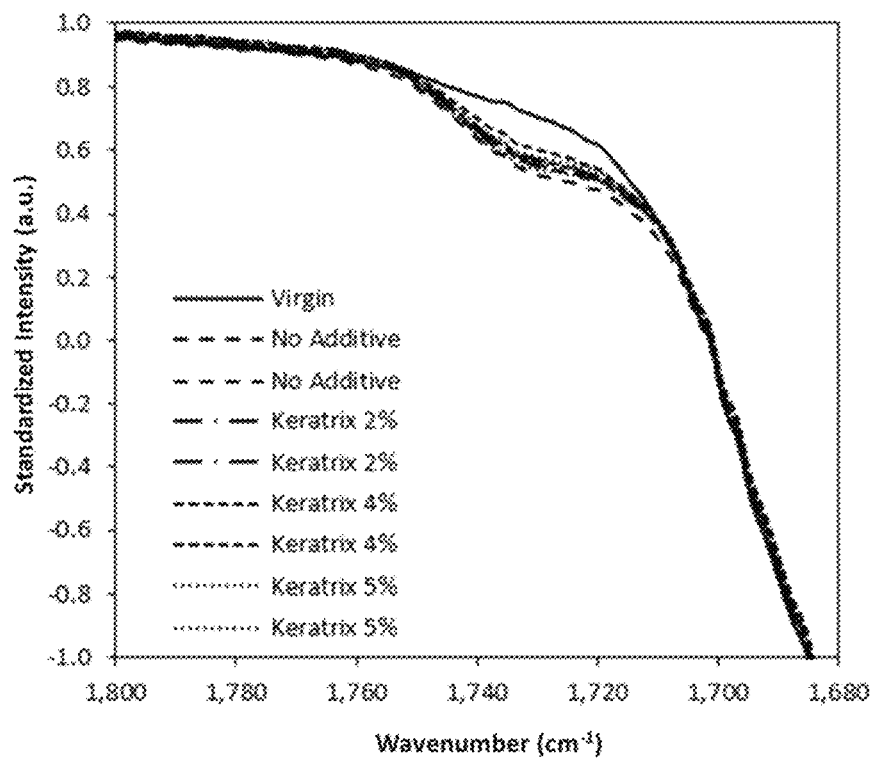
FIG. 48A depicts carbonyl peak region of FTIR spectra of hair after semi-simultaneous grafting with an exemplary PEG-diacrylate monomer with various amino acid or peptide mixture additives.
Figure 48B:
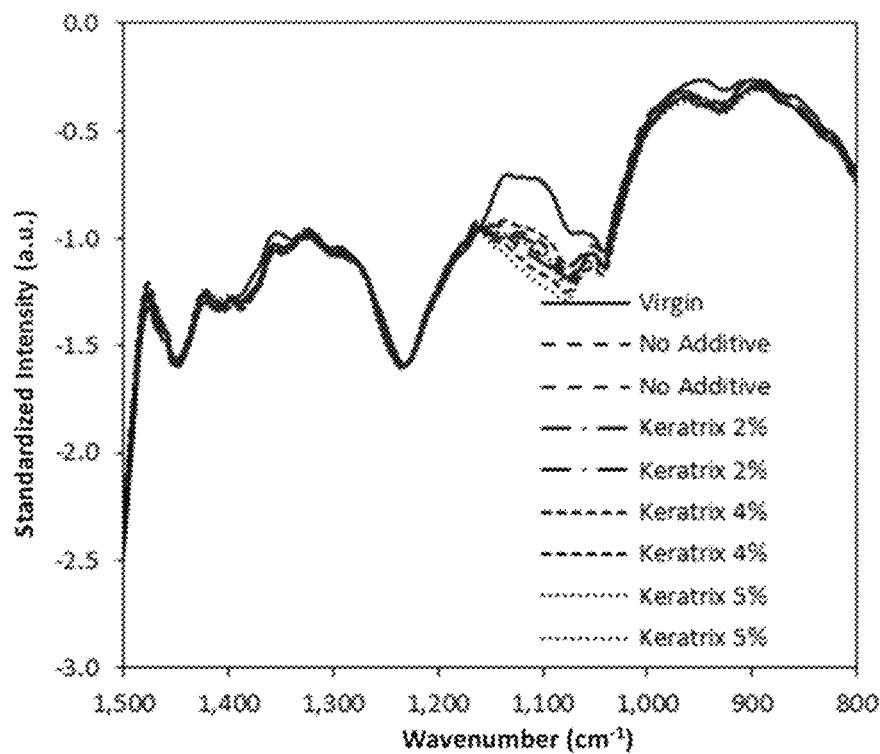
FIG. 48B depicts alkyl peak region of FTIR spectra of hair after semi-simultaneous grafting with an exemplary PEG-diacrylate monomer with various amino acid or peptide mixture additives.

A list of amino acid or peptide mixtures that are already used in personal care industries were also used as additives during grafting. These include blend of vegetable amino acids (sold under the trademark FISION® KeraVeg 18), amino acid blend (sold under the trademark PRODEW® 500), cetearamidoethyldiethonium succinoyl hydrolyzed pea protein (sold under the trademark Vegetamide 18MEA-NJ), cetearamidoethyl diethonium hydrolyzed rice protein (sold under the trademark Vegetamide 18MEA-MR), rice peptides and amino acids (sold under the trademark KERARICE™), carob tree hydrolysate (sold under the trademark KERATRIX™), hydrolyzed keratin (sold under the trademark Promois WK-PD), and low molecular weight vegetable peptides (sold under the trademark GLUADIN® Kera-P LM). The initial screening (Table 17) showed that when added at 2 wt % (with respect to the total grafting mixture) into grafting systems, most amino acid or peptide mixtures did not show any noticeable interference in the grafting efficiency. Furthermore, almost all amino acid or peptide mixture additives led to improved sensory properties. In particular, carob tree hydrolysate (sold under the trademark KERATRIX™) was shown to achieve the most favorable sensory properties. To further optimize the carob tree hydrolysate concentration, grafting with 2 wt %, 4 wt %, and 5 wt % of carob tree hydrolysate additive was further explored. FIG. 48 shows that very similar grafting was achieved at all three different carob tree hydrolysate concentrations. Blinded sensory evaluation also showed that hair tresses grafted with carob tree hydrolysate all led to improved sensory properties compared to the tress grafted with no additive. However, there was no discernable difference among the tresses with different carob tree hydrolysate concentrations. For that reason, 2 wt % was selected as the preferred carob tree hydrolysate concentration.

TABLE 17

Screening of exemplary amino acid or peptide mixtures as additives during semi-simultaneous grafting.

| Experiment | Additives | FTIR Results | Preferred Sensory Properties |
| --- | --- | --- | --- |
| I | rice peptides and amino acids (sold under the trademark KERARICE ™) hydrolyzed keratin (sold under the trademark Promois WK-PD) low molecular weight vegetable peptides (sold under the trademark GLUADIN ® Kera-P LM) | Lower grafting efficiency with rice peptides and amino acids (sold under the trademark KERARICE ™) | All better than no additive control |
| II | blend of vegetable amino acids (sold under the trademark FISION ® KeraVeg 18) amino acid blend (sold under the trademark PRODEW ® 500) carob tree hydrolysate (sold under the trademark KERATRIX ™) | Similar grafting efficiency | carob tree hydrolysate (sold under the trademark KERATRIX ™) |

TABLE 17-continued

Screening of exemplary amino acid or peptide mixtures as additives during semi-simultaneous grafting.

| Experiment | Additives | FTIR Results | Preferred Sensory Properties |
|---|---|---|---|
| III | cetearamidoethyldiethonium succinoyl hydrolyzed pea protein (sold under the trademark Vegetamide 18MEA-NJ) ceteraramidoethyl diethonium hydrolyzed rice protein (sold under the trademark Vegetamide 18MEA-MR) carob tree hydrolysate (sold under the trademark KERATRIX ™) | Lower grafting efficiency with cetearamidoethyldiethonium succinoyl hydrolyzed pea protein (sold under the trademark Vegetamide 18MEA-NJ) | carob tree hydrolysate (sold under the trademark KERATRIX ™) |

Amino Acids and N-Acetyl Amino Acids

Figure 49:
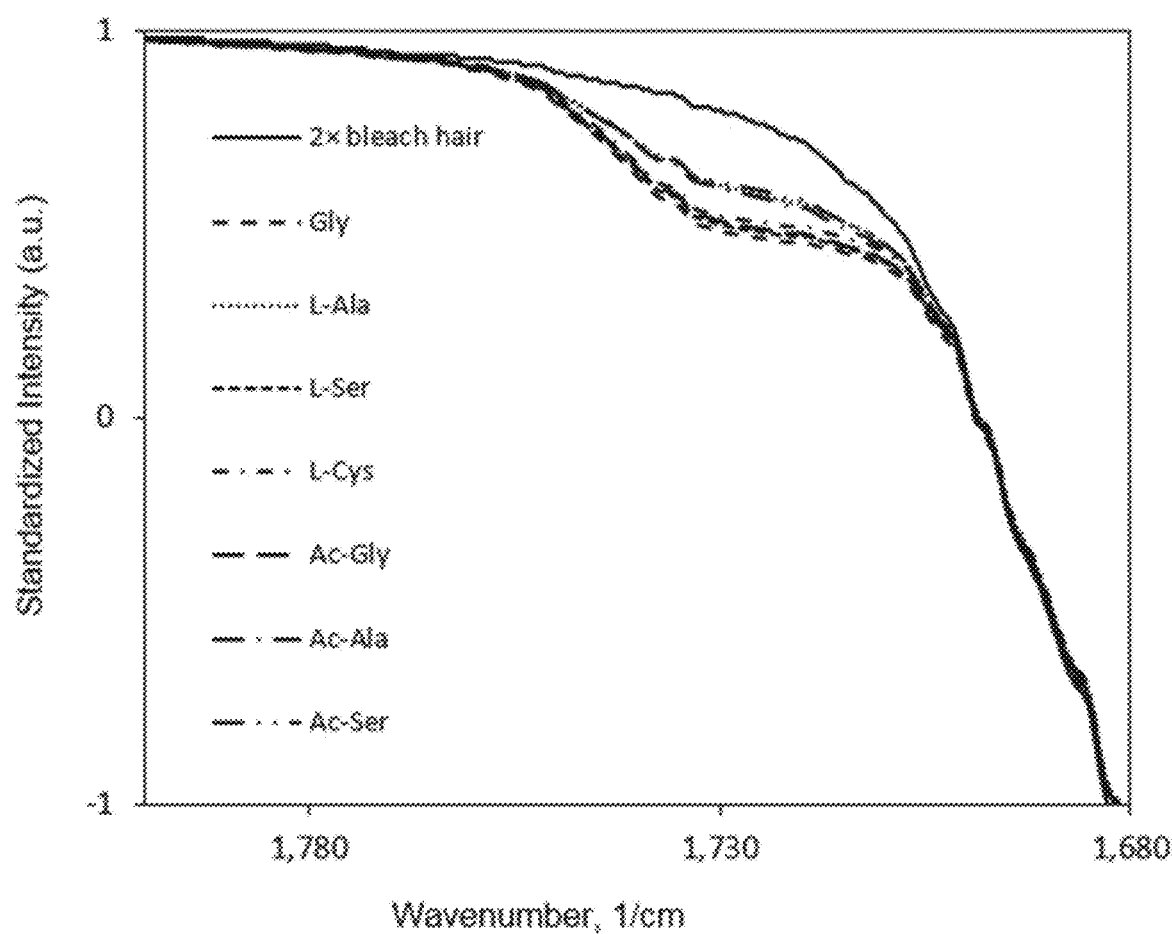
FIG. 49 depicts carbonyl peak region of FTIR spectra of hair after semi-simultaneous grafting with an exemplary PEG-diacrylate monomer with various amino acid or N-acetyl amino acid additives.

The types of amino acid and N-acetyl amino acids screened in this study include glycine (Gly), L-alanine (L-Ala), L-serine (L-Ser), L-cysteine (L-Cys), N-acetyl glycine (Ac-Gly), N-acetyl alanine (Ac-Ala) and N-acetyl serine (Ac-Ser). It was noticed that all hair tresses grafted using monomers with amino acids or N-acetyl amino acids as additives felt very soft and smooth. In FIG. 49, the higher peak intensity of grafting samples in the carbonyl peak region, compared with 2× bleach hair as control, demonstrate successful grafting of PEGDA in the presence of 2 wt % of the following amino acids and N-acetyl amino acids as additives Gly, L-Ala, L-Ser, L-Cys, Ac-Gly, Ac-Ala and Ac-Ser. The grafting efficiency of Gly, L-Ser, L-Cys and Ac-Gly was slightly higher than that of L-Ala, Ac-Ala and Ac-Ser, based on their peak intensity in the carbonyl peak region.

Figure 50:
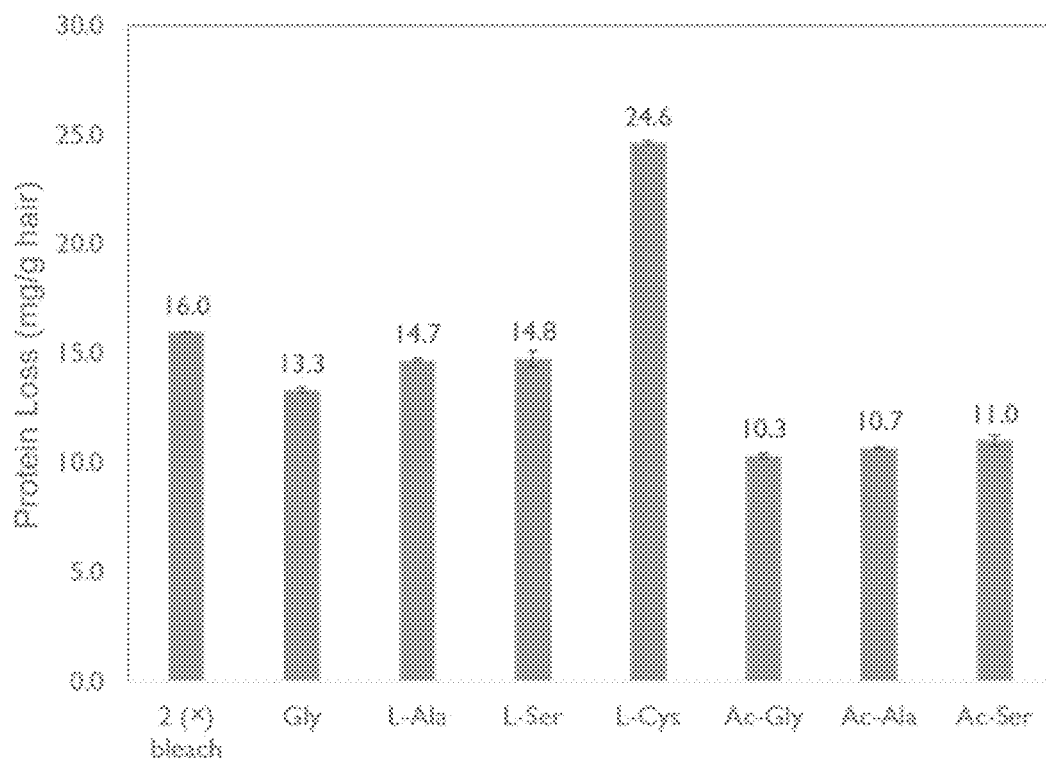
FIG. 50 depicts protein loss values of hair after semi-simultaneous grafting with an exemplary PEG-diacrylate monomer with various amino acid or N-acetyl amino acid additives.

Using the Lowry assay, the protein loss values for grafted hair samples with or without amino acids and N-acetyl amino acids additives were also determined. FIG. 50 showed that certain hair tresses, such as those grafted with Ac-Gly, Ac-Ala or Ac-Ser additives, had lower protein loss values compared with the untreated tress (2× bleach). This indicated that N-acetyl amino acids additives such as Ac-Gly, Ac-Ala or Ac-Ser may provide protection over hair cuticles during grafting and prevent protein loss thereafter.

Figure 51:
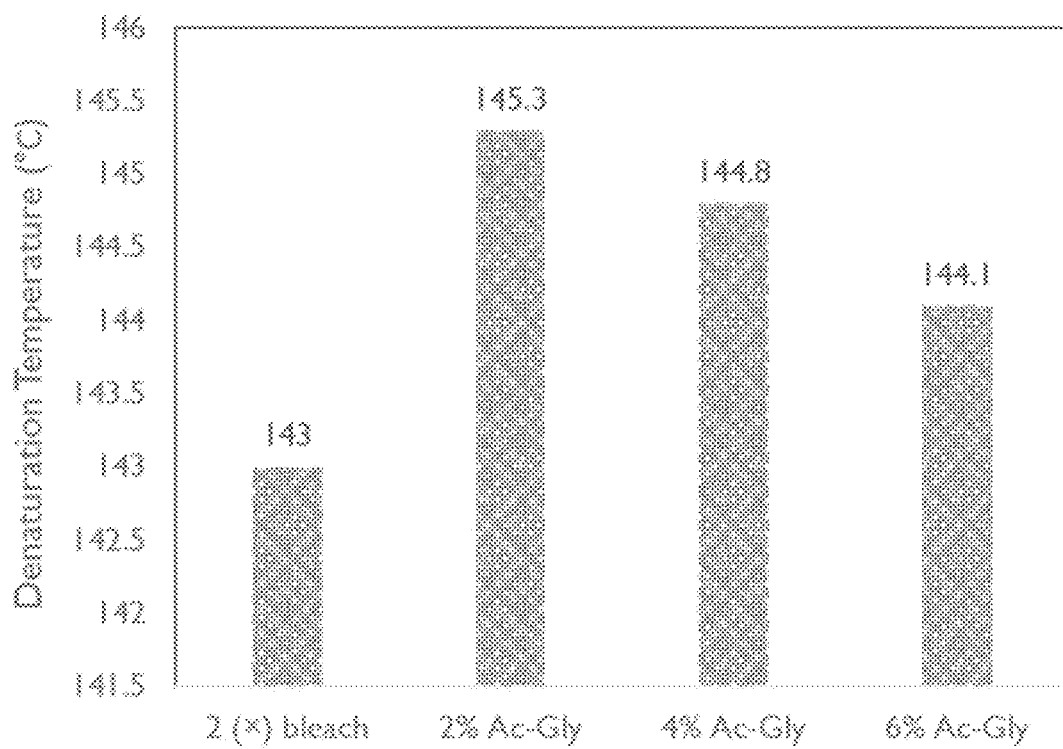
FIG. 51 depicts protein loss values of hair after semi-simultaneous grafting with an exemplary PEG-diacrylate monomer with various concentrations of an exemplary N-acetyl amino acid additive.

Because of the lowest protein loss value associated with it in FIG. 50 and its smallest size among all acetyl amino acids, Ac-Gly was selected for dose response study. 2× bleached brown hair tresses were treated by grafting of PEGDA 700 together with Ac-Gly as additive at 2 wt %, 4 wt %, and 6 wt % concentration. Differential scanning calorimety (DSC) analysis in FIG. 51 showed a slight increase in hair denaturation temperature ($T_d$) for the hair sample grafted with Ac-Gly additive at 2 wt %, 4 wt %, and 6 wt % concentration, suggesting the improvement in hair structural integrity by Ac-Gly. Altogether, the results suggested that the use of amino acids or N-acetyl amino acids like Ac-Gly as additives during grafting may bring in desired sensory properties or healthy benefits.

Acidifiers and Polycarboxylic Acids

Various acidifiers and polycarboxylic acids were explored as additional treatments to improve hair strength. Explored acidifiers and polycarboxylic acids included gluconolactone, citric acid, tartaric acid, and glutamic acid N,N-diacetic acid. Three different ways of including such treatments into a grafting process were explored: pre-treatment, post-treatment, and as additives during grafting. A mixture of gluconolactone (GL) and citric acid (CA) (mix: GLCA) was used as a model system. There were four main parameters that were explored for the application of solutions such as liquor ratio, reaction time, composition, and pH. The preferred parameters are shown in Table 18.

TABLE 18

Preferred parameters for semi-simultaneous grafting with gluconolactone and citric acid treatments

| Parameter | Range Investigated | Pre-Treatment | Additives | Post-Treatment |
|---|---|---|---|---|
| Liquor Ratio | 0.5:1 to 1.1:1 | 1.1:1 | 1.1:1 | 1.1:1 |
| Composition | 0.5% GL to 4% GL | 2% GL | 2% GL | 2% GL |
| | 0.5% CA to 4% CA | 2% CA | 2% CA | 2% CA |
| Reaction Time | 2 min to 1 h | 30 min | 30 min | 2-15 min |
| pH | 2-5 | 2 | N/A | 2-5 |

Gluconolactone/Citric Acid Pre-Treatment

Pre-treatment solutions of a mixture of gluconolactone and citric acid were applied to dry hair and left there for a certain period of time and then completely rinsed out of the hair. Grafting was then performed on the pre-treated tresses. Grafting performance was slightly decreased after pre-treatments for 15 and 30 minutes as observed by FTIR. In addition, hair denaturation temperature stayed about the same as that of the untreated hair only for the 30 minutes GLCA pre-treatment followed by grafting. No statistically significant benefits in terms of hair protein loss was observed after either 15 or 30 minutes of pre-treatment as compared to the grafting alone.

Gluconolactone/Citric Acid as Additives

The effects of addition of gluconolactone, citric acid, and a mixture of thereof either to the monomer solution or to the reducing solution also were explored. When added into monomer solution, a decrease in grafting efficiency was observed only in the presence of citric acid. Addition of citric acid and of the mixture of gluconolactone and citric acid into monomer solution contributed to the increase in the denaturation temperature, while addition of gluconolactone did not show any statistically significant benefits. Addition of gluconolactone and citric acid into reducing solution also did not show any statistically significant benefits.

Gluconolactone/Citric Acid Post-Treatment

Post-Treatment Time

Figure 52A:
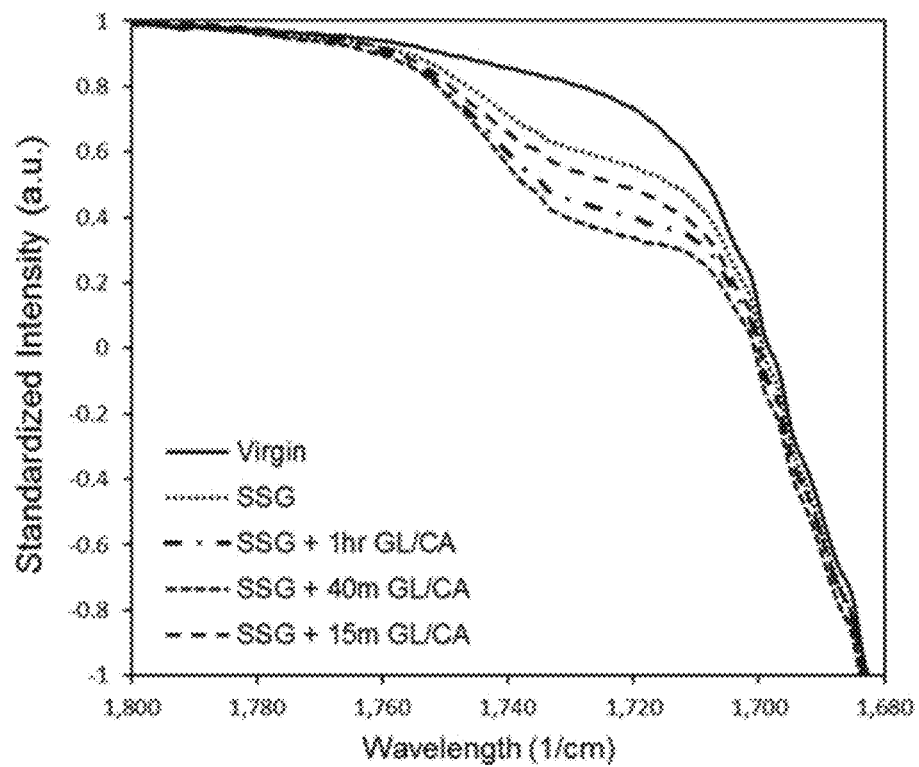
FIG. 52A depicts carbonyl peak region of FTIR spectra of hair after semi-simultaneous grafting with an exemplary PEG-diacrylate monomer with gluconolactone and citric acid with various post-treatment times.
Figure 52B:
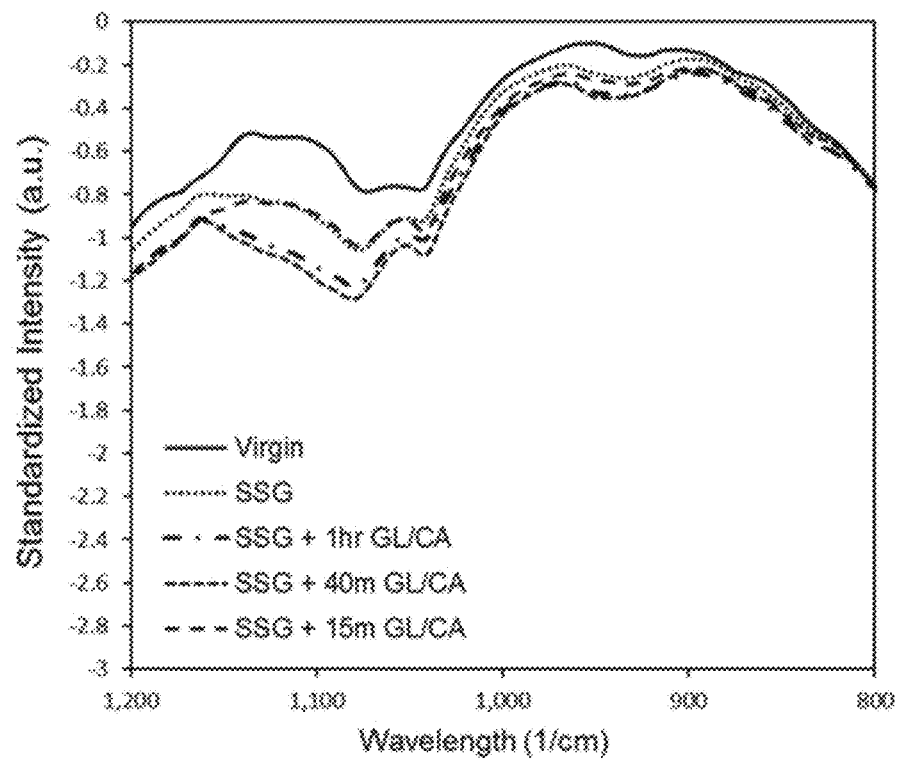
FIG. 52B depicts alkyl peak region of FTIR spectra of hair after semi-simultaneous grafting with an exemplary PEG-diacrylate monomer with gluconolactone and citric acid with various post-treatment times.
Figure 53A:
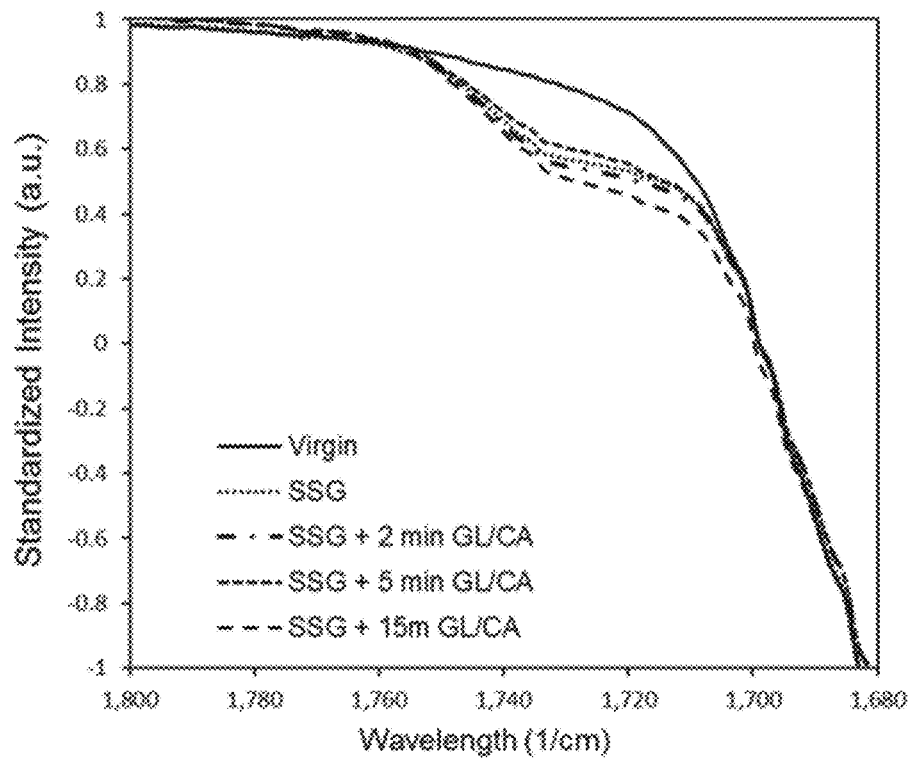
FIG. 53A depicts carbonyl peak region of FTIR spectra of hair after semi-simultaneous grafting with an exemplary PEG-diacrylate monomer with gluconolactone and citric acid with various post-treatment times.
Figure 53B:
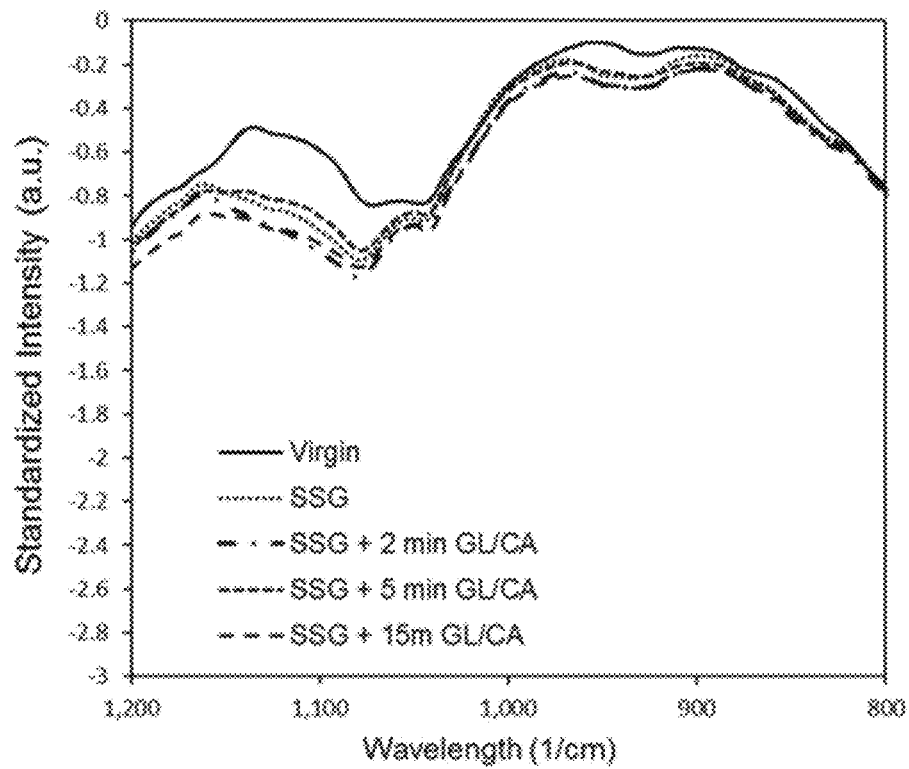
FIG. 53B depicts alkyl peak region of FTIR spectra of hair after semi-simultaneous grafting with an exemplary PEG-diacrylate monomer with gluconolactone and citric acid with various post-treatment times.

Post-treatment solutions were applied to the wet (towel dried) hair after grafting reaction was done and was completely rinsed out of the hair. The period of time of how long the post-treatment solution stays on hair was varied between 2 minutes and 1 hour to find the preferred conditions. For these experiments, the concentration of gluconolactone and citric acid was kept at 2 wt % each. Grafting after all conditions was confirmed by the presence of carbonyl peaks at 1730 cm$^{-1}$ and by the presence of —CH peaks in the FTIR spectra. All spectra shown are of hair tresses after thorough washing with sodium laureth sulfate (SLES) solution. As can be seen in FIGS. 52A, 52B, 53A, and 53B, grafting efficiency was not sacrificed, even further carbonyl peaks increased slightly after addition of gluconolactone and citric acid post-treatments. Without being bound by any theory, the further carbonyl peaks are possibly due to the additional carbonyl groups from the citric acid (FIG. 52A).

Figure 54:
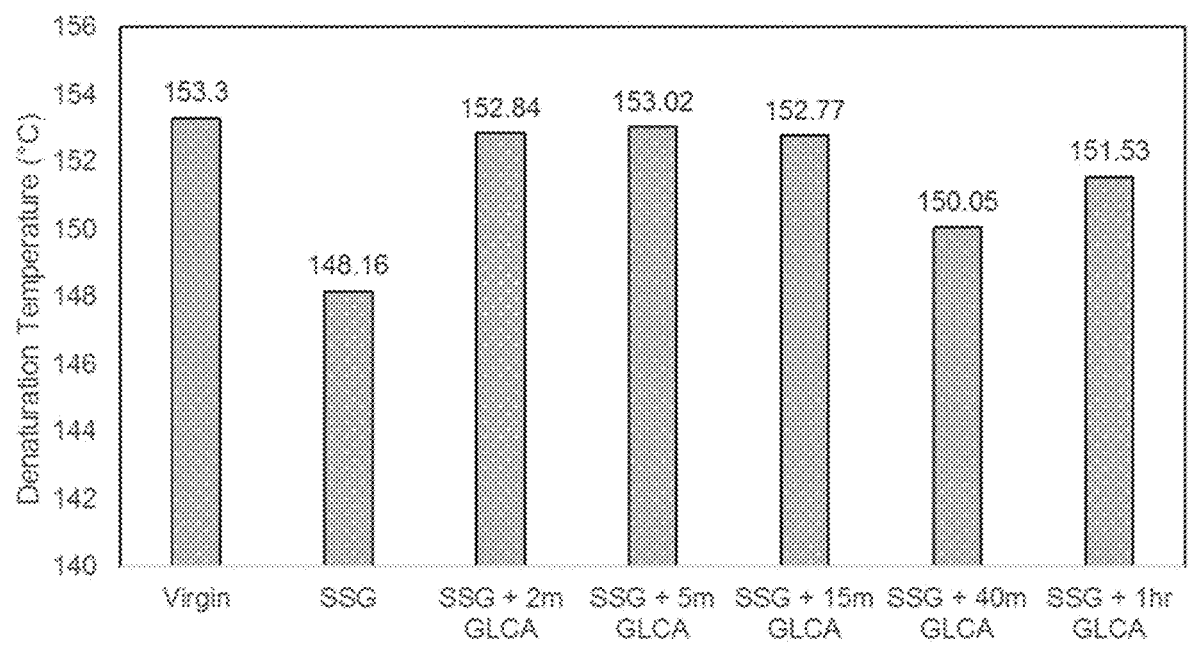
FIG. 54 depicts denaturation temperatures of untreated hair and of hair after semi-simultaneous grafting with an exemplary PEG-diacrylate monomer and post-treatment with gluconolactone and citric acid.

FIG. 54 represents denaturation temperatures ($T_d$) of the untreated hair (virgin) and hair after grafting and after gluconolactone and citric acid post-treatments. It was found that post-treatment times of 2, 5 or 15 minutes resulted in the $T_d$ similar to that of the untreated hair samples indicating that hair has not been damaged over the course of grafting and gluconolactone and citric acid post-treatments. Post-treatment for 2 minutes was found to be sufficient to bring the denaturation temperature to the level of the untreated hair indicating that no damage has been incurred on the hair samples.

Figure 55:
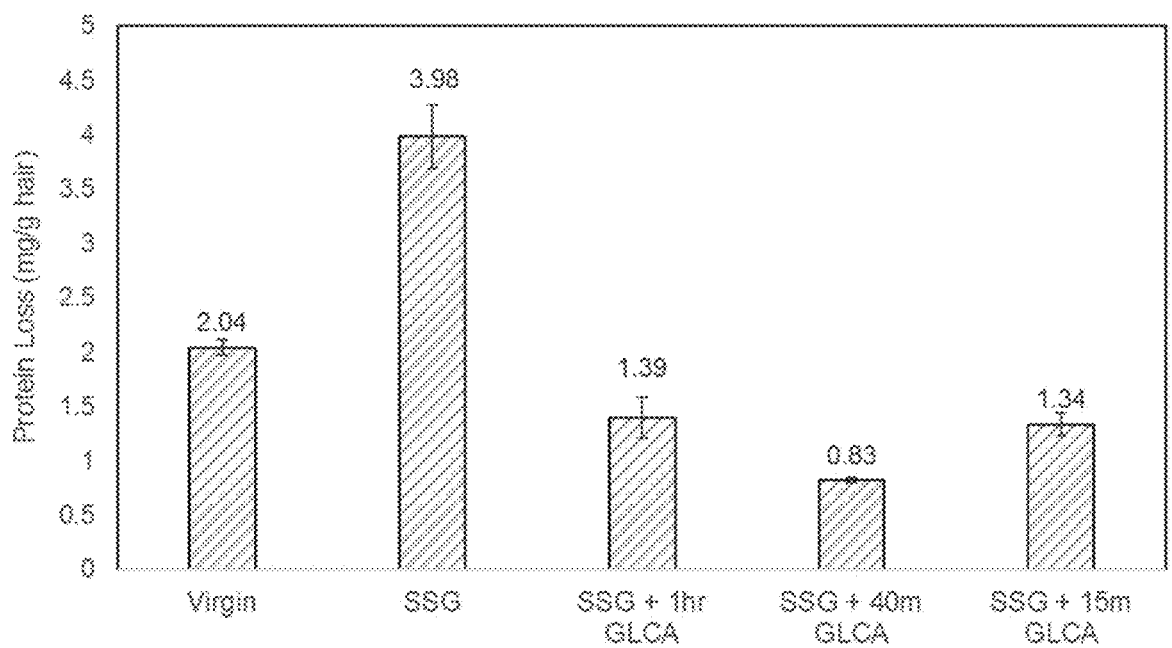
FIG. 55 depicts protein loss values of hair after semi-simultaneous grafting with an exemplary PEG-diacrylate monomer and a gluconolactone and citric acid post-treatment applied for various time periods.

FIG. 55 represents protein loss values for the untreated hair samples (virgin) and hair samples after semi-simultaneous grafting (SSG) and gluconolactone and citric acid (GLCA) post-treatments applied for the various period of times between 15 minutes and 1 hour. No dependence of time was found with respect to protein loss but addition of GLCA post-treatments dramatically lowered protein loss indicating healthier hair surface which prevents leaching out of the proteins.

pH

Figure 56A:
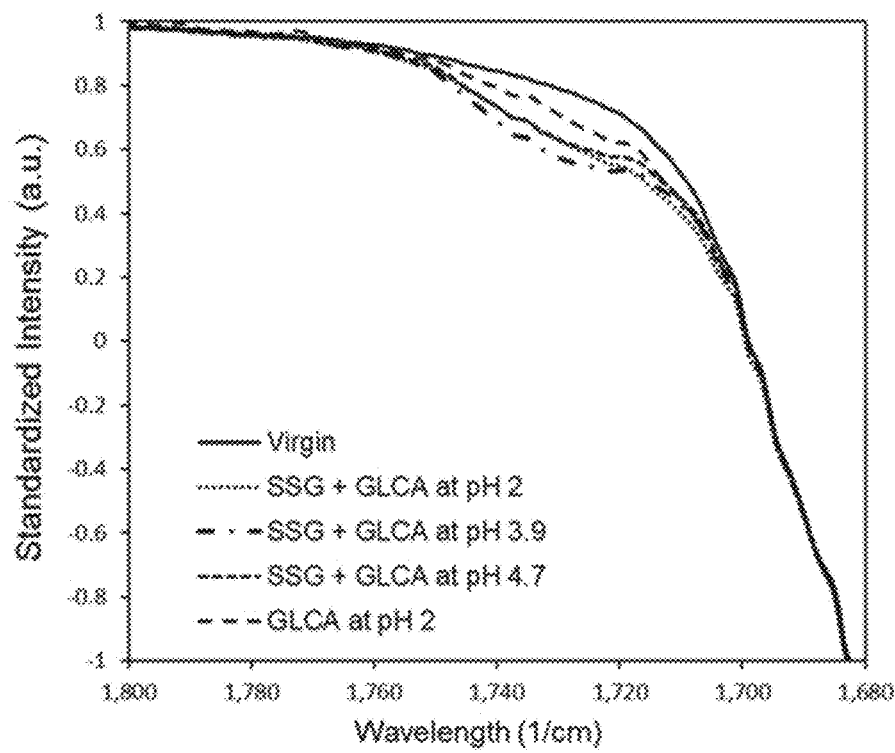
FIG. 56A depicts carbonyl peak region of FTIR spectra of hair after semi-simultaneous grafting with an exemplary PEG-diacrylate monomer and post-treatment with gluconolactone and citric acid at different pH values.
Figure 56B:
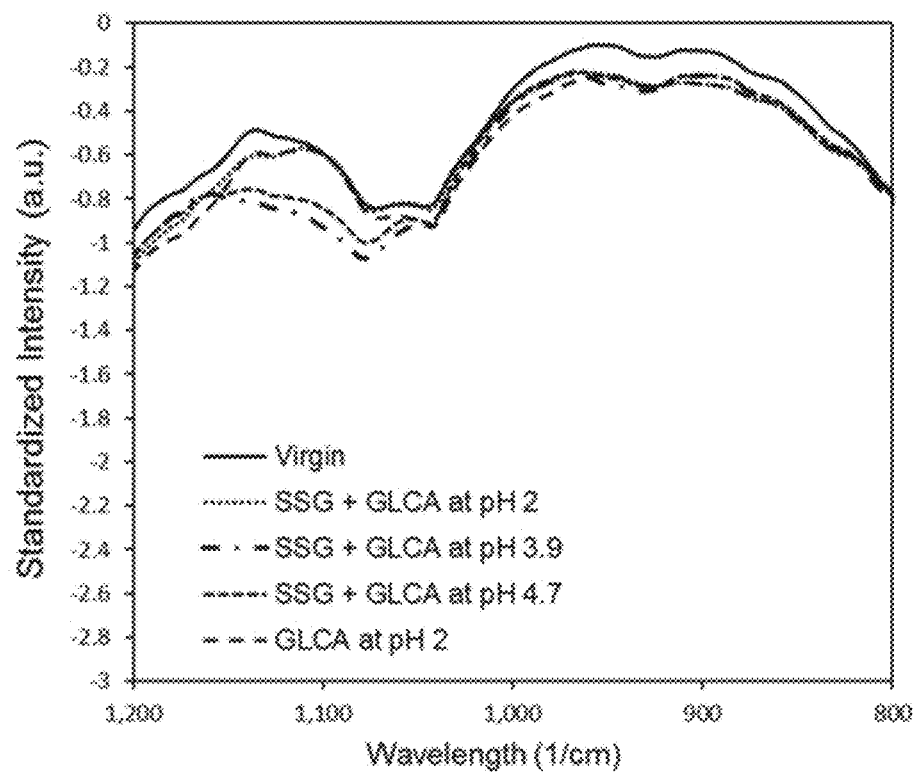
FIG. 56B depicts alkyl peak region of FTIR spectra of hair after semi-simultaneous grafting with an exemplary PEG-diacrylate monomer and post-treatment with gluconolactone and citric acid at different pH values.
Figure 57:
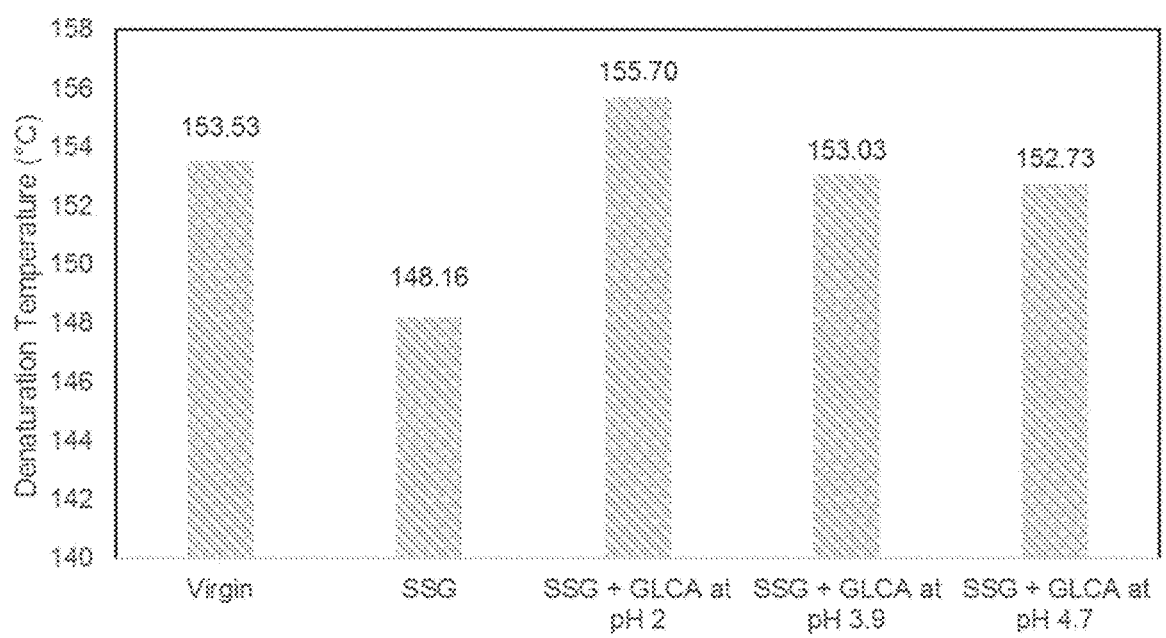
FIG. 57 depicts denaturation temperatures of untreated hair and of hair after semi-simultaneous grafting with an exemplary PEG-diacrylate monomer and post-treatment with gluconolactone and citric acid at different pH values.

The natural pH of the gluconolactone and citric acid mixture is around 2, so a wider pH range was explored. FIGS. 56A and 56B show FTIR spectra of hair samples after grafting and gluconolactone and citric acid post-treatments at various pH values. As can be seen, minimal changes in grafting efficiency were observed. In addition, denaturation temperature was the highest for the post-treatment at pH of 2 indicating improved hair strength as compared to the untreated, while post-treatments at pH values of 3.9 and 4.7 resulted in the unchanged $T_d$ compared to the untreated hair indicating no damage has been inflicted on the hair (FIG. 57).

Composition

Figure 58A:
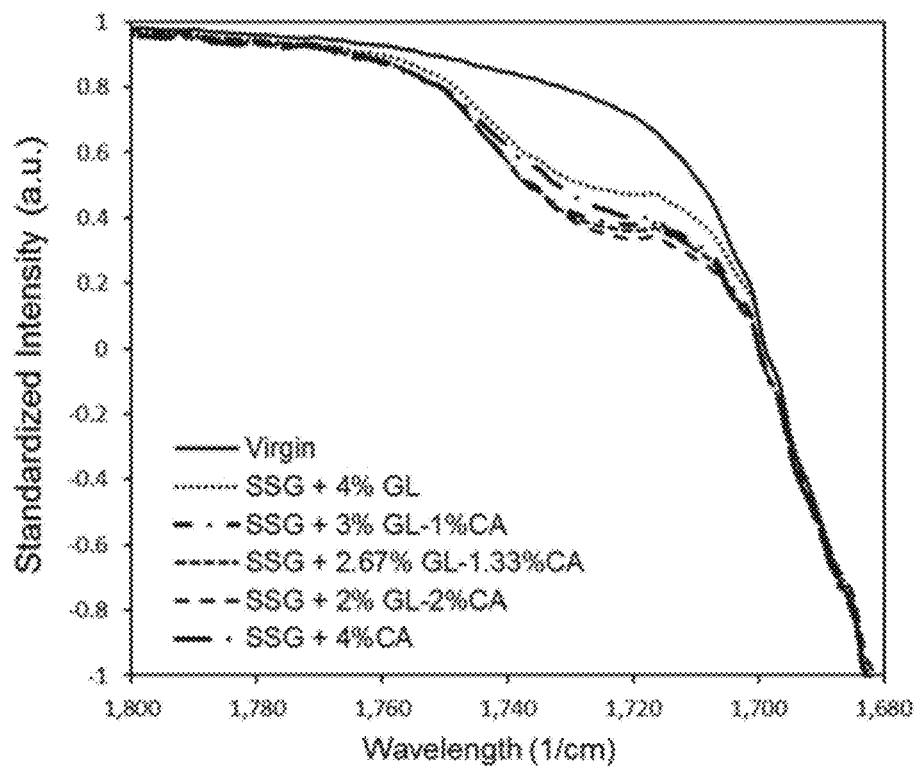
FIG. 58A depicts carbonyl peak region of FTIR spectra of hair after semi-simultaneous grafting with an exemplary PEG-diacrylate monomer and post-treatment with gluconolactone and citric acid at different concentrations.
Figure 58B:
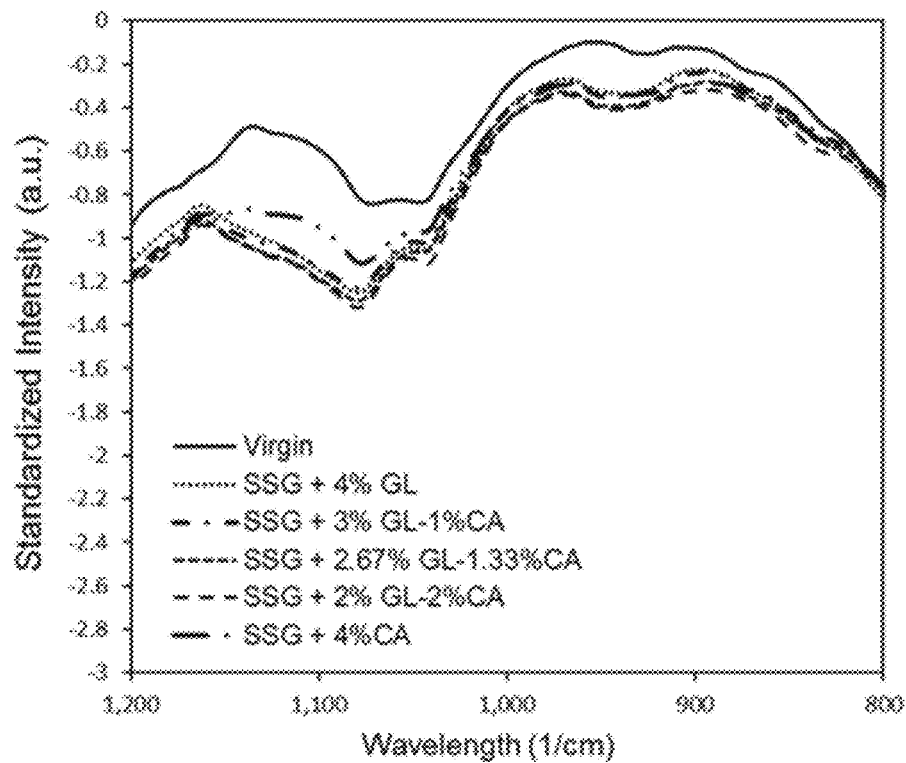
FIG. 58B depicts alkyl peak region of FTIR spectra of hair after semi-simultaneous grafting with an exemplary PEG-diacrylate monomer and post-treatment with gluconolactone and citric acid at different concentrations.
Figure 59:
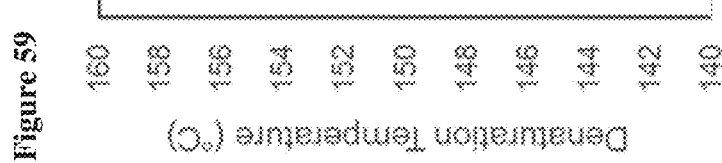
FIG. 59 depicts denaturation temperatures of untreated hair and of hair after semi-simultaneous grafting with an exemplary PEG-diacrylate monomer and post-treatment with gluconolactone and citric acid at different concentrations.

Another parameter that was explored for the gluconolactone and citric acid post-treatment was composition. The effect of using gluconolactone alone or citric acid alone was explored. For all experiments, the total concentration of these components was kept at 4 wt %. As can be seen from FIGS. 58A and 58B, grafting efficiency was not sacrificed with the various compositions. Varying concentrations of gluconolactone and citric acid or using these components alone at 4 wt % concentration results in the $T_d$ similar to that of untreated hair and no dependence on the concentration was observed (FIG. 59).

Addition of gluconolactone and citric acid mixture as pre-treatment, post-treatment, and as additives was explored. It was found that specifically when GLCA mixture was applied as a post-treatment, improvement in denaturation temperature of hair and decrease in protein loss, all of which indicate healthier hair state, were observed. In addition, it was found that post-treatment could be as short as 2 minutes long and was applicable over a wide pH range (2-4.7).

The gluconolactone and citric acid mixture was also incorporated into conditioner and used as a conditioner treatment after grafting. Neither denaturation temperature nor protein loss were affected by such incorporation meaning that GLCA could be easily incorporated into conditioners and improve the overall strength of the hair.

Gluconolactone and citric acid mixture was also explored as a leave-on treatment after grafting. It was found that low concentrations of gluconolactone and citric acid of either 1 wt % or 0.5 wt % each was sufficient for observed improved $T_d$ and protein loss benefits. The post-treatment could be left on the hair for up to 48 hours and is easily washed off with a shampoo and conditioner.

Such gluconolactone and citric acid (GLCA) post-treatment was also found especially beneficial on the damaged hair such as hair damaged by bleaching. It was found that denaturation temperature after grafting and GLCA post-treatment could be improved to the level of untreated (non-bleached, virgin) hair and protein loss could be dramatically decreased making the initially severely damaged hair stronger and less porous. Unlike commercial treatments, which make hair even more damaged (higher protein loss and lower denaturation temperatures), grafting followed by GLCA post-treatment makes hair stronger and healthier (FIGS. 60A and 60B).

Additional Polycarboxylic Acid Screening

Figure 61A:
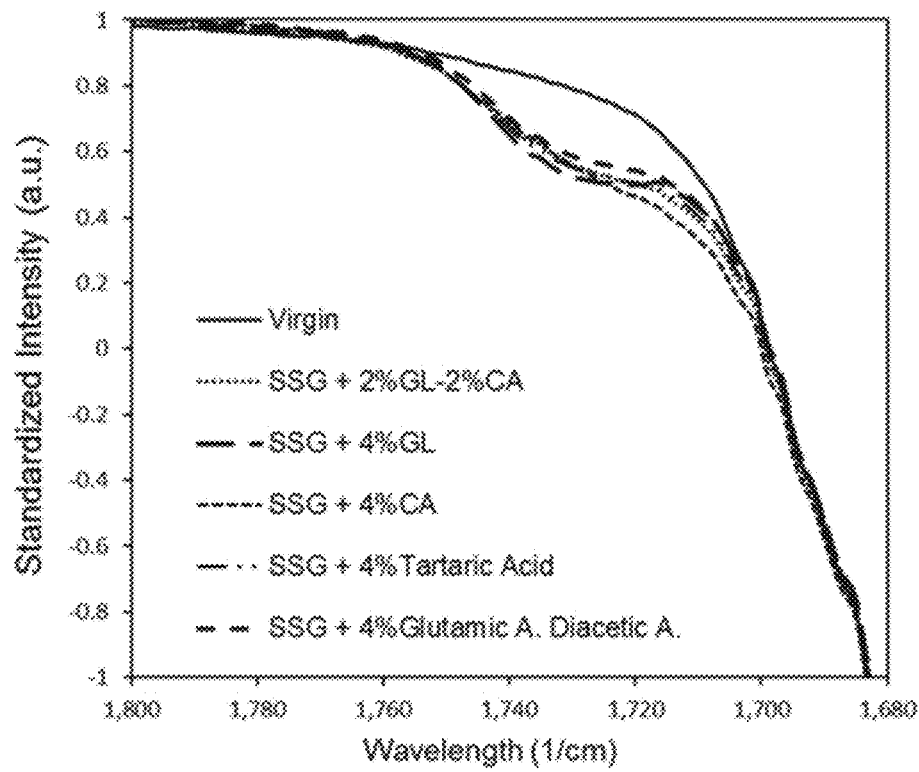
FIG. 61A depicts carbonyl peak region of FTIR spectra of hair after semi-simultaneous grafting with an exemplary PEG-diacrylate monomer and post-treatment with gluconolactone or various polycarboxylic acids.
Figure 61B:
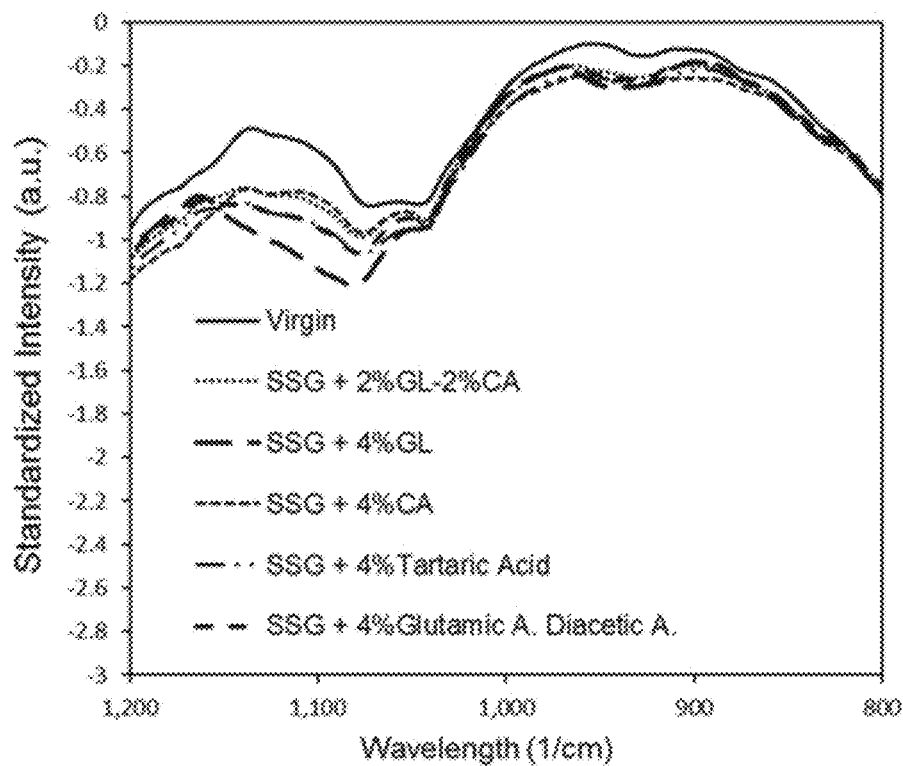
FIG. 61B depicts alkyl peak region of FTIR spectra of hair after semi-simultaneous grafting with an exemplary PEG-diacrylate monomer and post-treatment with gluconolactone or various polycarboxylic acids.
Figure 62:
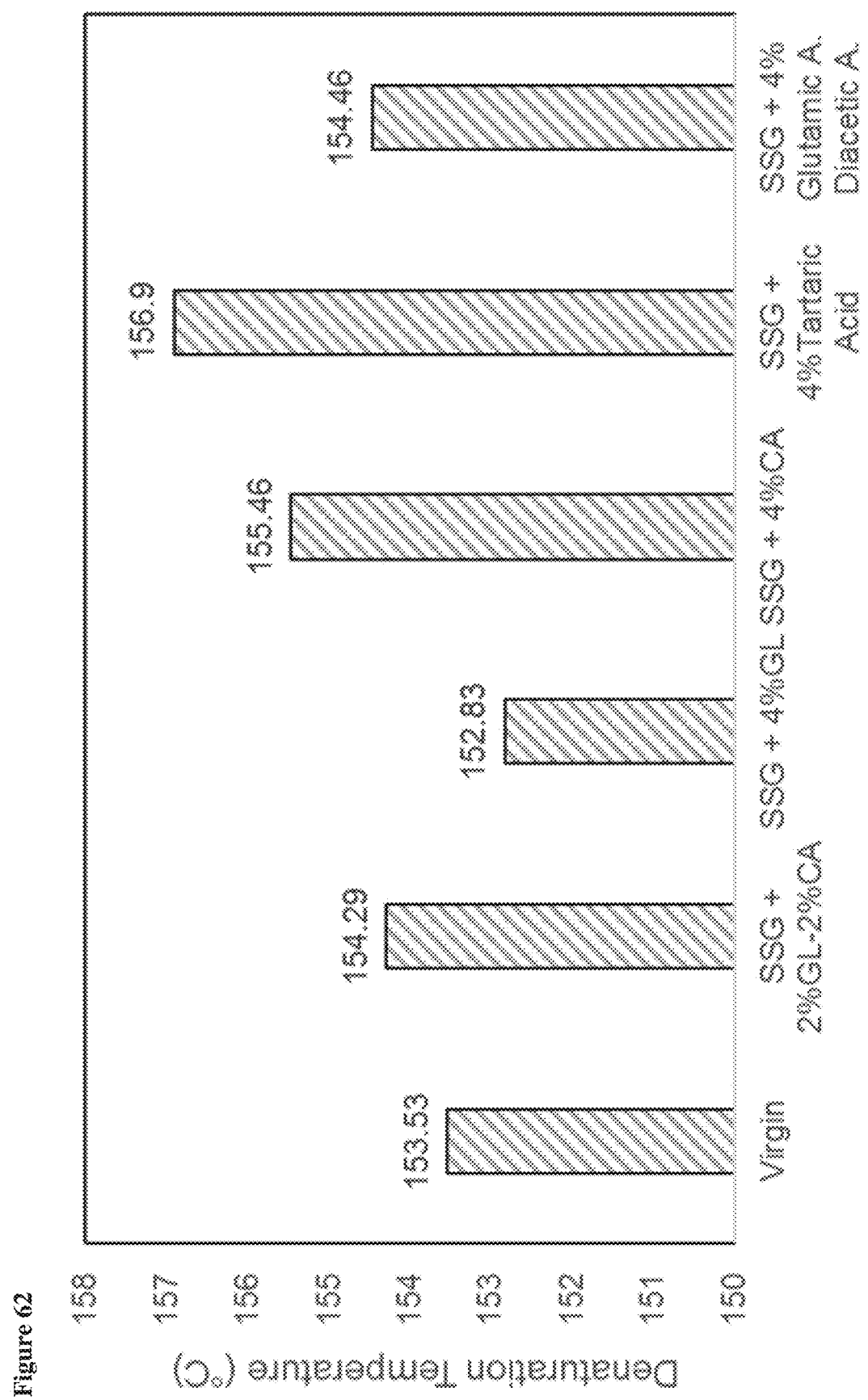
FIG. 62 depicts denaturation temperatures of untreated hair and of hair after semi-simultaneous grafting with an exemplary PEG-diacrylate monomer and post-treatment with gluconolactone or various polycarboxylic acids.
Figure 63A:
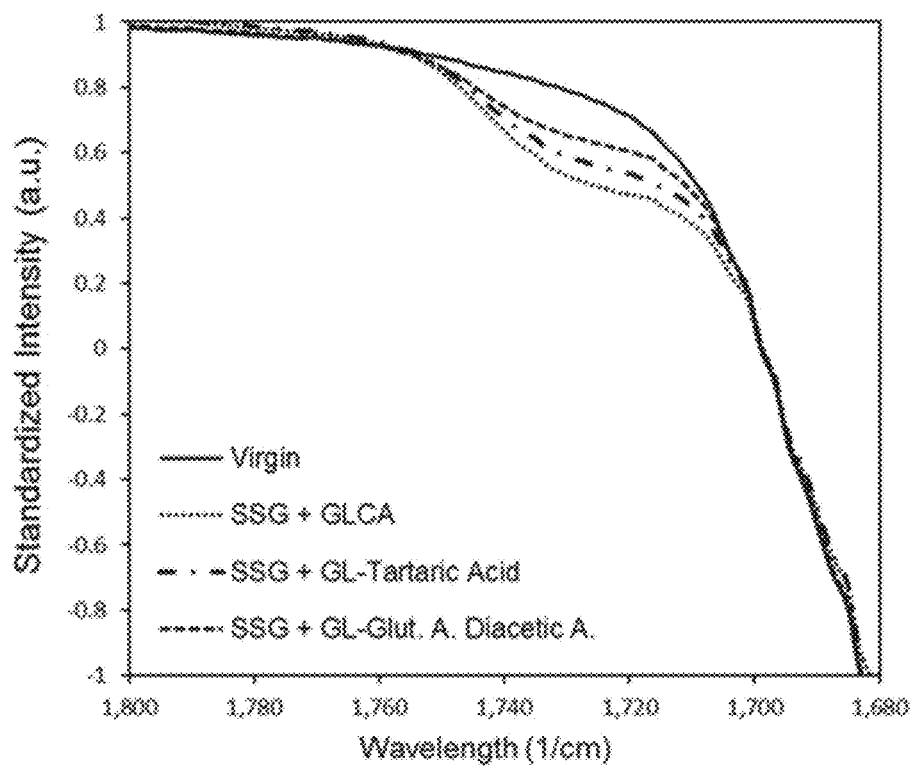
FIG. 63A depicts carbonyl peak region of FTIR spectra of hair after semi-simultaneous grafting with an exemplary PEG-diacrylate monomer and post-treatment with gluconolactone or various polycarboxylic acids.
Figure 63B:
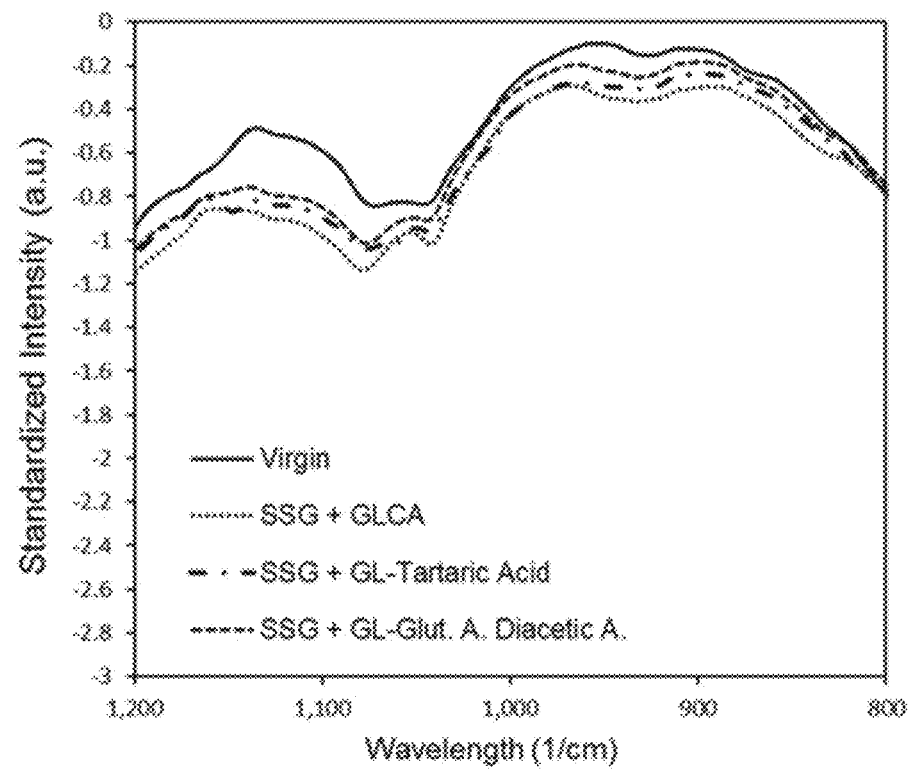
FIG. 63B depicts alkyl peak region of FTIR spectra of hair after semi-simultaneous grafting with an exemplary PEG-diacrylate monomer and post-treatment with gluconolactone or various polycarboxylic acids.
Figure 64:
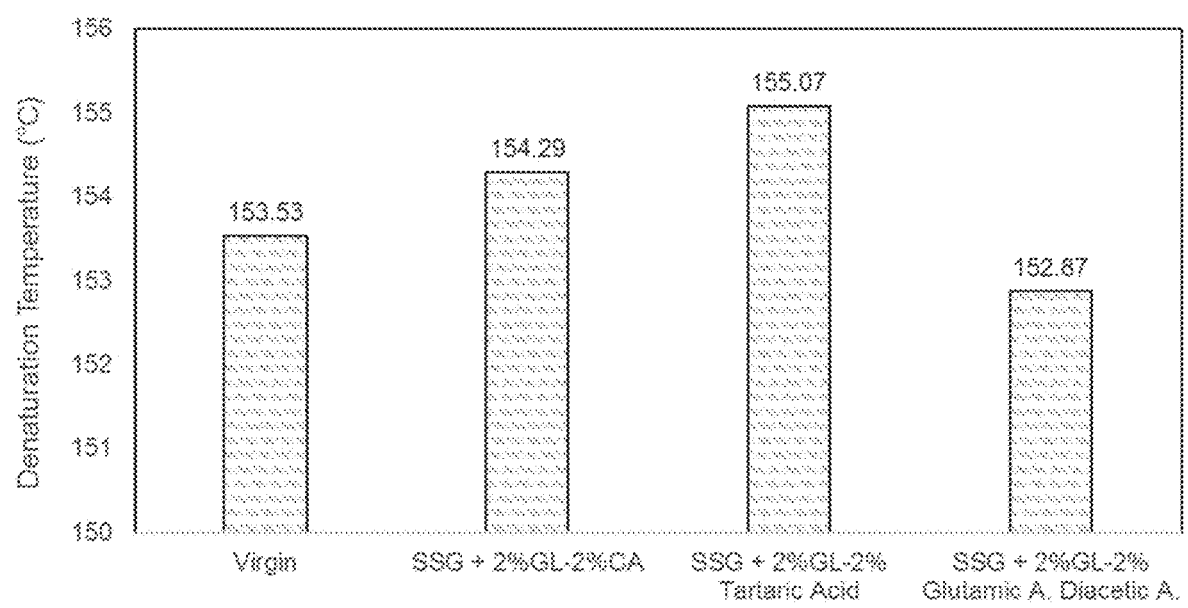
FIG. 64 depicts denaturation temperatures of untreated hair and of hair after semi-simultaneous grafting with an exemplary PEG-diacrylate monomer and post-treatment with gluconolactone or various polycarboxylic acids.

In addition to the gluconolactone and citric acid, the use of other polycarboxylic acids applied as a post-treatments after grafting process also was explored. Initial screening included gluconolactone and polycarboxylic acids such as citric acid, tartaric acid, and glutamic acid N,N-diacetic acid. As can be seen from FIGS. 61A and 61B, no sacrifice in grafting efficiency was observed after post-treatments with any of these materials. In addition, post-treatments with gluconolactone or various polycarboxylic acids, also did not show any sacrifice in grafting efficiency (FIGS. 63A and 63B). As can be seen from FIGS. 62 and 64 post-treatments that involved tartaric acid (either tartaric acid alone at 4 wt % or a mixture of gluconolactone and tartaric acid at 2 wt %-2 wt % concentration each) resulted in an increase in $T_d$ compared to the untreated hair indicating improved hair strength. Post-treatments with 4% gluconolactone alone and with a mixture of gluconolactone and glutamic acid N,N-diacetic acid resulted in slight decrease in $T_d$, however insignificant, indicating that hair did not get damaged after grafting and post-treatment process. None of the conditions showed dramatic decrease in $T_d$ indicating that hair did not get damaged after the grafting and post-treatment process.

Aside from gluconolactone and citric acid, the use of other polycarboxylic acids such as tartaric acid and glutamic acid N,N-diacetic acid led to desired properties.

Example 5—Long-Lasting In Vitro Performance

Figure 65A:
FIG. 65A depicts initial images of untreated hair and of hair after semi-simultaneous grafting with an exemplary PEG-diacrylate monomer.
Figure 65B:
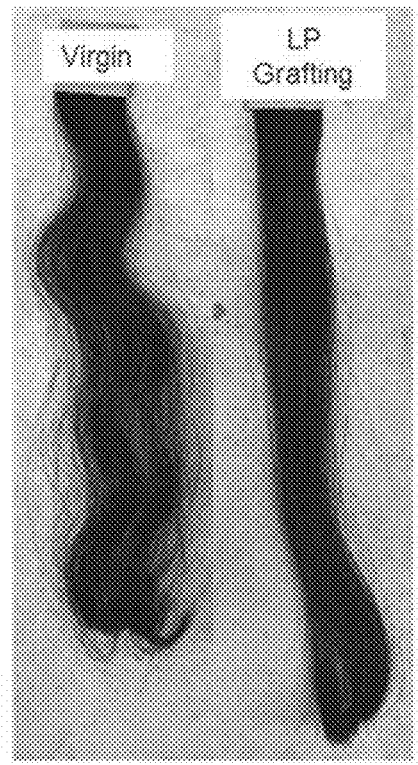
FIG. 65B depicts images of untreated hair and of hair after semi-simultaneous grafting with an exemplary PEG-diacrylate monomer after 15 shampoo and conditioner washes.

Long-lasting performance of the grafting process was first evaluated on the wavy frizzy hair tresses. 5 wt % ammonium thioglycolate reducing solution at a pH of about 9.5 and a liquor ratio of 1.1:1 was applied to wavy/frizzy hair tresses followed by application of PEG-diacrylate 1.5 k at a monomer-to-thiol ratio of about 0.2:1 in a semi-simultaneous process. The grafting treatment was carried out for 30 minutes. After thoroughly rinsing tresses, a post-treatment with a 2% gluconolactone and 2% citric acid solution was applied for 15 minutes. Hair was then blow dried and flat ironed. Tresses were washed 15 times with shampoo and conditioner to mimic long-lastingness over 1-2 months after received grafting treatment. As can be seen in FIGS. 65A and 65B, the initial straightening effect was well preserved after 15 washes.

Figure 66:
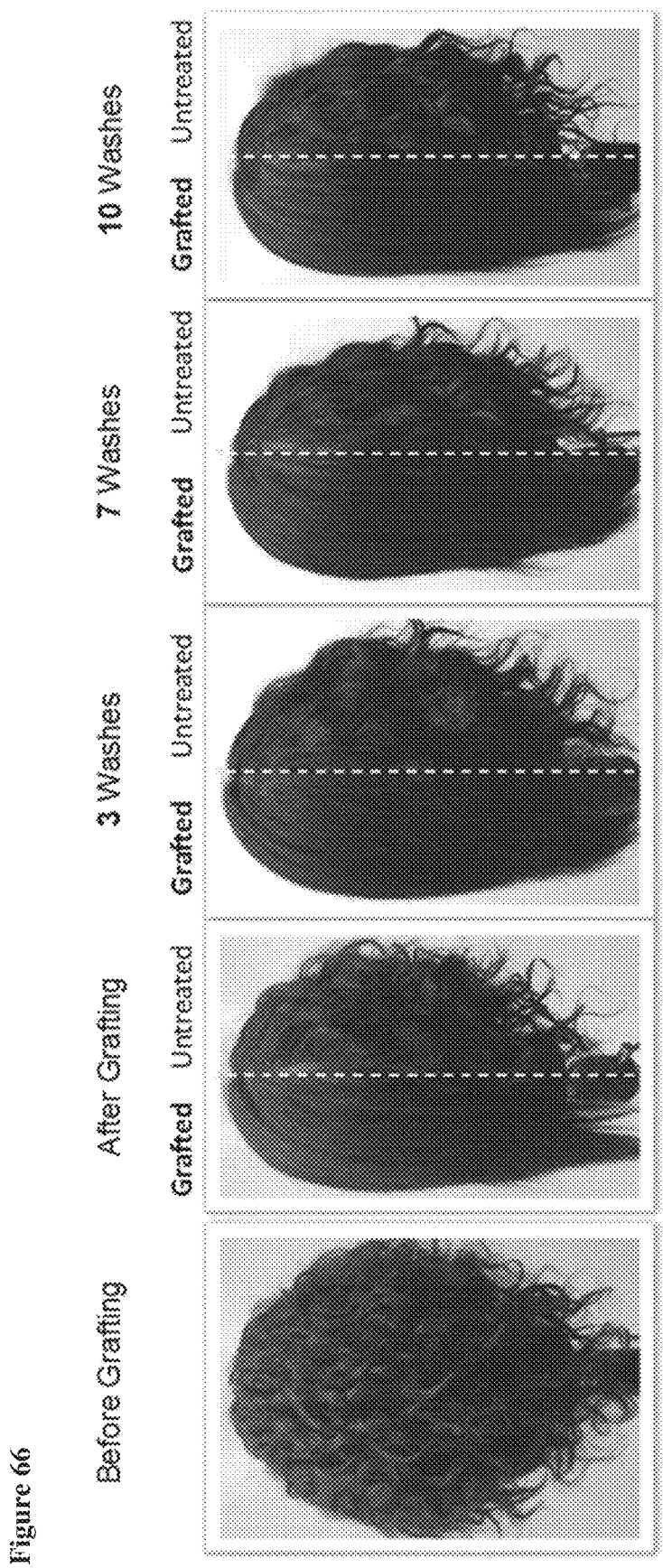
FIG. 66 depicts images showing a mannequin with wavy hair with one side grafted with an exemplary PEG-diacrylate monomer (left) and one side untreated (right) immediately after grafting and after 3, 7, and 10 washes, respectively.

Various testing on mannequin heads was conducted to evaluate the performance of a semi-simultaneous grafting process using 5 wt % ammonium thioglycolate reducing solution at a pH of about 9.5 and a liquor ratio of 1.1:1 followed by application of PEG-diacrylate 2 k at a monomer-to-thiol ratio of about 0.04:1. The grafting treatment was carried out for 30 minutes. After thoroughly rinsing the mannequin, a mixture of 2% gluconolactone and 2% citric acid was applied as a post-treatment for 15 minutes. Hair was then blow dried and flat ironed. FIG. 66 shows that grafting on a wavy/curly mannequin resulted in effective straightening and improved fiber alignment. Sensory evaluation also shows that the grafted hair felt smoother, softer, and more conditioned in comparison to the untreated hair. Both straightening and sensory benefits lasted for at least 10 times SLES washes (FIG. 66).

Figure 67:
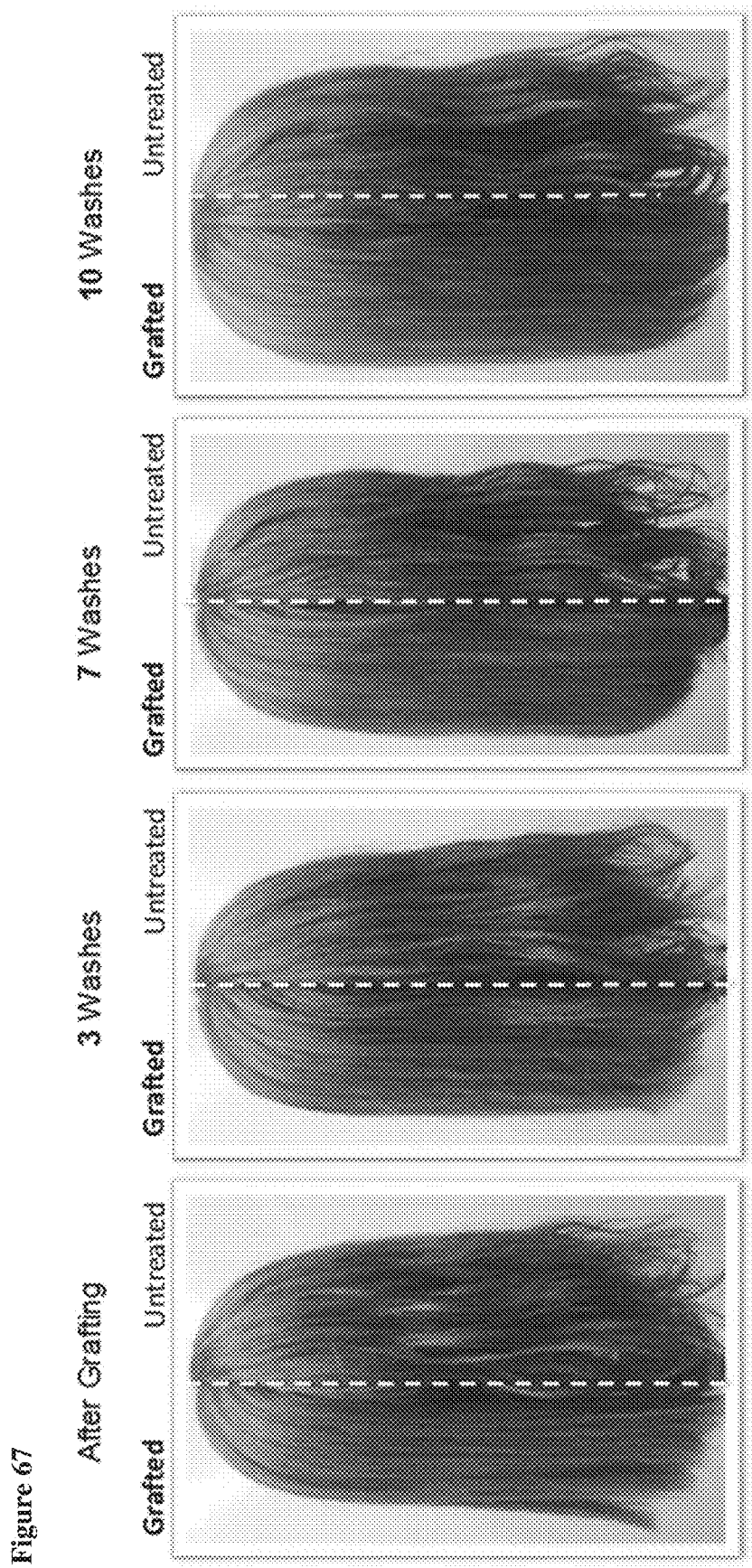
FIG. 67 depicts images showing a mannequin with frizzy hair with one side grafted with an exemplary PEG-diacrylate monomer (left) and one side untreated (right) immediately after grafting and after 3, 7, and 10 washes, respectively.

Grafting on a straight but frizzy mannequin under the conditions described above also resulted in much straighter, shinier, and less frizzy hair (FIG. 67). Sensory evaluation showed that the grafted hair felt softer, smoother, and more conditioned in comparison to the untreated hair. Washing studies showed that hair remained straight, smooth, soft, and conditioned for at least 10 SLES washes.

Figure 68:
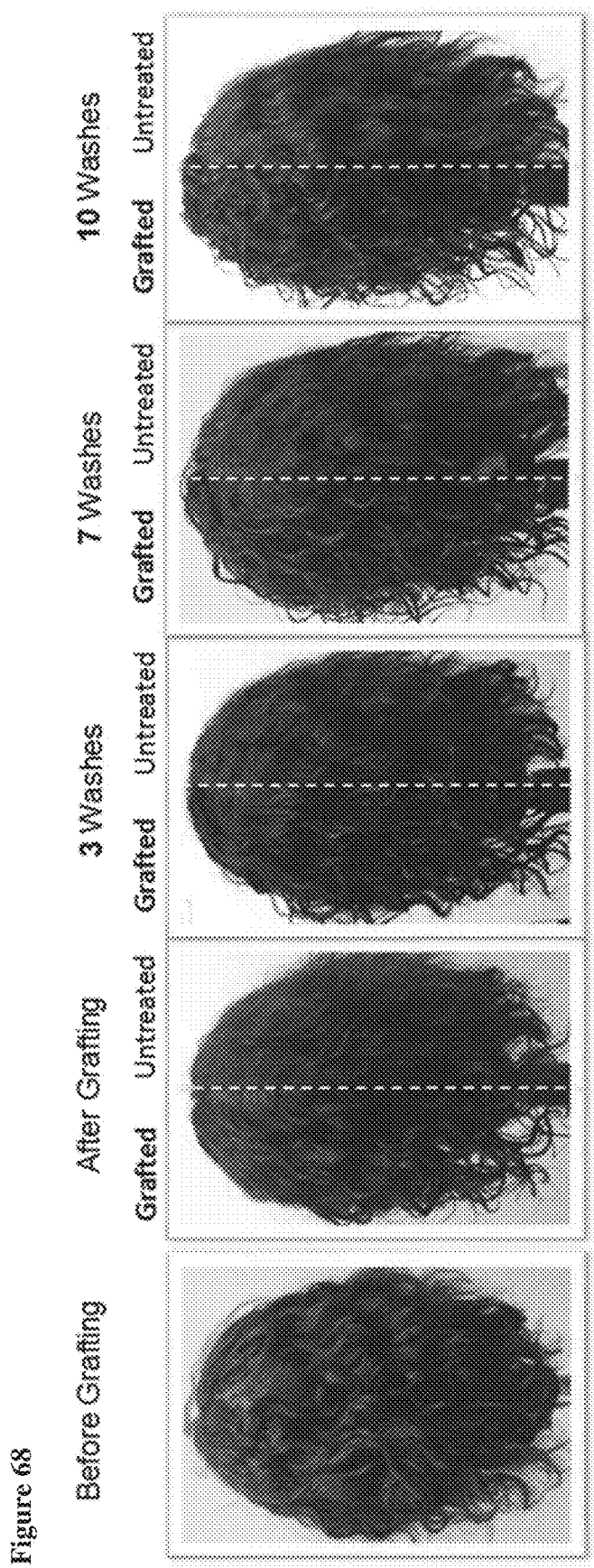
FIG. 68 depicts images showing a mannequin with wavy hair with one side grafted with an exemplary PEG-diacrylate monomer to enhance natural curl (left) and one side untreated (right) immediately after grafting and after 3, 7, and 10 washes, respectively.

Grafting on a wavy mannequin to enhance natural curl definition was also performed. It was clear that grafting resulted in much less frizzy and better curl definition in comparison to the untreated hair (FIG. 68). The curls remained well defined even after washing with SLES 10 times. Sensory evaluation also showed that the grafted hair feels softer, stronger, and more conditioned in comparison to the untreated hair.

Figure 69:
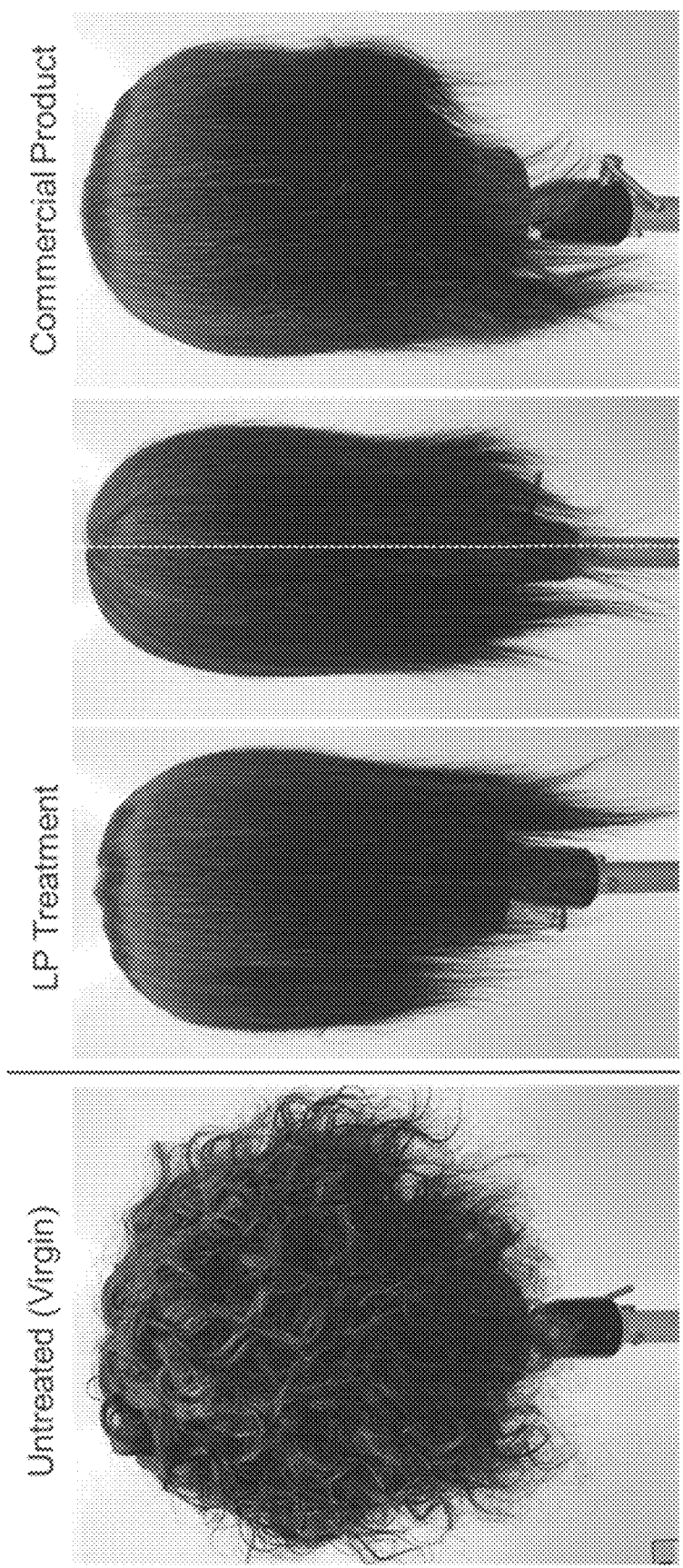
FIG. 69 depicts images showing a mannequin with wavy hair with one side grafted with an exemplary PEG-diacrylate monomer and post-treatment with gluconolactone and citric acid (left) and one side treated with a commercial product (right).
Figure 70A:
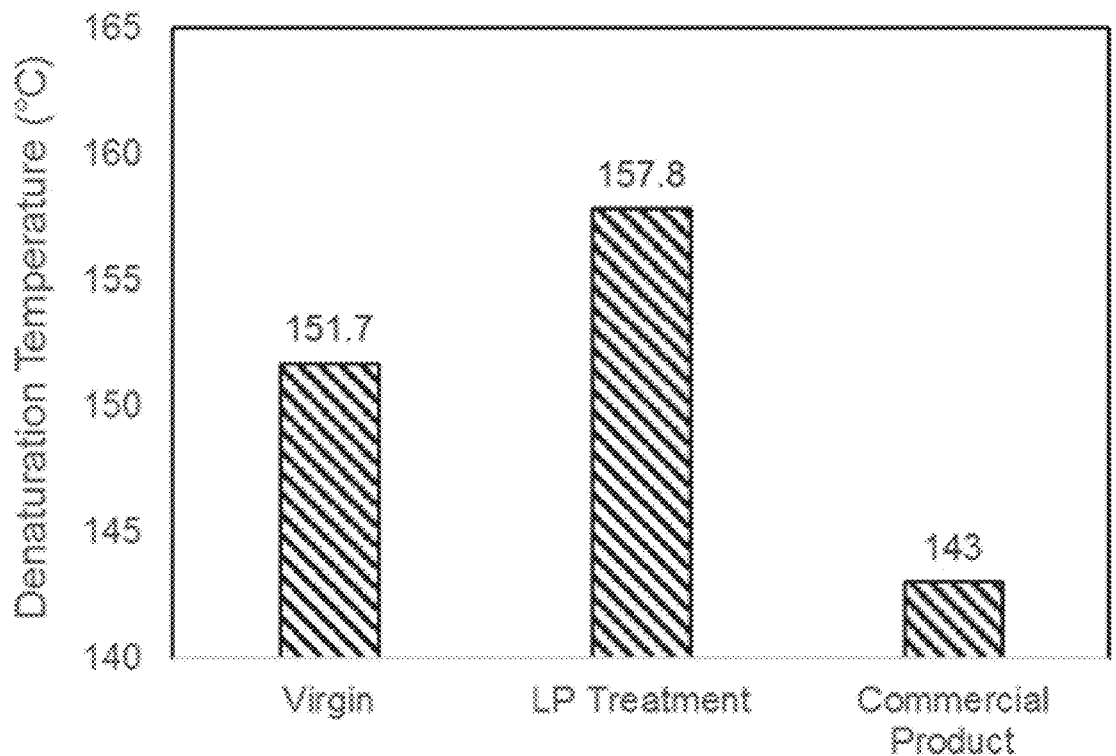
FIG. 70A depicts denaturation temperatures of untreated virgin hair, hair after semi-simultaneous grafting with an exemplary PEG-diacrylate monomer and post-treatment with gluconolactone and citric acid, and hair after treatment with a commercial product.
Figure 70B:
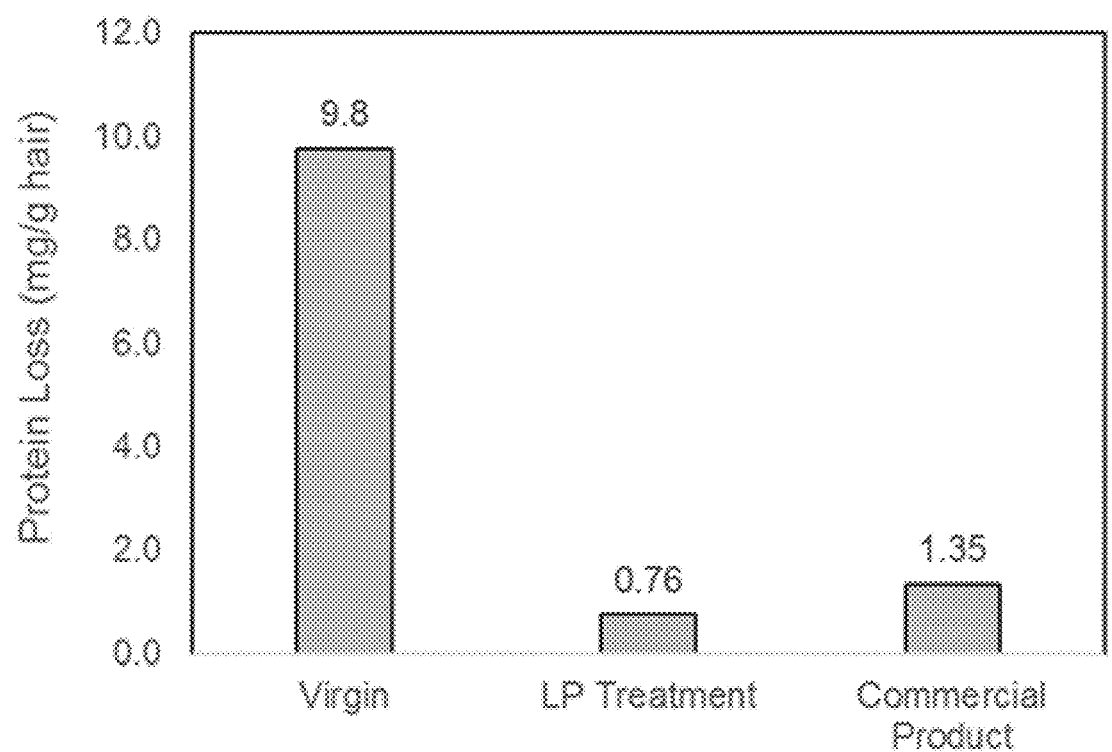
FIG. 70B depicts protein loss values of untreated virgin hair, hair after semi-simultaneous grafting with an exemplary PEG-diacrylate monomer and post-treatment with gluconolactone and citric acid, and hair after treatment with a commercial product.

FIG. 69 shows comparisons between commercial straightening treatment and the grafting process disclosed herein, which includes grafting with PEG-diacrylate molecules and post-treatment with polycarboxylic acids. Commercial straightening treatments used here are based on an ammonium thioglycolate reducing agent and consist of two main steps: a reduction step with ammonium thioglycolate and a neutralization step with hydrogen peroxide-based solution. The disclosed semi-simultaneous grafting process used 5 wt % ammonium thioglycolate reducing solution at a pH of about 9.5 and a liquor ratio of 1.1:1 followed by application of PEG-diacrylate 2 k at a monomer-to-thiol ratio of about 0.04:1. The grafting treatment was carried out for 30 minutes. After thoroughly rinsing the hair, a post-treatment of 2 wt % gluconolactone and 2 wt % citric acid was applied to the mannequin head. It can be seen that hair after grafting and post-treatment appears straighter and shinier. In addition, significantly higher denaturation temperature was observed after grafting and post-treatment (labeled LP treatment) in comparison to the commercial product (FIG. 70A). Hair treated with commercial product showed dramatic decrease in $T_d$ indicating severe hair damage. $T_d$ increases after grafting and post-treatment indicating hair becomes stronger. Furthermore, lower protein loss (meaning healthier and less porous hair), was observed after grafting and post-treatment (labeled LP treatment) compared to the hair treated with commercial product (FIG. 70B). The protein loss was almost doubled for the hair treated with commercial product as compared to the hair treated with the grafting process and post-treatment.

Example 6—Combining a Monomer with a Commercial Reducing Agent

Figure 71:
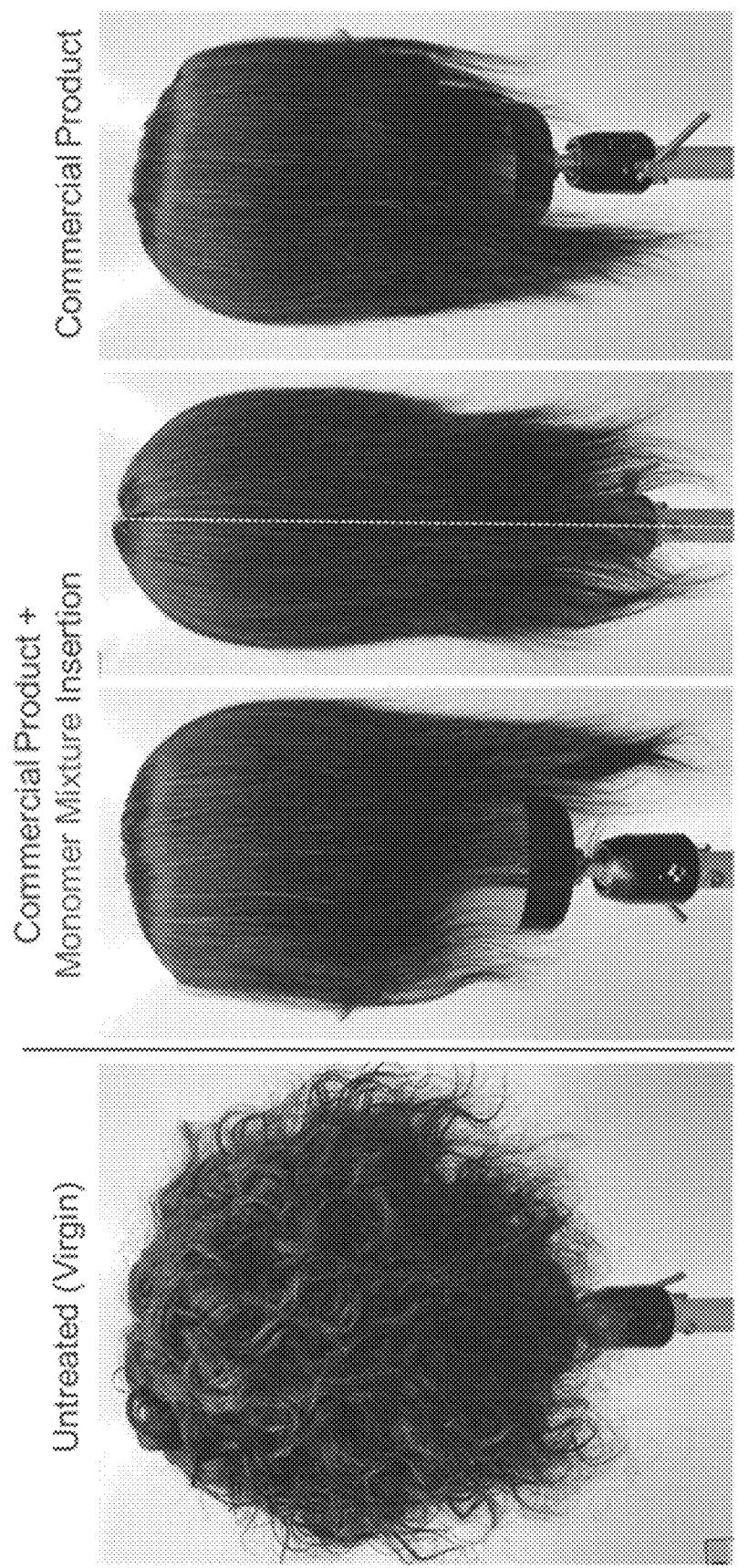
FIG. 71 depicts images showing a mannequin with wavy hair treated with a commercial product with one side grafted with an exemplary PEG-diacrylate monomer and N-acetyl amino acid additive (left) and no additional treatment (right).
Figure 72:
FIG. 72 depicts images showing a mannequin with frizzy hair treated with a commercial perming product with no additional treatment (left) and with one side grafted with an exemplary PEG-diacrylate monomer and N-acetyl amino acid additive (right).
Figure 73A:
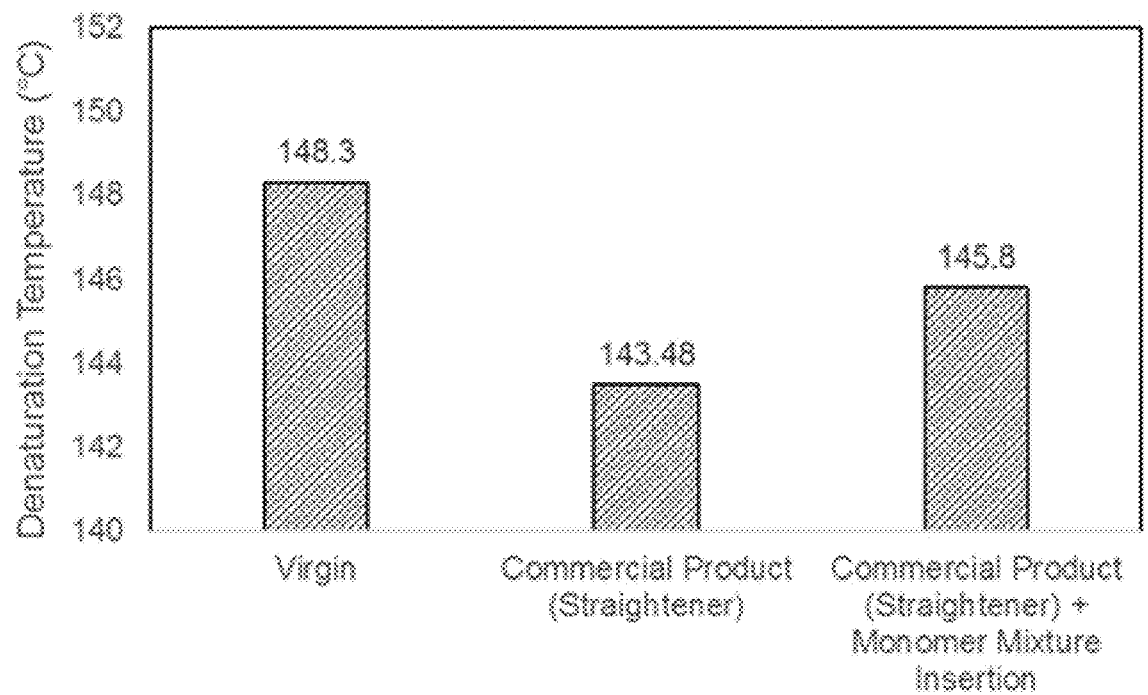
FIG. 73A depicts denaturation temperatures of untreated virgin hair, hair after straightening with a commercial product and insertion of a mixture of an exemplary PEG-diacrylate monomer and N-acetyl amino acid additive, and hair after straightening with a commercial product.
Figure 73B:
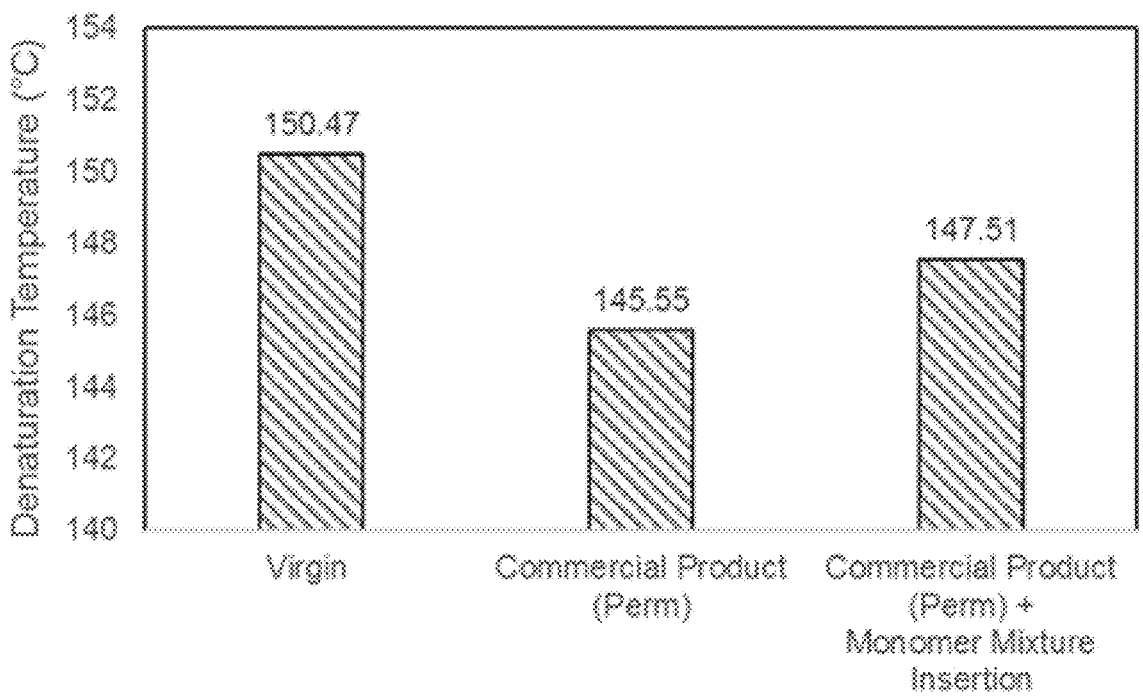
FIG. 73B depicts denaturation temperatures of untreated virgin hair, hair after perming with a commercial product and insertion of a mixture of an exemplary PEG-diacrylate monomer and N-acetyl amino acid additive, and hair after perming with a commercial product.

A typical reducing-agent-based commercial straightening and perm treatment consists of two main steps: a reduction step with ammonium thioglycolate and a neutralization step with hydrogen peroxide-based solution. Using available commercial treatments on the market, an option of insertion of the grafting monomer mixture into the process of the commercial treatment was explored. For example, for commercial straightening and perm treatments, a mixture of PEG-diacrylate 1.5 k at a monomer-to-thiol ratio of about 0.04:1 with 2 wt % N-acetyl glycine as an additive was applied right after the reduction step. The rest of the commercial treatment process was kept the same and followed the commercial kit instructions. It was found that after such insertion, straightening or curling (perm) performance was not sacrificed (FIGS. 71 and 72). For the straightening treatment, no sacrifice in performance was observed as hair on both sides appeared very straight in, and the monomer insertion side had favourable tactile differences according to a blinded sensory evaluation panel. In addition, after monomer insertion, denaturation temperatures were not as low as for the commercial treatments alone as can be seen in FIGS. 73A and 73B. This further suggests that addition of monomer mixture mitigates overall damage while still maintaining the end targeted performance.

Figure 74:
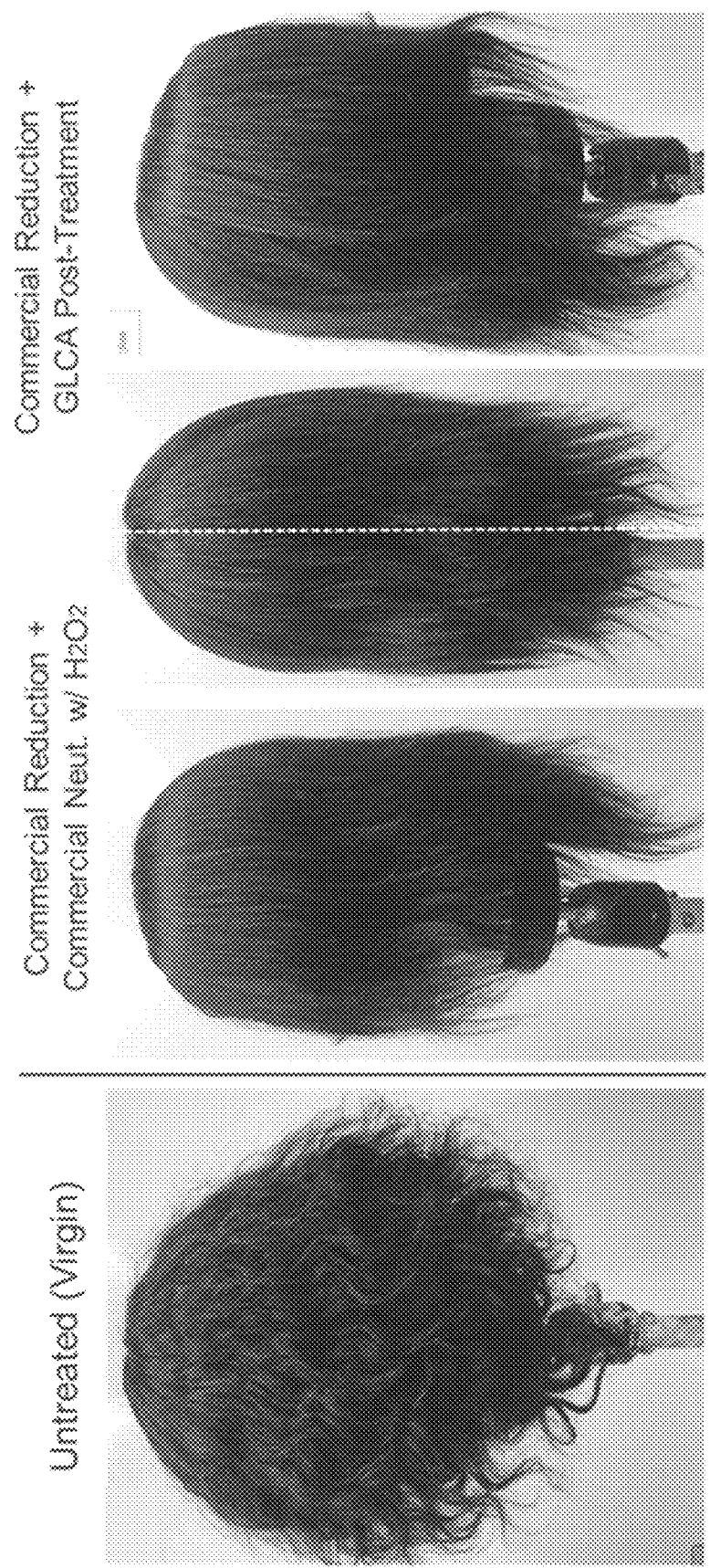
FIG. 74 depicts images showing a mannequin with wavy hair treated with a commercial reduction product with one side neutralized with hydrogen peroxide (left) and one side treated with gluconolactone and citric acid (right).
Figure 75A:
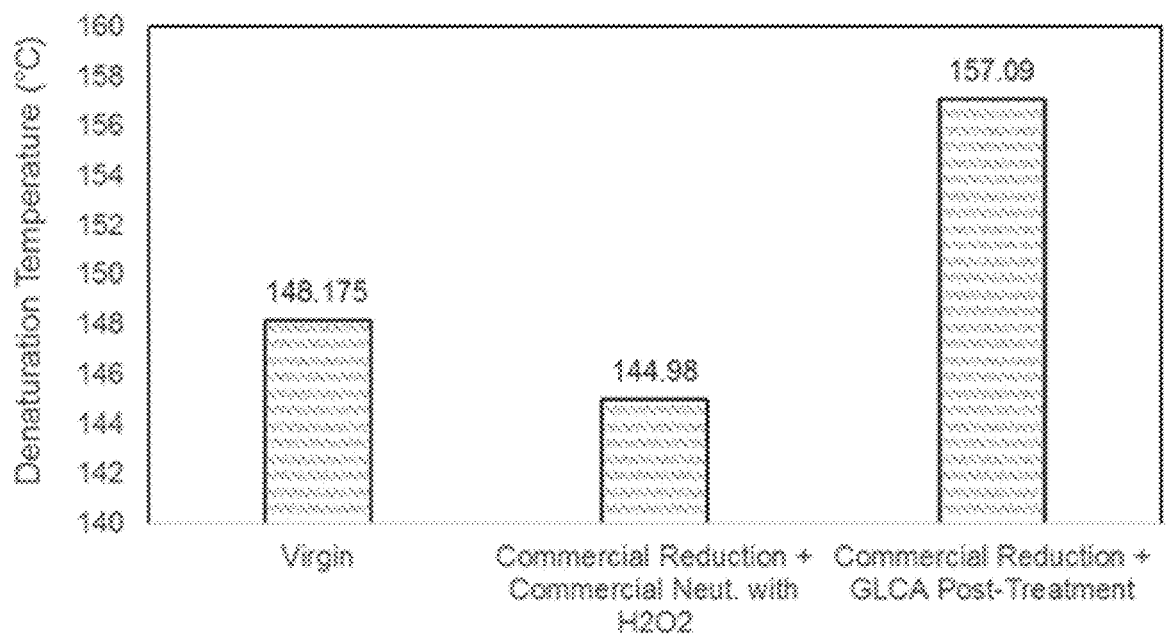
FIG. 75A depicts denaturation temperatures of untreated virgin hair, hair after commercial reduction product and neutralization with hydrogen peroxide, and hair after commercial reduction product and post-treatment with gluconolactone and citric acid.
Figure 75B:
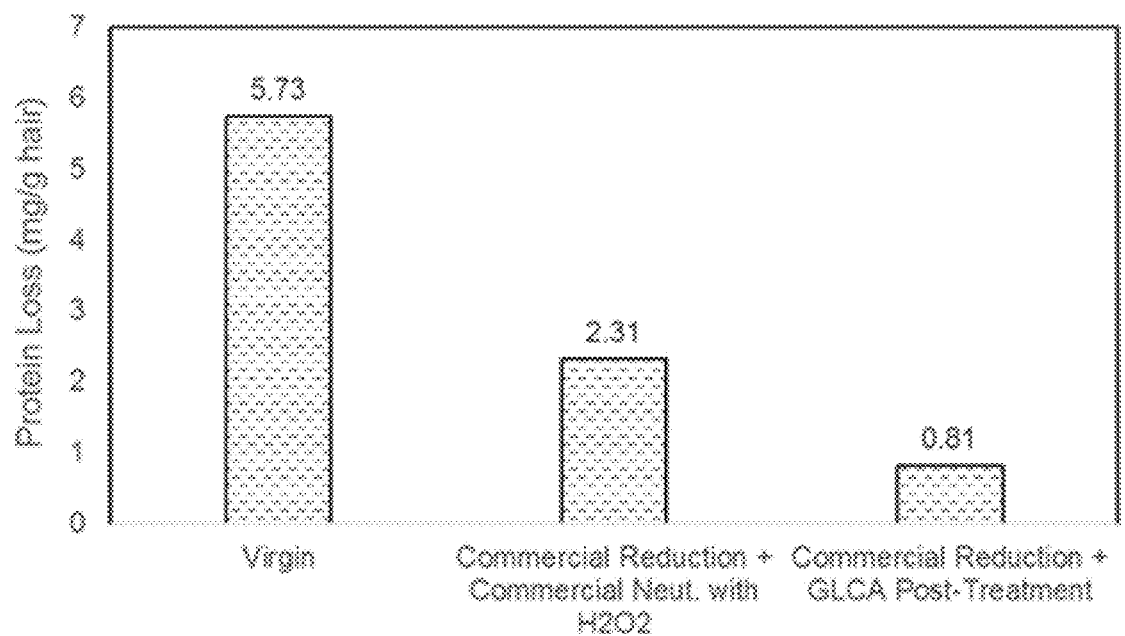
FIG. 75B depicts protein loss values of untreated virgin hair, hair after commercial reduction product and neutralization with hydrogen peroxide, and hair after commercial reduction product and post-treatment with gluconolactone and citric acid.

The potential of using gluconolactone and/or polycarboxylic acids as post-treatments was explored instead of the commercial neutralizers, which usually contain hydrogen peroxide. Hydrogen peroxide treatments, while designed to oxidize thiol bonds back to form cysteine bonds within the hair, sometimes result in severe hair damage in the case of either over or under oxidation. Thiol groups may convert to cysteic acid groups which makes hair more hydrophilic. On the other hand, the use of GLCA post-treatment showed that hair became stronger based on the increase in denaturation temperature and lower protein loss indicating less porous hair. Hence, it was proposed to use GLCA post-treatment instead of conventional neutralizers. FIG. 74 shows a mannequin head before treatment and after treatments with commercial reduction and commercial neutralizer on the left and commercial reduction and GLCA post-treatment on the right. As can be seen straightening performance was not sacrificed after GLCA post-treatment as both sides look similarly straight. Commercial treatment did result in lower denaturation temperature (FIG. 75A), while when GLCA post-treatment was used denaturation temperature showed dramatic increase. Similarly, protein loss increased after commercial treatment, while it was lower when GLCA post-treatment was used (FIG. 75B). This indicates that post-treatment with GLCA or other polycarboxylic acid could be used as an alternative to the conventional $H_2O_2$ based neutralizers without sacrifice in performance and with mitigation of hair damage.

Example 7—Long-Lasting In Vivo Performance

For the in vivo subjects, a semi-simultaneous grafting process used 5 wt % ammonium thioglycolate reducing solution at a pH of about 9.5 and a liquor ratio of 1.1:1 followed by application of PEG-diacrylate 1.5 k at a monomer-to-thiol ratio of about 0.04:1. The grafting treatment was carried out for 30 minutes. After thoroughly rinsing the hair, a post-treatment of 2 wt % gluconolactone and 2 wt % citric acid was applied to the subject's head. Hair was then blow dried and flat ironed.

FIGS. 76A and 76B show performance results after grafting on two subjects with different hair types. In both cases, the grafting process was designed to straighten originally wavy or curly hair. The subject in FIG. 76A had naturally wavy and frizzy hair which became very straight and smooth after the grafting treatment. The subject in FIG. 76B had bleached (damaged) and curly hair which also became straight and smooth after the treatment. As could be seen, after the grafting process, hair on both subjects appeared much straighter, shinier, and less frizzy. These subjects represented examples of using the grafting process as a straightening treatment, which could be done on either healthy hair or damaged (bleached) hair.

Figure 78:
FIG. 78 depicts images showing a subject with curly and frizzy hair before and after semi-simultaneous grafting with an exemplary PEG-diacrylate monomer and post-treatment with gluconolactone and citric acid.

Defrizzing and smoothing performance was shown on a subject with naturally straight frizzy hair in FIG. 77. After the grafting treatment, hair appeared much shinier, less frizzy and smooth with fibers well aligned. Similarly, defrizzing and smoothing performance was also achieved on naturally curly hair without the change in the natural hair shape (FIG. 78). Hair again appeared much shinier and less frizzy after the grafting treatment. This further showed how the grafting process could be used as a defrizzing/smoothing treatment without the change in natural hair shape.

Figure 79:
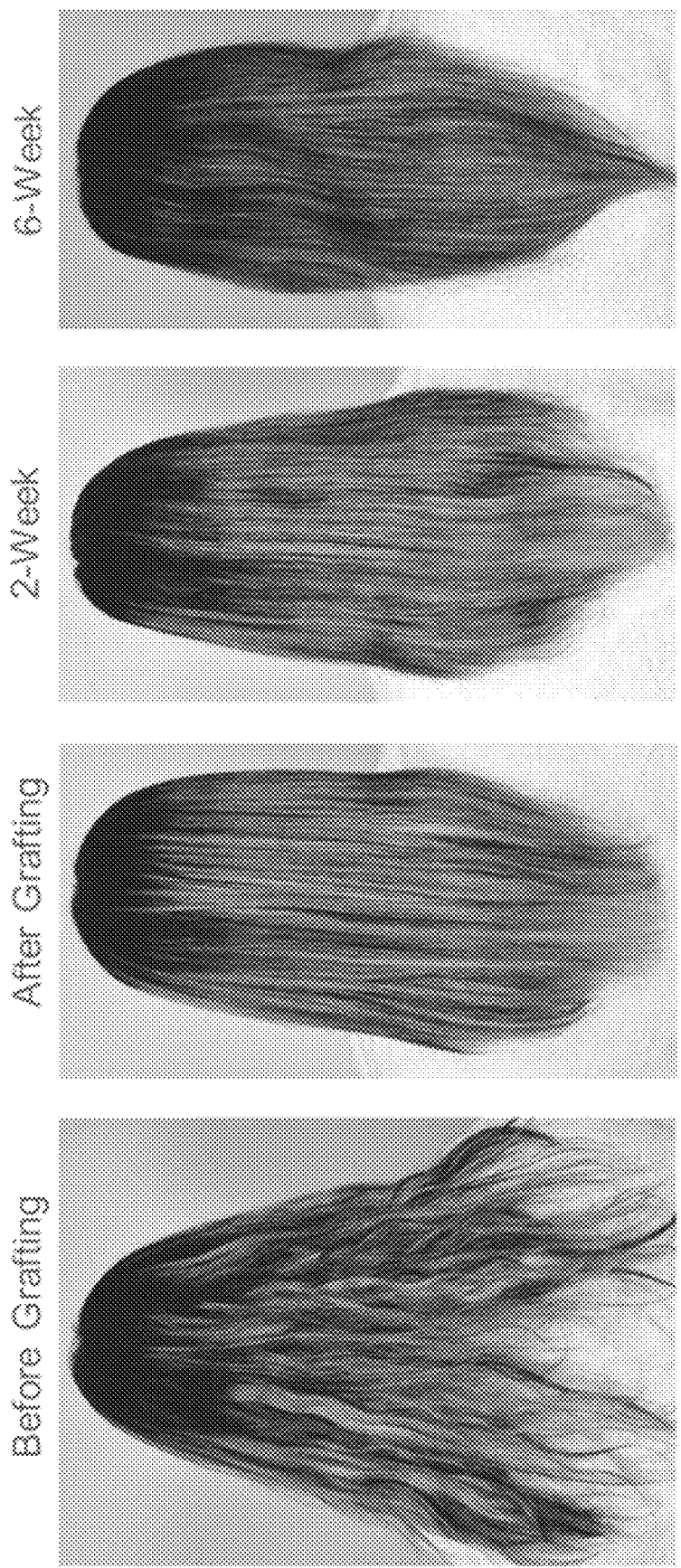
FIG. 79 depicts images showing a subject with bleached and curly hair before and after semi-simultaneous grafting with an exemplary PEG-diacrylate monomer and post-treatment with gluconolactone and citric acid at various time points.

The long-lastingness of the grafting process is presented in FIG. 79. The subject initially had curly, damaged (bleached) hair, which after grafting became much straighter, smoother, less frizzy, and more aligned. It can be seen that straightening performance is still there after 6 weeks (about 1.5 months).

INCORPORATION BY REFERENCE

The contents of the U.S. patents and U.S. patent applications mentioned or cited herein, are hereby incorporated by reference in their entirety to the same extent as if each individual U.S. patent or U.S. patent application was specifically and individually indicated to be incorporated by reference. Applicants reserve the right to physically incorporate into this application any and all materials and information from any such U.S. patents and U.S. patent applications.

EQUIVALENTS

The invention has been described broadly and generically herein. Those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. Further, each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

We claim:

1. A semi-simultaneous method for treating a keratin-containing material, comprising:
    i) providing a keratin-containing material sample comprising a plurality of disulfide bonds;
    ii) applying to the keratin-containing material sample for a period of time a mixture, comprising a reducing agent to produce a plurality of free thiol groups, thereby producing a reduced keratin-containing material sample comprising the plurality of free thiol groups; and
    iii) applying a monomer selected from a poly(ethylene glycol) (PEG) acrylate, a PEG-diacrylate, a succinimidyl-[(N-maleimidopropionamido)-diethyleneglycol] ester, a PEG-maleimide, a PEG-methyl ether maleimide, and a methoxy-PEG-maleimide to the reduced keratin-containing material sample, wherein the reduced keratin-containing material is not rinsed or washed between steps ii) and iii).

2. The method of claim 1, wherein the mixture comprising a reducing agent further comprises a catalyst.

3. A simultaneous method for treating a keratin-containing material, comprising:
    i) providing a keratin-containing material sample comprising a plurality of disulfide bonds; and
    ii) applying to the keratin-containing material sample for a period of time a mixture, comprising a reducing agent and a monomer selected from a poly(ethylene glycol) (PEG) acrylate, a PEG-diacrylate, a succinimidyl-[(N-maleimidopropionamido)-diethyleneglycol] ester, a PEG-maleimide, a PEG-methyl ether maleimide, and a methoxy-PEG-maleimide, thereby forming a plurality of free thiol groups which react with the monomer to form a plurality of covalent bonds between the free thiol groups and the monomer.

4. The method of claim 1, wherein the reducing agent is selected from the group consisting of ammonium thioglycolate, L-cysteine, N-acetyl L-cysteine, glutathione, ascorbic acid, beta-mercaptoethanol, 2-mercaptoethylamine, 2-mercaptoethylamine hydrochloride, dithiothreitol (DTT), thiolactic acid, thiosalicylic acid, tris-2-carboxyethylphosphine hydrochloride (TCEP), sodium hydrosulfite, sodium thiosulfate, potassium disulfite, sodium disulfite, sodium bisulfate, sodium bisulfite, ammonium bisulfite, thioglycolic acid, calcium thioglycolate, potassium thioglycolate, sodium thioglycolate, cysteine hydrochloride, ammonium thiolactate, thioglycerin, mercaptoprpionic acid, glycerol thioglycolate and dithiolbutylamine (DTBA).

5. The method of claim 1, wherein the monomer is a PEG-diacrylate.

6. The method of claim 1, wherein the molar ratio of the monomer to the free thiol groups is about 0.001:1 to about 2.5:1.

7. The method of claim 1, wherein the method further comprises a post-treatment after step iii), comprising applying to the reduced keratin-containing material sample modified with monomer for a period of time an additive, wherein the additive is selected from the group consisting of a fatty acid, a fatty alcohol, a fatty acid ester, an amino acid mixture, a peptide mixture, an acidifier, a polycarboxylic acid, or a mixture thereof.

8. The method of claim 1, wherein the keratin-containing material is selected from the group consisting of hair, eyebrows, eyelashes, fingernails and toenails.

9. The method of claim 3, wherein the reducing agent is selected from the group consisting of ammonium thioglycolate, L-cysteine, N-acetyl L-cysteine, glutathione, ascorbic acid, beta-mercaptoethanol, 2-mercaptoethylamine, 2-mercaptoethylamine hydrochloride, DTT, thiolactic acid, thiosalicylic acid, TCEP, sodium hydrosulfite, sodium thiosulfate, potassium disulfite, sodium disulfite, sodium bisulfate, sodium bisulfite, ammonium bisulfite, thioglycolic acid, calcium thioglycolate, potassium thioglycolate, sodium thioglycolate, cysteine hydrochloride, ammonium thiolactate, thioglycerin, mercaptoprpionic acid, glycerol thioglycolate and DTBA.

10. The method of claim 3, wherein the monomer is a PEG-diacrylate.

11. The method of claim 3, wherein the molar ratio of the monomer to the free thiol groups is about 0.001:1 to about 2.5:1.

12. The method of claim 3, wherein the mixture further comprises a catalyst selected from the group consisting of an amine, a phosphine, and a radical initiator.

13. The method of claim 3, wherein the keratin-containing material is selected from the group consisting of hair, eyebrows, eyelashes, fingernails and toenails.

14. The method of claim 1, wherein the method for treating a keratin-containing material improves one or more properties selected from the group consisting of a hydrophobicity, an elongation at break, a Young's modulus, an ultimate tensile strength, a protein loss value, and a denaturation temperature of the keratin-containing material.

15. The method of claim 3, wherein the method for treating a keratin-containing material improves one or more properties selected from the group consisting of a hydrophobicity, an elongation at break, a Young's modulus, an ultimate tensile strength, a protein loss value, and a denaturation temperature of the keratin-containing material.

* * * * *